US008580930B2

(12) United States Patent
Winston, Jr. et al.

(10) Patent No.: US 8,580,930 B2
(45) Date of Patent: Nov. 12, 2013

(54) HEPATOCYTE GROWTH FACTOR (HGF) BINDING PROTEINS

(75) Inventors: William M. Winston, Jr., Marlborough, MA (US); S. Kirk Wright, Waltham, MA (US); May Han, Brookline, MA (US); Lyne Breault, Roslindale, MA (US); Jie Lin, West Roxbury, MA (US); Bijan Etemad-Gilbertson, Jamaica Plain, MA (US); Christine Knuehl, Natick, MA (US); Jeno Gyuris, Lincoln, MA (US); Arnold Horwitz, San Leandro, CA (US)

(73) Assignee: AVEO Pharmaceuticals, Inc., Cambridge, MA (US)

(*) Notice: Subject to any disclaimer, the term of this patent is extended or adjusted under 35 U.S.C. 154(b) by 0 days.

(21) Appl. No.: 13/589,664

(22) Filed: Aug. 20, 2012

(65) Prior Publication Data

US 2013/0203963 A1 Aug. 8, 2013

Related U.S. Application Data

(62) Division of application No. 13/051,481, filed on Mar. 18, 2011, now Pat. No. 8,273,355, which is a division of application No. 12/632,765, filed on Dec. 7, 2009, now Pat. No. 7,943,344, which is a division of application No. 11/757,059, filed on Jun. 1, 2007, now Pat. No. 7,649,083.

(60) Provisional application No. 60/810,714, filed on Jun. 2, 2006, provisional application No. 60/860,509, filed on Nov. 21, 2006.

(51) Int. Cl.
*C07K 16/24* (2006.01)
*C07K 16/00* (2006.01)

(52) U.S. Cl.
USPC ............. 530/388.23; 530/388.15; 530/388.1; 530/387.1

(58) Field of Classification Search
None
See application file for complete search history.

(56) References Cited

U.S. PATENT DOCUMENTS

| | | | |
|---|---|---|---|
| 5,707,624 A | 1/1998 | Nickoloff et al. |
| 5,766,886 A | 6/1998 | Studnicka et al. |
| 5,997,868 A | 12/1999 | Goldberg et al. |
| 6,432,406 B1 | 8/2002 | Goldberg et al. |
| 6,881,557 B2 | 4/2005 | Foote |
| 7,220,410 B2 | 5/2007 | Kim et al. |
| 7,408,043 B2 | 8/2008 | Chung et al. |
| 7,459,536 B1 | 12/2008 | Cao et al. |
| 7,494,650 B2 | 2/2009 | Kim et al. |
| 7,632,926 B2 | 12/2009 | Kim et al. |
| 7,649,083 B2 | 1/2010 | Winston, Jr. et al. |
| 7,659,378 B2 | 2/2010 | Han et al. |
| 7,687,063 B2 | 3/2010 | Kim et al. |
| 7,718,174 B2 | 5/2010 | Chung et al. |
| 7,935,502 B2 | 5/2011 | Han et al. |
| 7,943,344 B2 | 5/2011 | Winston, Jr. et al. |
| 8,268,315 B2 | 9/2012 | Han et al. |
| 8,273,355 B2 | 9/2012 | Winston, Jr. et al. |
| 2005/0118643 A1 | 6/2005 | Burgess et al. |
| 2007/0036797 A1 | 2/2007 | Kim et al. |
| 2008/0038256 A1 | 2/2008 | Chung et al. |
| 2009/0104192 A1 | 4/2009 | Kim et al. |
| 2010/0221250 A1 | 9/2010 | Kim et al. |
| 2010/0278815 A1 | 11/2010 | Kim et al. |

FOREIGN PATENT DOCUMENTS

| | | |
|---|---|---|
| WO | WO 01/34650 A1 | 5/2001 |
| WO | WO 2005/017107 A2 | 2/2005 |
| WO | WO 2005/044848 A1 | 5/2005 |
| WO | WO 2005/107800 A1 | 11/2005 |
| WO | WO 2006/130773 A2 | 12/2006 |
| WO | WO 2007/115049 A2 | 10/2007 |

OTHER PUBLICATIONS

Australian Patent Office Search Report and Written Opinion dated Apr. 19, 2010.
Burgess et al. "Fully Human Monoclonal Antibodies to Hepatocyte Growth Factor With Therapeutic Potential Against Hepatocyte Growth Factor/C-Met-Dependent Human Tumors" (2006) Cancer Res. 66:3, pp. 1721-1729.
Burr et al. "Anti-Hepatocyte Growth Factor Antibody Inhibits Hepatocyte Proliferation During Liver Regeneration" Journal of Pathology, Chicester, Sussex, GB, vol. 185, (Jul. 1998) pp. 298-302.
Cao et al. "Neutralizing monoclonal antibodies to hepatocyte growth factor/scatter factor (HGF/SF) display antitumor activity in animal models" Proc. Natl. Acad. Sci. 2001 USA 98: 7443-7448.
Caulfield et al.. (1992) "A Pathogenic Monoclonal Antibody, G8, is Characteristic of Antierythrocyte Autoantibodies from Coombs'-Positive NZB Mice," The Journal of Immunology 148(7):2068-2073.
Database: GenBank, Accession No: X60424, 2004.
Database: GenBank, Accession No: X60425, 2004.
Database: GenBank, Accession No: X75096, 2006.
Hwang et al. "Use of human germline genes in a CDR homology-based approach to antibody humanization" Methods. May 2005;36(1):35-42.
International Search Report for PCT/2007/012939 dated Jan. 30, 2008.
International Search Report for PCT/2007/012950 dated Apr. 15, 2008.
Kim et al. "Systemic anti-hepatocyte growth factor monoclonal antibody thereapy induces the regression of intracranial glioma axenografts" (2006) *Clinical Cancer Research* 12: 1292-1298.
Monestier et al. (1994) "Molecular Analysis of Mercury-Induced Antinucleolar Antibodies in H-2s Mice," Journal of Immunology 152(2): 667-675.

(Continued)

*Primary Examiner* — Sharon Wen
(74) *Attorney, Agent, or Firm* — Goodwin Procter LLP

(57) ABSTRACT

The present invention provides a family of binding proteins that bind and neutralize the activity of hepatocyte growth factor (HGF), in particular human HGF. The binding proteins can be used as diagnostic and/or therapeutic agents. With regard to their therapeutic activity, the binding proteins can be used to treat certain HGF responsive disorders, for example, certain HGF responsive tumors.

9 Claims, 9 Drawing Sheets

(56) References Cited

OTHER PUBLICATIONS

R&D Systems, Inc. 1999 Catalog, p. 185, Cat. #MAB294, anti-human HGF monoclonal antibody.

Rubin et al. "Hepatocyte growth factor/scatter factor and its receptor, the c-met proto-oncogene product" Biochim Biophys Acta. Dec. 23, 1993;1155(3):357-71.

Studnicka et al. "Human-engineered monoclonal antibodies retain full specific binding activity by preserving non-CDR complementarity-modulating residues" Protein Eng. Jun. 1994;7(6):805-14.

Tan et al. ""Superhumanized" antibodies: reduction of immunogenic potential by complementarity-determining region grafting with human germline sequences: application to an anti-CD28" J Immunol. Jul. 15, 2002;169(2):1119-25.

Zaccolo et al. "Dimerization nof FAB Fragments Enables Ready Screening of Phage Antibodies that Affect Hepatocyte Growth Factor/Scatter Factor Activity on Target Cells" European Journal of Immunology, Weinheim, DE, vol. 27, No. 3, (1997), pp. 618-623.

Jun et al. "AMG 102, a fully human anti-hepatocyte growth factor/scatter factor neutralizing antibody, enhances the efficacy of temozolomide or docetaxel in U-87 MG cells and xenografts" Clin Cancer Res. Nov. 15, 2007;13(22 Pt 1):6735-42.

Complete Heavy Chain Variable Region Amino Acid Alignments

| Antibody | Signal Peptide | CDR1 | | CDR2 |
|---|---|---|---|---|
| 1A3 | MNFGLRLIFLVLVLKGVKC | EVQLVESGGGLVQPGGSLKLSCAASEFTFS | NYYMS | WVRQTPEKRLQWVAYISPGGGSSYYPASVKGRFTISRDNAKNTLYL |
| 2B8 | MGWSYIILFLVATATDVHS | QVQLQQPGAELVKPGTSVKLSCKASGYTFT | TYWMH | WVNQRPGQGLEWIGEINPTNGHTNYNEKFKSKATLTVDKSSSTAYM |
| 2F8 | MEWSWVFLFLLSVTAGVHC | QVQLKQSGAELVKPGTSVKMSCKASGYTFT | TYYIH | WVNQRPGQGLEWIGKIGPGSGSTYYNEMFKDKATLTVDTSSSTAYM |
| 3B6 | MEWPCIFLFLLSVTEGVHS | QVQLQQSGAELVRPGSSVKISCKASGYVFS | SYWMN | WVKQRPGQGLEWIGQIYPGDGSNYNGNFKGKATLTADKSSSTAYM |
| 3D11 | MAVPVLFLCLVAFPSCVLS | QVQLKESGPGLVAPSQSLSITCTVSGFSLT | SYSLH | WVRQPPGKGLEWLGVIWAG-GNTNYNSSLMSRLTIRKDNSKSQVFL |
| 1D3 | MNFGLRLIFLVLVLKGVKC | EVQLVESGGGLVQPGGSLKLSCAASGFTFS | DYYMS | WVRQTPEKRLEWVAYISSGGGSTYYPDSVKGRFTISRNAKNTLYL |
| 1F3 | MNFGLRLIFLVLVLKGVKC | EVQLVESGGGLVQSGGSLKLSCAASGFTFS | NYFMS | WVRQTPEKRLEWVAYISSGGGSTYYPDSVKGRFTISRDNAKNTLYL |
| 3A12 | MNFGLRLIFLVLVLKGVKC | EVQLVESGGGLVQPGGSLKISCAASGFTFS | NYFMS | WVRQTPEKRLEWVAYISSGGGSTYYPDSVKGRFTISRDNAKNTLYL |

CDR3

| | | | |
|---|---|---|---|
| (1A3 cont.) | QMSSLKSEDTAMYYCAR | QGDGYYGDYAMDY | WGQGTSVTVSS (SEQ ID NO: 2) |
| (2B8 cont.) | QLSSITSEDSAVYYCAR | NY----VGSIFDY | WGQGTTLTVSS (SEQ ID NO: 12) |
| (2F8 cont.) | QLSSITSDDSAVYFCAR | RG----LGRGFDY | WGQGTTLTVSS (SEQ ID NO: 22) |
| (3B6 cont.) | QLSSITSEDSAVYFCAS | QLG--LRENYFDY | WGQGTTLTVSS (SEQ ID NO: 32) |
| (3D11 cont.) | KMNSLQTDDTAMYYCAR | ER--------FAY | WGQGTLVTVSA (SEQ ID NO: 42) |
| (1D3 cont.) | QMSSLKSEDTAIYYCVR | QGDGYYGDYAMDY | WGQGTSVIVSS (SEQ ID NO: 52) |
| (1F3 cont.) | QMSSLKSEDTAMYYCVR | QGDGYYGDYAMDY | WGQGTSVTVSS (SEQ ID NO: 62) |
| (3A12 cont.) | QMNSLKSEDTAMYYCVR | QGDGYYGDYAMDY | WGQGTSVTVSS (SEQ ID NO: 72) |

FIG. 2

Heavy Chain CDR Amino Acid Alignments

| Antibody | CDR1 | | CDR2 | | CDR3 | |
|---|---|---|---|---|---|---|
| 1A3 | NYYMS | (SEQ ID NO: 5) | YISPGGGSSYYPASVKG | (SEQ ID NO: 6) | QGDGYYGDYAMDY | (SEQ ID NO: 7) |
| 2B8 | TYWMH | (SEQ ID NO: 15) | EINPTNGHTNYNEKFKS | (SEQ ID NO: 16) | NY~~~~VGSIFDY | (SEQ ID NO: 17) |
| 2F8 | TYYIH | (SEQ ID NO: 25) | KIGPSGSSTYYNEMFKD | (SEQ ID NO: 26) | RG~~~~LGRGFDY | (SEQ ID NO: 27) |
| 3B6 | SYWMN | (SEQ ID NO: 35) | QIYPGDGDSNYNGNFKG | (SEQ ID NO: 36) | QLG~~LRENYFDY | (SEQ ID NO: 37) |
| 3D11 | SYSLH | (SEQ ID NO: 45) | VIWAG~GNTNYNSSLMS | (SEQ ID NO: 46) | ER~~~~~~~~FAY | (SEQ ID NO: 47) |
| 1D3 | DYYMS | (SEQ ID NO: 55) | YISGGGSTYYPDSVKG | (SEQ ID NO: 56) | QGDGYYGDYAMDY | (SEQ ID NO: 57) |
| 1F3 | NYFMS | (SEQ ID NO: 65) | YISSGGGSTYYPDSVKG | (SEQ ID NO: 66) | QGDGYYGDYAMDY | (SEQ ID NO: 67) |
| 3A12 | NYFMS | (SEQ ID NO: 75) | YISSGGGSTYYPDSVKG | (SEQ ID NO: 76) | QGDGYYGDYAMDY | (SEQ ID NO: 77) |

FIG. 3

Complete Light (Kappa) Chain Variable Region Amino Acid Alignments

| Antibody | Signal Peptide | CDR1 | CDR2 |
|---|---|---|---|
| 1A3 | --MSVPTQVLGLLLLWLTDARC DIQMTQSPASLSVSVGETVTITC RASENIY----SNLA WYQQKQGKSPQLLVY AATNLAD GVPSRFSGSGSGTQFSLK |
| 2B8 | --MESQTLVFISILLWLYGADGN IVMTQSPKSMSMSVGERVTLSC KASENVV----SYVS WYQQKPAQSPKLLIY GASNRNT GVPDRFTGSCSATDFTLT |
| 2F8 | --METDTILLWVLLLWVPGSTGD IVLTQSPASLAVSLGQRATISC KASQSVDYDGNSYIN WYQKPGQPPKVLIY VASNLES GIPARFSGSG-GTDFTLN |
| 3B6 | MDMRTPAQFLGILLLWFPGIKC DIKMTQSPSSMYASLGERVTITC KASQDIK----SYLS WFQQKPGKSPKTLIY RVNRLVD GVPSRFSGSGQDSSLT |
| 3D11 | MDFQVQIFSFLLISASVKISRGQ IVLTQSPAIMSAYPGEKVTMTC SASSSVS----YNMH WYQQKSGTSPKRWIY DTSKLAS GVPARFSGSGSGTSYSLT |
| 1D3 | --MSVPTQVLGLLLLWLTDARC DIQMTQSPASLSVSVGETVTITC RTSENIY----SNLA WYQQKQGKSPQLLIY AATNLAD GVPSRFSGSGSGTQFSLR |
| 1F3 | --MSVPTQVLGLLLLWLTDARC DIQMTQSPASLSVSVGETVTITC RASENIY----SNLA WYQQKQGKSPQLLVY DATHLPD GVPSRFSGSGSGTQFSLK |
| 3A12 | --MSVPTQVLGLLLLWLTDARC DIQMTQSPASLSVSVGETVTITC RASENIY----INLA WYQQKQGKSPQLLVH AATKLAD GVPSRFSGSGSGTQYSLK |

CDR3

| | | |
|---|---|---|
| (1A3 cont.) | INSLQSEDFGTYYC QHFWGTPYT FGGGTKLEIK | (SEQ ID NO: 4) |
| (2B8 cont.) | ISSVRAEDLADYHC GQSYNYPYT FGGGTRLEIK | (SEQ ID NO: 14) |
| (2F8 cont.) | IHPVEEEDAATYYC QQSIEDPPT FGAGTKLELK | (SEQ ID NO: 24) |
| (3B6 cont.) | ITSLENEDMGIYYC LQYDEFPFT FGGGTKLEIK | (SEQ ID NO: 34) |
| (3D11 cont.) | ISSMEAEDAATYYC QQWSSNPLT FGAGTKLEIK | (SEQ ID NO: 44) |
| (1D3 cont.) | INSLQSEDFGRYYC QHFWGTPYT FGGGTKLEIK | (SEQ ID NO: 54) |
| (1F3 cont.) | INSLQSEDFGSYYC QHFWGTPYT FGGGTRLEIK | (SEQ ID NO: 64) |
| (3A12 cont.) | INSLQSEDFGSYYC QHFWGTPYT FGGGTKLEIK | (SEQ ID NO: 74) |

FIG. 4

Light (Kappa) Chain CDR Amino Acid Alignments

| Antibody | CDR1 | CDR2 | CDR3 |
|---|---|---|---|
| 1A3 | RASENIY----SNLA (SEQ ID NO: 8) | AATNLAD (SEQ ID NO: 9) | QHFWGTPYT (SEQ ID NO: 10) |
| 1D3 | RTSENIY----SNLA (SEQ ID NO: 58) | AATNLAD (SEQ ID NO: 59) | QHFWGTPYT (SEQ ID NO: 60) |
| 2B8 | KASENVV----SYVS (SEQ ID NO: 18) | GASNRNT (SEQ ID NO: 19) | GQSYNYPYT (SEQ ID NO: 20) |
| 2F8 | KASQSVDYDGNSYIN (SEQ ID NO: 28) | VASNLES (SEQ ID NO: 29) | QQSIEDPPT (SEQ ID NO: 30) |
| 3D11 | SASSSVS----YMH (SEQ ID NO: 48) | DTSKLAS (SEQ ID NO: 49) | QQWSSNPLT (SEQ ID NO: 50) |
| 3B6 | KASQDIK----SYLS (SEQ ID NO: 38) | RVNRLVD (SEQ ID NO: 39) | LQYDEFPFT (SEQ ID NO: 40) |
| 1F3 | RASENIY----SNLA (SEQ ID NO: 68) | DATHLPD (SEQ ID NO: 69) | QHFWGTPYT (SEQ ID NO: 70) |
| 3A12 | RASENIY----TNLA (SEQ ID NO: 78) | AATKLAD (SEQ ID NO: 79) | QHFWGTPYT (SEQ ID NO: 80) |

FIG. 5

| Kappa | Heavy | ka (1/Ms) | STDEV | kd (1/s) | STDEV | KD (pM) | STDEV |
|---|---|---|---|---|---|---|---|
| Chimeric 2B8 | Chimeric 2B8 | $2.3 \times 10^6$ | | $2.7 \times 10^{-5}$ | | 11.6 | |
| Hu2B8_Kv1-39.1 | Chimeric 2B8 | $2.8 \times 10^6$ | | $3.9 \times 10^{-5}$ | | 13.6 | |
| Hu2B8_Kv3-15.1 | Chimeric 2B8 | $3.1 \times 10^6$ | | $1.7 \times 10^{-5}$ | | 5.5 | |
| Chimeric 2B8 | Hu2B8_Hv1-f.1 | $2.4 \times 10^6$ | | $1.6 \times 10^{-3}$ | | 662.5 | |
| Chimeric 2B8 | Hu2B8_Hv5-a.1 | $2.4 \times 10^6$ | | $1.1 \times 10^{-5}$ | | 4.4 | |
| Chimeric 2B8 | Hu2B8_Hv5-51.1 | $2.1 \times 10^6$ | | $3.4 \times 10^{-5}$ | | 16.3 | |
| Hu2B8_Kv1-39.1 | Hu2B8_Hv1-f.1 | $7.1 \times 10^6$ | | $2.1 \times 10^{-3}$ | | 294.0 | |
| Hu2B8_Kv1-39.1 | Hu2B8_Hv5-a.1 | $2.6 \times 10^6$ | | $3.8 \times 10^{-5}$ | | 14.7 | |
| Hu2B8_Kv1-39.1 | Hu2B8_Hv5-51.1 | $2.0 \times 10^6$ | $4.2 \times 10^5$ | $1.7 \times 10^{-5}$ | $1.4 \times 10^{-5}$ | 8.1 | 5.3 |
| Hu2B8_Kv3-15.1 | Hu2B8_Hv1-f.1 | $7.8 \times 10^6$ | | $3.7 \times 10^{-3}$ | | 465.8 | |
| Hu2B8_Kv3-15.1 | Hu2B8_Hv5-a.1 | $2.2 \times 10^6$ | | $5.9 \times 10^{-5}$ | | 26.9 | |
| Hu2B8_Kv3-15.1 | Hu2B8_Hv5-51.1 | $1.9 \times 10^6$ | $4.7 \times 10^5$ | $2.3 \times 10^{-5}$ | $6.3 \times 10^{-6}$ | 12.0 | 0.4 |

Fig. 8

SEQUENCE LISTING

```
<160> NUMBER OF SEQ ID NOS: 216

<210> SEQ ID NO 1
<211> LENGTH: 424
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Synthetic Heavy Chain Variable Region 1A3

<400> SEQUENCE: 1
atgaactttg ggctcagatt gatttteett gtecttgttt taaaaggtgt gaagtgtgaa        60
gtgcagctgg tggagtctgg gggaggctta gtgcagcctg gagggtccct gaaactctcc       120
tgtgcagcct ctgaattcac tttcagtaac tattacatgt cttgggttcg ccagactcca       180
gagaagaggc tgcagtgggt cgcatacatt agtcctggtg gtggtagctc ctactatcca       240
```

```
gccagtgtga agggtcgatt caccatctcc agagacaatg ccagaacac cctgtacctg      300 caaatgagca gtctgaagtc tgaggacaca gccatgtatt actgtgcaag acaagggggat    360 ggttactacg ggactatgc tatggactac tggggtcaag gaacctcagt caccgtctcc      420
tcag                                                                   424
```

```
<210> SEQ ID NO 2
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Synthetic Heavy Chain Variable Region 1A3

<400> SEQUENCE: 2

Met Asn Phe Gly Leu Arg Leu Ile Phe Leu Val Leu Val Leu Lys Gly
1               5                   10                  15

Val Lys Cys Glu Val Gln Leu Val Glu Ser Gly Gly Gly Leu Val Gln
            20                  25                  30

Pro Gly Gly Ser Leu Lys Leu Ser Cys Ala Ala Ser Glu Phe Thr Phe
        35                  40                  45

Ser Asn Tyr Tyr Met Ser Trp Val Arg Gln Thr Pro Glu Lys Arg Leu
    50                  55                  60

Gln Trp Val Ala Tyr Ile Ser Pro Gly Gly Gly Ser Ser Tyr Tyr Pro
65                  70                  75                  80

Ala Ser Val Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Met
            100                 105                 110

Tyr Tyr Cys Ala Arg Gln Gly Asp Gly Tyr Tyr Gly Asp Tyr Ala Met
        115                 120                 125

Asp Tyr Trp Gly Gln Gly Thr Ser Val Thr Val Ser Ser
    130                 135                 140
```

```
<210> SEQ ID NO 3
<211> LENGTH: 382
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Synthetic Light (kappa) Chain Variable Region
      1A3

<400> SEQUENCE: 3
atgagtgtgc ccactcaggt cctggggttg ctgctgctgt ggcttacaga tgccagatgt      60
gacatccaga tgactcagtc tccagcctcc ctatctgttt ctgtgggaga aactgtcacc     120
atcacatgtc gagcaagtga gaatatttat agtaatttag catggtatca gcagaaacag    180
ggaaaatctc ctcagctcct ggtctatgct gcaacaaact agcagatgg tgtgccatca     240 aggttcagtg gcagtggatc aggcacacag ttttcctca agatcaacag cctgcagtct     300
gaagattttg ggacttatta ctgtcaacat ttttggggta ctccgtacac gttcggaggg    360
gggaccaagc tggaaataaa ac                                              382
```

```
<210> SEQ ID NO 4
<211> LENGTH: 127
<212> TYPE: PRT
```

```
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Synthetic Light (kappa) Chain Variable Region
      1A3

<400> SEQUENCE: 4

Met Ser Val Pro Thr Gln Val Leu Gly Leu Leu Leu Trp Leu Thr
1               5                   10                  15

Asp Ala Arg Cys Asp Ile Gln Met Thr Gln Ser Pro Ala Ser Leu Ser
            20                  25                  30

Val Ser Val Gly Glu Thr Val Thr Ile Thr Cys Arg Ala Ser Glu Asn
        35                  40                  45

Ile Tyr Ser Asn Leu Ala Trp Tyr Gln Gln Lys Gln Gly Lys Ser Pro
    50                  55                  60

Gln Leu Leu Val Tyr Ala Ala Thr Asn Leu Ala Asp Gly Val Pro Ser
65                  70                  75                  80

Arg Phe Ser Gly Ser Gly Ser Gly Thr Gln Phe Ser Leu Lys Ile Asn
                85                  90                  95

Ser Leu Gln Ser Glu Asp Phe Gly Thr Tyr Tyr Cys Gln His Phe Trp
            100                 105                 110

Gly Thr Pro Tyr Thr Phe Gly Gly Thr Lys Leu Glu Ile Lys
        115                 120                 125

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic Heavy Chain CDR1 1A3

<400> SEQUENCE: 5

Asn Tyr Tyr Met Ser
1               5

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic Heavy Chain CDR2 1A3

<400> SEQUENCE: 6

Tyr Ile Ser Pro Gly Gly Gly Ser Ser Tyr Tyr Pro Ala Ser Val Lys
1               5                   10                  15

Gly

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic Heavy Chain CDR3 1A3

<400> SEQUENCE: 7
```

```
Gln Gly Asp Gly Tyr Tyr Gly Asp Tyr Ala Met Asp Tyr
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic Light (kappa) Chain CDR1 1A3

<400> SEQUENCE: 8

Arg Ala Ser Glu Asn Ile Tyr Ser Asn Leu Ala
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic Light (kappa) Chain CDR2 1A3

<400> SEQUENCE: 9

Ala Ala Thr Asn Leu Ala Asp
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic Light (kappa) Chain CDR3 1A3

<400> SEQUENCE: 10

Gln His Phe Trp Gly Thr Pro Tyr Thr
1               5

<210> SEQ ID NO 11
<211> LENGTH: 412
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Synthetic Heavy Chain Variable Region 2B8

<400> SEQUENCE: 11
atgggatgga gctatatcat cctcttttg gtagcaacag ctacagatgt ccactcccag      60
gtccaactgc agcagcctgg ggctgaactg gtgaagcctg ggacttcagt gaagctgtcc    120
tgcaaggctt ctggctacac cttcaccacc tactggatgc actgggtgaa tcagaggcct    180
ggacaaggcc ttgagtggat tggagagatt aatcctacca acggtcatac taactacaat    240
gagaagttca gagcaaggc cacactgact gtagacaaat cctccagcac agcctacatg    300
caactcagca gcctgacatc tgaggactct gcggtctatt actgtgcaag aaactatgtt    360
ggtagcatct ttgactactg gggccaaggc accactctca cagtctcctc ag            412
```

```
<210> SEQ ID NO 12
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Synthetic Heavy Chain Variable Region 2B8

<400> SEQUENCE: 12

Met Gly Trp Ser Tyr Ile Ile Leu Phe Leu Val Ala Thr Ala Thr Asp
1               5                   10                  15

Val His Ser Gln Val Gln Leu Gln Gln Pro Gly Ala Glu Leu Val Lys
            20                  25                  30

Pro Gly Thr Ser Val Lys Leu Ser Cys Lys Ala Ser Gly Tyr Thr Phe
        35                  40                  45

Thr Thr Tyr Trp Met His Trp Val Asn Gln Arg Pro Gly Gln Gly Leu
    50                  55                  60

Glu Trp Ile Gly Glu Ile Asn Pro Thr Asn Gly His Thr Asn Tyr Asn
65                  70                  75                  80

Glu Lys Phe Lys Ser Lys Ala Thr Leu Thr Val Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Asn Tyr Val Gly Ser Ile Phe Asp Tyr Trp Gly
        115                 120                 125

Gln Gly Thr Thr Leu Thr Val Ser Ser
    130                 135

<210> SEQ ID NO 13
<211> LENGTH: 382
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Synthetic Light (kappa) Chain Variable Region
      2B8

<400> SEQUENCE: 13
atggaatcac agactctggt cttcatatcc atactgctct ggttatatgg tgctgatggg      60
aacattgtaa tgacccaatc tcccaaatcc atgtccatgt cagtaggaga gagggtcacc     120
ttgagctgca aggccagtga gaatgtggtt tcttatgtat cctggtatca acagaaacca     180
gcgcagtctc ctaaactgct gatatacggg gcatccaacc ggaacactgg ggtcccccgat    240 cgcttcacag gcagtggatc tgcaacagat ttcactctga ccatcagcag tgtgcgggct    300
gaagaccttg cagattatca ctgtgggcag agttacaact atccgtacac gttcggaggg    360
gggaccaggc tggaaataaa ac                                              382

<210> SEQ ID NO 14
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Synthetic Light (kappa) Chain Variable Region
      2B8

<400> SEQUENCE: 14
```

```
Met Glu Ser Gln Thr Leu Val Phe Ile Ser Ile Leu Leu Trp Leu Tyr
1               5                   10                  15

Gly Ala Asp Gly Asn Ile Val Met Thr Gln Ser Pro Lys Ser Met Ser
            20                  25                  30

Met Ser Val Gly Glu Arg Val Thr Leu Ser Cys Lys Ala Ser Glu Asn
                35                  40                  45

Val Val Ser Tyr Val Ser Trp Tyr Gln Gln Lys Pro Ala Gln Ser Pro
50                  55                  60

Lys Leu Leu Ile Tyr Gly Ala Ser Asn Arg Asn Thr Gly Val Pro Asp
65                  70                  75                  80

Arg Phe Thr Gly Ser Gly Ser Ala Thr Asp Phe Thr Leu Thr Ile Ser
                85                  90                  95

Ser Val Arg Ala Glu Asp Leu Ala Asp Tyr His Cys Gly Gln Ser Tyr
                100                 105                 110

Asn Tyr Pro Tyr Thr Phe Gly Gly Thr Arg Leu Glu Ile Lys
        115                 120                 125
```

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic Heavy Chain CDR1 2B8

<400> SEQUENCE: 15

```
Thr Tyr Trp Met His
1               5
```

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic Heavy Chain CDR2 2B8

<400> SEQUENCE: 16

```
Glu Ile Asn Pro Thr Asn Gly His Thr Asn Tyr Asn Glu Lys Phe Lys
1               5                   10                  15

Ser
```

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic Heavy Chain CDR3 2B8

<400> SEQUENCE: 17

```
Asn Tyr Val Gly Ser Ile Phe Asp Tyr
1               5
```

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Synthetic Light (kappa) Chain CDR1 2B8

<400> SEQUENCE: 18

Lys Ala Ser Glu Asn Val Val Ser Tyr Val Ser
1               5                   10

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Synthetic Light (kappa) Chain CDR2 2B8

<400> SEQUENCE: 19

Gly Ala Ser Asn Arg Asn Thr
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Synthetic Light (kappa) Chain CDR3 2B8

<400> SEQUENCE: 20

Gly Gln Ser Tyr Asn Tyr Pro Tyr Thr
1               5

<210> SEQ ID NO 21
<211> LENGTH: 412
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Synthetic Heavy Chain Variable Region 2F8

<400> SEQUENCE: 21

```
atggaatgga gctgggtctt tctcttcctc ctgtcagtaa ctgcaggtgt ccactgccag      60
gtccagctga agcagtctgg agctgagctg gtgaggcctg gacttcagt gaagatgtcc     120 tgcaaggctt ctggctacac cttcactacc tactatatac actgggtgaa tcagaggcct    180
ggacagggcc ttgagtggat tggaaagatt ggtcctggaa gtggtagtac ttactacaat    240
gagatgttca agacaaggc cacattgact gtagacacat cctccagcac agcctacatg    300
cagctcagca gcctgacatc tgacgactct gcggtctatt tctgtgcaag aaggggactg    360
ggacgtggct ttgactactg gggccaaggc accactctca cagtctcctc ag            412
```

<210> SEQ ID NO 22
<211> LENGTH: 137
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: Synthetic Heavy Chain Variable Region 2F8

```
<400> SEQUENCE: 22

Met Glu Trp Ser Trp Val Phe Leu Phe Leu Ser Val Thr Ala Gly
1               5                   10                  15

Val His Cys Gln Val Gln Leu Lys Gln Ser Gly Ala Glu Leu Val Arg
            20                  25                  30

Pro Gly Thr Ser Val Lys Met Ser Cys Lys Ala Ser Gly Tyr Thr Phe
        35                  40                  45

Thr Thr Tyr Tyr Ile His Trp Val Asn Gln Arg Pro Gly Gln Gly Leu
    50                  55                  60

Glu Trp Ile Gly Lys Ile Gly Pro Gly Ser Gly Ser Thr Tyr Tyr Asn
65                  70                  75                  80

Glu Met Phe Lys Asp Lys Ala Thr Leu Thr Val Asp Thr Ser Ser Ser
                85                  90                  95

Thr Ala Tyr Met Gln Leu Ser Ser Leu Thr Ser Asp Asp Ser Ala Val
            100                 105                 110

Tyr Phe Cys Ala Arg Arg Gly Leu Gly Arg Gly Phe Asp Tyr Trp Gly
        115                 120                 125

Gln Gly Thr Thr Leu Thr Val Ser Ser
    130                 135

<210> SEQ ID NO 23
<211> LENGTH: 394
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Synthetic Light (kappa) Chain Variable Region
      2F8

<400> SEQUENCE: 23
atggagacag acacaatcct gctatgggtg ctgctgctct ggttccagg ctccactggt     60 gacattgtgc tgacccaatc tccagcttct ttggctgtgt ctctagggca gagggccacc   120
atctcctgca aggccagcca aagtgttgat tatgatggta atagttatat caactggtac   180
caacagaaac caggacagcc acccaaagtc ctcatctatg ttgcatccaa tctagaatct   240
gggatcccag ccaggtttag tggcagtggg tctgggacag acttcaccct caacatccat   300
cctgtggagg aggaggatgc tgcaacctat tactgtcagc aaagtattga ggatcctccc   360
acgttcggtg ctgggaccaa gctggagctg aaac                               394

<210> SEQ ID NO 24
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Synthetic Light (kappa) Chain Variable Region
      2F8

<400> SEQUENCE: 24

Met Glu Thr Asp Thr Ile Leu Leu Trp Val Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Lys Ala Ser Gln Ser
        35                  40                  45
```

```
Val Asp Tyr Asp Gly Asn Ser Tyr Ile Asn Trp Tyr Gln Gln Lys Pro
    50                  55                  60

Gly Gln Pro Pro Lys Val Leu Ile Tyr Val Ala Ser Asn Leu Glu Ser
65                  70                  75                  80

Gly Ile Pro Ala Arg Phe Ser Gly Ser Gly Ser Gly Thr Asp Phe Thr
                85                  90                  95

Leu Asn Ile His Pro Val Glu Glu Asp Ala Ala Thr Tyr Tyr Cys
            100                 105                 110

Gln Gln Ser Ile Glu Asp Pro Pro Thr Phe Gly Ala Gly Thr Lys Leu
        115                 120                 125

Glu Leu Lys
    130

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic Heavy Chain CDR1 2F8

<400> SEQUENCE: 25

Thr Tyr Tyr Ile His
1               5

<210> SEQ ID NO 26
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic Heavy Chain CDR2 2F8

<400> SEQUENCE: 26

Lys Ile Gly Pro Gly Ser Gly Ser Thr Tyr Tyr Asn Glu Met Phe Lys
1               5                   10                  15

Asp

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic Heavy Chain CDR3 2F8

<400> SEQUENCE: 27

Arg Gly Leu Gly Arg Gly Phe Asp Tyr
1               5

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic Light (kappa) Chain CDR1 2F8
```

-continued

```
<400> SEQUENCE: 28

Lys Ala Ser Gln Ser Val Asp Tyr Asp Gly Asn Ser Tyr Ile Asn
1               5                   10                  15

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic Light (kappa) Chain CDR2 2F8

<400> SEQUENCE: 29

Val Ala Ser Asn Leu Glu Ser
1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic Light (kappa) Chain CDR3 2F8

<400> SEQUENCE: 30

Gln Gln Ser Ile Glu Asp Pro Pro Thr
1               5

<210> SEQ ID NO 31
<211> LENGTH: 418
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Synthetic Heavy Chain Variable Region 3B6

<400> SEQUENCE: 31
atggaatggc cttgtatctt tctcttcctc ctgtcagtaa ctgaaggtgt ccactcccag      60
gttcagctgc agcagtctgg ggctgaactg gtgaggcctg gtcctcagt gaagatttcc     120 tgcaaggctt ctggctatgt attcagtagc tactggatga actgggtgaa gcagaggcct    180
ggacagggtc ttgagtggat tggacagatt tatcctggag atggtgatag taactacaat    240
ggaaacttca agggtaaagc cacactgact gcagacaaat cctccagtac agcctacatg    300
cagctcagca gcctaacatc tgaggactct gcggtctatt tctgtgcatc ccagctcggg    360
ctacgtgaga actactttga ctactggggc caaggcacca ctctcacagt ctcctcag     418

<210> SEQ ID NO 32
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Synthetic Heavy Chain Variable Region 3B6

<400> SEQUENCE: 32

Met Glu Trp Pro Cys Ile Phe Leu Phe Leu Leu Ser Val Thr Glu Gly
1               5                   10                  15
```

```
Val His Ser Gln Val Gln Leu Gln Gln Ser Gly Ala Glu Leu Val Arg
        20                  25                  30

Pro Gly Ser Ser Val Lys Ile Ser Cys Lys Ala Ser Gly Tyr Val Phe
            35                  40                  45

Ser Ser Tyr Trp Met Asn Trp Val Lys Gln Arg Pro Gly Gln Gly Leu
50                  55                  60

Glu Trp Ile Gly Gln Ile Tyr Pro Gly Asp Gly Asp Ser Asn Tyr Asn
65                  70                  75                  80

Gly Asn Phe Lys Gly Lys Ala Thr Leu Thr Ala Asp Lys Ser Ser
                85                  90                  95

Thr Ala Tyr Met Gln Leu Ser Ser Leu Thr Ser Glu Asp Ser Ala Val
            100                 105                 110

Tyr Phe Cys Ala Ser Gln Leu Gly Leu Arg Glu Asn Tyr Phe Asp Tyr
            115                 120                 125

Trp Gly Gln Gly Thr Thr Leu Thr Val Ser Ser
        130                 135
```

<210> SEQ ID NO 33
<211> LENGTH: 388
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Synthetic Light (kappa) Chain Variable Region
      3B6

<400> SEQUENCE: 33

```
atggacatga ggacccctgc tcagtttctt ggaatcttgt tgctctggtt tccaggtatc    60
aaatgtgaca tcaagatgac ccagtctcca tcttccatgt atgcatctct aggagagaga   120
gtcacaatca cttgcaaggc gagtcaggac attaaaagct atttaagctg gttccagcag   180
aaaccaggga aatctcctaa gaccctgatc tatcgtgtaa acagattggt agatggggtc   240
ccatcaaggt tcagtggcag tggatctggg caagattctt ctctcaccat caccagcctg   300
gagaatgaag atatgggaat ttattattgt ctacagtatg atgagtttcc gttcacgttc   360 ggaggggga ccaagctgga aataaagc                                       388
```

<210> SEQ ID NO 34
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Synthetic Light (kappa) Chain Variable Region
      3B6

<400> SEQUENCE: 34

```
Met Asp Met Arg Thr Pro Ala Gln Phe Leu Gly Ile Leu Leu Leu Trp
1               5                   10                  15

Phe Pro Gly Ile Lys Cys Asp Ile Lys Met Thr Gln Ser Pro Ser Ser
            20                  25                  30

Met Tyr Ala Ser Leu Gly Glu Arg Val Thr Ile Thr Cys Lys Ala Ser
        35                  40                  45

Gln Asp Ile Lys Ser Tyr Leu Ser Trp Phe Gln Gln Lys Pro Gly Lys
    50                  55                  60

Ser Pro Lys Thr Leu Ile Tyr Arg Val Asn Arg Leu Val Asp Gly Val
65                  70                  75                  80
```

```
Pro Ser Arg Phe Ser Gly Ser Gly Ser Gly Gln Asp Ser Ser Leu Thr
                85                  90                  95

Ile Thr Ser Leu Glu Asn Glu Asp Met Gly Ile Tyr Tyr Cys Leu Gln
            100                 105                 110

Tyr Asp Glu Phe Pro Phe Thr Phe Gly Gly Gly Thr Lys Leu Glu Ile
        115                 120                 125

Lys

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic Heavy Chain CDR1 3B6

<400> SEQUENCE: 35

Ser Tyr Trp Met Asn
1               5

<210> SEQ ID NO 36
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic Heavy Chain CDR2 3B6

<400> SEQUENCE: 36

Gln Ile Tyr Pro Gly Asp Gly Asp Ser Asn Tyr Asn Gly Asn Phe Lys
1               5                   10                  15

Gly

<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic Heavy Chain CDR3 3B6

<400> SEQUENCE: 37

Gln Leu Gly Leu Arg Glu Asn Tyr Phe Asp Tyr
1               5                   10

<210> SEQ ID NO 38
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic Light (kappa) Chain CDR1 3B6

<400> SEQUENCE: 38

Lys Ala Ser Gln Asp Ile Lys Ser Tyr Leu Ser
1               5                   10

<210> SEQ ID NO 39
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic Light (kappa) Chain CDR2 3B6

<400> SEQUENCE: 39

Arg Val Asn Arg Leu Val Asp
1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic Light (kappa) Chain CDR3 3B6

<400> SEQUENCE: 40

Leu Gln Tyr Asp Glu Phe Pro Phe Thr
1               5

<210> SEQ ID NO 41
<211> LENGTH: 397
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Synthetic Heavy Chain Variable Region 3D11

<400> SEQUENCE: 41
atggctgtcc cggtgctgtt cctctgcctg gttgcatttc caagctgtgt cctgtcccag      60
gtacagctga aggagtcagg acctggcctg gtggcgccct cacagagcct gtccatcact     120
tgcactgtct ctgggttttc attaaccagc tatagtttac actgggttcg ccagcctcca     180
ggaaagggtc tggaatggct gggagtaata tgggctggtg aaacacaaa ttataattcg      240 tctctcatgt ccagactgac catcaggaaa gacaactcca agagccaagt tttcttaaaa     300
atgaacagtc tgcaaactga tgacacagcc atgtactact gtgccagaga gaggtttgct     360
tactggggcc aagggactct ggtcactgtc tctgcag                              397

<210> SEQ ID NO 42
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Synthetic Heavy Chain Variable Region 3D11

<400> SEQUENCE: 42

Met Ala Val Pro Val Leu Phe Leu Cys Leu Val Ala Phe Pro Ser Cys
1               5                   10                  15

Val Leu Ser Gln Val Gln Leu Lys Glu Ser Gly Pro Gly Leu Val Ala
            20                  25                  30

Pro Ser Gln Ser Leu Ser Ile Thr Cys Thr Val Ser Gly Phe Ser Leu
        35                  40                  45

Thr Ser Tyr Ser Leu His Trp Val Arg Gln Pro Pro Gly Lys Gly Leu
```

```
            50                  55                  60
Glu Trp Leu Gly Val Ile Trp Ala Gly Gly Asn Thr Asn Tyr Asn Ser
 65                  70                  75                  80

Ser Leu Met Ser Arg Leu Thr Ile Arg Lys Asp Asn Ser Lys Ser Gln
                 85                  90                  95

Val Phe Leu Lys Met Asn Ser Leu Gln Thr Asp Asp Thr Ala Met Tyr
            100                 105                 110

Tyr Cys Ala Arg Glu Arg Phe Ala Tyr Trp Gly Gln Gly Thr Leu Val
        115                 120                 125

Thr Val Ser Ala
        130

<210> SEQ ID NO 43
<211> LENGTH: 385
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Synthetic Light (kappa) Chain Variable Region
      3D11

<400> SEQUENCE: 43
atggattttc aagtgcagat tttcagcttc ctgctaatca gtgcctcagt caaatatcc      60 agaggacaaa ttgttctcac ccagtctcca gcaatcatgt ctgcatatcc aggggagaag   120
gtcaccatga cctgcagtgc cagctcaagt gtaagttaca tgcactggta ccagcagaag   180
tcaggcacct cccccaaaag atggatttat gacacatcca aactggcttc tggagtccct   240
gctcgcttca gtggcagtgg gtctgggacc tcttactccc tcacaatcag tagtatggag   300
gctgaagatg ctgccactta ttactgccag cagtggagta gtaacccact cacgttcggt   360
gctgggacca agctggagct gaaac                                          385

<210> SEQ ID NO 44
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Synthetic Light (kappa) Chain Variable Region
      3D11

<400> SEQUENCE: 44

Met Asp Phe Gln Val Gln Ile Phe Ser Phe Leu Leu Ile Ser Ala Ser
 1               5                  10                  15

Val Lys Ile Ser Arg Gly Gln Ile Val Leu Thr Gln Ser Pro Ala Ile
            20                  25                  30

Met Ser Ala Tyr Pro Gly Glu Lys Val Thr Met Thr Cys Ser Ala Ser
        35                  40                  45

Ser Ser Val Ser Tyr Met His Trp Tyr Gln Gln Lys Ser Gly Thr Ser
    50                  55                  60

Pro Lys Arg Trp Ile Tyr Asp Thr Ser Lys Leu Ala Ser Gly Val Pro
 65                  70                  75                  80

Ala Arg Phe Ser Gly Ser Gly Ser Gly Thr Ser Tyr Ser Leu Thr Ile
                 85                  90                  95

Ser Ser Met Glu Ala Glu Asp Ala Ala Thr Tyr Tyr Cys Gln Gln Trp
            100                 105                 110
```

-continued

Ser Ser Asn Pro Leu Thr Phe Gly Ala Gly Thr Lys Leu Glu Leu Lys
        115                 120                 125

<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic Heavy Chain CDR1 3D11

<400> SEQUENCE: 45

Ser Tyr Ser Leu His
1               5

<210> SEQ ID NO 46
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic Heavy Chain CDR2 3D11

<400> SEQUENCE: 46

Val Ile Trp Ala Gly Gly Asn Thr Asn Tyr Asn Ser Ser Leu Met Ser
1               5                   10                  15

<210> SEQ ID NO 47
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic Heavy Chain CDR3 3D11

<400> SEQUENCE: 47

Glu Arg Phe Ala Tyr
1               5

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic Light (kappa) Chain CDR1 3D11

<400> SEQUENCE: 48

Ser Ala Ser Ser Ser Val Ser Tyr Met His
1               5                   10

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic Light (kappa) Chain CDR2 3D11

<400> SEQUENCE: 49

Asp Thr Ser Lys Leu Ala Ser
1               5

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic Light (kappa) Chain CDR3 3D11

<400> SEQUENCE: 50

Gln Gln Trp Ser Ser Asn Pro Leu Thr
1               5

<210> SEQ ID NO 51
<211> LENGTH: 424
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Synthetic Heavy Chain Variable Region 1D3

<400> SEQUENCE: 51
atgaactttg ggctcagatt gattttcctt gtccttgttt taaaaggtgt gaagtgtgaa      60
gtgcagctgg tggagtctgg gggaggctta gtgcagcctg gagggtccct gaaactctcc    120
tgtgcagcct ctggattcac tttcagtgac tattacatgt cttgggttcg ccagactcca    180
gagaagaggc tggagtgggt cgcatacatt agtagtggtg gtggtagcac ctactatcca    240
gacagtgtga agggtcgatt caccatctcc cgagacaatg ccaagaacac cctgtacctg    300
caaatgagca gtctgaagtc tgaggacaca gccatatatt actgtgtgag acaaggggat    360
ggttattacg ggactatgc tatggactac tggggtcaag gaacctcagt catcgtctcc    420
tcag                                                                  424

<210> SEQ ID NO 52
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Synthetic Heavy Chain Variable Region 1D3

<400> SEQUENCE: 52

Met Asn Phe Gly Leu Arg Leu Ile Phe Leu Val Leu Val Leu Lys Gly
1               5                   10                  15

Val Lys Cys Glu Val Gln Leu Val Glu Ser Gly Gly Gly Leu Val Gln
            20                  25                  30

Pro Gly Gly Ser Leu Lys Leu Ser Cys Ala Ala Ser Gly Phe Thr Phe
        35                  40                  45

Ser Asp Tyr Tyr Met Ser Trp Val Arg Gln Thr Pro Glu Lys Arg Leu
    50                  55                  60

Glu Trp Val Ala Tyr Ile Ser Ser Gly Gly Gly Ser Thr Tyr Tyr Pro
65                  70                  75                  80

Asp Ser Val Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Ile

-continued

```
                    100                 105                 110
Tyr Tyr Cys Val Arg Gln Gly Asp Gly Tyr Tyr Gly Asp Tyr Ala Met
            115                 120                 125

Asp Tyr Trp Gly Gln Gly Thr Ser Val Ile Val Ser Ser
    130                 135                 140

<210> SEQ ID NO 53
<211> LENGTH: 382
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Synthetic Light (kappa) Chain Variable Region
      1D3

<400> SEQUENCE: 53
atgagtgtgc ccactcaggt cctggggttg ctgctgctgt ggcttacaga tgtcagatgt      60
gacatccaga tgactcagtc tccagcctcc ctatctgtat ctgtgggaga aactgtcacc     120
atcacatgtc gaacaagtga gaatatttac agtaatttag cgtggtatca gcagaaacag     180
ggaaaatctc ctcagctcct aatctatgct gcaacaaact tagcagatgg tgtgccatca     240
aggttcagtg gcagtggatc aggcacacag ttttcccctca ggatcaacag cctgcagtct     300
gaagattttg ggaggtatta ctgtcaacat tttggggga ctccgtacac gttcggaggg      360
gggaccaaac tggaaataaa ac                                              382

<210> SEQ ID NO 54
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Synthetic Light (kappa) Chain Variable Region
      1D3

<400> SEQUENCE: 54

Met Ser Val Pro Thr Gln Val Leu Gly Leu Leu Leu Trp Leu Thr
1               5                   10                  15

Asp Val Arg Cys Asp Ile Gln Met Thr Gln Ser Pro Ala Ser Leu Ser
            20                  25                  30

Val Ser Val Gly Glu Thr Val Thr Ile Thr Cys Arg Thr Ser Glu Asn
        35                  40                  45

Ile Tyr Ser Asn Leu Ala Trp Tyr Gln Gln Lys Gln Gly Lys Ser Pro
    50                  55                  60

Gln Leu Leu Ile Tyr Ala Ala Thr Asn Leu Ala Asp Gly Val Pro Ser
65                  70                  75                  80

Arg Phe Ser Gly Ser Gly Ser Gly Thr Gln Phe Ser Leu Arg Ile Asn
                85                  90                  95

Ser Leu Gln Ser Glu Asp Phe Gly Arg Tyr Tyr Cys Gln His Phe Trp
            100                 105                 110

Gly Thr Pro Tyr Thr Phe Gly Gly Gly Thr Lys Leu Glu Ile Lys
        115                 120                 125

<210> SEQ ID NO 55
<211> LENGTH: 5
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: Synthetic Heavy Chain CDR1 1D3

<400> SEQUENCE: 55

Asp Tyr Tyr Met Ser
1               5

<210> SEQ ID NO 56
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic Heavy Chain CDR2 1D3

<400> SEQUENCE: 56

Tyr Ile Ser Ser Gly Gly Gly Ser Thr Tyr Tyr Pro Asp Ser Val Lys
1               5                   10                  15

Gly

<210> SEQ ID NO 57
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic Heavy Chain CDR3 1D3

<400> SEQUENCE: 57

Gln Gly Asp Gly Tyr Tyr Gly Asp Tyr Ala Met Asp Tyr
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic Light (kappa) Chain CDR1 1D3

<400> SEQUENCE: 58

Arg Thr Ser Glu Asn Ile Tyr Ser Asn Leu Ala
1               5                   10

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic Light (kappa) Chain CDR2 1D3

<400> SEQUENCE: 59

Ala Ala Thr Asn Leu Ala Asp
1               5

<210> SEQ ID NO 60
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic Light (kappa) Chain CDR3 1D3

<400> SEQUENCE: 60

Gln His Phe Trp Gly Thr Pro Tyr Thr
1               5

<210> SEQ ID NO 61
<211> LENGTH: 424
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Synthetic Heavy Chain Variable Region 1F3

<400> SEQUENCE: 61
atgaactttg ggctcagatt gattttcctt gtccttgttt taaaaggtgt gaagtgtgag      60
gtgcagctgg tggagtctgg gggaggctta gtgcagtctg agggtccct gaaactctcc     120 tgtgcggcct ctggattcac tttcagtaac tatttcatgt cttgggttcg ccagactcca    180
gagaagaggc tggagtgggt cgcatatatt agtagtggtg gtggtagcac ctactatcca    240
gacagtgtga aggtcgatt caccatctct agagacaatg ccaagaacac cctgtacctg     300
caaatgagca gtctgaagtc tgaggacaca gccatgtatt actgtgtaag acaaggggat    360
ggttactacg gggactatgc tatggactac tggggtcaag gaacctcagt caccgtctcc    420
tcag                                                                 424

<210> SEQ ID NO 62
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Synthetic Heavy Chain Variable Region 1F3

<400> SEQUENCE: 62

Met Asn Phe Gly Leu Arg Leu Ile Phe Leu Val Leu Val Leu Lys Gly
1               5                   10                  15

Val Lys Cys Glu Val Gln Leu Val Glu Ser Gly Gly Gly Leu Val Gln
            20                  25                  30

Ser Gly Gly Ser Leu Lys Leu Ser Cys Ala Ala Ser Gly Phe Thr Phe
        35                  40                  45

Ser Asn Tyr Phe Met Ser Trp Val Arg Gln Thr Pro Glu Lys Arg Leu
    50                  55                  60

Glu Trp Val Ala Tyr Ile Ser Ser Gly Gly Gly Ser Thr Tyr Tyr Pro
65                  70                  75                  80

Asp Ser Val Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Met
            100                 105                 110

Tyr Tyr Cys Val Arg Gln Gly Asp Gly Tyr Tyr Gly Asp Tyr Ala Met
        115                 120                 125

Asp Tyr Trp Gly Gln Gly Thr Ser Val Thr Val Ser Ser
    130                 135                 140
```

<210> SEQ ID NO 63
<211> LENGTH: 382
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Synthetic Light (kappa) Chain Variable Region
      1F3

<400> SEQUENCE: 63

```
atgagtgtgc ccactcaggt cctggggttg ctgctgctgt ggcttacaga tgccagatgt    60
gacatccaga tgactcagtc tccagcctcc ctatctgtat ctgtgggaga aactgtcacc   120
atcacatgtc gagcaagtga gaatatttac agtaatttag catggtatca gcagaaacag   180
ggaaaatctc ctcagctcct ggtctatgat gcaacacact accagatgg tgtgccatca   240 aggttcagtg gcagtggatc aggcacacag ttttcccctca agatcaacag cctgcagtct   300
gaagattttg ggagttatta ctgtcaacat tttggggta ctccgtacac gtttggaggg   360
gggaccagac tggaaattaa ac                                           382
```

<210> SEQ ID NO 64
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Synthetic Light (kappa) Chain Variable Region
      1F3

<400> SEQUENCE: 64

```
Met Ser Val Pro Thr Gln Val Leu Gly Leu Leu Leu Trp Leu Thr
1               5                  10                  15

Asp Ala Arg Cys Asp Ile Gln Met Thr Gln Ser Pro Ala Ser Leu Ser
                20                  25                  30

Val Ser Val Gly Glu Thr Val Thr Ile Thr Cys Arg Ala Ser Glu Asn
            35                  40                  45

Ile Tyr Ser Asn Leu Ala Trp Tyr Gln Gln Lys Gln Gly Lys Ser Pro
        50                  55                  60

Gln Leu Leu Val Tyr Asp Ala Thr His Leu Pro Asp Gly Val Pro Ser
65                  70                  75                  80

Arg Phe Ser Gly Ser Gly Ser Gly Thr Gln Phe Ser Leu Lys Ile Asn
                85                  90                  95

Ser Leu Gln Ser Glu Asp Phe Gly Ser Tyr Tyr Cys Gln His Phe Trp
            100                 105                 110

Gly Thr Pro Tyr Thr Phe Gly Gly Gly Thr Arg Leu Glu Ile Lys
        115                 120                 125
```

<210> SEQ ID NO 65
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic Heavy Chain CDR1 1F3

<400> SEQUENCE: 65

```
Asn Tyr Phe Met Ser
1               5

<210> SEQ ID NO 66
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic Heavy Chain CDR2 1F3

<400> SEQUENCE: 66

Tyr Ile Ser Ser Gly Gly Gly Ser Thr Tyr Tyr Pro Asp Ser Val Lys
1               5                   10                  15

Gly

<210> SEQ ID NO 67
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic Heavy Chain CDR3 1F3

<400> SEQUENCE: 67

Gln Gly Asp Gly Tyr Tyr Gly Asp Tyr Ala Met Asp Tyr
1               5                   10

<210> SEQ ID NO 68
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic Light (kappa) Chain CDR1 1F3

<400> SEQUENCE: 68

Arg Ala Ser Glu Asn Ile Tyr Ser Asn Leu Ala
1               5                   10

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic Light (kappa) Chain CDR2 1F3

<400> SEQUENCE: 69

Asp Ala Thr His Leu Pro Asp
1               5

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic Light (kappa) Chain CDR3 1F3
```

<400> SEQUENCE: 70

Gln His Phe Trp Gly Thr Pro Tyr Thr
1               5

<210> SEQ ID NO 71
<211> LENGTH: 424
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Synthetic Heavy Chain Variable Region 3A12

<400> SEQUENCE: 71

```
atgaactttg ggctcagatt gattttcctt gtccttgttt taaaaggtgt gaagtgtgaa    60
gtgcagctgg tggagtctgg gggaggctta gtgcagcctg agggtccct gaaaatctcc    120
tgtgcagcct ctggatttac tttcagtaac tatttcatgt cttgggttcg ccagactcca   180
gagaagaggc tggagtgggt cgcatacatt agtagtggtg gtggtagcac ctactatcca   240
gacagtgtga agggtcgatt caccatctcc agagacaatg ccaagaacac cctgtacctg   300
caaatgaaca gtctgaagtc tgaggacaca gccatgtatt actgtgtaag acaaggagat   360
ggttactatg ggactatgc tatggactac tggggtcaag gaacctcagt caccgtctcc   420
tcag                                                                 424
```

<210> SEQ ID NO 72
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Synthetic Heavy Chain Variable Region 3A12

<400> SEQUENCE: 72

Met Asn Phe Gly Leu Arg Leu Ile Phe Leu Val Leu Val Leu Lys Gly
1               5                   10                  15

Val Lys Cys Glu Val Gln Leu Val Glu Ser Gly Gly Gly Leu Val Gln
            20                  25                  30

Pro Gly Gly Ser Leu Lys Ile Ser Cys Ala Ala Ser Gly Phe Thr Phe
        35                  40                  45

Ser Asn Tyr Phe Met Ser Trp Val Arg Gln Thr Pro Glu Lys Arg Leu
    50                  55                  60

Glu Trp Val Ala Tyr Ile Ser Ser Gly Gly Gly Ser Thr Tyr Tyr Pro
65                  70                  75                  80

Asp Ser Val Lys Gly Arg Phe Thr Ile Ser Arg Asp Asn Ala Lys Asn
                85                  90                  95

Thr Leu Tyr Leu Gln Met Asn Ser Leu Lys Ser Glu Thr Ala Met
            100                 105                 110

Tyr Tyr Cys Val Arg Gln Gly Asp Gly Tyr Tyr Gly Asp Tyr Ala Met
        115                 120                 125

Asp Tyr Trp Gly Gln Gly Thr Ser Val Thr Val Ser Ser
    130                 135                 140

<210> SEQ ID NO 73
<211> LENGTH: 382
<212> TYPE: DNA
<213> ORGANISM: Artificial Sequence
<220> FEATURE:

-continued

<223> OTHER INFORMATION: Description of Artificial Sequence: Synthetic
      polynucleotide
<220> FEATURE:
<223> OTHER INFORMATION: Synthetic Light (kappa) Chain Variable Region
      3A12

<400> SEQUENCE: 73

```
atgagtgtgc ccactcaggt cctggggttg ctgctgctgt ggcttacaga tgccagatgt      60
gacatccaga tgactcagtc gccagcctcc ctatctgtat ctgtgggaga aactgtcacc     120
atcacatgtc gagcaagtga gaatatttac attaatttag catggtatca gcagaaacag     180
ggaaaatctc ctcagctcct ggtccatgct gcaacaaagt tagcagatgg tgtgccatca     240
aggttcagtg gcagtggatc aggcacacag tattccctca agatcaacag cctgcagtct     300
gaagattttg ggagttatta ctgtcaacat ttttggggta ctccgtacac gttcggaggg     360
gggaccaaac tagaaataaa ac                                              382
```

<210> SEQ ID NO 74
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Synthetic Light (kappa) Chain Variable Region
      3A12

<400> SEQUENCE: 74

```
Met Ser Val Pro Thr Gln Val Leu Gly Leu Leu Leu Leu Trp Leu Thr
1               5                   10                  15

Asp Ala Arg Cys Asp Ile Gln Met Thr Gln Ser Pro Ala Ser Leu Ser
            20                  25                  30

Val Ser Val Gly Glu Thr Val Thr Ile Thr Cys Arg Ala Ser Glu Asn
        35                  40                  45

Ile Tyr Ile Asn Leu Ala Trp Tyr Gln Gln Lys Gln Gly Lys Ser Pro
    50                  55                  60

Gln Leu Leu Val His Ala Ala Thr Lys Leu Ala Asp Gly Val Pro Ser
65                  70                  75                  80

Arg Phe Ser Gly Ser Gly Ser Gly Thr Gln Tyr Ser Leu Lys Ile Asn
                85                  90                  95

Ser Leu Gln Ser Glu Asp Phe Gly Ser Tyr Tyr Cys Gln His Phe Trp
            100                 105                 110

Gly Thr Pro Tyr Thr Phe Gly Gly Gly Thr Lys Leu Glu Ile Lys
        115                 120                 125
```

<210> SEQ ID NO 75
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic Heavy Chain CDR1 3A12

<400> SEQUENCE: 75

```
Asn Tyr Phe Met Ser
1               5
```

<210> SEQ ID NO 76
<211> LENGTH: 17
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic Heavy Chain CDR2 3A12

<400> SEQUENCE: 76

Tyr Ile Ser Ser Gly Gly Gly Ser Thr Tyr Tyr Pro Asp Ser Val Lys
1               5                   10                  15

Gly

<210> SEQ ID NO 77
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic Heavy Chain CDR3 3A12

<400> SEQUENCE: 77

Gln Gly Asp Gly Tyr Tyr Gly Asp Tyr Ala Met Asp Tyr
1               5                   10

<210> SEQ ID NO 78
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic Light (kappa) Chain CDR1 3A12

<400> SEQUENCE: 78

Arg Ala Ser Glu Asn Ile Tyr Ile Asn Leu Ala
1               5                   10

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic Light (kappa) Chain CDR2 3A12

<400> SEQUENCE: 79

Ala Ala Thr Lys Leu Ala Asp
1               5

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic Light (kappa) Chain CDR3 3A12

<400> SEQUENCE: 80

Gln His Phe Trp Gly Thr Pro Tyr Thr
1               5

<210> SEQ ID NO 81
```

<211> LENGTH: 974
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Reference Mouse IgG1 Heavy Chain Constant Region (J00453)

<400> SEQUENCE: 81

| | |
|---|---|
| ccaaaacgac accccatct gtctatccac tggcccctgg atctgctgcc caaactaact | 60 |
| ccatggtgac cctgggatgc ctggtcaagg gctatttccc tgagccagtg acagtgacct | 120 |
| ggaactctgg atccctgtcc agcggtgtgc acaccttccc agctgtcctg gagtctgacc | 180 |
| tctacactct gagcagctca gtgactgtcc cctccagccc tcggcccagc gagaccgtca | 240 |
| cctgcaacgt tgcccacccg gccagcagca caaggtgga caagaaaatt gtgcccaggg | 300 |
| attgtggttg taagccttgc atatgtacag tcccagaagt atcatctgtc ttcatcttcc | 360 |
| ccccaaagcc caaggatgtg ctcaccatta ctctgactcc taaggtcacg tgtgttgtgg | 420 |
| tagacatcag caaggatgat cccgaggtcc agttcagctg gtttgtagat gatgtggagg | 480 |
| tgcacacagc tcagacgcaa ccccgggagg agcagttcaa cagcactttc cgctcagtca | 540 |
| gtgaacttcc catcatgcac caggactggc tcaatggcaa ggagttcaaa tgcagggtca | 600 |
| acagtgcagc tttccctgcc cccatcgaga aaaccatctc caaaaccaaa ggcagaccga | 660 |
| aggctccaca ggtgtacacc attccacctc caaggagca gatggccaag ataaagtca | 720 |
| gtctgacctg catgataaca gacttcttcc ctgaagacat tactgtggag tggcagtgga | 780 |
| atgggcagcc agcggagaac tacaagaaca ctcagcccat catgaacacg aatggctctt | 840 |
| acttcgtcta cagcaagctc aatgtgcaga agagcaactg ggaggcagga aatactttca | 900 |
| cctgctctgt gttacatgag ggcctgcaca accaccatac tgagaagagc ctctcccact | 960 |
| ctcctggtaa atga | 974 |

<210> SEQ ID NO 82
<211> LENGTH: 974
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Mouse IgG1 Heavy Chain Constant Region for 1A3, 1D3, 1F3, and 2B8

<400> SEQUENCE: 82

| | |
|---|---|
| ccaaaacgac accccatct gtctatccac tggcccctgg atctgctgcc caaactaact | 60 |
| ccatggtgac cctgggatgc ctggtcaagg gctatttccc tgagccagtg acagtgacct | 120 |
| ggaactctgg atccctgtcc agcggtgtgc acaccttccc agctgtcctg cagtctgacc | 180 |
| tctacactct gagcagctca gtgactgtcc cctccagcac ctggcccagc gagaccgtca | 240 |
| cctgcaacgt tgcccacccg gccagcagca caaggtgga caagaaaatt gtgcccaggg | 300 |
| attgtggttg taagccttgc atatgtacag tcccagaagt atcatctgtc ttcatcttcc | 360 |
| ccccaaagcc caaggatgtg ctcaccatta ctctgactcc taaggtcacg tgtgttgtgg | 420 |
| tagacatcag caaggatgat cccgaggtcc agttcagctg gtttgtagat gatgtggagg | 480 |
| tgcacacagc tcagacgcaa ccccgggagg agcagttcaa cagcactttc cgctcagtca | 540 |
| gtgaacttcc catcatgcac caggactggc tcaatggcaa ggagttcaaa tgcagggtca | 600 |

```
acagtgcagc tttccctgcc cccatcgaga aaaccatctc caaaaccaaa ggcagaccga      660
aggctccaca ggtgtacacc attccacctc ccaaggagca gatggccaag gataaagtca      720
gtctgacctg catgataaca gacttcttcc ctgaagacat tactgtggag tggcagtgga      780
atgggcagcc agcggagaac tacaagaaca ctcagcccat catggacaca gatggctctt      840
acttcgtcta cagcaagctc aatgtgcaga gagcaactg ggaggcagga aatactttca       900
cctgctctgt gttacatgag ggcctgcaca accaccatac tgagaagagc ctctcccact      960
ctcctggtaa atga                                                       974
```

<210> SEQ ID NO 83  
<211> LENGTH: 323  
<212> TYPE: DNA  
<213> ORGANISM: Artificial Sequence  
<220> FEATURE:  
<223> OTHER INFORMATION: Description of Artificial Sequence: Synthetic polynucleotide  
<220> FEATURE:  
<223> OTHER INFORMATION: Mouse Kappa Light Chain Constant Region

<400> SEQUENCE: 83

```
gggctgatgc tgcaccaact gtatccatct tcccaccatc cagtgagcag ttaacatctg       60
gaggtgcctc agtcgtgtgc ttcttgaaca acttctaccc caaagacatc aatgtcaagt      120
ggaagattga tggcagtgaa cgacaaaatg gcgtcctgaa cagttggact gatcaggaca      180
gcaaagacag cacctacagc atgagcagca ccctcacgtt gaccaaggac gagtatgaac      240
gacataacag ctatacctgt gaggccactc acaagacatc aacttcaccc attgtcaaga      300
gcttcaacag gaatgagtgt tag                                             323
```

<210> SEQ ID NO 84  
<211> LENGTH: 323  
<212> TYPE: DNA  
<213> ORGANISM: Artificial Sequence  
<220> FEATURE:  
<223> OTHER INFORMATION: Description of Artificial Sequence: Synthetic polynucleotide  
<220> FEATURE:  
<223> OTHER INFORMATION: Synthetic Mouse Kappa Light Chain Constant Region with Mutation

<400> SEQUENCE: 84

```
gggctgatgc tgcaccaact gtatccatct tcccaccatc cagtgagcag ttaacatctg       60
gaggtgcctc agtcgtgtgc ttcttgaaca acttctaccc caaagacatc aatgtcaagt      120
ggaagattga tggcagtgaa cgacaaaatg gcgtcctgaa cagttggact gatcaggaca      180
gcaaagacag cacctacagc atgagcagca ccctcatgtt gaccaaggac gagtatgaac      240
gacataacag ctatacctgt gaggccactc acaagacatc aacttcaccc attgtcaaga      300
gcttcaacag gaatgagtgt tag                                             323
```

<210> SEQ ID NO 85  
<211> LENGTH: 30  
<212> TYPE: DNA  
<213> ORGANISM: Artificial Sequence  
<220> FEATURE:  
<223> OTHER INFORMATION: Description of Artificial Sequence: Synthetic primer  
<220> FEATURE:  
<223> OTHER INFORMATION: Synthetic oligonucleotide primer BD SMART II A

<400> SEQUENCE: 85

```
aagcagtggt atcaacgcag agtacgcggg                                       30
```

```
<210> SEQ ID NO 86
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<223> OTHER INFORMATION: Synthetic oligonucleotide primer RACE CDS
<220> FEATURE:
<221> NAME/KEY: modified_base
<222> LOCATION: (27)..(27)
<223> OTHER INFORMATION: a, c, g, t or u

<400> SEQUENCE: 86 ttttttttttt tttttttttt tttttvn                                         27

<210> SEQ ID NO 87
<211> LENGTH: 45
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Synthetic oligonucleotide primer of Universal
      Primer Mix A

<400> SEQUENCE: 87
ctaatacgac tcactatagg gcaagcagtg gtatcaacgc agagt                      45

<210> SEQ ID NO 88
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Synthetic oligonucleotide primer of Universal
      Primer Mix A

<400> SEQUENCE: 88
ctaatacgac tcactatagg gc                                               22

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Synthetic IgG1 Constant Region specific primer

<400> SEQUENCE: 89
tatgcaaggc ttacaaccac a                                                21

<210> SEQ ID NO 90
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Synthetic IgG1 Constant Region specific primer
```

-continued

```
<400> SEQUENCE: 90
gccagtggat agacagatgg gggtgtcg                                       28

<210> SEQ ID NO 91
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Synthetic oligonucleotide primer

<400> SEQUENCE: 91
ctcattcctg ttgaagctct tgacaat                                        27

<210> SEQ ID NO 92
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Synthetic oligonucleotide primer

<400> SEQUENCE: 92
cgactgaggc acctccagat gtt                                            23

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Synthetic oligonucleotide primer T7

<400> SEQUENCE: 93
taatacgact cactataggg                                                20

<210> SEQ ID NO 94
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Synthetic oligonucleotide primer M13 Forward

<400> SEQUENCE: 94
gtaaaacgac ggccagt                                                   17

<210> SEQ ID NO 95
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Synthetic oligonucleotide primer M13 Reverse

<400> SEQUENCE: 95
caggaaacag ctatgacc                                                  18
```

```
<210> SEQ ID NO 96
<211> LENGTH: 63
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Synthetic oligonucleotide forward primer

<400> SEQUENCE: 96
ggggacaagt tgtacaaaa aagcaggctg ccaccatgaa ctttgggctc agattgattt      60
tcc                                                                  63

<210> SEQ ID NO 97
<211> LENGTH: 54
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Synthetic oligonucleotide reverse primer

<400> SEQUENCE: 97
ggggaccact tgtacaaga aagctgggtt catttaccag gagagtggga gagg            54

<210> SEQ ID NO 98
<211> LENGTH: 62
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Synthetic oligonucleotide forward primer

<400> SEQUENCE: 98
ggggacaagt tgtacaaaa aagcaggctg ccaccatggg atggagctat atcatcctct      60
tt                                                                   62

<210> SEQ ID NO 99
<211> LENGTH: 53
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Synthetic oligonucleotide reverse primer

<400> SEQUENCE: 99
ggggaccact tgtacaaga aagctgggtt catttaccag gagagtggga gag             53

<210> SEQ ID NO 100
<211> LENGTH: 62
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Synthetic oligonucleotide forward primer

<400> SEQUENCE: 100
ggggacaagt tgtacaaaa aagcaggctg ccaccatgga atcacagact ctggtcttca      60
ta                                                                   62
```

<210> SEQ ID NO 101
<211> LENGTH: 54
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Synthetic oligonucleotide reverse primer

<400> SEQUENCE: 101
ggggaccact tgtacaaga aagctgggtc taacactcat tcctgttgaa gctc        54

<210> SEQ ID NO 102
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Synthetic oligonucleotide 5 prime hHGF NheI
      primer

<400> SEQUENCE: 102
actggctagc atgtgggtga ccaaactcct                                  30

<210> SEQ ID NO 103
<211> LENGTH: 46
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Synthetic oligonucleotide 3 prime hHGF NotI
      his tag primer

<400> SEQUENCE: 103
gtgatggtga tggtgatggc ggccgcatga ctgtggtacc ttatat                46

<210> SEQ ID NO 104
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Synthetic oligonucleotide 5 prime His IgFc
      primer

<400> SEQUENCE: 104
actggcggcc gccatcacca tcaccatcac                                  30

<210> SEQ ID NO 105
<211> LENGTH: 31
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Synthetic oligonucleotide 3 prime IgFc BamHI
      primer

<400> SEQUENCE: 105
actgggatcc tcactattta cccggggaca g                                31

```
<210> SEQ ID NO 106
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Synthetic hHGF-Fc (G555E) sense primer

<400> SEQUENCE: 106
catgatgtcc acgaaagagg agatgag                                               27

<210> SEQ ID NO 107
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Synthetic hHGF-Fc (G555E) antisense primer

<400> SEQUENCE: 107
ctcatctcct ctttcgtgga catcatg                                               27

<210> SEQ ID NO 108
<211> LENGTH: 37
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Synthetic hHGF-Fc (C561R) sense primer

<400> SEQUENCE: 108
ggaagaggag atgagaaacg caaacaggtt ctcaatg                                    37

<210> SEQ ID NO 109
<211> LENGTH: 37
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Synthetic hHGF-Fc (C561R) antisense primer

<400> SEQUENCE: 109
cattgagaac ctgtttgcgt ttctcatctc ctcttcc                                    37

<210> SEQ ID NO 110
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Synthetic Fragment 1 Primer for mHGF alpha
      chain 5 prime NheI

<400> SEQUENCE: 110
atcggctagc atgatgtggg ggaccaaac                                             29

<210> SEQ ID NO 111
<211> LENGTH: 36
<212> TYPE: DNA
<213> ORGANISM: Artificial Sequence
```

-continued

```
<220> FEATURE:
<223> OTHER INFORMATION: Description of Artificial Sequence: Synthetic
      primer
<220> FEATURE:
<223> OTHER INFORMATION: Synthetic Fragment 1 Primer for mHGF alpha
      chain 5 prime NheI

<400> SEQUENCE: 111
ggttttgttt tgttgacgcc caacatttac cctaag                           36

<210> SEQ ID NO 112
<211> LENGTH: 36
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Synthetic Fragment 2 Primer for hHGF beta chain
      aa V495-L585

<400> SEQUENCE: 112
ccaaaacaaa acaactgcgg gttgtaaatg ggattc                           36

<210> SEQ ID NO 113
<211> LENGTH: 40
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Synthetic Fragment 2 Primer for hHGF beta chain
      aa V495-L585

<400> SEQUENCE: 113
tctagaccaa aattacttcg aacgagctgg acgttaggac                       40

<210> SEQ ID NO 114
<211> LENGTH: 40
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Synthetic Fragment 3 Primer for mHGF beta chain
      C-terminus 3 prime NotI

<400> SEQUENCE: 114
agatctggtt ttaatgaagc ttgctcgacc tgcaatcctg                       40

<210> SEQ ID NO 115
<211> LENGTH: 48
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Synthetic Fragment 3 Primer for mHGF beta chain
      C-terminus 3 prime NotI

<400> SEQUENCE: 115
cactaccact accactaccg ccggcgtgtt gaacatacag ttttaatg              48

<210> SEQ ID NO 116
<211> LENGTH: 38
<212> TYPE: DNA
<213> ORGANISM: Artificial Sequence
```

```
<220> FEATURE:
<223> OTHER INFORMATION: Description of Artificial Sequence: Synthetic
      primer
<220> FEATURE:
<223> OTHER INFORMATION: Synthetic mutagenesis primer 1

<400> SEQUENCE: 116
catcaccatc accatcacta agcgggtctg gtgccacg                              38

<210> SEQ ID NO 117
<211> LENGTH: 38
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Synthetic mutagenesis primer 2

<400> SEQUENCE: 117
cgtggcacca gacccgctta gtgatggtga tggtgatg                              38

<210> SEQ ID NO 118
<211> LENGTH: 2922
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: nucleotide sequence of synthetic hHGF-Fc
      protein

<400> SEQUENCE: 118
atgtgggtga ccaaactcct gccagccctg ctgctgcagc atgtcctcct gcatctcctc      60
ctgctcccca tcgccatccc ctatgcagag ggacaaagga aagaagaaa tacaattcat       120 gaattcaaaa aatcagcaaa gactacccta atcaaaatag atccagcact gaagataaaa      180
accaaaaaag tgaatactgc agaccaatgt gctaatagat gtactaggaa taaggactt       240 ccattcactt gcaaggcttt tgtttttgat aaagcaagaa acaatgcct ctggttcccc       300 ttcaatagca tgtcaagtgg agtgaaaaaa gaatttggcc atgaatttga cctctatgaa      360
aacaaagact acattagaaa ctgcatcatt ggtaaaggac gcagctacaa gggaacagta      420
tctatcacta gagtggcat caaatgtcag ccctggagtt ccatgatacc acacgaacac       480 agcttttttgc cttcgagcta tcggggtaaa gacctacagg aaaactactg tcgaaatcct      540
cgaggggaag aaggggggacc ctggtgtttc acaagcaatc agaggtacg ctacgaagtc      600 tgtgacattc ctcagtgttc agaagttgaa tgcatgacct gcaatgggga gagttatcga      660
ggtctcatgg atcatacaga atcaggcaag atttgtcagc gctgggatca tcagacacca      720
caccggcaca aattcttgcc tgaaagatat cccgacaagg gctttgatga taattattgc      780
cgcaatcccg atggccagcc gaggccatgg tgctatactc ttgaccctca caccgctgg      840 gagtactgtg caattaaaac atgcgctgac aatactatga tgacactga tgttcctttg       900 gaaacaactg aatgcatcca aggtcaagga gaaggctaca gggcactgt caataccatt       960 tggaatggaa ttccatgtca gcgttgggat tctcagtatc ctcacgagca tgacatgact      1020
cctgaaaatt tcaagtgcaa ggacctacga gaaaattact gccgaaatcc agatgggtct      1080
gaatcaccct ggtgtttac cactgatcca aacatccgag ttggctactg ctcccaaatt      1140
ccaaactgtg atatgtcaca tggacaagat tgttatcgtg ggaatggcaa aaattatatg      1200
ggcaacttat cccaaacaag atctggacta acatgttcaa tgtgggacaa gaacatggaa      1260
```

```
gacttacatc gtcatatctt ctgggaacca gatgcaagta agctgaatga gaattactgc    1320
cgaaatccag atgatgatgc tcatggaccc tggtgctaca cgggaaatcc actcattcct    1380
tgggattatt gccctatttc tcgttgtgaa ggtgatacca cacctacaat agtcaattta    1440
gaccatcccg taatatcttg tgccaaaacg aaacaattgc gagttgtaaa tgggattcca    1500
acacgaacaa acataggatg gatggttagt ttgagataca gaaataaaca tatctgcgga    1560
ggatcattga taaaggagag ttgggttctt actgcacgac agtgtttccc ttctcgagac    1620
ttgaaagatt atgaagcttg gcttggaatt catgatgtcc acggaagagg agatgagaaa    1680
tgcaaacagg ttctcaatgt ttcccagctg gtatatggcc ctgaaggatc agatctggtt    1740
ttaatgaagc ttgccaggcc tgctgtcctg gatgattttg ttagtacgat tgatttacct    1800
aattatggat gcacaattcc tgaaaagacc agttgcagtg tttatggctg gggctacact    1860
ggattgatca actatgatgg cctattacga gtggcacatc tctatataat gggaaatgag    1920
aaatgcagcc agcatcatcg agggaaggtg actctgaatg agtctgaaat atgtgctggg    1980
gctgaaaaga ttggatcagg accatgtgag ggggattatg gtggcccact tgtttgtgag    2040
caacataaaa tgagaatggt tcttggtgtc attgttcctg gtcgtggatg tgccattcca    2100
aatcgtcctg gtattttgt ccgagtagca tattatgcaa aatggataca caaaattatt    2160
ttaacatata aggtaccaca gtcatgcggc cgccatcacc atcaccatca ctccgcgggt    2220
ctggtgccac gcggtagtga caaaactcac acatgcccac cgtgcccagc acctgaactc    2280 ctgggggac cgtcagtctt cctcttcccc ccaaaaccca aggacaccct catgatctcc    2340
cggacccctg aggtcacatg cgtggtggtg gacgtgagcc acgaagaccc tgaggtcaag    2400
ttcaactggt acgtggacgg cgtggaggtg cataatgcca agacaaagcc gcgggaggag    2460
cagtacaaca gcacgtaccg tgtggtcagc gtcctcaccg tcctgcacca ggactggctg    2520
aatggcaagg agtacaagtg caaggtctcc aacaaagccc tcccagcccc catcgagaaa    2580
accatctcca aagccaaagg gcagccccga gaaccacagg tgtacaccct gcccccatcc    2640
cgggaggaga tgaccaagaa ccaggtcagc ctgacctgcc tggtcaaagg cttctatccc    2700
agcgacatcg ccgtggagtg ggagagcaat gggcagccgg agaacaacta caagaccacg    2760
cctcccgtgc tggactccga cggctccttc ttcctctata gcaagctcac cgtggacaag    2820
agcaggtggc agcaggggaa cgtcttctca tgctccgtga tgcatgaggc tctgcacaac    2880
cactacacgc agaagagcct ctccctgtcc ccgggtaaat ag                       2922
```

<210> SEQ ID NO 119
<211> LENGTH: 919
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: amino acid sequence of synthetic hHGF-Fc
      protein

<400> SEQUENCE: 119

Pro Ala Leu Lys Ile Lys Thr Lys Lys Val Asn Thr Ala Asp Gln Cys
1               5                   10                  15

Ala Asn Arg Cys Thr Arg Asn Lys Gly Leu Pro Phe Thr Cys Lys Ala
            20                  25                  30

Phe Val Phe Asp Lys Ala Arg Lys Gln Cys Leu Trp Phe Pro Phe Asn
        35                  40                  45

-continued

```
Ser Met Ser Ser Gly Val Lys Lys Glu Phe Gly His Glu Phe Asp Leu
     50                  55                  60

Tyr Glu Asn Lys Asp Tyr Ile Arg Asn Cys Ile Ile Gly Lys Gly Arg
 65                  70                  75                  80

Ser Tyr Lys Gly Thr Val Ser Ile Thr Lys Ser Gly Ile Lys Cys Gln
                 85                  90                  95

Pro Trp Ser Ser Met Ile Pro His Glu His Ser Phe Leu Pro Ser Ser
                100                 105                 110

Tyr Arg Gly Lys Asp Leu Gln Glu Asn Tyr Cys Arg Asn Pro Arg Gly
            115                 120                 125

Glu Glu Gly Gly Pro Trp Cys Phe Thr Ser Asn Pro Glu Val Arg Tyr
    130                 135                 140

Glu Val Cys Asp Ile Pro Gln Cys Ser Glu Val Glu Cys Met Thr Cys
145                 150                 155                 160

Asn Gly Glu Ser Tyr Arg Gly Leu Met Asp His Thr Glu Ser Gly Lys
                165                 170                 175

Ile Cys Gln Arg Trp Asp His Gln Thr Pro His Arg His Lys Phe Leu
            180                 185                 190

Pro Glu Arg Tyr Pro Asp Lys Gly Phe Asp Asp Asn Tyr Cys Arg Asn
    195                 200                 205

Pro Asp Gly Gln Pro Arg Pro Trp Cys Tyr Thr Leu Asp Pro His Thr
210                 215                 220

Arg Trp Glu Tyr Cys Ala Ile Lys Thr Cys Ala Asp Asn Thr Met Asn
225                 230                 235                 240

Asp Thr Asp Val Pro Leu Glu Thr Thr Glu Cys Ile Gln Gly Gln Gly
                245                 250                 255

Glu Gly Tyr Arg Gly Thr Val Asn Thr Ile Trp Asn Gly Ile Pro Cys
            260                 265                 270

Gln Arg Trp Asp Ser Gln Tyr Pro His Glu His Asp Met Thr Pro Glu
    275                 280                 285

Asn Phe Lys Cys Lys Asp Leu Arg Glu Asn Tyr Cys Arg Asn Pro Asp
    290                 295                 300

Gly Ser Glu Ser Pro Trp Cys Phe Thr Thr Asp Pro Asn Ile Arg Val
305                 310                 315                 320

Gly Tyr Cys Ser Gln Ile Pro Asn Cys Asp Met Ser His Gly Gln Asp
                325                 330                 335

Cys Tyr Arg Gly Asn Gly Lys Asn Tyr Met Gly Asn Leu Ser Gln Thr
            340                 345                 350

Arg Ser Gly Leu Thr Cys Ser Met Trp Asp Lys Asn Met Glu Asp Leu
    355                 360                 365

His Arg His Ile Phe Trp Glu Pro Asp Ala Ser Lys Leu Asn Glu Asn
    370                 375                 380

Tyr Cys Arg Asn Pro Asp Asp Asp Ala His Gly Pro Trp Cys Tyr Thr
385                 390                 395                 400

Gly Asn Pro Leu Ile Pro Trp Asp Tyr Cys Pro Ile Ser Arg Cys Glu
                405                 410                 415

Gly Asp Thr Thr Pro Thr Ile Val Asn Leu Asp His Pro Val Ile Ser
            420                 425                 430

Cys Ala Lys Thr Lys Gln Leu Arg Val Val Asn Gly Ile Pro Thr Arg
    435                 440                 445

Thr Asn Ile Gly Trp Met Val Ser Leu Arg Tyr Arg Asn Lys His Ile
    450                 455                 460

Cys Gly Gly Ser Leu Ile Lys Glu Ser Trp Val Leu Thr Ala Arg Gln
465                 470                 475                 480
```

```
Cys Phe Pro Ser Arg Asp Leu Lys Asp Tyr Glu Ala Trp Leu Gly Ile
            485                 490                 495

His Asp Val His Gly Arg Gly Asp Glu Lys Cys Lys Gln Val Leu Asn
        500                 505                 510

Val Ser Gln Leu Val Tyr Gly Pro Glu Gly Ser Asp Leu Val Leu Met
            515                 520                 525

Lys Leu Ala Arg Pro Ala Val Leu Asp Asp Phe Val Ser Thr Ile Asp
530                 535                 540

Leu Pro Asn Tyr Gly Cys Thr Ile Pro Glu Lys Thr Ser Cys Ser Val
545                 550                 555                 560

Tyr Gly Trp Gly Tyr Thr Gly Leu Ile Asn Tyr Asp Gly Leu Leu Arg
                565                 570                 575

Val Ala His Leu Tyr Ile Met Gly Asn Glu Lys Cys Ser Gln His His
            580                 585                 590

Arg Gly Lys Val Thr Leu Asn Glu Ser Glu Ile Cys Ala Gly Ala Glu
        595                 600                 605

Lys Ile Gly Ser Gly Pro Cys Glu Gly Asp Tyr Gly Gly Pro Leu Val
            610                 615                 620

Cys Glu Gln His Lys Met Arg Met Val Leu Gly Val Ile Val Pro Gly
625                 630                 635                 640

Arg Gly Cys Ala Ile Pro Asn Arg Pro Gly Ile Phe Val Arg Val Ala
                645                 650                 655

Tyr Tyr Ala Lys Trp Ile His Lys Ile Ile Leu Thr Tyr Lys Val Pro
            660                 665                 670

Gln Ser Cys Gly Arg His His His His His Ser Ala Gly Leu Val
        675                 680                 685

Pro Arg Gly Ser Asp Lys Thr His Thr Cys Pro Pro Cys Pro Ala Pro
    690                 695                 700

Glu Leu Leu Gly Gly Pro Ser Val Phe Leu Phe Pro Pro Lys Pro Lys
705                 710                 715                 720

Asp Thr Leu Met Ile Ser Arg Thr Pro Glu Val Thr Cys Val Val Val
                725                 730                 735

Asp Val Ser His Glu Asp Pro Glu Val Lys Phe Asn Trp Tyr Val Asp
            740                 745                 750

Gly Val Glu Val His Asn Ala Lys Thr Lys Pro Arg Glu Glu Gln Tyr
        755                 760                 765

Asn Ser Thr Tyr Arg Val Val Ser Val Leu Thr Val Leu His Gln Asp
    770                 775                 780

Trp Leu Asn Gly Lys Glu Tyr Lys Cys Lys Val Ser Asn Lys Ala Leu
785                 790                 795                 800

Pro Ala Pro Ile Glu Lys Thr Ile Ser Lys Ala Lys Gly Gln Pro Arg
                805                 810                 815

Glu Pro Gln Val Tyr Thr Leu Pro Pro Ser Arg Glu Glu Met Thr Lys
            820                 825                 830

Asn Gln Val Ser Leu Thr Cys Leu Val Lys Gly Phe Tyr Pro Ser Asp
        835                 840                 845

Ile Ala Val Glu Trp Glu Ser Asn Gly Gln Pro Glu Asn Asn Tyr Lys
    850                 855                 860

Thr Thr Pro Pro Val Leu Asp Ser Asp Gly Ser Phe Phe Leu Tyr Ser
865                 870                 875                 880

Lys Leu Thr Val Asp Lys Ser Arg Trp Gln Gln Gly Asn Val Phe Ser
                885                 890                 895

Cys Ser Val Met His Glu Ala Leu His Asn His Tyr Thr Gln Lys Ser
```

Leu Ser Leu Ser Pro Gly Lys
    915

<210> SEQ ID NO 120
<211> LENGTH: 2901
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Synthetic mhm (V495-L585)-Fc chimeric protein

<400> SEQUENCE: 120

| | | | | | |
|---|---|---|---|---|---|
| atgatgtggg | ggaccaaact | tctgccggtc | ctgttgctgc | agcatgtcct | cctgcacctc | 60 |
| ctcctgcttc | atgtcgccat | ccctatgca | gaaggacaga | agaaaagaag | aaatacactt | 120 |
| catgaattta | aaaagtcagc | aaaaactact | cttaccaagg | aagacccatt | actgaagatt | 180 |
| aaaaccaaaa | aagtgaactc | tgcagatgag | tgtgccaaca | ggtgtatcag | gaacagggc | 240 |
| tttacgttca | cttgcaaggc | cttcgttttt | gataagtcaa | gaaaacgatg | ctactggtat | 300 |
| cctttcaata | gtatgtcaag | tggagtgaaa | aaagggtttg | gccatgaatt | tgacctctat | 360 |
| gaaaacaaag | actatattag | aaactgcatc | attggtaaag | gaggcagcta | taaagggacg | 420 |
| gtatccatca | ctaagagtgg | catcaaatgc | cagccttgga | attccatgat | cccccatgaa | 480 |
| cacagctatc | gcggtaaaga | cctacaggaa | aactactgtc | gaaatcctcg | aggggaagaa | 540 |
| gggggaccct | ggtgtttcac | aagcaatcca | gaggtacgct | acgaagtctg | tgacattcct | 600 |
| cagtgttcag | aagttgaatg | catgacctgc | aatggtgaaa | gctacagagg | tcccatggat | 660 |
| cacacagaat | caggcaagac | ttgtcagcgc | tgggaccagc | agacaccaca | ccggcacaag | 720 |
| ttcttgccag | aaagatatcc | cgacaagggc | tttgatgata | ttattgccg | caatcctgat | 780 |
| ggcaagccga | ggccatggtg | ctacactctt | gaccctgaca | cccctttggga | gtattgtgca | 840 |
| attaaaacgt | gcgctcacag | tgctgtgaat | gagactgatg | tccctatgga | aacaactgaa | 900 |
| tgcattcaag | gccaaggaga | aggttacagg | ggaaccagca | ataccatttg | gaatggaatt | 960 |
| ccctgtcagc | gttgggattc | gcagtaccct | cacaagcatg | atatcactcc | cgagaacttc | 1020 |
| aaaatgcaag | accttagaga | aaattattgc | cgcaatccag | atggggctga | atcaccatgg | 1080 |
| tgttttacca | ctgacccaaa | catccgagtt | ggctactgct | ctcaaattcc | caagtgtgac | 1140 |
| gtgtcaagtg | gacaagattg | ttatcgtggc | aatgggaaaa | attacatggg | caacttatcc | 1200 |
| aaaacaaggt | ctggacttac | atgttccatg | tgggacaaga | atatggagga | tttacaccgt | 1260 |
| catatcttct | gggagccaga | tgctagcaaa | ttgaataaga | attactgccg | gaatcctgat | 1320 |
| gatgatgccc | atggaccttg | gtgctacacg | gggaatcctc | ttattccttg | ggattattgc | 1380 |
| cctatttccc | gttgtgaagg | agatactaca | cctacaattg | tcaatttgga | ccatcctgta | 1440 |
| atatcctgtg | ccaaaacaaa | acaactgcgg | gttgtaaatg | ggattccaac | acgaacaaac | 1500 |
| ataggatgga | tggttagttt | gagatacaga | aataaacata | tctgcggagg | atcattgata | 1560 |
| aaggagagtt | gggttcttac | tgcacgacag | tgttttcctt | ctcgagactt | gaaagattat | 1620 |
| gaagcttggc | ttggaattca | tgatgtccac | ggaagaggag | atgagaaatg | caaacaggtt | 1680 |
| ctcaatgttt | cccagctggt | atatggccct | gaaggatcag | atctggtttt | aatgaagctt | 1740 |
| gctcgacctg | caatcctgga | taactttgtc | agtacaattg | atttacctag | ttatggttgt | 1800 |
| acaatccctg | aaaagaccac | ttgcagtatt | tacggctggg | gctacactgg | attgatcaac | 1860 |

-continued

```
gcggatggtt tattacgagt agctcatctg tatattatgg ggaatgagaa atgcagtcag    1920
caccatcaag gcaaggtgac tttgaatgag tctgagttat gtgctggggc tgaaaagatt    1980
ggatcaggac catgtgaggg agattatggt ggcccactca tttgtgaaca acacaaaatg    2040
agaatggttc ttggtgtcat tgttcctggt cgtggatgtg ccatcccaaa tcgtcctggt    2100
atttttgttc gagtagcata ttatgcaaaa tggatacaca aagtaatttt gacatacaag    2160
ttgtgcggcc gccatcacca tcaccatcac tccgcgggtc tggtgccacg cggtagtgac    2220
aaaactcaca catgcccacc gtgcccagca cctgaactcc tggggggacc gtcagtcttc    2280
ctcttccccc caaaacccaa ggacaccctc atgatctccc ggacccctga ggtcacatgc    2340
gtggtggtgg acgtgagcca cgaagaccct gaggtcaagt tcaactggta cgtggacggc    2400
gtggaggtgc ataatgccaa gacaaagccg cgggaggagc agtacaacag cacgtaccgt    2460
gtggtcagcg tcctcaccgt cctgcaccag gactggctga atggcaagga gtacaagtgc    2520
aaggtctcca acaaagccct cccagccccc atcgagaaaa ccatctccaa agccaaaggg    2580
cagccccgag aaccacaggt gtacaccctg cccccatccc gggaggagat gaccaagaac    2640
caggtcagcc tgacctgcct ggtcaaaggc ttctatccca gcgacatcgc cgtggagtgg    2700
gagagcaatg ggcagccgga gaacaactac aagaccacgc ctcccgtgct ggactccgac    2760
ggctccttct tcctctatag caagctcacc gtggacaaga gcaggtggca gcaggggaac    2820
gtcttctcat gctccgtgat gcatgaggct ctgcacaacc actacacgca gaagagcctc    2880
tccctgtccc cgggtaaata g                                               2901
```

<210> SEQ ID NO 121
<211> LENGTH: 911
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: synthetic mhm-Fc Active form

<400> SEQUENCE: 121

```
Pro Leu Leu Lys Ile Lys Thr Lys Lys Val Asn Ser Ala Asp Glu Cys
1               5                   10                  15

Ala Asn Arg Cys Ile Arg Asn Arg Gly Phe Thr Phe Thr Cys Lys Ala
            20                  25                  30

Phe Val Phe Asp Lys Ser Arg Lys Arg Cys Tyr Trp Tyr Pro Phe Asn
        35                  40                  45

Ser Met Ser Ser Gly Val Lys Lys Gly Phe Gly His Glu Phe Asp Leu
    50                  55                  60

Tyr Glu Asn Lys Asp Tyr Ile Arg Asn Cys Ile Ile Gly Lys Gly Gly
65                  70                  75                  80

Ser Tyr Lys Gly Thr Val Ser Ile Thr Lys Ser Gly Ile Lys Cys Gln
                85                  90                  95

Pro Trp Asn Ser Met Ile Pro His Glu His Ser Tyr Arg Gly Lys Asp
            100                 105                 110

Leu Gln Glu Asn Tyr Cys Arg Asn Pro Arg Gly Glu Glu Gly Gly Pro
        115                 120                 125

Trp Cys Phe Thr Ser Asn Pro Glu Val Arg Tyr Glu Val Cys Asp Ile
    130                 135                 140

Pro Gln Cys Ser Glu Val Glu Cys Met Thr Cys Asn Gly Glu Ser Tyr
145                 150                 155                 160

Arg Gly Pro Met Asp His Thr Glu Ser Gly Lys Thr Cys Gln Arg Trp
```

```
                     165                 170                 175
Asp Gln Gln Thr Pro His Arg His Lys Phe Leu Pro Glu Arg Tyr Pro
            180                 185                 190
Asp Lys Gly Phe Asp Asp Asn Tyr Cys Arg Asn Pro Asp Gly Lys Pro
            195                 200                 205
Arg Pro Trp Cys Tyr Thr Leu Asp Pro Asp Thr Pro Trp Glu Tyr Cys
            210                 215                 220
Ala Ile Lys Thr Cys Ala His Ser Ala Val Asn Glu Thr Asp Val Pro
225                 230                 235                 240
Met Glu Thr Thr Glu Cys Ile Gln Gly Gln Gly Glu Gly Tyr Arg Gly
            245                 250                 255
Thr Ser Asn Thr Ile Trp Asn Gly Ile Pro Cys Gln Arg Trp Asp Ser
            260                 265                 270
Gln Tyr Pro His Lys His Asp Ile Thr Pro Glu Asn Phe Lys Cys Lys
            275                 280                 285
Asp Leu Arg Glu Asn Tyr Cys Arg Asn Pro Asp Gly Ala Glu Ser Pro
            290                 295                 300
Trp Cys Phe Thr Thr Asp Pro Asn Ile Arg Val Gly Tyr Cys Ser Gln
305                 310                 315                 320
Ile Pro Lys Cys Asp Val Ser Ser Gly Gln Asp Cys Tyr Arg Gly Asn
                        325                 330                 335
Gly Lys Asn Tyr Met Gly Asn Leu Ser Lys Thr Arg Ser Gly Leu Thr
            340                 345                 350
Cys Ser Met Trp Asp Lys Asn Met Glu Asp Leu His Arg His Ile Phe
            355                 360                 365
Trp Glu Pro Asp Ala Ser Lys Leu Asn Lys Asn Tyr Cys Arg Asn Pro
            370                 375                 380
Asp Asp Asp Ala His Gly Pro Trp Cys Tyr Thr Gly Asn Pro Leu Ile
385                 390                 395                 400
Pro Trp Asp Tyr Cys Pro Ile Ser Arg Cys Glu Gly Asp Thr Thr Pro
                        405                 410                 415
Thr Ile Val Asn Leu Asp His Pro Val Ile Ser Cys Ala Lys Thr Lys
            420                 425                 430
Gln Leu Arg Val Val Asn Gly Ile Pro Thr Arg Thr Asn Ile Gly Trp
            435                 440                 445
Met Val Ser Leu Arg Tyr Arg Asn Lys His Ile Cys Gly Gly Ser Leu
            450                 455                 460
Ile Lys Glu Ser Trp Val Leu Thr Ala Arg Gln Cys Phe Pro Ser Arg
465                 470                 475                 480
Asp Leu Lys Asp Tyr Glu Ala Trp Leu Gly Ile His Asp Val His Gly
                        485                 490                 495
Arg Gly Asp Glu Lys Cys Lys Gln Val Leu Asn Val Ser Gln Leu Val
            500                 505                 510
Tyr Gly Pro Glu Gly Ser Asp Leu Val Leu Met Lys Leu Ala Arg Pro
            515                 520                 525
Ala Ile Leu Asp Asn Phe Val Ser Thr Ile Asp Leu Pro Ser Tyr Gly
            530                 535                 540
Cys Thr Ile Pro Glu Lys Thr Thr Cys Ser Ile Tyr Gly Trp Gly Tyr
545                 550                 555                 560
Thr Gly Leu Ile Asn Ala Asp Gly Leu Leu Arg Val Ala His Leu Tyr
                        565                 570                 575
Ile Met Gly Asn Glu Lys Cys Ser Gln His His Gln Gly Lys Val Thr
            580                 585                 590
```

```
Leu Asn Glu Ser Glu Leu Cys Ala Gly Ala Glu Lys Ile Gly Ser Gly
            595                 600                 605
Pro Cys Glu Gly Asp Tyr Gly Pro Leu Ile Cys Glu Gln His Lys
    610                 615                 620
Met Arg Met Val Leu Gly Val Ile Val Pro Gly Arg Gly Cys Ala Ile
625                 630                 635                 640
Pro Asn Arg Pro Gly Ile Phe Val Arg Val Ala Tyr Tyr Ala Lys Trp
                645                 650                 655
Ile His Lys Val Ile Leu Thr Tyr Lys Leu Cys Gly Arg His His
            660                 665                 670
His His His Ser Ala Gly Leu Val Pro Arg Gly Ser Asp Lys Thr His
        675                 680                 685
Thr Cys Pro Pro Cys Pro Ala Pro Glu Leu Leu Gly Gly Pro Ser Val
690                 695                 700
Phe Leu Phe Pro Pro Lys Pro Lys Asp Thr Leu Met Ile Ser Arg Thr
705                 710                 715                 720
Pro Glu Val Thr Cys Val Val Val Asp Val Ser His Glu Asp Pro Glu
                725                 730                 735
Val Lys Phe Asn Trp Tyr Val Asp Gly Val Glu Val His Asn Ala Lys
            740                 745                 750
Thr Lys Pro Arg Glu Glu Gln Tyr Asn Ser Thr Tyr Arg Val Val Ser
        755                 760                 765
Val Leu Thr Val Leu His Gln Asp Trp Leu Asn Gly Lys Glu Tyr Lys
    770                 775                 780
Cys Lys Val Ser Asn Lys Ala Leu Pro Ala Pro Ile Glu Lys Thr Ile
785                 790                 795                 800
Ser Lys Ala Lys Gly Gln Pro Arg Glu Pro Gln Val Tyr Thr Leu Pro
                805                 810                 815
Pro Ser Arg Glu Glu Met Thr Lys Asn Gln Val Ser Leu Thr Cys Leu
            820                 825                 830
Val Lys Gly Phe Tyr Pro Ser Asp Ile Ala Val Glu Trp Glu Ser Asn
        835                 840                 845
Gly Gln Pro Glu Asn Asn Tyr Lys Thr Thr Pro Pro Val Leu Asp Ser
    850                 855                 860
Asp Gly Ser Phe Phe Leu Tyr Ser Lys Leu Thr Val Asp Lys Ser Arg
865                 870                 875                 880
Trp Gln Gln Gly Asn Val Phe Ser Cys Ser Val Met His Glu Ala Leu
                885                 890                 895
His Asn His Tyr Thr Gln Lys Ser Leu Ser Leu Ser Pro Gly Lys
            900                 905                 910

<210> SEQ ID NO 122
<211> LENGTH: 1398
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Full length Heavy Chain (1A3 Variable Region
      and IgG1 Constant Region)

<400> SEQUENCE: 122
atgaactttg ggctcagatt gattttcctt gtccttgttt taaaaggtgt gaagtgtgaa      60
gtgcagctgg tggagtctgg gggaggctta gtgcagcctg gagggtccct gaaactctcc    120
tgtgcagcct ctgaattcac tttcagtaac tattacatgt cttgggttcg ccagactcca    180
```

-continued

```
gagaagaggc tgcagtgggt cgcatacatt agtcctggtg gtggtagctc ctactatcca    240
gccagtgtga agggtcgatt caccatctcc agagacaatg ccaagaacac cctgtacctg    300
caaatgagca gtctgaagtc tgaggacaca gccatgtatt actgtgcaag acaaggggat    360
ggttactacg gggactatgc tatggactac tggggtcaag gaacctcagt caccgtctcc    420
tcagccaaaa cgacaccccc atctgtctat ccactggccc ctggatctgc tgcccaaact    480
aactccatgg tgaccctggg atgcctggtc aagggctatt tccctgagcc agtgacagtg    540
acctggaact ctggatccct gtccagcggt gtgcacacct cccagctgt cctgcagtct    600 gacctctaca ctctgagcag ctcagtgact gtcccctcca gcacctggcc cagcgagacc    660
gtcacctgca acgttgccca cccggccagc agcaccaagg tggacaagaa aattgtgccc    720
agggattgtg gttgtaagcc ttgcatatgt acagtcccag aagtatcatc tgtcttcatc    780
ttccccccaa agcccaagga tgtgctcacc attactctga ctcctaaggt cacgtgtgtt    840
gtggtagaca tcagcaagga tgatcccgag gtccagttca gctggtttgt agatgatgtg    900
gaggtgcaca cagctcagac gcaaccccgg gaggagcagt tcaacagcac tttccgctca    960
gtcagtgaac ttcccatcat gcaccaggac tggctcaatg gcaaggagtt caaatgcagg   1020
gtcaacagtg cagctttccc tgcccccatc gagaaaacca tctccaaaac caaaggcaga   1080
ccgaaggctc cacaggtgta caccattcca cctcccaagg agcagatggc caaggataaa   1140
gtcagtctga cctgcatgat aacagacttc ttccctgaag acattactgt ggagtggcag   1200
tggaatgggc agccagcgga gaactacaag aacactcagc ccatcatgga cacagatggc   1260
tcttacttcg tctacagcaa gctcaatgtg cagaagagca ctgggaggc aggaaatact   1320 ttcacctgct ctgtgttaca tgagggcctg cacaaccacc atactgagaa gagcctctcc   1380
cactctcctg gtaaatga                                                1398
```

<210> SEQ ID NO 123
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Full Length 1A3 Heavy Chain (1A3 Variable
      Region and IgG1 Constant Region)

<400> SEQUENCE: 123

```
Glu Val Gln Leu Val Glu Ser Gly Gly Gly Leu Val Gln Pro Gly Gly
1               5                   10                  15

Ser Leu Lys Leu Ser Cys Ala Ala Ser Glu Phe Thr Phe Ser Asn Tyr
            20                  25                  30

Tyr Met Ser Trp Val Arg Gln Thr Pro Glu Lys Arg Leu Gln Trp Val
        35                  40                  45

Ala Tyr Ile Ser Pro Gly Gly Gly Ser Ser Tyr Pro Ala Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Gln Gly Asp Gly Tyr Tyr Gly Asp Tyr Ala Met Asp Tyr Trp
            100                 105                 110

Gly Gln Gly Thr Ser Val Thr Val Ser Ser Ala Lys Thr Thr Pro Pro
        115                 120                 125
```

```
Ser Val Tyr Pro Leu Ala Pro Gly Ser Ala Ala Gln Thr Asn Ser Met
            130                 135                 140

Val Thr Leu Gly Cys Leu Val Lys Gly Tyr Phe Pro Glu Pro Val Thr
145                 150                 155                 160

Val Thr Trp Asn Ser Gly Ser Leu Ser Ser Gly Val His Thr Phe Pro
                165                 170                 175

Ala Val Leu Gln Ser Asp Leu Tyr Thr Leu Ser Ser Val Thr Val
            180                 185                 190

Pro Ser Ser Thr Trp Pro Ser Glu Thr Val Thr Cys Asn Val Ala His
            195                 200                 205

Pro Ala Ser Ser Thr Lys Val Asp Lys Lys Ile Val Pro Arg Asp Cys
210                 215                 220

Gly Cys Lys Pro Cys Ile Cys Thr Val Pro Glu Val Ser Ser Val Phe
225                 230                 235                 240

Ile Phe Pro Pro Lys Pro Lys Asp Val Leu Thr Ile Thr Leu Thr Pro
            245                 250                 255

Lys Val Thr Cys Val Val Val Asp Ile Ser Lys Asp Asp Pro Glu Val
            260                 265                 270

Gln Phe Ser Trp Phe Val Asp Asp Val Glu Val His Thr Ala Gln Thr
            275                 280                 285

Gln Pro Arg Glu Glu Gln Phe Asn Ser Thr Phe Arg Ser Val Ser Glu
290                 295                 300

Leu Pro Ile Met His Gln Asp Trp Leu Asn Gly Lys Glu Phe Lys Cys
305                 310                 315                 320

Arg Val Asn Ser Ala Ala Phe Pro Ala Pro Ile Glu Lys Thr Ile Ser
                325                 330                 335

Lys Thr Lys Gly Arg Pro Lys Ala Pro Gln Val Tyr Thr Ile Pro Pro
            340                 345                 350

Pro Lys Glu Gln Met Ala Lys Asp Lys Val Ser Leu Thr Cys Met Ile
            355                 360                 365

Thr Asp Phe Phe Pro Glu Asp Ile Thr Val Glu Trp Gln Trp Asn Gly
            370                 375                 380

Gln Pro Ala Glu Asn Tyr Lys Asn Thr Gln Pro Ile Met Asp Thr Asp
385                 390                 395                 400

Gly Ser Tyr Phe Val Tyr Ser Lys Leu Asn Val Gln Lys Ser Asn Trp
                405                 410                 415

Glu Ala Gly Asn Thr Phe Thr Cys Ser Val Leu His Glu Gly Leu His
            420                 425                 430

Asn His His Thr Glu Lys Ser Leu Ser His Ser Pro Gly Lys
            435                 440                 445
```

<210> SEQ ID NO 124
<211> LENGTH: 705
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Full Length Light Chain (1A3 Kappa Variable Region and Constant Region)

<400> SEQUENCE: 124

```
atgagtgtgc ccactcaggt cctggggttg ctgctgctgt ggcttacaga tgccagatgt    60
gacatccaga tgactcagtc tccagcctcc ctatctgttt ctgtgggaga aactgtcacc   120
atcacatgtc gagcaagtga gaatatttat agtaatttag catggtatca gcagaaacag   180
```

```
ggaaaatctc ctcagctcct ggtctatgct gcaacaaact tagcagatgg tgtgccatca    240
aggttcagtg gcagtggatc aggcacacag ttttccctca agatcaacag cctgcagtct    300
gaagattttg ggacttatta ctgtcaacat ttttggggta ctccgtacac gttcggaggg    360
gggaccaagc tggaaataaa acgggctgat gctgcaccaa ctgtatccat cttcccacca    420
tccagtgagc agttaacatc tggaggtgcc tcagtcgtgt gcttcttgaa caacttctac    480
cccaaagaca tcaatgtcaa gtggaagatt gatggcagtg aacgacaaaa tggcgtcctg    540
aacagttgga ctgatcagga cagcaaagac agcacctaca gcatgagcag caccctcatg    600
ttgaccaagg acgagtatga acgacataac agctatacct gtgaggccac tcacaagaca    660
tcaacttcac ccattgtcaa gagcttcaac aggaatgagt gttag                    705
```

<210> SEQ ID NO 125
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Full Length Light Chain (1A3 Kappa Variable
      Region and Constant Region)

<400> SEQUENCE: 125

```
Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Phe Ser Leu Lys Ile Asn Ser Leu Gln Ser
65                  70                  75                  80

Glu Asp Phe Gly Thr Tyr Tyr Cys Gln His Phe Trp Gly Thr Pro Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Met Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 126
<211> LENGTH: 1386
<212> TYPE: DNA
<213> ORGANISM: Artificial Sequence
<220> FEATURE:

-continued

<220> FEATURE:
<223> OTHER INFORMATION: Description of Artificial Sequence: Synthetic
polynucleotide
<220> FEATURE:
<223> OTHER INFORMATION: Full Length Heavy Chain (2B8 Variable Region
and IgG1 Constant Region)

<400> SEQUENCE: 126

```
atgggatgga gctatatcat cctcttttg gtagcaacag ctacagatgt ccactcccag      60
gtccaactgc agcagcctgg ggctgaactg gtgaagcctg gacttcagt gaagctgtcc     120
tgcaaggctt ctggctacac cttcaccacc tactggatgc actgggtgaa tcagaggcct    180
ggacaaggcc ttgagtggat tggagagatt aatcctacca acggtcatac taactacaat    240
gagaagttca gagcaaggc cacactgact gtagacaaat cctccagcac agcctacatg     300
caactcagca gcctgacatc tgaggactct gcggtctatt actgtgcaag aaactatgtt    360
ggtagcatct ttgactactg gggccaaggc accactctca cagtctcctc agccaaaacg    420
acacccccat ctgtctatcc actggcccct ggatctgctg cccaaactaa ctccatggtg    480
accctgggat gcctggtcaa gggctatttc cctgagccag tgacagtgac ctggaactct    540
ggatccctgt ccagcggtgt gcacaccttc ccagctgtcc tgcagtctga cctctacact    600
ctgagcagct cagtgactgt cccctccagc acctggccca gcgagaccgt cacctgcaac    660
gttgcccacc cggccagcag caccaaggtg gacaagaaaa ttgtgcccag ggattgtggt    720
tgtaagcctt gcatatgtac agtcccagaa gtatcatctg tcttcatctt ccccccaaag    780
cccaaggatg tgctcaccat tactctgact cctaaggtca cgtgtgttgt ggtagacatc    840
agcaaggatg atcccgaggt ccagttcagc tggtttgtag atgatgtgga ggtgcacaca    900
gctcagacgc aaccccggga ggagcagttc aacagcactt tccgctcagt cagtgaactt    960
cccatcatgc accaggactg gctcaatggc aaggagttca atgcagggt caacagtgca   1020
gctttcctg cccccatcga gaaaccatc tccaaaacca aggcagacc gaaggctcca    1080
caggtgtaca ccattccacc tcccaaggag cagatggcca aggataaagt cagtctgacc   1140
tgcatgataa cagacttctt ccctgaagac attactgtgg agtggcagtg gaatgggcag   1200
ccagcggaga actacaagaa cactcagccc atcatggaca cagatggctc ttacttcgtc   1260
tacagcaagc tcaatgtgca gaagagcaac tgggaggcag aaatactttt cacctgctct   1320
gtgttacatg agggcctgca caaccaccat actgagaaga gcctctccca ctctcctggt   1380
aaatga                                                              1386
```

<210> SEQ ID NO 127
<211> LENGTH: 442
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: Full Length Heavy Chain (2B8 Variable Region
and IgG1 Constant Region)

<400> SEQUENCE: 127

```
Gln Val Gln Leu Gln Gln Pro Gly Ala Glu Leu Val Lys Pro Gly Thr
1               5                   10                  15

Ser Val Lys Leu Ser Cys Lys Ala Ser Gly Tyr Thr Phe Thr Thr Tyr
            20                  25                  30

Trp Met His Trp Val Asn Gln Arg Pro Gly Gln Gly Leu Glu Trp Ile
        35                  40                  45

Gly Glu Ile Asn Pro Thr Asn Gly His Thr Asn Tyr Asn Glu Lys Phe
```

```
                50             55             60
Lys Ser Lys Ala Thr Leu Thr Val Asp Lys Ser Ser Thr Ala Tyr
 65              70                  75                  80

Met Gln Leu Ser Ser Leu Thr Ser Glu Asp Ser Ala Val Tyr Tyr Cys
                 85                  90                  95

Ala Arg Asn Tyr Val Gly Ser Ile Phe Asp Tyr Trp Gly Gln Gly Thr
                100                 105                 110

Thr Leu Thr Val Ser Ser Ala Lys Thr Thr Pro Pro Ser Val Tyr Pro
                115                 120                 125

Leu Ala Pro Gly Ser Ala Ala Gln Thr Asn Ser Met Val Thr Leu Gly
                130                 135                 140

Cys Leu Val Lys Gly Tyr Phe Pro Glu Pro Val Thr Val Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Val Thr Val Pro Ser Ser Thr
                180                 185                 190

Trp Pro Ser Glu Thr Val Thr Cys Asn Val Ala His Pro Ala Ser Ser
                195                 200                 205

Thr Lys Val Asp Lys Lys Ile Val Pro Arg Asp Cys Gly Cys Lys Pro
210                 215                 220

Cys Ile Cys Thr Val Pro Glu Val Ser Ser Val Phe Ile Phe Pro Pro
225                 230                 235                 240

Lys Pro Lys Asp Val Leu Thr Ile Thr Leu Thr Pro Lys Val Thr Cys
                245                 250                 255

Val Val Val Asp Ile Ser Lys Asp Asp Pro Glu Val Gln Phe Ser Trp
                260                 265                 270

Phe Val Asp Asp Val Glu Val His Thr Ala Gln Thr Gln Pro Arg Glu
                275                 280                 285

Glu Gln Phe Asn Ser Thr Phe Arg Ser Val Ser Glu Leu Pro Ile Met
290                 295                 300

His Gln Asp Trp Leu Asn Gly Lys Glu Phe Lys Cys Arg Val Asn Ser
305                 310                 315                 320

Ala Ala Phe Pro Ala Pro Ile Glu Lys Thr Ile Ser Lys Thr Lys Gly
                325                 330                 335

Arg Pro Lys Ala Pro Gln Val Tyr Thr Ile Pro Pro Pro Lys Glu Gln
                340                 345                 350

Met Ala Lys Asp Lys Val Ser Leu Thr Cys Met Ile Thr Asp Phe Phe
                355                 360                 365

Pro Glu Asp Ile Thr Val Glu Trp Gln Trp Asn Gly Gln Pro Ala Glu
                370                 375                 380

Asn Tyr Lys Asn Thr Gln Pro Ile Met Asp Thr Asp Gly Ser Tyr Phe
385                 390                 395                 400

Val Tyr Ser Lys Leu Asn Val Gln Lys Ser Asn Trp Glu Ala Gly Asn
                405                 410                 415

Thr Phe Thr Cys Ser Val Leu His Glu Gly Leu His Asn His His Thr
                420                 425                 430

Glu Lys Ser Leu Ser His Ser Pro Gly Lys
                435                 440

<210> SEQ ID NO 128
<211> LENGTH: 705
<212> TYPE: DNA
<213> ORGANISM: Artificial Sequence
<220> FEATURE:
```

<223> OTHER INFORMATION: Description of Artificial Sequence: Synthetic
polynucleotide
<220> FEATURE:
<223> OTHER INFORMATION: Full Length Light Chain (2B8 Kappa Variable
Region and Constant Region)

<400> SEQUENCE: 128

```
atggaatcac agactctggt cttcatatcc atactgctct ggttatatgg tgctgatggg      60
aacattgtaa tgacccaatc tcccaaatcc atgtccatgt cagtaggaga gagggtcacc     120
ttgagctgca aggccagtga gaatgtggtt tcttatgtat cctggtatca acagaaacca     180
gcgcagtctc ctaaactgct gatatacggg gcatccaacc ggaacactgg ggtccccgat     240
cgcttcacag gcagtggatc tgcaacagat ttcactctga ccatcagcag tgtgcgggct     300
gaagaccttg cagattatca ctgtgggcag agttacaact atccgtacac gttcggaggg     360
gggaccaggc tggaaataaa acgggctgat gctgcaccaa ctgtatccat cttcccacca     420
tccagtgagc agttaacatc tggaggtgcc tcagtcgtgt gcttcttgaa caacttctac     480
cccaaagaca tcaatgtcaa gtggaagatt gatggcagtg aacgacaaaa tggcgtcctg     540
aacagttgga ctgatcagga cagcaaagac agcacctaca gcatgagcag cacccctcacg    600
ttgaccaagg acgagtatga acgacataac agctatacct gtgaggccac tcacaagaca    660
tcaacttcac ccattgtcaa gagcttcaac aggaatgagt gttag                    705
```

<210> SEQ ID NO 129
<211> LENGTH: 214
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: Full Length Light Chain (2B8 Kappa Variable
Region and Constant Region)

<400> SEQUENCE: 129

```
Asn Ile Val Met Thr Gln Ser Pro Lys Ser Met Ser Met Ser Val Gly
 1               5                  10                  15

Glu Arg Val Thr Leu Ser Cys Lys Ala Ser Glu Asn Val Val Ser Tyr
            20                  25                  30

Val Ser Trp Tyr Gln Gln Lys Pro Ala Gln Ser Pro Lys Leu Leu Ile
        35                  40                  45

Tyr Gly Ala Ser Asn Arg Asn Thr Gly Val Pro Asp Arg Phe Thr Gly
    50                  55                  60

Ser Gly Ser Ala Thr Asp Phe Thr Leu Thr Ile Ser Ser Val Arg Ala
65                  70                  75                  80

Glu Asp Leu Ala Asp Tyr His Cys Gly Gln Ser Tyr Asn Tyr Pro Tyr
                85                  90                  95

Thr Phe Gly Gly Gly Thr Arg Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
```

```
                180             185             190
Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 130
<211> LENGTH: 1386
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Full Length Heavy Chain (2F8 Variable Region
      and IgG1 Constant Region)

<400> SEQUENCE: 130

| | |
|---|---|
| atggaatgga gctgggtctt tctcttcctc ctgtcagtaa ctgcaggtgt ccactgccag | 60 |
| gtccagctga agcagtctgg agctgagctg gtgaggcctg gacttcagt gaagatgtcc | 120 |
| tgcaaggctt ctggctacac cttcactacc tactatatac actgggtgaa tcagaggcct | 180 |
| ggacagggcc ttgagtggat tggaaagatt ggtcctggaa gtggtagtac ttactacaat | 240 |
| gagatgttca agacaaggc cacattgact gtagacacat cctccagcac agcctacatg | 300 |
| cagctcagca gcctgacatc tgacgactct gcggtctatt tctgtgcaag aaggggactg | 360 |
| ggacgtggct ttgactactg gggccaaggc accactctca cagtctcctc agccaaaacg | 420 |
| acacccccat ctgtctatcc actggcccct ggatctgctg cccaaactaa ctccatggtg | 480 |
| accctgggat gcctggtcaa gggctatttc cctgagccag tgacagtgac ctggaactct | 540 |
| ggatccctgt ccagcggtgt gcacaccttc ccagctgtcc tgcagtctga cctctacact | 600 |
| ctgagcagct cagtgactgt cccctccagc acctggccca gcgagaccgt cacctgcaac | 660 |
| gttgcccacc cggccagcag caccaaggtg gacaagaaaa ttgtgcccag ggattgtggt | 720 |
| tgtaagcctt gcatatgtac agtcccagaa gtatcatctg tcttcatctt cccccccaaag | 780 |
| cccaaggatg tgctcaccat tactctgact cctaaggtca cgtgtgttgt ggtagacatc | 840 |
| agcaaggatg atcccgaggt ccagttcagc tggtttgtag atgatgtgga ggtgcacaca | 900 |
| gctcagacgc aaccccggga ggagcagttc aacagcactt tccgctcagt cagtgaactt | 960 |
| cccatcatgc accaggactg gctcaatggc aaggagttca atgcagggt caacagtgca | 1020 |
| gctttccctg cccccatcga gaaaaccatc tccaaaacca aggcagacc gaaggctcca | 1080 |
| caggtgtaca ccattccacc tcccaaggag cagatggcca aggataaagt cagtctgacc | 1140 |
| tgcatgataa cagacttctt ccctgaagac attactgtgg agtggcagtg gaatgggcag | 1200 |
| ccagcggaga actacaagaa cactcagccc atcatggaca cagatggctc ttacttcgtc | 1260 |
| tacagcaagc tcaatgtgca gaagagcaac tgggaggcag gaaatacttt cacctgctct | 1320 |
| gtgttacatg agggcctgca caaccaccat actgagaaga gcctctccca ctctcctggt | 1380 |
| aaatga | 1386 |

<210> SEQ ID NO 131
<211> LENGTH: 442
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Full Length Heavy Chain (2F8 Variable Region and IgG1 Constant Region)

<400> SEQUENCE: 131

| | | | | | | | | | | | | | | |
|---|---|---|---|---|---|---|---|---|---|---|---|---|---|---|
|Gln|Val|Gln|Leu|Lys|Gln|Ser|Gly|Ala|Glu|Leu|Val|Arg|Pro|Gly|Thr|
|1| | | |5| | | | |10| | | | |15|
|Ser|Val|Lys|Met|Ser|Cys|Lys|Ala|Ser|Gly|Tyr|Thr|Phe|Thr|Thr|Tyr|
| | | |20| | | | |25| | | | |30| | |
|Tyr|Ile|His|Trp|Val|Asn|Gln|Arg|Pro|Gly|Gln|Gly|Leu|Glu|Trp|Ile|
| | | |35| | | | |40| | | | |45| | |
|Gly|Lys|Ile|Gly|Pro|Gly|Ser|Gly|Ser|Thr|Tyr|Tyr|Asn|Glu|Met|Phe|
| |50| | | | |55| | | | |60| | | | |
|Lys|Asp|Lys|Ala|Thr|Leu|Thr|Val|Asp|Thr|Ser|Ser|Ser|Thr|Ala|Tyr|
|65| | | | |70| | | | |75| | | | |80|
|Met|Gln|Leu|Ser|Ser|Leu|Thr|Ser|Asp|Asp|Ser|Ala|Val|Tyr|Phe|Cys|
| | | | |85| | | | |90| | | | |95| |
|Ala|Arg|Arg|Gly|Leu|Gly|Arg|Gly|Phe|Asp|Tyr|Trp|Gly|Gln|Gly|Thr|
| | | |100| | | | |105| | | | |110| | |
|Thr|Leu|Thr|Val|Ser|Ser|Ala|Lys|Thr|Thr|Pro|Pro|Ser|Val|Tyr|Pro|
| | | |115| | | | |120| | | | |125| | |
|Leu|Ala|Pro|Gly|Ser|Ala|Ala|Gln|Thr|Asn|Ser|Met|Val|Thr|Leu|Gly|
| | | |130| | | | |135| | | | |140| | |
|Cys|Leu|Val|Lys|Gly|Tyr|Phe|Pro|Glu|Pro|Val|Thr|Val|Thr|Trp|Asn|
|145| | | | |150| | | | |155| | | | |160|
|Ser|Gly|Ser|Leu|Ser|Ser|Gly|Val|His|Thr|Phe|Pro|Ala|Val|Leu|Gln|
| | | | |165| | | | |170| | | | |175| |
|Ser|Asp|Leu|Tyr|Thr|Leu|Ser|Ser|Ser|Val|Thr|Val|Pro|Ser|Ser|Thr|
| | | | |180| | | | |185| | | | |190| |
|Trp|Pro|Ser|Glu|Thr|Val|Thr|Cys|Asn|Val|Ala|His|Pro|Ala|Ser|Ser|
| | | | |195| | | | |200| | | | |205| |
|Thr|Lys|Val|Asp|Lys|Lys|Ile|Val|Pro|Arg|Asp|Cys|Gly|Cys|Lys|Pro|
| | | |210| | | | |215| | | | |220| | |
|Cys|Ile|Cys|Thr|Val|Pro|Glu|Val|Ser|Ser|Val|Phe|Ile|Phe|Pro|Pro|
|225| | | | |230| | | | |235| | | | |240|
|Lys|Pro|Lys|Asp|Val|Leu|Thr|Ile|Thr|Leu|Thr|Pro|Lys|Val|Thr|Cys|
| | | | |245| | | | |250| | | | |255| |
|Val|Val|Val|Asp|Ile|Ser|Lys|Asp|Asp|Pro|Glu|Val|Gln|Phe|Ser|Trp|
| | | |260| | | | |265| | | | |270| | |
|Phe|Val|Asp|Asp|Val|Glu|Val|His|Thr|Ala|Gln|Thr|Gln|Pro|Arg|Glu|
| | | |275| | | | |280| | | | |285| | |
|Glu|Gln|Phe|Asn|Ser|Thr|Phe|Arg|Ser|Val|Ser|Glu|Leu|Pro|Ile|Met|
| | | |290| | | | |295| | | | |300| | |
|His|Gln|Asp|Trp|Leu|Asn|Gly|Lys|Glu|Phe|Lys|Cys|Arg|Val|Asn|Ser|
|305| | | | |310| | | | |315| | | | |320|
|Ala|Ala|Phe|Pro|Ala|Pro|Ile|Glu|Lys|Thr|Ile|Ser|Lys|Thr|Lys|Gly|
| | | | |325| | | | |330| | | | |335| |
|Arg|Pro|Lys|Ala|Pro|Gln|Val|Tyr|Thr|Ile|Pro|Pro|Pro|Lys|Glu|Gln|
| | | | |340| | | | |345| | | | |350| |
|Met|Ala|Lys|Asp|Lys|Val|Ser|Leu|Thr|Cys|Met|Ile|Thr|Asp|Phe|Phe|
| | | |355| | | | |360| | | | |365| | |
|Pro|Glu|Asp|Ile|Thr|Val|Glu|Trp|Gln|Trp|Asn|Gly|Gln|Pro|Ala|Glu|
| | | |370| | | | |375| | | | |380| | |
|Asn|Tyr|Lys|Asn|Thr|Gln|Pro|Ile|Met|Asp|Thr|Asp|Gly|Ser|Tyr|Phe|
|385| | | | |390| | | | |395| | | | |400|
|Val|Tyr|Ser|Lys|Leu|Asn|Val|Gln|Lys|Ser|Asn|Trp|Glu|Ala|Gly|Asn|

```
                    405                 410                 415
Thr Phe Thr Cys Ser Val Leu His Glu Gly Leu His Asn His His Thr
            420                 425                 430

Glu Lys Ser Leu Ser His Ser Pro Gly Lys
        435                 440

<210> SEQ ID NO 132
<211> LENGTH: 717
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Full Length Light Chain (2F8 Kappa Variable
      Region and Constant Region)

<400> SEQUENCE: 132
atggagacag acacaatcct gctatgggtg ctgctgctct ggttccagg  ctccactggt      60 gacattgtgc tgacccaatc tccagcttct ttggctgtgt ctctagggca gagggccacc    120
atctcctgca aggccagcca agtgttgat tatgatggta atagttatat caactggtac     180
caacagaaac caggacagcc acccaaagtc ctcatctatg ttgcatccaa tctagaatct    240
gggatcccag ccaggtttag tggcagtggg tctgggacag acttcaccct caacatccat    300
cctgtggagg aggaggatgc tgcaacctat tactgtcagc aaagtattga ggatcctccc    360
acgttcggtg ctgggaccaa gctggagctg aaacgggctg atgctgcacc aactgtatcc    420
atcttcccac catccagtga gcagttaaca tctggaggtg cctcagtcgt gtgcttcttg    480
aacaacttct accccaaaga catcaatgtc aagtggaaga ttgatggcag tgaacgacaa    540
aatggcgtcc tgaacagttg gactgatcag gacagcaaag acagcaccta cagcatgagc    600
agcacccTca cgttgaccaa ggacgagtat gaacgacata acagctatac ctgtgaggcc    660
actcacaaga catcaacttc acccattgtc aagagcttca caggaatga gtgttag       717

<210> SEQ ID NO 133
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Full Length Light Chain (2F8 Kappa Variable
      Region and Constant Region)

<400> SEQUENCE: 133

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asn Ser Tyr Ile Asn Trp Tyr Gln Gln Lys Pro Gly Gln Pro Pro
        35                  40                  45

Lys Val Leu Ile Tyr Val Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Ile
                85                  90                  95

Glu Asp Pro Pro Thr Phe Gly Ala Gly Thr Lys Leu Glu Leu Lys Arg
            100                 105                 110
```

```
Ala Asp Ala Ala Pro Thr Val Ser Ile Phe Pro Pro Ser Ser Glu Gln
            115                 120                 125
Leu Thr Ser Gly Gly Ala Ser Val Val Cys Phe Leu Asn Asn Phe Tyr
        130                 135                 140
Pro Lys Asp Ile Asn Val Lys Trp Lys Ile Asp Gly Ser Glu Arg Gln
145                 150                 155                 160
Asn Gly Val Leu Asn Ser Trp Thr Asp Gln Asp Ser Lys Asp Ser Thr
                165                 170                 175
Tyr Ser Met Ser Ser Thr Leu Thr Leu Thr Lys Asp Glu Tyr Glu Arg
            180                 185                 190
His Asn Ser Tyr Thr Cys Glu Ala Thr His Lys Thr Ser Thr Ser Pro
        195                 200                 205
Ile Val Lys Ser Phe Asn Arg Asn Glu Cys
    210                 215
```

<210> SEQ ID NO 134
<211> LENGTH: 1392
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Full Length Heavy Chain (3B6 Variable Region and IgG1 Constant Region)

<400> SEQUENCE: 134

```
atggaatggc cttgtatctt tctcttcctc ctgtcagtaa ctgaaggtgt ccactcccag      60
gttcagctgc agcagtctgg ggctgaactg gtgaggcctg gtcctcagt gaagatttcc     120
tgcaaggctt ctggctatgt attcagtagc tactggatga actgggtgaa gcagaggcct    180
ggacagggtc ttgagtggat tggacagatt tatcctggag atggtgatag taactacaat    240
ggaaacttca gggtaaagc cacactgact gcagacaaat cctccagtac agcctacatg    300
cagctcagca gcctaacatc tgaggactct gcggtctatt tctgtgcatc ccagctcggg   360
ctacgtgaga actactttga ctactggggc caaggcacca ctctcacagt ctcctcagcc   420
aaaacgacac ccccatctgt ctatccactg gcccctggat ctgctgccca aactaactcc   480
atggtgaccc tgggatgcct ggtcaagggc tatttccctg agccagtgac agtgacctgg   540
aactctggat ccctgtccag cggtgtgcac accttcccag ctgtcctgca gtctgacctc   600
tacactctga gcagctcagt gactgtcccc tccagcacct ggcccagcga ccgtcacc     660
tgcaacgttg cccacccggc cagcagcacc aaggtggaca gaaaaattgt gcccaggat    720
tgtggttgta agccttgcat atgtacagtc ccagaagtat catctgtctt catcttcccc   780
ccaaagccca aggatgtgct caccattact ctgactccta aggtcacgtg tgttgtggta   840
gacatcagca aggatgatcc cgaggtccag ttcagctggt ttgtagatga tgtggaggtg   900
cacacagctc agacgcaacc ccgggaggag cagttcaaca gcactttccg ctcagtcagt   960
gaacttccca tcatgcacca ggactggctc aatggcaagg agttcaaatg cagggtcaac  1020
agtgcagctt tccctgcccc catcgagaaa accatctcca aaaccaaagg cagaccgaag  1080
gctccacagg tgtacaccat tccacctccc aaggagcaga tggccaagga taaagtcagt  1140
ctgacctgca tgataacaga cttcttccct gaagacatta ctgtggagtg cagtggaat  1200
gggcagccag cggagaacta caagaacact cagcccatca tggacacaga tggctcttac  1260
ttcgtctaca gcaagctcaa tgtgcagaag agcaactggg aggcaggaaa tactttcacc  1320
```

```
tgctctgtgt tacatgaggg cctgcacaac caccatactg agaagagcct ctcccactct    1380
cctggtaaat ga                                                        1392
```

<210> SEQ ID NO 135
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Full Length Heavy Chain (3B6 Variable Region
      and IgG1 Constant Region)

<400> SEQUENCE: 135

```
Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Val Phe Ser Ser Tyr
            20                  25                  30

Trp Met Asn Trp Val Lys Gln Arg Pro Gly Gln Gly Leu Glu Trp Ile
        35                  40                  45

Gly Gln Ile Tyr Pro Gly Asp Gly Asp Ser Asn Tyr Asn Gly Asn Phe
    50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Phe Cys
                85                  90                  95

Ala Ser Gln Leu Gly Leu Arg Glu Asn Tyr Phe Asp Tyr Trp Gly Gln
            100                 105                 110

Gly Thr Thr Leu Thr Val Ser Ser Ala Lys Thr Thr Pro Pro Ser Val
        115                 120                 125

Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Pro Ser
            180                 185                 190

Ser Thr Trp Pro Ser Glu Thr Val Thr Cys Asn Val Ala His Pro Ala
        195                 200                 205

Ser Ser Thr Lys Val Asp Lys Lys Ile Val Pro Arg Asp Cys Gly Cys
    210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
                245                 250                 255

Thr Cys Val Val Val Asp Ile Ser Lys Asp Asp Pro Glu Val Gln Phe
            260                 265                 270

Ser Trp Phe Val Asp Asp Val Glu Val His Thr Ala Gln Thr Gln Pro
        275                 280                 285

Arg Glu Glu Gln Phe Asn Ser Thr Phe Arg Ser Val Ser Glu Leu Pro
    290                 295                 300

Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr
                325                 330                 335
```

Lys Gly Arg Pro Lys Ala Pro Gln Val Tyr Thr Ile Pro Pro Pro Lys
              340                 345                 350

Glu Gln Met Ala Lys Asp Lys Val Ser Leu Thr Cys Met Ile Thr Asp
              355                 360                 365

Phe Phe Pro Glu Asp Ile Thr Val Glu Trp Gln Trp Asn Gly Gln Pro
      370                 375                 380

Ala Glu Asn Tyr Lys Asn Thr Gln Pro Ile Met Asp Thr Asp Gly Ser
385                 390                 395                 400

Tyr Phe Val Tyr Ser Lys Leu Asn Val Gln Lys Ser Asn Trp Glu Ala
              405                 410                 415

Gly Asn Thr Phe Thr Cys Ser Val Leu His Glu Gly Leu His Asn His
              420                 425                 430

His Thr Glu Lys Ser Leu Ser His Ser Pro Gly Lys
              435                 440

<210> SEQ ID NO 136
<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Full Length Light Chain (3B6 Kappa Variable
      Region and Constant Region)

<400> SEQUENCE: 136

```
atggacatga ggacccctgc tcagtttctt ggaatcttgt tgctctggtt tccaggtatc    60
aaatgtgaca tcaagatgac ccagtctcca tcttccatgt atgcatctct aggagagaga   120
gtcacaatca cttgcaaggc gagtcaggac attaaaagct atttaagctg gttccagcag   180
aaaccaggga aatctcctaa gaccctgatc tatcgtgtaa acagattggt agatggggtc   240
ccatcaaggt tcagtggcag tggatctggg caagattctt ctctcaccat caccagcctg   300
gagaatgaag atatgggaat ttattattgt ctacagtatg atgagtttcc gttcacgttc   360 ggaggggggaccaagctgga aataaagcgg gctgatgctg caccaactgt atccatcttc   420
ccaccatcca gtgagcagtt aacatctgga ggtgcctcag tcgtgtgctt cttgaacaac   480
ttctacccca agacatcaa tgtcaagtgg aagattgatg cagtgaacg acaaaatggc    540 gtcctgaaca gttggactga tcaggacagc aaagacagca cctacagcat gagcagcacc   600
ctcacgttga ccaaggacga gtatgaacga cataacagct atacctgtga ggccactcac   660
aagacatcaa cttcacccat tgtcaagagc ttcaacagga atgagtgtta g            711
```

<210> SEQ ID NO 137
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Full Length Light Chain (3B6 Kappa Variable
      Region and Constant Region)

<400> SEQUENCE: 137

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Lys Ser Tyr
            20                  25                  30

```
Leu Ser Trp Phe Gln Gln Lys Pro Gly Lys Ser Pro Lys Thr Leu Ile
         35                  40                  45
Tyr Arg Val Asn Arg Leu Val Asp Gly Val Pro Ser Arg Phe Ser Gly
     50                  55                  60
Ser Gly Ser Gly Gln Asp Ser Ser Leu Thr Ile Thr Ser Leu Glu Asn
 65                  70                  75                  80
Glu Asp Met Gly Ile Tyr Tyr Cys Leu Gln Tyr Asp Glu Phe Pro Phe
                 85                  90                  95
Thr Phe Gly Gly Gly Thr Lys Leu Glu Ile Lys Arg Ala Asp Ala Ala
                100                 105                 110
Pro Thr Val Ser Ile Phe Pro Pro Ser Ser Glu Gln Leu Thr Ser Gly
            115                 120                 125
Gly Ala Ser Val Val Cys Phe Leu Asn Asn Phe Tyr Pro Lys Asp Ile
        130                 135                 140
Asn Val Lys Trp Lys Ile Asp Gly Ser Glu Arg Gln Asn Gly Val Leu
145                 150                 155                 160
Asn Ser Trp Thr Asp Gln Asp Ser Lys Asp Ser Thr Tyr Ser Met Ser
                165                 170                 175
Ser Thr Leu Thr Leu Thr Lys Asp Glu Tyr Glu Arg His Asn Ser Tyr
            180                 185                 190
Thr Cys Glu Ala Thr His Lys Thr Ser Thr Ser Pro Ile Val Lys Ser
        195                 200                 205
Phe Asn Arg Asn Glu Cys
    210

<210> SEQ ID NO 138
<211> LENGTH: 1361
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Full Length Heavy Chain (3D11 Variable Region
      and IgG1 Constant Region)

<400> SEQUENCE: 138
atggctgtcc cggtgctgtt cctctgcctg gttgcatttc caagctgtgt cctgtcccag      60
gtacagctga aggagtcagg acctggcctg gtggcgccct cacagagcct gtccatcact     120
tgcactgtct ctgggttttc attaaccagc tatagtttac actgggttcg ccagcctcca     180
ggaaagggtc tggaatggct gggagtaata tgggctggtg aaacacaaa ttataattcg     240 tctctcatgt ccagactgac catcaggaaa gacaactcca agagccaagt tttcttaaaa     300
atgaacagtc tgcaaactga tgacacagcc atgtactact gtgccagaga gaggtttgct     360
tactggggcc aagggactct ggtcactgtc tctgcagcca aaacgacacc cccatctgtc     420
tatccactgg cccctggatc tgctgcccaa actaactcca tggtgaccct gggatgcctg     480
gtcaagggct atttccctga gccagtgaca gtgacctgga ctctggatcc ctgtccagc     540 ggtgtgcaca ccttcccagc tgtcctgcag tctgacctct acactctgag cagctcagtg     600
actgtcccct ccagcacctg gcccagcgag accgtcacct gcaacgttgc ccacccggcc     660
agcagcacca aggtggacaa gaaaattgtg cccagggatt gtggttgtaa gccttgcata     720
tgtacagtcc cagaagtatc atctgtcttc atcttccccc caaagcccaa ggatgtgctc     780
accattactc tgactcctaa ggtcacgtgt gttgtggtag acatcagcaa ggatgatccc     840
gaggtccagt tcagctggtt tgtagatgat gtggaggtgc acacagctca gacgcaaccc     900
```

```
cgggaggagc agttcaacag cactttccgc tcagtcagtg aacttcccat catgcaccag    960
gactggctca atggcaagga gttcaaatgc agggtcaaca gtgcagcttt ccctgccccc   1020
atcgagaaaa ccatctccaa aaccaaaggc agaccgaagg ctccacaggt gtacaccatt   1080
ccacctccca aggagcagat ggccaaggat aaagtcagtc tgacctgcat gataacagac   1140
ttcttccctg aagacattac tgtggagtgg cagtggaatg ggcagccagc ggagaactac   1200
aagaacactc agcccatcat ggacacagat ggctcttact tcgtctacag caagctcaat   1260
gtgcagaaga gcaactggga ggcaggaaat actttcacct gctctgtgtt acatgagggc   1320
ctgcacaacc accatactga tcccactctc ctggtaaatg a                       1361
```

<210> SEQ ID NO 139
<211> LENGTH: 437
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Full Length Heavy Chain (3D11 Variable Region
      and IgG1 Constant Region)

<400> SEQUENCE: 139

```
Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Ser Leu His Trp Val Arg Gln Pro Pro Gly Lys Gly Leu Glu Trp Leu
        35                  40                  45

Gly Val Ile Trp Ala Gly Gly Asn Thr Asn Tyr Asn Ser Ser Leu Met
    50                  55                  60

Ser Arg Leu Thr Ile Arg Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg Glu Arg Phe Ala Tyr Trp Gly Gln Gly Thr Leu Val Thr Val Ser
            100                 105                 110

Ala Ala Lys Thr Thr Pro Pro Ser Val Tyr Pro Leu Ala Pro Gly Ser
        115                 120                 125

Ala Ala Gln Thr Asn Ser Met Val Thr Leu Gly Cys Leu Val Lys Gly
    130                 135                 140

Tyr Phe Pro Glu Pro Val Thr Val Thr Trp Asn Ser Gly Ser Leu Ser
145                 150                 155                 160

Ser Gly Val His Thr Phe Pro Ala Val Leu Gln Ser Asp Leu Tyr Thr
                165                 170                 175

Leu Ser Ser Ser Val Thr Val Pro Ser Ser Thr Trp Pro Ser Glu Thr
            180                 185                 190

Val Thr Cys Asn Val Ala His Pro Ala Ser Ser Thr Lys Val Asp Lys
        195                 200                 205

Lys Ile Val Pro Arg Asp Cys Gly Cys Lys Pro Cys Ile Cys Thr Val
    210                 215                 220

Pro Glu Val Ser Ser Val Phe Ile Phe Pro Pro Lys Pro Lys Asp Val
225                 230                 235                 240

Leu Thr Ile Thr Leu Thr Pro Lys Val Thr Cys Val Val Val Asp Ile
                245                 250                 255

Ser Lys Asp Asp Pro Glu Val Gln Phe Ser Trp Phe Val Asp Asp Val
            260                 265                 270
```

```
Glu Val His Thr Ala Gln Thr Gln Pro Arg Glu Gln Phe Asn Ser
            275                 280                 285
Thr Phe Arg Ser Val Ser Glu Leu Pro Ile Met His Gln Asp Trp Leu
        290                 295                 300
Asn Gly Lys Glu Phe Lys Cys Arg Val Asn Ser Ala Ala Phe Pro Ala
305                 310                 315                 320
Pro Ile Glu Lys Thr Ile Ser Lys Thr Lys Gly Arg Pro Lys Ala Pro
                325                 330                 335
Gln Val Tyr Thr Ile Pro Pro Pro Lys Glu Gln Met Ala Lys Asp Lys
            340                 345                 350
Val Ser Leu Thr Cys Met Ile Thr Asp Phe Phe Pro Glu Asp Ile Thr
        355                 360                 365
Val Glu Trp Gln Trp Asn Gly Gln Pro Ala Glu Asn Tyr Lys Asn Thr
    370                 375                 380
Gln Pro Ile Met Asp Thr Asp Gly Ser Tyr Phe Val Tyr Ser Lys Leu
385                 390                 395                 400
Asn Val Gln Lys Ser Asn Trp Glu Ala Gly Asn Thr Phe Thr Cys Ser
                405                 410                 415
Val Leu His Glu Gly Leu His Asn His His Thr Glu Lys Ser Leu Ser
            420                 425                 430
His Ser Pro Gly Lys
            435

<210> SEQ ID NO 140
<211> LENGTH: 708
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Full Length Light Chain (3D11 Kappa Variable
      Region and Constant Region)

<400> SEQUENCE: 140
atggattttc aagtgcagat tttcagcttc ctgctaatca gtgcctcagt caaaatatcc        60
agaggacaaa ttgttctcac ccagtctcca gcaatcatgt ctgcatatcc aggggagaag       120
gtcaccatga cctgcagtgc cagctcaagt gtaagttaca tgcactggta ccagcagaag       180
tcaggcacct cccccaaaag atggatttat gacacatcca aactggcttc tggagtccct       240
gctcgcttca gtggcagtgg gtctgggacc tcttactccc tcacaatcag tagtatggag       300
gctgaagatg ctgccactta ttactgccag cagtggagta gtaacccact cacgttcggt       360
gctgggacca gctggagct gaaacgggct gatgctgcac caactgtatc catcttccca       420
ccatccagtg agcagttaac atctggaggt gcctcagtcg tgtgcttctt gaacaacttc       480
taccccaaag acatcaatgt caagtggaag attgatggca gtgaacgaca aaatggcgtc       540
ctgaacagtt ggactgatca ggacagcaaa gacagcacct acagcatgag cagcaccctc       600
acgttgacca aggacgagta tgaacgacat aacagctata cctgtgaggc cactcacaag       660
acatcaactt cacccattgt caagagcttc aacaggaatg agtgttag                    708

<210> SEQ ID NO 141
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide
```

-continued

```
<220> FEATURE:
<223> OTHER INFORMATION: Full Length Light Chain (3D11 Kappa Variable
      Region and Constant Region)

<400> SEQUENCE: 141

Gln Ile Val Leu Thr Gln Ser Pro Ala Ile Met Ser Ala Tyr Pro Gly
1               5                   10                  15

Glu Lys Val Thr Met Thr Cys Ser Ala Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys Arg Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210

<210> SEQ ID NO 142
<211> LENGTH: 1398
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Full Length Heavy Chain (1D3 Variable Region
      and IgG1 Constant Region)

<400> SEQUENCE: 142
atgaactttg ggctcagatt gattttcctt gtccttgttt taaaaggtgt gaagtgtgaa      60
gtgcagctgg tggagtctgg gggaggctta gtgcagcctg agggtccct gaaactctcc      120 tgtgcagcct ctggattcac tttcagtgac tattacatgt cttgggttcg ccagactcca     180
gagaagaggc tggagtgggt cgcatacatt agtagtggtg gtggtagcac ctactatcca     240
gacagtgtga aggggtcgatt caccatctcc cgagacaatg ccaagaacac cctgtacctg     300
caaatgagca gtctgaagtc tgaggacaca gccatatatt actgtgtgag acaaggggat     360
ggttattacg gggactatgc tatggactac tggggtcaag gaacctcagt catcgtctcc     420
tcagccaaaa cgacaccccc atctgtctat ccactggccc ctggatctgc tgcccaaact     480
aactccatgg tgaccctggg atgcctggtc aagggctatt ccctgagcc agtgacagtg     540
```

```
acctggaact ctggatccct gtccagcggt gtgcacacct tcccagctgt cctgcagtct    600
gacctctaca ctctgagcag ctcagtgact gtccccccca gcacctggcc cagcgagacc    660
gtcacctgca acgttgccca cccggccagc agcaccaagg tggacaagaa aattgtgccc    720
agggattgtg gttgtaagcc ttgcatatgt acagtcccag aagtatcatc tgtcttcatc    780
ttccccccaa agcccaagga tgtgctcacc attactctga ctcctaaggt cacgtgtgtt    840
gtggtagaca tcagcaagga tgatcccgag gtccagttca gctggtttgt agatgatgtg    900
gaggtgcaca cagctcagac gcaaccccgg gaggagcagt tcaacagcac tttccgctca    960
gtcagtgaac ttcccatcat gcaccaggac tggctcaatg gcaaggagtt caaatgcagg   1020
gtcaacagtg cagctttccc tgcccccatc gagaaaacca tctccaaaac caaaggcaga   1080
ccgaaggctc cacaggtgta caccattcca cctcccaagg agcagatggc caaggataaa   1140
gtcagtctga cctgcatgat aacagacttc ttccctgaag acattactgt ggagtggcag   1200
tggaatgggc agccagcgga gaactacaag aacactcagc ccatcatgga cacagatggc   1260
tcttacttcg tctacagcaa gctcaatgtg cagaagagca ctgggaggc aggaaatact   1320
ttcacctgct ctgtgttaca tgagggcctg cacaaccacc atactgagaa gagcctctcc   1380
cactctcctg gtaaatga                                                  1398
```

<210> SEQ ID NO 143
<211> LENGTH: 446
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Full Length Heavy chain (1D3 Variable Region and IgG1 Constant Region)

<400> SEQUENCE: 143

```
Glu Val Gln Leu Val Glu Ser Gly Gly Gly Leu Val Gln Pro Gly Gly
 1               5                  10                  15

Ser Leu Lys Leu Ser Cys Ala Ala Ser Gly Phe Thr Phe Ser Asp Tyr
            20                  25                  30

Tyr Met Ser Trp Val Arg Gln Thr Pro Glu Lys Arg Leu Glu Trp Val
        35                  40                  45

Ala Tyr Ile Ser Ser Gly Gly Gly Ser Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Ile Tyr Tyr Cys
                85                  90                  95

Val Arg Gln Gly Asp Gly Tyr Tyr Gly Asp Tyr Ala Met Asp Tyr Trp
            100                 105                 110

Gly Gln Gly Thr Ser Val Ile Val Ser Ser Ala Lys Thr Thr Pro Pro
        115                 120                 125

Ser Val Tyr Pro Leu Ala Pro Gly Ser Ala Ala Gln Thr Asn Ser Met
    130                 135                 140

Val Thr Leu Gly Cys Leu Val Lys Gly Tyr Phe Pro Glu Pro Val Thr
145                 150                 155                 160

Val Thr Trp Asn Ser Gly Ser Leu Ser Ser Gly Val His Thr Phe Pro
                165                 170                 175

Ala Val Leu Gln Ser Asp Leu Tyr Thr Leu Ser Ser Ser Val Thr Val
            180                 185                 190
```

```
Pro Ser Ser Thr Trp Pro Ser Glu Thr Val Thr Cys Asn Val Ala His
        195                 200                 205

Pro Ala Ser Ser Thr Lys Val Asp Lys Lys Ile Val Pro Arg Asp Cys
        210                 215                 220

Gly Cys Lys Pro Cys Ile Cys Thr Val Pro Glu Val Ser Ser Val Phe
225                 230                 235                 240

Ile Phe Pro Pro Lys Pro Lys Asp Val Leu Thr Ile Thr Leu Thr Pro
                245                 250                 255

Lys Val Thr Cys Val Val Val Asp Ile Ser Lys Asp Asp Pro Glu Val
                260                 265                 270

Gln Phe Ser Trp Phe Val Asp Asp Val Glu Val His Thr Ala Gln Thr
            275                 280                 285

Gln Pro Arg Glu Glu Gln Phe Asn Ser Thr Phe Arg Ser Val Ser Glu
        290                 295                 300

Leu Pro Ile Met His Gln Asp Trp Leu Asn Gly Lys Glu Phe Lys Cys
305                 310                 315                 320

Arg Val Asn Ser Ala Ala Phe Pro Ala Pro Ile Glu Lys Thr Ile Ser
                325                 330                 335

Lys Thr Lys Gly Arg Pro Lys Ala Pro Gln Val Tyr Thr Ile Pro Pro
                340                 345                 350

Pro Lys Glu Gln Met Ala Lys Asp Lys Val Ser Leu Thr Cys Met Ile
            355                 360                 365

Thr Asp Phe Phe Pro Glu Asp Ile Thr Val Glu Trp Gln Trp Asn Gly
        370                 375                 380

Gln Pro Ala Glu Asn Tyr Lys Asn Thr Gln Pro Ile Met Asp Thr Asp
385                 390                 395                 400

Gly Ser Tyr Phe Val Tyr Ser Lys Leu Asn Val Gln Lys Ser Asn Trp
                405                 410                 415

Glu Ala Gly Asn Thr Phe Thr Cys Ser Val Leu His Glu Gly Leu His
                420                 425                 430

Asn His His Thr Glu Lys Ser Leu Ser His Ser Pro Gly Lys
            435                 440                 445

<210> SEQ ID NO 144
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Full Length Light Chain (1D3 Kappa Variable
      Region and Constant Region)

<400> SEQUENCE: 144
atgagtgtgc ccactcaggt cctggggttg ctgctgctgt ggcttacaga tgtcagatgt      60
gacatccaga tgactcagtc tccagcctcc ctatctgtat ctgtgggaga aactgtcacc     120
atcacatgtc gaacaagtga aaatatttac agtaatttag cgtggtatca gcagaaacag     180
ggaaaatctc ctcagctcct aatctatgct gcaacaaact tagcagatgg tgtgccatca     240
aggttcagtg gcagtggatc aggcacacag ttttcccctca ggatcaacag cctgcagtct     300
gaagattttg gaggtatta ctgtcaacat ttttggggga ctccgtacac gttcggaggg     360
gggaccaaac tggaaataaa acgggctgat gctgcaccaa ctgtatccat cttcccacca     420
tccagtgagc agttaacatc tggaggtgcc tcagtcgtgt gcttcttgaa caacttctac     480
cccaaagaca tcaatgtcaa gtggaagatt gatggcagtg aacgacaaaa tggcgtcctg     540
```

```
aacagttgga ctgatcagga cagcaaagac agcacctaca gcatgagcag caccctcacg    600
ttgaccaagg acgagtatga acgacataac agctatacct gtgaggccac tcacaagaca    660
tcaacttcac ccattgtcaa gagcttcaac aggaatgagt gttag                    705
```

<210> SEQ ID NO 145  
<211> LENGTH: 214  
<212> TYPE: PRT  
<213> ORGANISM: Artificial Sequence  
<220> FEATURE:  
<223> OTHER INFORMATION: Description of Artificial Sequence: Synthetic polypeptide  
<220> FEATURE:  
<223> OTHER INFORMATION: Full Length Light Chain (1D3 Kappa Variable Region and Constant Region)

<400> SEQUENCE: 145

```
Asp Ile Gln Met Thr Gln Ser Pro Ala Ser Leu Ser Val Ser Val Gly
1               5                   10                  15

Glu Thr Val Thr Ile Thr Cys Arg Thr Ser Glu Asn Ile Tyr Ser Asn
            20                  25                  30

Leu Ala Trp Tyr Gln Gln Lys Gln Gly Lys Ser Pro Gln Leu Leu Ile
        35                  40                  45

Tyr Ala Ala Thr Asn Leu Ala Asp Gly Val Pro Ser Arg Phe Ser Gly
    50                  55                  60

Ser Gly Ser Gly Thr Gln Phe Ser Leu Arg Ile Asn Ser Leu Gln Ser
65                  70                  75                  80

Glu Asp Phe Gly Arg Tyr Tyr Cys Gln His Phe Trp Gly Thr Pro Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 146  
<211> LENGTH: 1398  
<212> TYPE: DNA  
<213> ORGANISM: Artificial Sequence  
<220> FEATURE:  
<223> OTHER INFORMATION: Description of Artificial Sequence: Synthetic polynucleotide  
<220> FEATURE:  
<223> OTHER INFORMATION: Full Length Heavy Chain (1F3 Variable Region and IgG1 Constant Region)

<400> SEQUENCE: 146

```
atgaactttg ggctcagatt gattttcctt gtccttgttt taaaaggtgt gaagtgtgag    60
gtgcagctgg tggagtctgg gggaggctta gtgcagtctg agggtccct  gaaactctcc    120
```

```
tgtgcggcct ctggattcac tttcagtaac tatttcatgt cttgggttcg ccagactcca    180
gagaagaggc tggagtgggt cgcatatatt agtagtggtg gtggtagcac ctactatcca    240
gacagtgtga agggtcgatt caccatctct agagacaatg ccaagaacac cctgtacctg    300
caaatgagca gtctgaagtc tgaggacaca gccatgtatt actgtgtaag acaagggggat   360 ggttactacg gggactatgc tatggactac tggggtcaag aacctcagt caccgtctcc     420 tcagccaaaa cgacaccccc atctgtctat ccactggccc ctggatctgc tgcccaaact    480
aactccatgg tgaccctggg atgcctggtc aagggctatt ccctgagcc agtgacagtg     540 acctggaact ctggatccct gtccagcggt gtgcacacct cccagctgt cctgcagtct    600 gacctctaca ctctgagcag ctcagtgact gtcccctcca gcacctggcc cagcgagacc    660
gtcacctgca cgttgccca cccggccagc agcaccaagg tggacaagaa aattgtgccc    720
agggattgtg gttgtaagcc ttgcatatgt acagtcccag aagtatcatc tgtcttcatc    780
ttccccccaa agcccaagga tgtgctcacc attactctga ctcctaaggt cacgtgtgtt    840
gtggtagaca tcagcaagga tgatcccgag gtccagttca gctggtttgt agatgatgtg    900
gaggtgcaca cagctcagac gcaaccccgg gaggagcagt tcaacagcac tttccgctca    960
gtcagtgaac ttcccatcat gcaccaggac tggctcaatg gcaaggagtt caaatgcagg   1020
gtcaacagtg cagcttttccc tgcccccatc gagaaaacca tctccaaaac caaaggcaga   1080
ccgaaggctc cacaggtgta caccattcca cctcccaagg agcagatggc caaggataaa   1140
gtcagtctga cctgcatgat aacagacttc ttccctgaag acattactgt ggagtggcag   1200
tggaatgggc agccagcgga gaactacaag aacactcagc ccatcatgga cacagatggc   1260
tcttacttcg tctacagcaa gctcaatgtg cagaagagca ctgggaggc aggaaatact   1320 ttcacctgct ctgtgttaca tgagggcctg cacaaccacc atactgagaa gagcctctcc   1380
cactctcctg gtaaatga                                                  1398
```

<210> SEQ ID NO 147
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Full Length Heavy Chain (1F3 Variable Region
      and IgG1 Constant Region)

<400> SEQUENCE: 147

```
Glu Val Gln Leu Val Glu Ser Gly Gly Gly Leu Val Gln Ser Gly Gly
1               5                   10                  15

Ser Leu Lys Leu Ser Cys Ala Ala Ser Gly Phe Thr Phe Ser Asn Tyr
            20                  25                  30

Phe Met Ser Trp Val Arg Gln Thr Pro Glu Lys Arg Leu Glu Trp Val
        35                  40                  45

Ala Tyr Ile Ser Ser Gly Gly Gly Ser Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Val Arg Gln Gly Asp Gly Tyr Tyr Gly Asp Tyr Ala Met Asp Tyr Trp
            100                 105                 110

Gly Gln Gly Thr Ser Val Thr Val Ser Ser Ala Lys Thr Thr Pro Pro
```

```
            115                 120                 125
Ser Val Tyr Pro Leu Ala Pro Gly Ser Ala Gln Thr Asn Ser Met
    130                 135                 140

Val Thr Leu Gly Cys Leu Val Lys Gly Tyr Phe Pro Glu Pro Val Thr
145                 150                 155                 160

Val Thr Trp Asn Ser Gly Ser Leu Ser Ser Gly Val His Thr Phe Pro
                165                 170                 175

Ala Val Leu Gln Ser Asp Leu Tyr Thr Leu Ser Ser Ser Val Thr Val
                180                 185                 190

Pro Ser Ser Thr Trp Pro Ser Glu Thr Val Thr Cys Asn Val Ala His
                195                 200                 205

Pro Ala Ser Ser Thr Lys Val Asp Lys Lys Ile Val Pro Arg Asp Cys
    210                 215                 220

Gly Cys Lys Pro Cys Ile Cys Thr Val Pro Glu Val Ser Ser Val Phe
225                 230                 235                 240

Ile Phe Pro Pro Lys Pro Lys Asp Val Leu Thr Ile Thr Leu Thr Pro
                245                 250                 255

Lys Val Thr Cys Val Val Val Asp Ile Ser Lys Asp Asp Pro Glu Val
                260                 265                 270

Gln Phe Ser Trp Phe Val Asp Asp Val Glu Val His Thr Ala Gln Thr
    275                 280                 285

Gln Pro Arg Glu Glu Gln Phe Asn Ser Thr Phe Arg Ser Val Ser Glu
    290                 295                 300

Leu Pro Ile Met His Gln Asp Trp Leu Asn Gly Lys Glu Phe Lys Cys
305                 310                 315                 320

Arg Val Asn Ser Ala Ala Phe Pro Ala Pro Ile Glu Lys Thr Ile Ser
                325                 330                 335

Lys Thr Lys Gly Arg Pro Lys Ala Pro Gln Val Tyr Thr Ile Pro Pro
                340                 345                 350

Pro Lys Glu Gln Met Ala Lys Asp Lys Val Ser Leu Thr Cys Met Ile
    355                 360                 365

Thr Asp Phe Phe Pro Glu Asp Ile Thr Val Glu Trp Gln Trp Asn Gly
    370                 375                 380

Gln Pro Ala Glu Asn Tyr Lys Asn Thr Gln Pro Ile Met Asp Thr Asp
385                 390                 395                 400

Gly Ser Tyr Phe Val Tyr Ser Lys Leu Asn Val Gln Lys Ser Asn Trp
                405                 410                 415

Glu Ala Gly Asn Thr Phe Thr Cys Ser Val Leu His Glu Gly Leu His
                420                 425                 430

Asn His His Thr Glu Lys Ser Leu Ser His Ser Pro Gly Lys
                435                 440                 445

<210> SEQ ID NO 148
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Full Length Light Chain (1F3 Kappa Variable
      Region and Constant Region)

<400> SEQUENCE: 148
atgagtgtgc ccactcaggt cctgggggttg ctgctgctgt ggcttacaga tgccagatgt      60
gacatccaga tgactcagtc tccagcctcc ctatctgtat ctgtgggaga aactgtcacc     120
```

-continued

```
atcacatgtc gagcaagtga gaatatttac agtaatttag catggtatca gcagaaacag      180
ggaaaatctc ctcagctcct ggtctatgat gcaacacact taccagatgg tgtgccatca      240
aggttcagtg gcagtggatc aggcacacag ttttcccctca agatcaacag cctgcagtct     300
gaagattttg ggagttatta ctgtcaacat tttggggta ctccgtacac gtttggaggg       360
gggaccagac tggaaattaa acgggctgat gctgcaccaa ctgtatccat cttcccacca      420
tccagtgagc agttaacatc tggaggtgcc tcagtcgtgt gcttcttgaa caacttctac      480
cccaaagaca tcaatgtcaa gtggaagatt gatggcagtg aacgacaaaa tggcgtcctg      540
aacagttgga ctgatcagga cagcaaagac agcacctaca gcatgagcag caccctcacg      600
ttgaccaagg acgagtatga acgacataac agctatacct gtgaggccac tcacaagaca      660
tcaacttcac ccattgtcaa gagcttcaac aggaatgagt gttag                      705
```

<210> SEQ ID NO 149
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Full Length Light Chain (1F3 Kappa Variable
      Region and Constant Region)

<400> SEQUENCE: 149

```
Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Asp Ala Thr His Leu Pro Asp Gly Val Pro Ser Arg Phe Ser Gly
    50                  55                  60

Ser Gly Ser Gly Thr Gln Phe Ser Leu Lys Ile Asn Ser Leu Gln Ser
65                  70                  75                  80

Glu Asp Phe Gly Ser Tyr Tyr Cys Gln His Phe Trp Gly Thr Pro Tyr
                85                  90                  95

Thr Phe Gly Gly Gly Thr Arg Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 150
<211> LENGTH: 1398
<212> TYPE: DNA

<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Full Length Heavy Chain (3A12 Variable Region and IgG1 Constant Region)

<400> SEQUENCE: 150

```
atgaactttg ggctcagatt gattttcctt gtccttgttt taaaaggtgt gaagtgtgaa      60
gtgcagctgg tggagtctgg gggaggctta gtgcagcctg agggtccct gaaaatctcc     120
tgtgcagcct ctggatttac tttcagtaac tatttcatgt cttgggttcg ccagactcca     180
gagaagaggc tggagtgggt cgcatacatt agtagtggtg gtggtagcac ctactatcca     240
gacagtgtga aggtcgatt caccatctcc agagacaatg ccaagaacac cctgtacctg     300
caaatgaaca gtctgaagtc tgaggacaca gccatgtatt actgtgtaag acaaggagat     360
ggttactatg gggactatgc tatggactac tggggtcaag gaacctcagt caccgtctcc     420
tcagccaaaa cgacaccccc atctgtctat ccactggccc ctggatctgc tgcccaaact     480
aactccatgg tgaccctggg atgcctggtc aagggctatt ccctgagcc agtgacagtg     540
acctggaact ctggatccct gtccagcggt gtgcacacct cccagctgt cctgcagtct     600
gacctctaca ctctgagcag ctcagtgact gtccctcca gcacctggcc cagcgagacc     660
gtcacctgca acgttgccca ccggccagc agcaccaagg tggacaagaa aattgtgccc     720
agggattgtg gttgtaagcc ttgcatatgt acagtcccag aagtatcatc tgtcttcatc     780
ttcccccca agcccaagga tgtgctcacc attactctga ctcctaaggt cacgtgtgtt     840
gtggtagaca tcagcaagga tgatcccgag gtccagttca gctggtttgt agatgatgtg     900
gaggtgcaca cagctcagac gcaaccccgg gaggagcagt tcaacagcac tttccgctca     960
gtcagtgaac ttcccatcat gcaccaggac tggctcaatg gcaaggagtt caaatgcagg    1020
gtcaacagtg cagctttccc tgcccccatc gagaaaacca tctccaaaac caaaggcaga    1080
ccgaaggctc cacaggtgta caccattcca cctcccaagg agcagatggc aaggataaa     1140
gtcagtctga cctgcatgat aacagacttc ttccctgaag acattactgt ggagtggcag    1200
tggaatgggc agccagcgga gaactacaag aacactcagc ccatcatgga cacagatggc    1260
tcttacttcg tctacagcaa gctcaatgtg cagaagagca ctgggaggc aggaaatact    1320
ttcacctgct ctgtgttaca tgagggcctg cacaaccacc atactgagaa gagcctctcc    1380
cactctcctg gtaaatga                                                 1398
```

<210> SEQ ID NO 151
<211> LENGTH: 446
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Full Length Heavy Chain (3A12 Variable Region and IgG1 Constant Region)

<400> SEQUENCE: 151

```
Glu Val Gln Leu Val Glu Ser Gly Gly Gly Leu Val Gln Pro Gly Gly
 1               5                  10                  15

Ser Leu Lys Ile Ser Cys Ala Ala Ser Gly Phe Thr Phe Ser Asn Tyr
            20                  25                  30

Phe Met Ser Trp Val Arg Gln Thr Pro Glu Lys Arg Leu Glu Trp Val
        35                  40                  45
```

Ala Tyr Ile Ser Ser Gly Gly Ser Thr Tyr Tyr Pro Asp Ser Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Ser Glu Asp Thr Ala Met Tyr Tyr Cys
                 85                  90                  95

Val Arg Gln Gly Asp Gly Tyr Tyr Gly Asp Tyr Ala Met Asp Tyr Trp
            100                 105                 110

Gly Gln Gly Thr Ser Val Thr Val Ser Ser Ala Lys Thr Thr Pro Pro
        115                 120                 125

Ser Val Tyr Pro Leu Ala Pro Gly Ser Ala Ala Gln Thr Asn Ser Met
130                 135                 140

Val Thr Leu Gly Cys Leu Val Lys Gly Tyr Phe Pro Glu Pro Val Thr
145                 150                 155                 160

Val Thr Trp Asn Ser Gly Ser Leu Ser Ser Gly Val His Thr Phe Pro
                165                 170                 175

Ala Val Leu Gln Ser Asp Leu Tyr Thr Leu Ser Ser Ser Val Thr Val
            180                 185                 190

Pro Ser Ser Thr Trp Pro Ser Glu Thr Val Thr Cys Asn Val Ala His
        195                 200                 205

Pro Ala Ser Ser Thr Lys Val Asp Lys Lys Ile Val Pro Arg Asp Cys
210                 215                 220

Gly Cys Lys Pro Cys Ile Cys Thr Val Pro Glu Val Ser Ser Val Phe
225                 230                 235                 240

Ile Phe Pro Pro Lys Pro Lys Asp Val Leu Thr Ile Thr Leu Thr Pro
                245                 250                 255

Lys Val Thr Cys Val Val Val Asp Ile Ser Lys Asp Asp Pro Glu Val
            260                 265                 270

Gln Phe Ser Trp Phe Val Asp Asp Val Glu Val His Thr Ala Gln Thr
        275                 280                 285

Gln Pro Arg Glu Glu Gln Phe Asn Ser Thr Phe Arg Ser Val Ser Glu
290                 295                 300

Leu Pro Ile Met His Gln Asp Trp Leu Asn Gly Lys Glu Phe Lys Cys
305                 310                 315                 320

Arg Val Asn Ser Ala Ala Phe Pro Ala Pro Ile Glu Lys Thr Ile Ser
                325                 330                 335

Lys Thr Lys Gly Arg Pro Lys Ala Pro Gln Val Tyr Thr Ile Pro Pro
            340                 345                 350

Pro Lys Glu Gln Met Ala Lys Asp Lys Val Ser Leu Thr Cys Met Ile
        355                 360                 365

Thr Asp Phe Phe Pro Glu Asp Ile Thr Val Glu Trp Gln Trp Asn Gly
370                 375                 380

Gln Pro Ala Glu Asn Tyr Lys Asn Thr Gln Pro Ile Met Asp Thr Asp
385                 390                 395                 400

Gly Ser Tyr Phe Val Tyr Ser Lys Leu Asn Val Gln Lys Ser Asn Trp
                405                 410                 415

Glu Ala Gly Asn Thr Phe Thr Cys Ser Val Leu His Glu Gly Leu His
            420                 425                 430

Asn His His Thr Glu Lys Ser Leu Ser His Ser Pro Gly Lys
        435                 440                 445

<210> SEQ ID NO 152
<211> LENGTH: 705
<212> TYPE: DNA

<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Full Length Light Chain (3A12 Kappa Variable
Region and Constant Region)

<400> SEQUENCE: 152

```
atgagtgtgc ccactcaggt cctggggttg ctgctgctgt ggcttacaga tgccagatgt    60
gacatccaga tgactcagtc gccagcctcc ctatctgtat ctgtgggaga aactgtcacc   120
atcacatgtc gagcaagtga gaatatttac attaatttag catggtatca gcagaaacag   180
ggaaaatctc ctcagctcct ggtccatgct gcaacaaagt tagcagatgg tgtgccatca   240
aggttcagtg gcagtggatc aggcacacag tattccctca agatcaacag cctgcagtct   300
gaagattttg ggagttatta ctgtcaacat ttttggggta ctccgtacac gttcggaggg   360
gggaccaaac tagaaataaa acgggctgat gctgcaccaa ctgtatccat cttcccacca   420
tccagtgagc agttaacatc tggaggtgcc tcagtcgtgt gcttcttgaa caacttctac   480
cccaaagaca tcaatgtcaa gtggaagatt gatggcagtg aacgacaaaa tggcgtcctg   540
aacagttgga ctgatcagga cagcaaagac agcacctaca gcatgagcag caccctcacg   600
ttgaccaagg acgagtatga acgacataac agctatacct gtgaggccac tcacaagaca   660
tcaacttcac ccattgtcaa gagcttcaac aggaatgagt gttag               705
```

<210> SEQ ID NO 153
<211> LENGTH: 214
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: Full Length Light Chain (3A12 Kappa Variable
Region and Constant Region)

<400> SEQUENCE: 153

```
Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ile Asn
            20                  25                  30

Leu Ala Trp Tyr Gln Gln Lys Gln Gly Lys Ser Pro Gln Leu Leu Val
        35                  40                  45

His Ala Ala Thr Lys Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175
```

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 154
<211> LENGTH: 1404
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Full Length Chimeric 2B8 Heavy Chain

<400> SEQUENCE: 154

```
atgggatgga gctatatcat cctcttttg gtagcaacag ctacagatgt ccactcccag      60
gtccaactgc agcagcctgg ggctgaactg gtgaagcctg ggacttcagt gaagctgtcc    120
tgcaaggctt ctggctacac cttcaccacc tactggatgc actgggtgaa tcagaggcct    180
ggacaaggcc ttgagtggat tggagagatt aatcctacca acggtcatac taactacaat    240
gagaagttca gagcaaggc cacactgact gtagacaaat cctccagcac agcctacatg    300
caactcagca gcctgacatc tgaggactct gcggtctatt actgtgcaag aaactatgtt    360
ggtagcatct ttgactactg gggccaaggc accactctca ccgtctcctc agcctccacc    420
aagggcccat cggtcttccc cctggcaccc tcctccaaga gcacctctgg gggcacagcg    480
gccctgggct gcctggtcaa ggactacttc cccgaaccgg tgacggtgtc gtggaactca    540
ggcgccctga ccagcggcgt gcacaccttc ccggctgtcc tacagtcctc aggactctac    600
tccctcagca gcgtggtgac cgtgccctcc agcagcttgg gcacccagac ctacatctgc    660
aacgtgaatc acaagcccag caacaccaag gtggacaaga agttgagcc caaatcttgt    720 gacaaaactc acacatgccc accgtgccca gcacctgaac tcctgggggg accgtcagtc    780
ttcctcttcc cccaaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccgcgggagg agcagtacaa cagcacgtac    960
cgtgtggtca gcgtcctcac cgtcctgcac caggactggc tgaatggcaa ggagtacaag   1020
tgcaaggtct ccaacaaagc cctcccagcc cccatcgaga aaaccatctc caaagccaaa   1080
gggcagcccc gagaaccaca ggtgtacacc ctgcccccat cccgggatga gctgaccaag   1140
aaccaggtca gcctgacctg cctggtcaaa ggcttctatc ccagcgacat cgccgtggag   1200
tgggagagca atgggcagcc ggagaacaac tacaagacca cgcctcccgt gctggactcc   1260
gacggctcct tcttcctcta cagcaagctc accgtggaca gagcaggtg gcagcagggg   1320 aacgtcttct catgctccgt gatgcatgag gctctgcaca accactacac gcagaagagc   1380 ctctcccctgt ctccgggtaa atga                                          1404
```

<210> SEQ ID NO 155
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:

<223> OTHER INFORMATION: Full Length Chimeric 2B8 Heavy Chain

<400> SEQUENCE: 155

```
Gln Val Gln Leu Gln Gln Pro Gly Ala Glu Leu Val Lys Pro Gly Thr
 1               5                  10                  15
Ser Val Lys Leu Ser Cys Lys Ala Ser Gly Tyr Thr Phe Thr Thr Tyr
            20                  25                  30
Trp Met His Trp Val Asn Gln Arg Pro Gly Gln Gly Leu Glu Trp Ile
        35                  40                  45
Gly Glu Ile Asn Pro Thr Asn Gly His Thr Asn Tyr Asn Glu Lys Phe
    50                  55                  60
Lys Ser Lys Ala Thr Leu Thr Val Asp Lys Ser Ser Ser Thr Ala Tyr
65                  70                  75                  80
Met Gln Leu Ser Ser Leu Thr Ser Glu Asp Ser Ala Val Tyr Tyr Cys
                85                  90                  95
Ala Arg Asn Tyr Val Gly Ser Ile Phe Asp Tyr Trp Gly Gln Gly Thr
            100                 105                 110
Thr Leu Thr Val Ser Ser Ala Ser Thr Lys Gly Pro Ser Val Phe Pro
        115                 120                 125
Leu Ala Pro Ser Ser Lys Ser Thr Ser Gly Gly Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Lys Lys Val Glu Pro Lys Ser Cys Asp Lys Thr
    210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Asp Glu Leu Thr Lys Asn Gln Val Ser Leu Thr Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Val Leu Asp
385                 390                 395                 400
Ser Asp Gly Ser Phe Phe Leu Tyr Ser Lys Leu Thr Val Asp Lys Ser
```

```
                    405                 410                 415
Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 156
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Full Length Chimeric 2B8 Light Chain

<400> SEQUENCE: 156
atggaatcac agactctggt cttcatatcc atactgctct ggttatatgg tgctgatggg      60
aacattgtaa tgacccaatc tcccaaatcc atgtccatgt cagtaggaga gagggtcacc     120
ttgagctgca aggccagtga gaatgtggtt tcttatgtat cctggtatca acagaaacca     180
gcgcagtctc ctaaactgct gatatacggg gcatccaacc ggaacactgg ggtcccgat      240 cgcttcacag gcagtggatc tgcaacagat tcactctga ccatcagcag tgtgcgggct      300
gaagaccttg cagattatca ctgtgggcag agttacaact atccgtacac gttcggaggg     360
gggaccaggc tggaaataaa acgaactgtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgccc tccaatcggg taactcccag     540
gagagtgtca cagagcagga cagcaaggac agcacctaca gcctcagcag cacccctgacg    600 ctgagcaaag cagactacga gaaacacaaa gtctacgcct gcgaagtcac ccatcagggc     660
ctgagctcgc ccgtcacaaa gagcttcaac aggggagagt gttga                    705

<210> SEQ ID NO 157
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Full Length Chimeric 2B8 Light Chain

<400> SEQUENCE: 157

Asn Ile Val Met Thr Gln Ser Pro Lys Ser Met Ser Met Ser Val Gly
1               5                   10                  15

Glu Arg Val Thr Leu Ser Cys Lys Ala Ser Glu Asn Val Val Ser Tyr
            20                  25                  30

Val Ser Trp Tyr Gln Gln Lys Pro Ala Gln Ser Pro Lys Leu Leu Ile
        35                  40                  45

Tyr Gly Ala Ser Asn Arg Asn Thr Gly Val Pro Asp Arg Phe Thr Gly
    50                  55                  60

Ser Gly Ser Ala Thr Asp Phe Thr Leu Thr Ile Ser Ser Val Arg Ala
65                  70                  75                  80

Glu Asp Leu Ala Asp Tyr His Cys Gly Gln Ser Tyr Asn Tyr Pro Tyr
                85                  90                  95

Thr Phe Gly Gly Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
```

```
                    115                 120                 125
Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 158
<211> LENGTH: 412
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Synthetic Humanized Hu2B8 Hv1-f.1 Heavy Chain
      Variable Region

<400> SEQUENCE: 158
atggactgca cctggaggat cctcctcttg gtggcagcag ctacaggcac ccacgccgag      60
gtccagctgg tacagtctgg ggctgaggtg aagaagcctg ggctacagt gaaaatctcc     120 tgcaaggttt ctggatacac cttcaccacc tactggatgc actgggtgca acaggcccct    180
ggaaaagggc ttgagtggat gggagagatt aatcctacca acggtcatac taactacaat    240
gagaagttcc agggcagagt caccataacc gcggacacgt ctacagacac agcctacatg    300
gagctgagca gcctgagatc tgaggacacg gccgtgtatt actgtgcaac aaactatgtt    360
ggtagcatct ttgactactg gggccaagga accctggtca ccgtctcctc ag            412

<210> SEQ ID NO 159
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Synthetic Humanized Hu2B8 Hv1-f.1 Heavy Chain
      Variable Region

<400> SEQUENCE: 159

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Thr Tyr
            20                  25                  30

Trp Met His Trp Val Gln Gln Ala Pro Gly Lys Gly Leu Glu Trp Met
        35                  40                  45

Gly Glu Ile Asn Pro Thr Asn Gly His Thr Asn Tyr Asn Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95
```

Ala Thr Asn Tyr Val Gly Ser Ile Phe Asp Tyr Trp Gly Gln Gly Thr
            100                 105                 110

Leu Val Thr Val Ser Ser
        115

<210> SEQ ID NO 160
<211> LENGTH: 992
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Synthetic Human IgG1 Heavy Chain Constant
      Region

<400> SEQUENCE: 160
cctccaccaa gggcccatcg gtcttccccc tggcaccctc ctccaagagc acctctgggg     60
gcacagcggc cctgggctgc ctggtcaagg actacttccc cgaaccggtg acggtgtcgt    120
ggaactcagg cgccctgacc agcggcgtgc acaccttccc ggctgtccta cagtcctcag    180
gactctactc cctcagcagc gtggtgaccg tgccctccag cagcttgggc acccagacct    240
acatctgcaa cgtgaatcac aagcccagca acaccaaggt ggacaagaaa gttgagccca    300
aatcttgtga caaaactcac acatgcccac cgtgcccagc acctgaactc ctggggggac    360
cgtcagtctt cctcttcccc ccaaaaccca aggacaccct catgatctcc cggacccctg    420
aggtcacatg cgtggtggtg gacgtgagcc acgaagaccc tgaggtcaag ttcaactggt    480
acgtggacgg cgtggaggtg cataatgcca agacaaagcc gcgggaggag cagtacaaca    540
gcacgtaccg tgtggtcagc gtcctcaccg tcctgcacca ggactggctg aatggcaagg    600
agtacaagtg caaggtctcc aacaaagccc tcccagcccc catcgagaaa accatctcca    660
aagccaaagg gcagccccga gaaccacagg tgtacaccct gcccccatcc cgggatgagc    720
tgaccaagaa ccaggtcagc ctgacctgcc tggtcaaagg cttctatccc agcgacatcg    780
ccgtggagtg ggagagcaat gggcagccgg agaacaacta caagaccacg cctcccgtgc    840
tggactccga cggctccttc ttcctctaca gcaagctcac cgtggacaag agcaggtggc    900
agcaggggaa cgtcttctca tgctccgtga tgcatgaggc tctgcacaac cactacacgc    960
agaagagcct ctccctgtct ccgggtaaat ga                                  992

<210> SEQ ID NO 161
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Synthetic Human IgG1 Heavy Chain Constant
      Region

<400> SEQUENCE: 161

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

```
Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 162
<211> LENGTH: 1404
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Full Length Humanized Hu2B8 Heavy Chain
      (Hv1f.1 Variable Region)

<400> SEQUENCE: 162
atggactgca cctggaggat cctcctcttg gtggcagcag ctacaggcac ccacgccgag      60
gtccagctgg tacagtctgg ggctgaggtg aagaagcctg ggctacagt gaaaatctcc     120 tgcaaggttt ctggatacac cttcaccacc tactggatgc actgggtgca acaggcccct    180
ggaaaagggc ttgagtggat gggagagatt aatcctacca acgtcatac taactacaat    240 gagaagttcc aggcagagt caccataacc gcggacacgt ctacagacac agcctacatg    300
gagctgagca gcctgagatc tgaggacacg gccgtgtatt actgtgcaac aaactatgtt    360
ggtagcatct ttgactactg gggccaagga accctggtca ccgtctcctc agcctccacc    420
aagggcccat cggtcttccc cctggcaccc tcctccaaga gcacctctgg gggcacagcg    480
```

```
gccctgggct gcctggtcaa ggactacttc cccgaaccgg tgacggtgtc gtggaactca    540
ggcgccctga ccagcggcgt gcacaccttc ccggctgtcc tacagtcctc aggactctac    600
tcccctcagca gcgtggtgac cgtgccctcc agcagcttgg gcacccagac ctacatctgc    660
aacgtgaatc acaagcccag caacaccaag gtggacaaga agttgagcc caaatcttgt      720
gacaaaactc acacatgccc accgtgccca gcacctgaac tcctggggg accgtcagtc       780
ttcctcttcc ccccaaaacc caaggacacc ctcatgatct cccggacccc tgaggtcaca      840
tgcgtggtgg tggacgtgag ccacgaagac cctgaggtca agttcaactg gtacgtggac      900
ggcgtggagg tgcataatgc caagacaaag ccgcgggagg agcagtacaa cagcacgtac      960
cgtgtggtca gcgtcctcac cgtcctgcac caggactggc tgaatggcaa ggagtacaag     1020
tgcaaggtct ccaacaaagc cctcccagcc cccatcgaga aaaccatctc caaagccaaa    1080
gggcagcccc gagaaccaca ggtgtacacc ctgcccccat cccgggatga gctgaccaag    1140
aaccaggtca gcctgacctg cctggtcaaa ggcttctatc ccagcgacat cgccgtggag    1200
tgggagagca tgggcagcc ggagaacaac tacaagacca cgcctcccgt gctggactcc    1260
gacggctcct tcttcctcta cagcaagctc accgtggaca gagcaggtg gcagcagggg    1320
aacgtcttct catgctccgt gatgcatgag gctctgcaca accactacac gcagaagagc    1380
ctctccctgt ctccgggtaa atga                                            1404
```

<210> SEQ ID NO 163  
<211> LENGTH: 448  
<212> TYPE: PRT  
<213> ORGANISM: Artificial Sequence  
<220> FEATURE:  
<223> OTHER INFORMATION: Description of Artificial Sequence: Synthetic polypeptide  
<220> FEATURE:  
<223> OTHER INFORMATION: Full Length Humanized Hu2B8 Heavy Chain (Hv1f.1 Variable Region)

<400> SEQUENCE: 163

```
Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Thr Tyr
                20                  25                  30

Trp Met His Trp Val Gln Gln Ala Pro Gly Lys Gly Leu Glu Trp Met
            35                  40                  45

Gly Glu Ile Asn Pro Thr Asn Gly His Thr Asn Tyr Asn Glu Lys Phe
        50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asn Tyr Val Gly Ser Ile Phe Asp Tyr Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175
```

```
Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 164
<211> LENGTH: 412
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Humanized Hu2B8 Hv5a.1 Heavy Chain Variable
      Region

<400> SEQUENCE: 164
atggggtcaa ccgccatcct cgccctcctc ctggctgttc tccaaggagt ctgtgccgaa     60
gtgcagctgg tgcagtctgg agcagaggtg aaaaagcccg gggagtctct gaggatctcc    120
tgtaagggtt ctggatacag ctttaccacc tactggatgc actgggtgcg ccagatgccc    180
gggaaaggcc tggagtggat gggggagatt aatcctacca acgtcatac taactacaat    240 ccgtccttcc aaggccacgt caccatctca gctgacaagt ccatcagcac tgcctacctg    300
cagtggagca gcctgaaggc ctcggacacc gccatgtatt actgtgcgag aaactatgtt    360
ggtagcatct ttgactactg gggccaagga accctggtca ccgtctcctc ag            412
```

<210> SEQ ID NO 165
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Humanized Hu2B8 Hv5a.1 Heavy Chain Variable
      Region

<400> SEQUENCE: 165

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Thr Tyr
            20                  25                  30

Trp Met His Trp Val Arg Gln Met Pro Gly Lys Gly Leu Glu Trp Met
        35                  40                  45

Gly Glu Ile Asn Pro Thr Asn Gly His Thr Asn Tyr Asn Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asn Tyr Val Gly Ser Ile Phe Asp Tyr Trp Gly Gln Gly Thr
            100                 105                 110

Leu Val Thr Val Ser Ser
        115

<210> SEQ ID NO 166
<211> LENGTH: 1404
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Full length Humanized Hu2B8 Heavy Chain
      (Hv5a.1 Variable Region)

<400> SEQUENCE: 166
atggggtcaa ccgccatcct cgccctcctc ctggctgttc tccaaggagt ctgtgccgaa      60
gtgcagctgg tgcagtctgg agcagaggtg aaaaagcccg ggagtctct gaggatctcc     120 tgtaagggtt ctggatacag ctttaccacc tactggatgc actgggtgcg ccagatgccc     180
gggaaaggcc tggagtggat gggggagatt aatcctacca acggtcatac taactacaat     240
ccgtccttcc aaggccacgt caccatctca gctgacaagt ccatcagcac tgcctacctg     300
cagtggagca gcctgaaggc ctcggacacc gccatgtatt actgtgcgag aaactatgtt     360
ggtagcatct ttgactactg gggccaagga accctggtca ccgtctcctc agcctccacc     420
aagggcccat cggtcttccc cctggcaccc tcctccaaga gcacctctgg gggcacagcg     480
gccctgggct gcctggtcaa ggactacttc cccgaaccgg tgacggtgtc gtggaactca     540
ggcgccctga ccagcggcgt gcacaccttc ccggctgtcc tacagtcctc aggactctac     600
tccctcagca gcgtggtgac cgtgccctcc agcagcttgg gcacccagac ctacatctgc     660
aacgtgaatc acaagcccag caacaccaag gtggacaaga agttgagcc caaatcttgt     720 gacaaaactc acacatgccc accgtgccca gcacctgaac tcctgggggg accgtcagtc     780
ttcctcttcc cccaaaaacc caaggacacc ctcatgatct cccggacccc tgaggtcaca     840
tgcgtggtgg tggacgtgag ccacgaagac cctgaggtca agttcaactg gtacgtggac     900

```
ggcgtggagg tgcataatgc aagacaaag ccgcgggagg agcagtacaa cagcacgtac    960
cgtgtggtca gcgtcctcac cgtcctgcac caggactggc tgaatggcaa ggagtacaag   1020
tgcaaggtct ccaacaaagc cctcccagcc cccatcgaga aaaccatctc caaagccaaa   1080
gggcagcccc gagaaccaca ggtgtacacc ctgcccccat cccgggatga gctgaccaag   1140
aaccaggtca gcctgacctg cctggtcaaa ggcttctatc ccagcgacat cgccgtggag   1200
tgggagagca atgggcagcc ggagaacaac tacaagacca cgcctcccgt gctggactcc   1260
gacggctcct tcttcctcta cagcaagctc accgtggaca agagcaggtg gcagcagggg   1320
aacgtcttct catgctccgt gatgcatgag gctctgcaca accactacac gcagaagagc   1380
ctctccctgt ctccgggtaa atga                                          1404
```

<210> SEQ ID NO 167
<211> LENGTH: 448
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Full length Humanized Hu2B8 Heavy Chain (Hv5a.1 Variable Region)

<400> SEQUENCE: 167

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Thr Tyr
            20                  25                  30

Trp Met His Trp Val Arg Gln Met Pro Gly Lys Gly Leu Glu Trp Met
        35                  40                  45

Gly Glu Ile Asn Pro Thr Asn Gly His Thr Asn Tyr Asn Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asn Tyr Val Gly Ser Ile Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255
```

-continued

```
Thr Pro Glu Val Thr Cys Val Val Asp Val Ser His Glu Asp Pro
        260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 168
<211> LENGTH: 412
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Humanized Hu2B8 Hv5-51.1 Heavy Chain Variable
      Region

<400> SEQUENCE: 168

```
atggggtcaa ccgccatcct cgccctcctc ctggctgttc tccaaggagt ctgtgccgaa    60
gtgcagctgg tgcagtctgg agcagaggtg aaaaagcccg gggagtctct gaagatctcc   120
tgtaagggtt ctggatacag ctttaccacc tactggatgc actgggtgcg ccagatgccc   180
gggaaaggcc tggagtggat gggggagatt aatcctacca acggtcatac taactacaat   240
ccgtccttcc aaggccaggt caccatctca gctgacaagt ccatcagcac tgcctacctg   300
cagtggagca gcctgaaggc ctcggacacc gccatgtatt actgtgcgag aaactatgtt   360
ggtagcatct ttgactactg gggccaagga accctggtca ccgtctcctc ag           412
```

<210> SEQ ID NO 169
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Humanized Hu2B8 Hv5-51.1 Heavy Chain Variable
      Sequence

<400> SEQUENCE: 169

```
Glu Val Gln Leu Val Gln Ser Gly Ala Glu Val Lys Lys Pro Gly Glu
```

```
                1               5                    10                  15
         Ser Leu Lys Ile Ser Cys Lys Gly Ser Gly Tyr Ser Phe Thr Thr Tyr
                         20                  25                  30

Trp Met His Trp Val Arg Gln Met Pro Gly Lys Gly Leu Glu Trp Met
                         35                  40                  45

Gly Glu Ile Asn Pro Thr Asn Gly His Thr Asn Tyr Asn Pro Ser Phe
                 50                  55                  60

Gln Gly Gln Val Thr Ile Ser Ala Asp Lys Ser Ile Ser Thr Ala Tyr
         65                  70                  75                  80

Leu Gln Trp Ser Ser Leu Lys Ala Ser Asp Thr Ala Met Tyr Tyr Cys
                         85                  90                  95

Ala Arg Asn Tyr Val Gly Ser Ile Phe Asp Tyr Trp Gly Gln Gly Thr
                         100                 105                 110

Leu Val Thr Val Ser Ser
                 115
```

<210> SEQ ID NO 170
<211> LENGTH: 1404
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Full Length Humanized Hu2B8 Heavy Chain (Hv5-51.1 Variable Region)

<400> SEQUENCE: 170

```
atgggGtcaa ccgccatcct cgccctcctc ctggctgttc tccaaggagt ctgtgccgaa      60
gtgcagctgg tgcagtctgg agcagaggtg aaaaagcccg ggagtctct gaagatctcc     120
tgtaagggtt ctggatacag ctttaccacc tactggatgc actgggtgcg ccagatgccc     180
gggaaaggcc tggagtggat gggggagatt aatcctacca acggtcatac taactacaat     240
ccgtccttcc aaggccaggt caccatctca gctgacaagt ccatcagcac tgcctacctg     300
cagtggagca gcctgaaggc ctcggacacc gccatgtatt actgtgcgag aaactatgtt     360
ggtagcatct ttgactactg gggccaagga accctggtca ccgtctcctc agcctccacc     420
aagggcccat cggtcttccc cctggcaccc tcctccaaga gcacctctgg gggcacagcg     480
gccctgggct gcctggtcaa ggactacttc cccgaaccgg tgacggtgtc gtggaactca     540
ggcgccctga ccagcggcgt gcacaccttc ccggctgtcc tacagtcctc aggactctac     600
tccctcagca gcgtggtgac cgtgccctcc agcagcttgg gcacccagac ctacatctgc     660
aacgtgaatc acaagcccag caacaccaag gtggacaaga agttgagcc caaatcttgt     720
gacaaaactc acacatgccc accgtgccca gcacctgaac tcctgggggg accgtcagtc     780
ttcctcttcc ccccaaaacc caaggacacc ctcatgatct cccggacccc tgaggtcaca     840
tgcgtggtgg tggacgtgag ccacgaagac cctgaggtca agttcaactg gtacgtggac     900
ggcgtggagg tgcataatgc caagacaaag ccgcggagg agcagtacaa cagcacgtac     960
cgtgtggtca gcgtcctcac cgtcctgcac caggactggc tgaatggcaa ggagtacaag    1020
tgcaaggtct ccaacaaagc cctcccagcc cccatcgaga aaaccatctc caaagccaaa    1080
gggcagcccc gagaaccaca ggtgtacacc ctgcccccat cccgggatga gctgaccaag    1140
aaccaggtca gcctgacctg cctggtcaaa ggcttctatc ccagcgacat cgccgtggag    1200
tgggagagca atgggcagcc ggagaacaac tacaagacca cgcctcccgt gctggactcc    1260
gacggctcct tcttcctcta cagcaagctc accgtggaca agagcaggtg gcagcagggg    1320
```

-continued aacgtcttct catgctccgt gatgcatgag gctctgcaca accactacac gcagaagagc    1380
ctctccctgt ctccgggtaa atga                                           1404

<210> SEQ ID NO 171
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Full Length Humanized Hu2B8 Heavy Chain
      (Hv5-51.1 Variable Region)

<400> SEQUENCE: 171

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Thr Tyr
            20                  25                  30

Trp Met His Trp Val Arg Gln Met Pro Gly Lys Gly Leu Glu Trp Met
        35                  40                  45

Gly Glu Ile Asn Pro Thr Asn Gly His Thr Asn Tyr Asn Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asn Tyr Val Gly Ser Ile Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
```

```
                 325                 330                 335
Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 172
<211> LENGTH: 388
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Humanized Hu2B8 Kv1-39.1 Kappa Chain Variable
      Region

<400> SEQUENCE: 172
atggacatga gggtccccgc tcagctcctg gggctcctgc tactctggct ccgaggtgcc      60
agatgtgaca tccagatgac ccagtctcca tcctccctgt ctgcatctgt aggagacaga     120
gtcaccatca cttgcaaggc cagtgagaat gtggtttctt atgtatcctg gtatcagcag     180
aaaccaggga aagcccctaa gctcctgatc tatggggcat ccaaccggaa cactggggtc     240
ccatcaaggt tcagtggcag tggatctggg acagatttca ctctcaccat cagcagtctg     300
caacctgaag attttgcaac ttactactgt gggcagagtt acaactatcc gtacacgttt     360
ggccagggga ccaagctgga gatcaaac                                        388

<210> SEQ ID NO 173
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Humanized Hu2B8 Kv1-39.1 Kappa Chain Variable
      Region

<400> SEQUENCE: 173

Asp Ile Gln Met Thr Gln Ser Pro Ser Ser Leu Ser Ala Ser Val Gly
1               5                   10                  15

Asp Arg Val Thr Ile Thr Cys Lys Ala Ser Glu Asn Val Val Ser Tyr
            20                  25                  30

Val Ser Trp Tyr Gln Gln Lys Pro Gly Lys Ala Pro Lys Leu Leu Ile
        35                  40                  45

Tyr Gly Ala Ser Asn Arg Asn Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
        Glu Asp Phe Ala Thr Tyr Tyr Cys Gly Gln Ser Tyr Asn Tyr Pro Tyr
                    85                  90                  95

Thr Phe Gly Gln Gly Thr Lys Leu Glu Ile Lys
                    100                 105

<210> SEQ ID NO 174
<211> LENGTH: 323
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Human Kappa Chain Constant Region (Km(3)
      allotype) (allele 2)

<400> SEQUENCE: 174
gaactgtggc tgcaccatct gtcttcatct tcccgccatc tgatgagcag ttgaaatctg      60
gaactgcctc tgttgtgtgc ctgctgaata acttctatcc cagagaggcc aaagtacagt    120
ggaaggtgga taacgccctc caatcgggta actcccagga gagtgtcaca gagcaggaca    180
gcaaggacag cacctacagc ctcagcagca ccctgacgct gagcaaagca gactacgaga    240
aacacaaagt ctacgcctgc gaagtcaccc atcagggcct gagctcgccc gtcacaaaga    300
gcttcaacag gggagagtgt tga                                           323

<210> SEQ ID NO 175
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Kappa Chain Constant Region (Km(3)
      allotype) (allele 2)

<400> SEQUENCE: 175

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 176
<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Full Length Humanized Hu2B8 Light Chain
      (Kv-39.1 Variable Region)

<400> SEQUENCE: 176
```

```
atggacatga gggtccccgc tcagctcctg gggtcctgc tactctggct ccgaggtgcc        60
agatgtgaca tccagatgac ccagtctcca tcctccctgt ctgcatctgt aggagacaga       120
gtcaccatca cttgcaaggc cagtgagaat gtggtttctt atgtatcctg gtatcagcag       180
aaaccaggga aagcccctaa gctcctgatc tatggggcat ccaaccggaa cactggggtc       240
ccatcaaggt tcagtggcag tggatctggg acagatttca ctctcaccat cagcagtctg       300
caacctgaag attttgcaac ttactactgt gggcagagtt acaactatcc gtacacgttt       360
ggccagggga ccaagctgga gatcaaacga actgtggctg caccatctgt cttcatcttc       420
ccgccatctg atgagcagtt gaaatctgga actgcctctg ttgtgtgcct gctgaataac       480
ttctatccca gagaggccaa agtacagtgg aaggtggata acgccctcca atcgggtaac       540
tcccaggaga gtgtcacaga gcaggacagc aaggacagca cctacagcct cagcagcacc       600
ctgacgctga gcaaagcaga ctacgagaaa cacaaagtct acgcctgcga agtcacccat       660
cagggcctga gctcgcccgt cacaaagagc ttcaacaggg gagagtgttg a                711
```

<210> SEQ ID NO 177
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Full Length Humanized Hu2B8 Light Chain
      (Kv-39.1 Variable Region)

<400> SEQUENCE: 177

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Glu Asn Val Val Ser Tyr
            20                  25                  30

Val Ser Trp Tyr Gln Gln Lys Pro Gly Lys Ala Pro Lys Leu Leu Ile
        35                  40                  45

Tyr Gly Ala Ser Asn Arg Asn Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gly Gln Ser Tyr Asn Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 178
<211> LENGTH: 382
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Humanized Hu2B8 Kv3-15.1 Light Chain Variable
      Region

<400> SEQUENCE: 178
atggaagccc cagcgcagct tctcttcctc ctgctactct ggctcccaga taccactgga      60
gaaatagtga tgacgcagtc tccagccacc ctgtctgtgt ctccagggga aagagccacc     120
ctctcctgca aggccagtga gaatgtggtt tcttatgtat cctggtacca gcagaaacct     180
ggccaggctc ccaggctcct catctatggg gcatccaacc ggaacactgg tatcccagcc     240
aggttcagtg gcagtgggtc tgggacagag ttcactctca ccatcagcag cctgcagtct     300
gaagattttg cagtttatta ctgtgggcag agttacaact atccgtacac gtttggccag     360
gggaccaagc tggagatcaa ac                                              382

<210> SEQ ID NO 179
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Humanized Hu2B8 Kv3-15.1 Light Chain Variable
      Region

<400> SEQUENCE: 179

Glu Ile Val Met Thr Gln Ser Pro Ala Thr Leu Ser Val Ser Pro Gly
1               5                   10                  15

Glu Arg Ala Thr Leu Ser Cys Lys Ala Ser Glu Asn Val Val Ser Tyr
            20                  25                  30

Val Ser Trp Tyr Gln Gln Lys Pro Gly Gln Ala Pro Arg Leu Leu Ile
        35                  40                  45

Tyr Gly Ala Ser Asn Arg Asn Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gly Gln Ser Tyr Asn Tyr Pro Tyr
                85                  90                  95

Thr Phe Gly Gln Gly Thr Lys Leu Glu Ile Lys
            100                 105

<210> SEQ ID NO 180
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Full Length Humanized Hu2B8 Light Chain
      (Kv3-15.1 Variable Region)

<400> SEQUENCE: 180
atggaagccc cagcgcagct tctcttcctc ctgctactct ggctcccaga taccactgga      60

```
gaaatagtga tgacgcagtc tccagccacc ctgtctgtgt ctccagggga aagagccacc    120
ctctcctgca aggccagtga aatgtggtt tcttatgtat cctggtacca gcagaaacct    180
ggccaggctc ccaggctcct catctatggg gcatccaacc ggaacactgg tatcccagcc    240
aggttcagtg gcagtgggtc tgggacagag ttcactctca ccatcagcag cctgcagtct    300
gaagattttg cagtttatta ctgtgggcag agttacaact atccgtacac gtttggccag    360
gggaccaagc tggagatcaa acgaactgtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacgccc tccaatcggg taactcccag    540
gagagtgtca cagagcagga cagcaaggac agcacctaca gcctcagcag caccctgacg    600
ctgagcaaag cagactacga aaacacaaa gtctacgcct gcgaagtcac ccatcagggc    660
ctgagctcgc ccgtcacaaa gagcttcaac aggggagagt gttga                   705
```

<210> SEQ ID NO 181
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Full Length Humanized Hu2B8 Light Chain (Kv3-15.1 Variable Region)

<400> SEQUENCE: 181

```
Glu Ile Val Met Thr Gln Ser Pro Ala Thr Leu Ser Val Ser Pro Gly
1               5                   10                  15

Glu Arg Ala Thr Leu Ser Cys Lys Ala Ser Glu Asn Val Val Ser Tyr
            20                  25                  30

Val Ser Trp Tyr Gln Gln Lys Pro Gly Gln Ala Pro Arg Leu Leu Ile
        35                  40                  45

Tyr Gly Ala Ser Asn Arg Asn Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gly Gln Ser Tyr Asn Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 182

```
<211> LENGTH: 412
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Humanized LR2B8HC Heavy Chain Variable Region

<400> SEQUENCE: 182
atgggctggt catatattat tctctttctt gttgctaccg ctaccgatgt gcactctcaa    60
gtccaactcg tacaaccagg cgctgaagtc gtaaaacccg gaacatctgt taaactctca   120
tgcaaagcct caggatacac tttcacaact tactggatgc attgggtcaa tcaagccccc   180
ggacaaggcc tcgaatggat tggcgaaatt aacccaacta acggacatac taattataat   240
gaaaaattta aggcaaagc tacactcacc gtcgataaat caacctctac agcttatatg    300
gaactttcat ccctgagatc agaagataca gccgtctact attgcgccag aaactacgta   360
ggatcaatat cgattactg gggtcaaggc actctcctca cagtcagctc ag            412

<210> SEQ ID NO 183
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Humanized LR2B8HC Heavy Chain Variable Region

<400> SEQUENCE: 183

Gln Val Gln Leu Val Gln Pro Gly Ala Glu Val Val Lys Pro Gly Thr
1               5                   10                  15

Ser Val Lys Leu Ser Cys Lys Ala Ser Gly Tyr Thr Phe Thr Thr Tyr
            20                  25                  30

Trp Met His Trp Val Asn Gln Ala Pro Gly Gln Gly Leu Glu Trp Ile
        35                  40                  45

Gly Glu Ile Asn Pro Thr Asn Gly His Thr Asn Tyr Asn Glu Lys Phe
    50                  55                  60

Lys Gly Lys Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Tyr Val Gly Ser Ile Phe Asp Tyr Trp Gly Gln Gly Thr
            100                 105                 110

Leu Leu Thr Val Ser Ser
        115

<210> SEQ ID NO 184
<211> LENGTH: 992
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Human IgG1 Heavy Chain Constant Region (G1m(3)
      allotype) (allele 1)

<400> SEQUENCE: 184
ccagcacaaa gggcccatcg tcttccccc tggcaccctc ctccaagagc acctctgggg    60
gcacagcggc cctgggctgc ctggtcaagg actacttccc cgaaccggtg acggtgtcgt   120
```

```
ggaactcagg cgccctgacc agcggcgtgc acaccttccc ggctgtccta cagtcctcag    180
gactctactc cctcagcagc gtggtgaccg tgccctccag cagcttgggc acccagacct    240
acatctgcaa cgtgaatcac aagcccagca acaccaaggt ggacaagaga gttgagccca    300
aatcttgtga caaaactcac acatgtccac cgtgcccagc acctgaactc ctggggggac    360
cgtcagtctt cctcttcccc ccaaaaccca aggacaccct catgatctcc cggacccctg    420
aggtcacatg cgtggtggtg gacgtgagcc acgaagaccc tgaggtcaag ttcaactggt    480
acgtggacgg cgtggaggtg cataatgcca agacaaagcc gcgggaggag cagtacaaca    540
gcacgtaccg tgtggtcagc gtcctcaccg tcctgcacca ggactggctg aatggcaagg    600
agtacaagtg caaggtctcc aacaaagccc tcccagcccc catcgagaaa accatctcca    660
aagccaaagg gcagccccga gaaccacagg tgtacaccct gcccccatcc cgggaggaga    720
tgaccaagaa ccaggtcagc ctgacctgcc tggtcaaagg cttctatccc agcgacatcg    780
ccgtggagtg ggagagcaat gggcagccgg agaacaacta caagaccacg cctcccgtgc    840
tggactccga cggctccttc ttcctctata gcaagctcac cgtggacaag agcaggtggc    900
agcaggggaa cgtcttctca tgctccgtga tgcatgaggc tctgcacaac cactacacgc    960
agaagagcct ctccctgtcc ccgggtaaat ga                                  992
```

<210> SEQ ID NO 185
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human IgG1 Heavy Chain Constant Region (G1m(3)
      allotype) (allele 1 or 2)

<400> SEQUENCE: 185

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190
```

```
His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330
```

<210> SEQ ID NO 186
<211> LENGTH: 1404
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Full Length Humanized LR2B8HC Heavy Chain

<400> SEQUENCE: 186

```
atgggctggt catatattat tctctttctt gttgctaccg ctaccgatgt gcactctcaa      60
gtccaactcg tacaaccagg cgctgaagtc gtaaacccg  gaacatctgt taaactctca    120
tgcaaagcct caggatacac tttcacaact tactggatgc attgggtcaa tcaagccccc    180
ggacaaggcc tcgaatggat tggcgaaatt aacccaacta acggacatac taattataat    240
gaaaaattta agggcaaagc tacactcacc gtcgataaat caacctctac agcttatatg    300
gaactttcat ccctgagatc agaagataca gccgtctact attgcgccag aaactacgta    360
ggatcaatat tcgattactg gggtcaaggc actctcctca gtcagctc  agccagcaca     420 aagggcccat cggtcttccc cctggcaccc tcctccaaga gcacctctgg gggcacagcg    480
gccctgggct gcctggtcaa ggactacttc cccgaaccgg tgacggtgtc gtggaactca    540
ggcgccctga ccagcggcgt gcacaccttc ccggctgtcc tacagtcctc aggactctac    600
tccctcagca gcgtggtgac cgtgccctcc agcagcttgg gcacccagac ctacatctgc    660
aacgtgaatc acaagcccag caacaccaag gtggacaaga gagttgagcc caaatcttgt    720
gacaaaactc acacatgtcc accgtgccca gcacctgaac tcctgggggg accgtcagtc    780
ttcctcttcc cccaaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccgcgggagg agcagtacaa cagcacgtac    960
cgtgtggtca gcgtcctcac cgtcctgcac caggactggc tgaatggcaa ggagtacaag   1020
tgcaaggtct ccaacaaagc cctcccagcc cccatcgaga aaaccatctc caaagccaaa   1080
gggcagcccc gagaaccaca ggtgtacacc ctgcccccat cccgggagga tgaccaag     1140 aaccaggtca gcctgacctg cctggtcaaa ggcttctatc ccagcgacat cgccgtggag   1200
```

```
tgggagagca atgggcagcc ggagaacaac tacaagacca cgcctcccgt gctggactcc    1260
gacggctcct tcttcctcta tagcaagctc accgtggaca agagcaggtg gcagcagggg    1320
aacgtcttct catgctccgt gatgcatgag gctctgcaca accactacac gcagaagagc    1380
ctctccctgt ccccgggtaa atga                                           1404
```

<210> SEQ ID NO 187
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Full Length Humanized LR2B8HC Heavy Chain

<400> SEQUENCE: 187

```
Gln Val Gln Leu Val Gln Pro Gly Ala Glu Val Val Lys Pro Gly Thr
1               5                   10                  15

Ser Val Lys Leu Ser Cys Lys Ala Ser Gly Tyr Thr Phe Thr Thr Tyr
            20                  25                  30

Trp Met His Trp Val Asn Gln Ala Pro Gly Gln Gly Leu Glu Trp Ile
        35                  40                  45

Gly Glu Ile Asn Pro Thr Asn Gly His Thr Asn Tyr Asn Glu Lys Phe
    50                  55                  60

Lys Gly Lys Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Tyr Val Gly Ser Ile Phe Asp Tyr Trp Gly Gln Gly Thr
            100                 105                 110

Leu Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320
```

```
Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 188
<211> LENGTH: 412
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Humanized LRMR2B8HC Heavy Chain Variable Region

<400> SEQUENCE: 188
atgggttggt catatattat actctttctc gtagccaccg ccaccgacgt acactctcag      60
gttcaactcg tacacccggg cgccgaagtc aagaaaccag gaacatcagt caaactctca     120
tgtaaagcaa gcggatacac ctttactact tattggatgc attgggtaag acaagccccc     180
ggacaaggac tcgaatggat aggcgaaata aatcccacta atggacatac aaattataat     240
caaaaatttc aaggacgcgc tacactcacc gtcgataaat caacctcaac cgcatacatg     300
gaactcagct ccctccgatc cgaagacact gccgtttatt attgtgccag aaactatgta     360
ggatctattt tcgattactg gggacaagga acacttctca ccgtaagctc ag             412

<210> SEQ ID NO 189
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Humanized LRMR2B8HC Heavy Chain Variable
      Region

<400> SEQUENCE: 189

Gln Val Gln Leu Val Gln Pro Gly Ala Glu Val Lys Lys Pro Gly Thr
1               5                   10                  15

Ser Val Lys Leu Ser Cys Lys Ala Ser Gly Tyr Thr Phe Thr Thr Tyr
            20                  25                  30

Trp Met His Trp Val Arg Gln Ala Pro Gly Gln Gly Leu Glu Trp Ile
            35                  40                  45

Gly Glu Ile Asn Pro Thr Asn Gly His Thr Asn Tyr Asn Gln Lys Phe
        50                  55                  60

Gln Gly Arg Ala Thr Leu Thr Val Asp Lys Ser Thr Ser Thr Ala Tyr
65                  70                  75                  80
```

```
Met Glu Leu Ser Ser Leu Arg Ser Glu Asp Thr Ala Val Tyr Tyr Cys
                 85                  90                  95

Ala Arg Asn Tyr Val Gly Ser Ile Phe Asp Tyr Trp Gly Gln Gly Thr
            100                 105                 110

Leu Leu Thr Val Ser Ser
        115

<210> SEQ ID NO 190
<211> LENGTH: 1404
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Full Length Humanized LRMR2B8HC Heavy Chain

<400> SEQUENCE: 190
atgggttggt catatattat actctttctc gtagccaccg ccaccgacgt acactctcag     60
gttcaactcg tacaacccgg cgccgaagtc aagaaaccag aacatcagt caaactctca    120 tgtaaagcaa gcggatacac ctttactact tattggatgc attgggtaag acaagccccc    180
ggacaaggac tcgaatggat aggcgaaata atcccacta atggacatac aaattataat    240
caaaaatttc aaggacgcgc tacactcacc gtcgataaat caacctcaac cgcatacatg    300
gaactcagct ccctccgatc cgaagacact gccgtttatt attgtgccag aaactatgta    360
ggatctattt tcgattactg gggacaagga acacttctca ccgtaagctc agccagcaca    420
aagggcccat cggtcttccc cctggcaccc tcctccaaga gcacctctgg gggcacagcg    480
gccctgggct gcctggtcaa ggactacttc cccgaaccgg tgacggtgtc gtggaactca    540
ggcgccctga ccagcggcgt gcacaccttc ccggctgtcc tacagtcctc aggactctac    600
tccctcagca gcgtggtgac cgtgccctcc agcagcttgg gcacccagac ctacatctgc    660
aacgtgaatc acaagcccag caacaccaag gtggacaaga gagttgagcc caaatcttgt    720
gacaaaactc acacatgtcc accgtgccca gcacctgaac tcctgggggg accgtcagtc    780
ttcctcttcc cccccaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccgcgggagg agcagtacaa cagcacgtac    960
cgtgtggtca gcgtcctcac cgtcctgcac caggactggc tgaatggcaa ggagtacaag   1020
tgcaaggtct ccaacaaagc cctcccagcc cccatcgaga aaaccatctc caaagccaaa   1080
gggcagcccc gagaaccaca ggtgtacacc ctgcccccat cccgggagga gatgaccaag   1140
aaccaggtca gcctgacctg cctggtcaaa ggcttctatc ccagcgacat cgccgtggag   1200
tgggagagca atgggcagcc ggagaacaac tacaagacca cgcctcccgt gctggactcc   1260
gacggctcct tcttcctcta tagcaagctc accgtggaca agagcaggtg gcagcagggg   1320
aacgtcttct catgctccgt gatgcatgag gctctgcaca accactacac gcagaagagc   1380
ctctccctgt ccccgggtaa atga                                          1404

<210> SEQ ID NO 191
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

<223> OTHER INFORMATION: Full Length Humanized LRMR2B8HC Heavy Chain

<400> SEQUENCE: 191

```
Gln Val Gln Leu Val Gln Pro Gly Ala Glu Val Lys Pro Gly Thr
1               5                   10                  15

Ser Val Lys Leu Ser Cys Lys Ala Ser Gly Tyr Thr Phe Thr Thr Tyr
            20                  25                  30

Trp Met His Trp Val Arg Gln Ala Pro Gly Gln Gly Leu Glu Trp Ile
        35                  40                  45

Gly Glu Ile Asn Pro Thr Asn Gly His Thr Asn Tyr Asn Gln Lys Phe
    50                  55                  60

Gln Gly Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Tyr Val Gly Ser Ile Phe Asp Tyr Trp Gly Gln Gly Thr
            100                 105                 110

Leu Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Val Leu Asp
385                 390                 395                 400

Ser Asp Gly Ser Phe Phe Leu Tyr Ser Lys Leu Thr Val Asp Lys Ser
```

Arg Trp Gln Gln Gly Asn Val Phe Ser Cys Ser Val Met His Glu Ala
            405                 410                 415
Leu His Asn His Tyr Thr Gln Lys Ser Leu Ser Leu Ser Pro Gly Lys
        420                 425                 430
            435                 440                 445

<210> SEQ ID NO 192
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Humanized LR2B8LC Light Chain Variable Region

<400> SEQUENCE: 192
atggaaagtc agacccttgt attcatctct attcttcttt ggttgtatgg agcagacggc    60
gacattgtga tgacccaatc ccccgatagt atggccatga gtgtaggaga aagagtcacc   120
cttaattgca aagcctccga aaatgtcgtt tcatatgtgt cttggtatca acaaaaaccc   180
ggccaatcac ccaaacttct catatacggc gcttcaaaca gaaacacagg cgttcccgac   240
agatttagtg gatccggatc agctacagat ttcacccctta ccatcagttc agttcaagca   300
gaagacgttg cagactatca ttgcggacaa tcttataact acccttacac attcggacaa   360

<210> SEQ ID NO 193
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Humanized LR2B8LC Light Chain Variable Region

<400> SEQUENCE: 193

Asp Ile Val Met Thr Gln Ser Pro Asp Ser Met Ala Met Ser Val Gly
1               5                   10                  15

Glu Arg Val Thr Leu Asn Cys Lys Ala Ser Glu Asn Val Val Ser Tyr
            20                  25                  30

Val Ser Trp Tyr Gln Gln Lys Pro Gly Gln Ser Pro Lys Leu Leu Ile
        35                  40                  45

Tyr Gly Ala Ser Asn Arg Asn Thr Gly Val Pro Asp Arg Phe Ser Gly
    50                  55                  60

Ser Gly Ser Ala Thr Asp Phe Thr Leu Thr Ile Ser Ser Val Gln Ala
65                  70                  75                  80

Glu Asp Val Ala Asp Tyr His Cys Gly Gln Ser Tyr Asn Tyr Pro Tyr
                85                  90                  95

Thr Phe Gly Gln Gly Thr Lys Leu Glu Ile Lys
            100                 105

<210> SEQ ID NO 194
<211> LENGTH: 323
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Human Kappa Chain Constant Region (Km(3)
      allotype) (allele 1)

<400> SEQUENCE: 194

```
gtacggtggc tgcaccatct gtcttcatct tcccgccatc tgatgagcag ttgaaatctg      60
gaactgcctc tgttgtgtgc ctgctgaata acttctatcc cagagaggcc aaagtacagt     120
ggaaggtgga taacgccctc caatcgggta actcccagga gagtgtcaca gagcaggaca     180
gcaaggacag cacctacagc ctcagcagca ccctgacgct gagcaaagca gactacgaga     240
aacacaaagt ctacgcctgc gaagtcaccc atcagggcct gagctcgccc gtcacaaaga     300
gcttcaacag gggagagtgt tag                                             323
```

<210> SEQ ID NO 195
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Kappa Chain Constant Region (Km(3)
      allotype) (allele 1)

<400> SEQUENCE: 195

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 196
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Full Length Humanized LR2B8LC Light Chain

<400> SEQUENCE: 196

```
atggaaagtc agacccttgt attcatctct attcttcttt ggttgtatgg agcagacggc      60
gacattgtga tgacccaatc ccccgatagt atggccatga gtgtaggaga aagagtcacc     120
cttaattgca aagcctccga aaatgtcgtt tcatatgtgt cttggtatca acaaaaaccc     180
ggccaatcac ccaaacttct catatacggc gcttcaaaca gaaacacagg cgttcccgac     240
agatttagtg gatccggatc agctacagat ttcacccctta ccatcagttc agttcaagca     300
gaagacgttg cagactatca ttgcggacaa tcttataact acccttacac attcggacaa     360
ggaaccaaac tcgaaattaa acgtacggtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgccc tccaatcggg taactcccag     540
gagagtgtca cagagcagga cagcaaggac agcacctaca gcctcagcag cacccctgacg     600
```
ctgagcaaag cagactacga gaaacacaaa gtctacgcct gcgaagtcac ccatcagggc    660
ctgagctcgc ccgtcacaaa gagcttcaac aggggagagt gttag                    705

<210> SEQ ID NO 197
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Full Length Humanized LR2B8LC Light Chain

<400> SEQUENCE: 197

Asp Ile Val Met Thr Gln Ser Pro Asp Ser Met Ala Met Ser Val Gly
1               5                   10                  15

Glu Arg Val Thr Leu Asn Cys Lys Ala Ser Glu Asn Val Val Ser Tyr
            20                  25                  30

Val Ser Trp Tyr Gln Gln Lys Pro Gly Gln Ser Pro Lys Leu Leu Ile
        35                  40                  45

Tyr Gly Ala Ser Asn Arg Asn Thr Gly Val Pro Asp Arg Phe Ser Gly
    50                  55                  60

Ser Gly Ser Ala Thr Asp Phe Thr Leu Thr Ile Ser Ser Val Gln Ala
65                  70                  75                  80

Glu Asp Val Ala Asp Tyr His Cys Gly Gln Ser Tyr Asn Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 198
<211> LENGTH: 382
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Humanized LRMR2B8LC Light Chain Variable Region

<400> SEQUENCE: 198
atggaatccc aaacccttgt tttcatctct atccttctct ggctttatgg cgccgacgga    60
gacatcgtaa tgacacaatc ccctgactct cttgctatga gcttgggcga acgagtaaca   120
cttaactgca aagcatccga aaatgtcgta tcttacgtat cctggtatca gcaaaaacct   180
ggtcaaagtc ctaaacttct tatatatggt gcaagtaatc gtgaaagtgg cgtcccagac   240

```
agatttagcg gttcaggttc agcaactgac tttacactta caatttctag cgttcaggcc    300
gaagacgttg cagactatca ttgtggacaa tcttataact atccttatac tttcggacaa    360
ggcactaaac ttgaaattaa ac                                             382
```

<210> SEQ ID NO 199
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Humanized LRMR2B8LC Light Chain Variable Region

<400> SEQUENCE: 199

```
Asp Ile Val Met Thr Gln Ser Pro Asp Ser Leu Ala Met Ser Leu Gly
1               5                   10                  15
Glu Arg Val Thr Leu Asn Cys Lys Ala Ser Glu Asn Val Val Ser Tyr
            20                  25                  30
Val Ser Trp Tyr Gln Gln Lys Pro Gly Gln Ser Pro Lys Leu Leu Ile
        35                  40                  45
Tyr Gly Ala Ser Asn Arg Glu Ser Gly Val Pro Asp Arg Phe Ser Gly
    50                  55                  60
Ser Gly Ser Ala Thr Asp Phe Thr Leu Thr Ile Ser Ser Val Gln Ala
65                  70                  75                  80
Glu Asp Val Ala Asp Tyr His Cys Gly Gln Ser Tyr Asn Tyr Pro Tyr
                85                  90                  95
Thr Phe Gly Gln Gly Thr Lys Leu Glu Ile Lys
            100                 105
```

<210> SEQ ID NO 200
<211> LENGTH: 705
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Full Length Humanized LRMR2B8LC Light Chain

<400> SEQUENCE: 200

```
atggaatccc aaacccttgt tttcatctct atccttctct ggctttatgg cgccgacgga    60
gacatcgtaa tgacacaatc ccctgactct cttgctatga gcttgggcga acgagtaaca   120
cttaactgca agcatccga aaatgtcgta tcttacgtat cctggtatca gcaaaaacct    180
ggtcaaagtc ctaaacttct tatatatggt gcaagtaatc gtgaaagtgg cgtcccagac   240
agatttagcg gttcaggttc agcaactgac tttacactta caatttctag cgttcaggcc   300
gaagacgttg cagactatca ttgtggacaa tcttataact atccttatac tttcggacaa   360
ggcactaaac ttgaaattaa acgtacggtg gctgcaccat ctgtcttcat cttcccgcca   420
tctgatgagc agttgaaatc tggaactgcc tctgttgtgt gcctgctgaa taacttctat   480
cccagagagg ccaaagtaca gtggaaggtg gataacgccc tccaatcggg taactcccag   540
gagagtgtca cagagcagga cagcaaggac agcacctaca gcctcagcag caccctgacg   600
ctgagcaaag cagactacga gaaacacaaa gtctacgcct gcgaagtcac ccatcagggc   660
ctgagctcgc ccgtcacaaa gagcttcaac aggggagagt gttag                  705
```

```
<210> SEQ ID NO 201
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Full Length Humanized LRMR2B8LC Light Chain

<400> SEQUENCE: 201

Asp Ile Val Met Thr Gln Ser Pro Asp Ser Leu Ala Met Ser Leu Gly
1               5                   10                  15

Glu Arg Val Thr Leu Asn Cys Lys Ala Ser Gln Asn Val Ser Tyr
            20                  25                  30

Val Ser Trp Tyr Gln Gln Lys Pro Gly Gln Ser Pro Lys Leu Leu Ile
        35                  40                  45

Tyr Gly Ala Ser Asn Arg Glu Ser Gly Val Pro Asp Arg Phe Ser Gly
    50                  55                  60

Ser Gly Ser Ala Thr Asp Phe Thr Leu Thr Ile Ser Ser Val Gln Ala
65                  70                  75                  80

Glu Asp Val Ala Asp Tyr His Cys Gly Gln Ser Tyr Asn Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 202
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Heavy Chain CDR2 sequence of Humanized Hu2B8
      Hv1f.1 antibody

<400> SEQUENCE: 202

Glu Ile Asn Pro Thr Asn Gly His Thr Asn Tyr Asn Glu Lys Phe Gln
1               5                   10                  15

Gly

<210> SEQ ID NO 203
<211> LENGTH: 17
<212> TYPE: PRT
<213> ORGANISM: Artificial Sequence
<220> FEATURE:
<223> OTHER INFORMATION: Description of Artificial Sequence: Synthetic
```

```
        peptide
<220> FEATURE:
<223> OTHER INFORMATION: Heavy Chain CDR2 sequence of humanized Hu2B8
      Hv5a.1 antibody

<400> SEQUENCE: 203

Glu Ile Asn Pro Thr Asn Gly His Thr Asn Tyr Asn Pro Ser Phe Gln
1               5                   10                  15

Gly

<210> SEQ ID NO 204
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Heavy Chain CDR2 sequence of humanized LR2B8HC
      antibody

<400> SEQUENCE: 204

Glu Ile Asn Pro Thr Asn Gly His Thr Asn Tyr Asn Glu Lys Phe Lys
1               5                   10                  15

Gly

<210> SEQ ID NO 205
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Heavy Chain CDR2 sequence of humanized
      LRMR2B8HC antibody

<400> SEQUENCE: 205

Glu Ile Asn Pro Thr Asn Gly His Thr Asn Tyr Asn Gln Lys Phe Gln
1               5                   10                  15

Gly

<210> SEQ ID NO 206
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Light Chain CDR2 sequence of humanized
      LRMR2B8LC antibody

<400> SEQUENCE: 206

Gly Ala Ser Asn Arg Glu Ser
1               5

<210> SEQ ID NO 207
<211> LENGTH: 992
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Human IgG1 Heavy Chain Constant Region (G1m(3)
      allotype) (allele 2)

<400> SEQUENCE: 207
```

-continued

```
cctccaccaa gggcccatcg gtcttccccc tggcaccctc ctccaagagc acctctgggg      60
gcacagcggc cctgggctgc ctggtcaagg actacttccc cgaaccggtg acggtgtcgt     120
ggaactcagg cgccctgacc agcggcgtgc acaccttccc ggctgtccta cagtcctcag     180
gactctactc cctcagcagc gtggtgaccg tgccctccag cagcttgggc acccagacct     240
acatctgcaa cgtgaatcac aagcccagca acaccaaggt ggacaagaga gttgagccca     300
aatcttgtga caaaactcac acatgcccac cgtgcccagc acctgaactc ctggggggac     360
cgtcagtctt cctcttcccc ccaaaaccca aggacaccct catgatctcc cggacccctg     420
aggtcacatg cgtggtggtg gacgtgagcc acgaagaccc tgaggtcaag ttcaactggt     480
acgtggacgg cgtggaggtg cataatgcca agacaaagcc gcgggaggag cagtacaaca     540
gcacgtaccg tgtggtcagc gtcctcaccg tcctgcacca ggactggctg aatggcaagg     600
agtacaagtg caaggtctcc aacaaagccc tcccagcccc catcgagaag accatctcca     660
aagccaaagg gcagccccga gaaccacagg tgtacaccct gcccccatcc cgggaggaga     720
tgaccaagaa ccaggtcagc ctgacctgcc tggtcaaagg cttctatccc agcgacatcg     780
ccgtggagtg ggagagcaat gggcagccgg agaacaacta caagaccacg cctcccgtgc     840
tggactccga cggctccttc ttcctctaca gcaagctcac cgtggacaag agcaggtggc     900 agcagggaa cgtcttctca tgctccgtga tgcatgaggc tctgcacaac cactacacgc     960
agaagagcct ctccctgtct ccgggtaaat ga                                    992
```

<210> SEQ ID NO 208
<211> LENGTH: 330
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Human IgG1 Heavy Chain Constant Region (G1m(3) allotype) (allele 1 or 2)

<400> SEQUENCE: 208

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
```

```
                165                 170                 175
Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 209
<211> LENGTH: 1404
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Full Length Humanized Hu2B8 Heavy Chain
      (Hv5-51.1 Variable region)

<400> SEQUENCE: 209
atggggtcaa ccgccatcct cgccctcctc ctggctgttc tccaaggagt ctgtgccgaa      60
gtgcagctgg tgcagtctgg agcagaggtg aaaaagcccg ggagtctct gaagatctcc     120 tgtaagggtt ctggatacag ctttaccacc tactggatgc actgggtgcg ccagatgccc     180
gggaaaggcc tggagtggat gggggagatt aatcctacca acggtcatac taactacaat     240
ccgtccttcc aaggccaggt caccatctca gctgacaagt ccatcagcac tgcctacctg     300
cagtggagca gcctgaaggc ctcggacacc gccatgtatt actgtgcgag aaactatgtt     360
ggtagcatct ttgactactg gggccaagga accctggtca ccgtctcctc agcctccacc     420
aagggcccat cggtcttccc cctggcaccc tcctccaaga gcacctctgg gggcacagcg     480
gccctgggct gcctggtcaa ggactacttc cccgaaccgg tgacggtgtc gtggaactca     540
ggcgccctga ccagcggcgt gcacaccttc ccggctgtcc tacagtcctc aggactctac     600
tccctcagca gcgtggtgac cgtgccctcc agcagcttgg gcacccagac ctacatctgc     660
aacgtgaatc acaagcccag caacaccaag gtggacaaga gagttgagcc caaatcttgt     720
gacaaaactc acacatgccc accgtgccca gcacctgaac tcctgggggg accgtcagtc     780
ttcctcttcc cccaaaaacc caaggacacc ctcatgatct cccggacccc tgaggtcaca     840
tgcgtggtgg tggacgtgag ccacgaagac cctgaggtca agttcaactg gtacgtggac     900
ggcgtggagg tgcataatgc caagacaaag ccgcgggagg agcagtacaa cagcacgtac     960
cgtgtggtca gcgtcctcac cgtcctgcac caggactggc tgaatggcaa ggagtacaag    1020
```

-continued

```
tgcaaggtct ccaacaaagc cctcccagcc cccatcgaga agaccatctc caaagccaaa    1080
gggcagcccc gagaaccaca ggtgtacacc ctgcccccat cccgggagga gatgaccaag    1140
aaccaggtca gcctgacctg cctggtcaaa ggcttctatc ccagcgacat cgccgtggag    1200
tgggagagca atgggcagcc ggagaacaac tacaagacca cgcctcccgt gctggactcc    1260
gacggctcct tcttcctcta cagcaagctc accgtggaca agagcaggtg gcagcagggg    1320
aacgtcttct catgctccgt gatgcatgag gctctgcaca accactacac gcagaagagc    1380
ctctccctgt ctccgggtaa atga                                           1404
```

<210> SEQ ID NO 210
<211> LENGTH: 448
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Full Length Humanized Hu2B8 Heavy Chain (Hv5-51.1 Variable region)

<400> SEQUENCE: 210

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Thr Tyr
            20                  25                  30

Trp Met His Trp Val Arg Gln Met Pro Gly Lys Gly Leu Glu Trp Met
        35                  40                  45

Gly Glu Ile Asn Pro Thr Asn Gly His Thr Asn Tyr Asn Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asn Tyr Val Gly Ser Ile Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
```

|  |  |  |  | 275 |  |  |  | 280 |  |  |  | 285 |  |  |
|---|---|---|---|---|---|---|---|---|---|---|---|---|---|---|
| Lys | Thr | Lys | Pro | Arg | Glu | Glu | Gln | Tyr | Asn | Ser | Thr | Tyr | Arg | Val | Val |
|  |  |  |  | 290 |  |  |  | 295 |  |  |  | 300 |  |  |  |
| Ser | Val | Leu | Thr | Val | Leu | His | Gln | Asp | Trp | Leu | Asn | Gly | Lys | Glu | Tyr |
| 305 |  |  |  |  | 310 |  |  |  |  | 315 |  |  |  |  | 320 |
| Lys | Cys | Lys | Val | Ser | Asn | Lys | Ala | Leu | Pro | Ala | Pro | Ile | Glu | Lys | Thr |
|  |  |  |  | 325 |  |  |  |  | 330 |  |  |  |  | 335 |  |
| Ile | Ser | Lys | Ala | Lys | Gly | Gln | Pro | Arg | Glu | Pro | Gln | Val | Tyr | Thr | Leu |
|  |  |  | 340 |  |  |  |  | 345 |  |  |  |  | 350 |  |  |
| Pro | Pro | Ser | Arg | Glu | Glu | Met | Thr | Lys | Asn | Gln | Val | Ser | Leu | Thr | Cys |
|  |  | 355 |  |  |  |  | 360 |  |  |  |  | 365 |  |  |  |
| Leu | Val | Lys | Gly | Phe | Tyr | Pro | Ser | Asp | Ile | Ala | Val | Glu | Trp | Glu | Ser |
| 370 |  |  |  |  | 375 |  |  |  |  | 380 |  |  |  |  |  |
| Asn | Gly | Gln | Pro | Glu | Asn | Asn | Tyr | Lys | Thr | Thr | Pro | Pro | Val | Leu | Asp |
| 385 |  |  |  |  | 390 |  |  |  |  | 395 |  |  |  |  | 400 |
| Ser | Asp | Gly | Ser | Phe | Phe | Leu | Tyr | Ser | Lys | Leu | Thr | Val | Asp | Lys | Ser |
|  |  |  |  | 405 |  |  |  |  | 410 |  |  |  |  | 415 |  |
| Arg | Trp | Gln | Gln | Gly | Asn | Val | Phe | Ser | Cys | Ser | Val | Met | His | Glu | Ala |
|  |  |  | 420 |  |  |  |  | 425 |  |  |  |  | 430 |  |  |
| Leu | His | Asn | His | Tyr | Thr | Gln | Lys | Ser | Leu | Ser | Leu | Ser | Pro | Gly | Lys |
|  |  |  | 435 |  |  |  |  | 440 |  |  |  |  | 445 |  |  |

<210> SEQ ID NO 211
<211> LENGTH: 2209
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Synthetic HGF mhm (V495-L585)

<400> SEQUENCE: 211

```
atgatgtggg ggaccaaaact tctgccggtc ctgttgctgc agcatgtcct cctgcacctc      60
ctcctgcttc atgtcgccat ccctatgca gaaggacaga agaaaagaag aaatacactt      120
catgaattta aaagtcagc aaaaactact cttaccaagg aagacccatt actgaagatt      180
aaaaccaaaa aagtgaactc tgcagatgag tgtgccaaca gtgtatcag aacaggggc      240
tttacgttca cttgcaaggc cttcgttttt gataagtcaa gaaacgatg ctactggtat      300
ccttttcaata gtatgtcaag tggagtgaaa aaagggtttg ccatgaatt tgacctctat      360
gaaaacaaag actatattag aaactgcatc attggtaaag gaggcagcta taagggacg      420
gtatccatca ctaagagtgg catcaaatgc cagccttgga attccatgat ccccatgaa      480
cacagctttt tgccttcgag ctatcgcggt aaagacctac aggaaaacta ctgtcgaaat      540
cctcgaggg aagaagggg accctggtgt tcacaagca atccagaggt acgctacgaa      600
gtctgtgaca ttcctcagtg ttcagaagtt gaatgcatga cctgcaatgg tgaaagctac      660
agaggtccca tggatcacac agaatcaggc aagacttgtc agcgctggga ccagcagaca      720
ccacaccggc acaagttctt gccagaaaga tatcccgaca gggctttgaa tgataattat      780
tgccgcaatc ctgatggcaa gccgaggcca tggtgctaca ctcttgaccc tgacaccact      840
tgggagtatt gtgcaattaa acgtgcgct cacagtgctg tgaatgagac tgatgtccct      900
atggaaacaa ctgaatgcat tcaaggccaa ggagaaggtt acaggggaac cagcaatacc      960
atttggaatg gaattccctg tcagcgttgg gattcgcagt accctcacaa gcatgatat      1020
actcccgaga acttcaaatg caaggacctt agagaaaatt attgccgcaa tccagatggg      1080
```

```
gctgaatcac catggtgttt taccactgac ccaaacatcc gagttggcta ctgctctcag   1140
attcccaagt gtgacgtgtc aagtggacaa gattgttatc gtggcaatgg gaaaaattac   1200
atgggcaact tatccaaaac aaggtctgga cttacatgtt ccatgtggga caagaatatg   1260
gaggatttac accgtcatat cttctgggag ccagatgcta gcaaattgaa taagaattac   1320
tgccggaatc ctgatgatga tgcccatgga ccttggtgct acacggggaa tcctcttatt   1380
ccttgggatt attgccctat ttcccgttgt gaaggagata ctacacctac aattgtcaat   1440
ttggaccatc ctgtaatatc ctgtgccaaa acaaaacaac tgcgggttgt aaatgggatt   1500
ccaacacgaa caaacatagg atggatggtt agtttgagat acagaaataa acatatctgc   1560
ggaggatcat tgataaagga gagttgggtt cttactgcac gacagtgttt cccttctcga   1620
gacttgaaag attatgaagc ttggcttgga attcatgatg tccacggaag aggagatgag   1680
aaatgcaaac aggttctcaa tgtttcccag ctggtatatg gccctgaagg atcagatctg   1740
gttttaatga agcttgctcg acctgcaatc ctggataact ttgtcagtac aattgattta   1800
cctagttatg gttgtacaat ccctgaaaag accacttgca gtatttacgg ctggggctac   1860
actggattga tcaacgcgga tggttttata cgagtagctc atctgtatat tatggggaat   1920
gagaaatgca gtcagcacca tcaaggcaag gtgactttga atgagtctga gttatgtgct   1980
ggggctgaaa agattggatc aggaccatgt gaggagatt atggtggccc actcatttgt   2040
gaacaacaca aaatgagaat ggttcttggt gtcattgttc ctggtcgtgg atgtgccatc   2100
ccaaatcgtc ctgttatttt tgttcgagta gcatattatg caaatggat acacaaagta   2160 attttgacat acaagttgtg cggccgccat caccatcacc atcactaag            2209
```

<210> SEQ ID NO 212
<211> LENGTH: 680
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Synthetic HGF mhm495-585 active

<400> SEQUENCE: 212

```
Pro Leu Leu Lys Ile Lys Thr Lys Lys Val Asn Ser Ala Asp Glu Cys
 1               5                  10                  15

Ala Asn Arg Cys Ile Arg Asn Arg Gly Phe Thr Phe Thr Cys Lys Ala
                20                  25                  30

Phe Val Phe Asp Lys Ser Arg Lys Arg Cys Tyr Trp Tyr Pro Phe Asn
            35                  40                  45

Ser Met Ser Ser Gly Val Lys Lys Gly Phe Gly His Glu Phe Asp Leu
        50                  55                  60

Tyr Glu Asn Lys Asp Tyr Ile Arg Asn Cys Ile Ile Gly Lys Gly Gly
 65                  70                  75                  80

Ser Tyr Lys Gly Thr Val Ser Ile Thr Lys Ser Gly Ile Lys Cys Gln
                85                  90                  95

Pro Trp Asn Ser Met Ile Pro His Glu His Ser Phe Leu Pro Ser Ser
            100                 105                 110

Tyr Arg Gly Lys Asp Leu Gln Glu Asn Tyr Cys Arg Asn Pro Arg Gly
        115                 120                 125

Glu Glu Gly Gly Pro Trp Cys Phe Thr Ser Asn Pro Glu Val Arg Tyr
    130                 135                 140

Glu Val Cys Asp Ile Pro Gln Cys Ser Glu Val Glu Cys Met Thr Cys
```

```
            145                 150                 155                 160
Asn Gly Glu Ser Tyr Arg Gly Pro Met Asp His Thr Glu Ser Gly Lys
                165                 170                 175

Thr Cys Gln Arg Trp Asp Gln Gln Thr Pro His Arg His Lys Phe Leu
                180                 185                 190

Pro Glu Arg Tyr Pro Asp Lys Gly Phe Asp Asp Asn Tyr Cys Arg Asn
                195                 200                 205

Pro Asp Gly Lys Pro Arg Pro Trp Cys Tyr Thr Leu Asp Pro Asp Thr
    210                 215                 220

Thr Trp Glu Tyr Cys Ala Ile Lys Thr Ala His Ser Ala Val Asn
225                 230                 235                 240

Glu Thr Asp Val Pro Met Glu Thr Thr Glu Cys Ile Gln Gly Gln Gly
                    245                 250                 255

Glu Gly Tyr Arg Gly Thr Ser Asn Thr Ile Trp Asn Gly Ile Pro Cys
                260                 265                 270

Gln Arg Trp Asp Ser Gln Tyr Pro His Lys His Asp Ile Thr Pro Glu
                275                 280                 285

Asn Phe Lys Cys Lys Asp Leu Arg Glu Asn Tyr Cys Arg Asn Pro Asp
    290                 295                 300

Gly Ala Glu Ser Pro Trp Cys Phe Thr Thr Asp Pro Asn Ile Arg Val
305                 310                 315                 320

Gly Tyr Cys Ser Gln Ile Pro Lys Cys Asp Val Ser Ser Gly Gln Asp
                325                 330                 335

Cys Tyr Arg Gly Asn Gly Lys Asn Tyr Met Gly Asn Leu Ser Lys Thr
                340                 345                 350

Arg Ser Gly Leu Thr Cys Ser Met Trp Asp Lys Asn Met Glu Asp Leu
    355                 360                 365

His Arg His Ile Phe Trp Glu Pro Asp Ala Ser Lys Leu Asn Lys Asn
    370                 375                 380

Tyr Cys Arg Asn Pro Asp Asp Ala His Gly Pro Trp Cys Tyr Thr
385                 390                 395                 400

Gly Asn Pro Leu Ile Pro Trp Asp Tyr Cys Pro Ile Ser Arg Cys Glu
                405                 410                 415

Gly Asp Thr Thr Pro Thr Ile Val Asn Leu Asp His Pro Val Ile Ser
                420                 425                 430

Cys Ala Lys Thr Lys Gln Leu Arg Val Val Asn Gly Ile Pro Thr Arg
            435                 440                 445

Thr Asn Ile Gly Trp Met Val Ser Leu Arg Tyr Arg Asn Lys His Ile
    450                 455                 460

Cys Gly Gly Ser Leu Ile Lys Glu Ser Trp Val Leu Thr Ala Arg Gln
465                 470                 475                 480

Cys Phe Pro Ser Arg Asp Leu Lys Asp Tyr Glu Ala Trp Leu Gly Ile
                485                 490                 495

His Asp Val His Gly Arg Gly Asp Glu Lys Cys Lys Gln Val Leu Asn
                500                 505                 510

Val Ser Gln Leu Val Tyr Gly Pro Glu Gly Ser Asp Leu Val Leu Met
            515                 520                 525

Lys Leu Ala Arg Pro Ala Ile Leu Asp Asn Phe Val Ser Thr Ile Asp
    530                 535                 540

Leu Pro Ser Tyr Gly Cys Thr Ile Pro Glu Lys Thr Cys Ser Ile
545                 550                 555                 560

Tyr Gly Trp Gly Tyr Thr Gly Leu Ile Asn Ala Asp Gly Leu Leu Arg
                565                 570                 575
```

```
Val Ala His Leu Tyr Ile Met Gly Asn Glu Lys Cys Ser Gln His His
            580                 585                 590

Gln Gly Lys Val Thr Leu Asn Glu Ser Glu Leu Cys Ala Gly Ala Glu
        595                 600                 605

Lys Ile Gly Ser Gly Pro Cys Glu Gly Asp Tyr Gly Gly Pro Leu Ile
    610                 615                 620

Cys Glu Gln His Lys Met Arg Met Val Leu Gly Val Ile Val Pro Gly
625                 630                 635                 640

Arg Gly Cys Ala Ile Pro Asn Arg Pro Val Ile Phe Val Arg Val Ala
                645                 650                 655

Tyr Tyr Ala Lys Trp Ile His Lys Val Ile Leu Thr Tyr Lys Leu Cys
            660                 665                 670

Gly Arg His His His His His His
        675                 680

<210> SEQ ID NO 213
<211> LENGTH: 2194
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Synthetic HGF mhm (I499-R556)

<400> SEQUENCE: 213
atgatgtggg ggaccaaact tctgccggtc ctgttgctgc agcatgtcct cctgcacctc        60
ctcctgcttc atgtcgccat ccctatgca gaaggacaga agaaagaag aaatacactt        120 catgaattta aaaagtcagc aaaaactact cttaccaagg aagacccatt actgaagatt       180
aaaaccaaaa agtgaactc tgcagatgag tgtgccaaca ggtgtatcag gaacaggggc       240
tttacgttca cttgcaaggc cttcgttttt gataagtcaa gaaaacgatg ctactggtat       300
cctttcaata gtatgtcaag tggagtgaaa aaagggtttg ccatgaatt tgacctctat        360 gaaaacaaag actatattag aaactgcatc attggtaaag gaggcagcta taaagggacg       420
gtatccatca ctaagagtgg catcaaatgc agccttggaa attccatgat cccccatgaa       480
cacagctatc gcggtaaaga cctacaggaa aactactgtc gaaatcctcg aggggaagaa       540 gggggacct ggtgtttcac aagcaatcca gaggtacgct acgaagtctg tgacattcct       600
cagtgttcag aagttgaatg catgaccttgc aatggtgaaa gctacagagg tcccatggat       660
cacacagaat caggcaagac ttgtcagcgc tgggaccagc agacaccaca ccggcacaag       720
ttcttgccag aaagatatcc cgacaagggc tttgatgata ttattgccg caatcctgat       780 ggcaagccga ggccatggtg ctacactctt gaccctgaca cccttggga gtattgtgca       840 attaaaacgt gcgctcacag tgctgtgaat gagactgatg tccctatgga acaactgaa       900 tgcattcaag ccaaggaga aggttacagg ggaaccagca ataccatttg aatggaatt       960 ccctgtcagc gttgggattc gcagtaccct cacaagcatg atatcactcc cgagaacttc      1020
aaatgcaagg accttagaga aaattattgc cgcaatccag atggggctga atcaccatgg      1080
tgttttacca ctgacccaaa catccgagtt ggctactgct ctcagattcc caagtgtgac      1140
gtgtcaagtg acaagattg ttatcgtggc aatgggaaaa attacatggg caacttatcc      1200
aaaacaaggt ctggacttac atgttccatg tgggacaaga atatggagga tttacaccgt      1260
catatcttct gggagccaga tgctagcaaa ttgaataaga attactgccg gaatcctgat      1320
gatgatgccc atggaccttg gtgctacacg gggaatcctc ttattccttg ggattattgc      1380
```

```
cctatttccc gttgtgaagg agatactaca cctacaattg tcaatttgga ccatcctgta    1440
atatcctgtg ccaaaacaaa acaactgcgg gttgtaaatg ggattccaac acgaacaaac    1500
ataggatgga tggttagttt gagatacaga aataaacata tctgcggagg atcattgata    1560
aaggagagtt gggttcttac tgcacgacag tgtttccctt ctcgagactt gaaagattat    1620
gaagcttggc ttggaattca tgatgtccac ggaagaggag aggagaaaag aaaacagatt    1680
ctcaatattt cccagctggt atatggccct gaaggatcag atctggtttt actgaagctt    1740
gctcgacctg caatcctgga taactttgtc agtacaattg atttacctag ttatggttgt    1800
acaatccctg aaaagaccac ttgcagtatt tacggctggg gctacactgg attgatcaac    1860
gcggatggtt tattacgagt agctcatctg tatattatgg ggaatgagaa atgcagtcag    1920
caccatcaag gcaaggtgac tttgaatgag tctgagttat gtgctggggc tgaaaagatt    1980
ggatcaggac catgtgaggg agattatggt ggcccactca tttgtgaaca acacaaaatg    2040
agaatggttc ttggtgtcat tgttcctggt cgtggatgtg ccatcccaaa tcgtcctggt    2100 attttgttc gagtagcata ttatgcaaaa tggatacaca aagtaatttt gacatacaag    2160
ttgtgcggcc gccatcacca tcaccatcac taag                                2194
```

<210> SEQ ID NO 214  
<211> LENGTH: 675  
<212> TYPE: PRT  
<213> ORGANISM: Artificial Sequence  
<220> FEATURE:  
<223> OTHER INFORMATION: Description of Artificial Sequence: Synthetic polypeptide  
<220> FEATURE:  
<223> OTHER INFORMATION: Synthetic HGF mhm 499-556 active

<400> SEQUENCE: 214

```
Pro Leu Leu Lys Ile Lys Thr Lys Lys Val Asn Ser Ala Asp Glu Cys
1               5                   10                  15

Ala Asn Arg Cys Ile Arg Asn Arg Gly Phe Thr Phe Thr Cys Lys Ala
            20                  25                  30

Phe Val Phe Asp Lys Ser Arg Lys Arg Cys Tyr Trp Tyr Pro Phe Asn
        35                  40                  45

Ser Met Ser Ser Gly Val Lys Lys Gly Phe Gly His Glu Phe Asp Leu
    50                  55                  60

Tyr Glu Asn Lys Asp Tyr Ile Arg Asn Cys Ile Ile Gly Lys Gly Gly
65                  70                  75                  80

Ser Tyr Lys Gly Thr Val Ser Ile Thr Lys Ser Gly Ile Lys Cys Gln
                85                  90                  95

Pro Trp Asn Ser Met Ile Pro His Glu His Ser Tyr Arg Gly Lys Asp
            100                 105                 110

Leu Gln Glu Asn Tyr Cys Arg Asn Pro Arg Gly Glu Glu Gly Gly Pro
        115                 120                 125

Trp Cys Phe Thr Ser Asn Pro Glu Val Arg Tyr Glu Val Cys Asp Ile
    130                 135                 140

Pro Gln Cys Ser Glu Val Glu Cys Met Thr Cys Asn Gly Glu Ser Tyr
145                 150                 155                 160

Arg Gly Pro Met Asp His Thr Glu Ser Gly Lys Thr Cys Gln Arg Trp
                165                 170                 175

Asp Gln Gln Thr Pro His Arg His Lys Phe Leu Pro Glu Arg Tyr Pro
            180                 185                 190

Asp Lys Gly Phe Asp Asp Asn Tyr Cys Arg Asn Pro Asp Gly Lys Pro
        195                 200                 205
```

-continued

```
Arg Pro Trp Cys Tyr Thr Leu Asp Pro Asp Thr Pro Trp Glu Tyr Cys
    210                 215                 220

Ala Ile Lys Thr Cys Ala His Ser Ala Val Asn Glu Thr Asp Val Pro
225                 230                 235                 240

Met Glu Thr Thr Glu Cys Ile Gln Gly Gln Gly Glu Gly Tyr Arg Gly
                245                 250                 255

Thr Ser Asn Thr Ile Trp Asn Gly Ile Pro Cys Gln Arg Trp Asp Ser
            260                 265                 270

Gln Tyr Pro His Lys His Asp Ile Thr Pro Glu Asn Phe Lys Cys Lys
        275                 280                 285

Asp Leu Arg Glu Asn Tyr Cys Arg Asn Pro Asp Gly Ala Glu Ser Pro
    290                 295                 300

Trp Cys Phe Thr Thr Asp Pro Asn Ile Arg Val Gly Tyr Cys Ser Gln
305                 310                 315                 320

Ile Pro Lys Cys Asp Val Ser Ser Gly Gln Asp Cys Tyr Arg Gly Asn
                325                 330                 335

Gly Lys Asn Tyr Met Gly Asn Leu Ser Lys Thr Arg Ser Gly Leu Thr
            340                 345                 350

Cys Ser Met Trp Asp Lys Asn Met Glu Asp Leu His Arg His Ile Phe
        355                 360                 365

Trp Glu Pro Asp Ala Ser Lys Leu Asn Lys Asn Tyr Cys Arg Asn Pro
    370                 375                 380

Asp Asp Asp Ala His Gly Pro Trp Cys Tyr Thr Gly Asn Pro Leu Ile
385                 390                 395                 400

Pro Trp Asp Tyr Cys Pro Ile Ser Arg Cys Glu Gly Asp Thr Thr Pro
                405                 410                 415

Thr Ile Val Asn Leu Asp His Pro Val Ile Ser Cys Ala Lys Thr Lys
            420                 425                 430

Gln Leu Arg Val Val Asn Gly Ile Pro Thr Arg Thr Asn Ile Gly Trp
        435                 440                 445

Met Val Ser Leu Arg Tyr Arg Asn Lys His Ile Cys Gly Gly Ser Leu
    450                 455                 460

Ile Lys Glu Ser Trp Val Leu Thr Ala Arg Gln Cys Phe Pro Ser Arg
465                 470                 475                 480

Asp Leu Lys Asp Tyr Glu Ala Trp Leu Gly Ile His Asp Val His Gly
                485                 490                 495

Arg Gly Glu Glu Lys Arg Lys Gln Ile Leu Asn Ile Ser Gln Leu Val
            500                 505                 510

Tyr Gly Pro Glu Gly Ser Asp Leu Val Leu Leu Lys Leu Ala Arg Pro
        515                 520                 525

Ala Ile Leu Asp Asn Phe Val Ser Thr Ile Asp Leu Pro Ser Tyr Gly
    530                 535                 540

Cys Thr Ile Pro Glu Lys Thr Thr Cys Ser Ile Tyr Gly Trp Gly Tyr
545                 550                 555                 560

Thr Gly Leu Ile Asn Ala Asp Gly Leu Leu Arg Val Ala His Leu Tyr
                565                 570                 575

Ile Met Gly Asn Glu Lys Cys Ser Gln His His Gln Gly Lys Val Thr
            580                 585                 590

Leu Asn Glu Ser Glu Leu Cys Ala Gly Ala Glu Lys Ile Gly Ser Gly
        595                 600                 605

Pro Cys Glu Gly Asp Tyr Gly Gly Pro Leu Ile Cys Glu Gln His Lys
    610                 615                 620

Met Arg Met Val Leu Gly Val Ile Val Pro Gly Arg Gly Cys Ala Ile
625                 630                 635                 640
```

Pro Asn Arg Pro Gly Ile Phe Val Arg Val Ala Tyr Tyr Ala Lys Trp
            645                 650                 655

Ile His Lys Val Ile Leu Thr Tyr Lys Leu Cys Gly Arg His His His
        660                 665                 670

His His His
        675

<210> SEQ ID NO 215
<211> LENGTH: 2194
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Synthetic HGF mhm (W507-L585)

<400> SEQUENCE: 215

| | | | | | |
|---|---|---|---|---|---|
| atgatgtggg | ggaccaaact | tctgccggtc | ctgttgctgc | agcatgtcct | cctgcacctc | 60 |
| ctcctgcttc | atgtcgccat | cccctatgca | gaaggacaga | gaaaagaag | aaatacactt | 120 |
| catgaattta | aaaagtcagc | aaaaactact | cttaccaagg | aagacccatt | actgaagatt | 180 |
| aaaaccaaaa | aagtgaactc | tgcagatgag | tgtgccaaca | ggtgtatcag | gaacaggggc | 240 |
| tttacgttca | cttgcaaggc | cttcgttttt | gataagtcaa | gaaaacgatg | ctactggtat | 300 |
| cctttcaata | gtatgtcaag | tggagtgaaa | aagggtttg | gccatgaatt | tgacctctat | 360 |
| gaaaacaaag | actatattag | aaactgcatc | attggtaaag | gaggcagcta | taaagggacg | 420 |
| gtatccatca | ctaagagtgg | catcaaatgc | cagccttgga | attccatgat | ccccatgaa | 480 |
| cacagctatc | gcgtaaaga | cctacaggaa | aactactgtc | gaaatcctcg | aggggaagaa | 540 |
| gggggaccct | ggtgtttcac | aagcaatcca | gaggtacgct | acgaagtctg | tgacattcct | 600 |
| cagtgttcag | aagttgaatg | catgacctgc | aatggtgaaa | gctacagagg | tcccatggat | 660 |
| cacacagaat | caggcaagac | ttgtcagcgc | tgggaccagc | agacaccaca | ccggcacaag | 720 |
| ttcttgccag | aaagatatcc | cgacaagggc | tttgatgata | ttattgccg | caatcctgat | 780 |
| ggcaagccga | ggccatggtg | ctacactctt | gaccctgaca | cccttggga | gtattgtgca | 840 |
| attaaaacgt | gcgctcacag | tgctgtgaat | gagactgatg | tccctatgga | acaactgaa | 900 |
| tgcattcaag | gccaaggaga | aggttacagg | ggaaccagca | ataccatttg | gaatggaatt | 960 |
| ccctgtcagc | gttgggattc | gcagtaccct | cacaagcatg | atatcactcc | cgagaacttc | 1020 |
| aaatgcaagg | accttagaga | aaattattgc | cgcaatccag | atgggctga | atcaccatgg | 1080 |
| tgttttacca | ctgacccaaa | catccgagtt | ggctactgct | ctcagattcc | caagtgtgac | 1140 |
| gtgtcaagtg | gacaagattg | ttatcgtggc | aatgggaaaa | attacatggg | caacttatcc | 1200 |
| aaaacaaggt | ctggacttac | atgttccatg | tgggacaaga | atatggagga | tttacaccgt | 1260 |
| catatcttct | gggagccaga | tgctagcaaa | ttgaataaga | attactgccg | gaatcctgat | 1320 |
| gatgatgccc | atggaccttg | gtgctacacg | gggaatcctc | ttattccttg | ggattattgc | 1380 |
| cctatttccc | gttgtgaagg | agatactaca | cctacaattg | tcaatttgga | ccatcctgta | 1440 |
| atatcctgtg | ccaaaacaaa | acaactgcgg | gttgtaaatg | ggattccaac | acaacaaca | 1500 |
| gtaggatgga | tggttagttt | gagatacaga | aataaacata | tctgcggagg | atcattgata | 1560 |
| aaggagagtt | gggttcttac | tgcacgacag | tgtttccctt | ctcgagactt | gaaagattat | 1620 |
| gaagcttggc | ttggaattca | tgatgtccac | ggaagaggag | atgagaaatg | caaacaggtt | 1680 |
| ctcaatgttt | cccagctggt | atatggccct | gaaggatcag | atctggtttt | aatgaagctt | 1740 |

```
gctcgacctg caatcctgga taactttgtc agtacaattg atttacctag ttatggttgt    1800
acaatccctg aaaagaccac ttgcagtatt tacggctggg gctacactgg attgatcaac    1860
gcggatggtt tattacgagt agctcatctg tatattatgg ggaatgagaa atgcagtcag    1920
caccatcaag gcaaggtgac tttgaatgag tctgagttat gtgctggggc tgaaaagatt    1980
ggatcaggac catgtgaggg agattattgg tggcccactca tttgtgaaca acacaaaatg    2040
agaatggttc ttggtgtcat tgttcctggt cgtggatgtg ccatcccaaa tcgtcctggt    2100
atttttgttc gagtagcata ttatgcaaaa tggatacaca agtaatttt gacatacaag    2160 ttgtgcggcc gccatcacca tcaccatcac taag                                2194
```

<210> SEQ ID NO 216
<211> LENGTH: 675
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Synthetic HGF mhm507-585 active

<400> SEQUENCE: 216

```
Pro Leu Leu Lys Ile Lys Thr Lys Lys Val Asn Ser Ala Asp Glu Cys
1               5                   10                  15

Ala Asn Arg Cys Ile Arg Asn Arg Gly Phe Thr Phe Thr Cys Lys Ala
                20                  25                  30

Phe Val Phe Asp Lys Ser Arg Lys Arg Cys Tyr Trp Tyr Pro Phe Asn
            35                  40                  45

Ser Met Ser Ser Gly Val Lys Lys Gly Phe Gly His Glu Phe Asp Leu
        50                  55                  60

Tyr Glu Asn Lys Asp Tyr Ile Arg Asn Cys Ile Ile Gly Lys Gly Gly
65                  70                  75                  80

Ser Tyr Lys Gly Thr Val Ser Ile Thr Lys Ser Gly Ile Lys Cys Gln
                85                  90                  95

Pro Trp Asn Ser Met Ile Pro His Glu His Ser Tyr Arg Gly Lys Asp
            100                 105                 110

Leu Gln Glu Asn Tyr Cys Arg Asn Pro Arg Gly Glu Glu Gly Gly Pro
        115                 120                 125

Trp Cys Phe Thr Ser Asn Pro Glu Val Arg Tyr Glu Val Cys Asp Ile
130                 135                 140

Pro Gln Cys Ser Glu Val Glu Cys Met Thr Cys Asn Gly Glu Ser Tyr
145                 150                 155                 160

Arg Gly Pro Met Asp His Thr Glu Ser Gly Lys Thr Cys Gln Arg Trp
                165                 170                 175

Asp Gln Gln Thr Pro His Arg His Lys Phe Leu Pro Glu Arg Tyr Pro
            180                 185                 190

Asp Lys Gly Phe Asp Asp Asn Tyr Cys Arg Asn Pro Asp Gly Lys Pro
        195                 200                 205

Arg Pro Trp Cys Tyr Thr Leu Asp Pro Asp Thr Pro Trp Glu Tyr Cys
    210                 215                 220

Ala Ile Lys Thr Cys Ala His Ser Ala Val Asn Glu Thr Asp Val Pro
225                 230                 235                 240

Met Glu Thr Thr Glu Cys Ile Gln Gly Gln Gly Glu Gly Tyr Arg Gly
                245                 250                 255

Thr Ser Asn Thr Ile Trp Asn Gly Ile Pro Cys Gln Arg Trp Asp Ser
            260                 265                 270
```

```
Gln Tyr Pro His Lys His Asp Ile Thr Pro Glu Asn Phe Lys Cys Lys
        275                 280                 285

Asp Leu Arg Glu Asn Tyr Cys Arg Asn Pro Asp Gly Ala Glu Ser Pro
        290                 295                 300

Trp Cys Phe Thr Thr Asp Pro Asn Ile Arg Val Gly Tyr Cys Ser Gln
305                 310                 315                 320

Ile Pro Lys Cys Asp Val Ser Ser Gly Gln Asp Cys Tyr Arg Gly Asn
                325                 330                 335

Gly Lys Asn Tyr Met Gly Asn Leu Ser Lys Thr Arg Ser Gly Leu Thr
            340                 345                 350

Cys Ser Met Trp Asp Lys Asn Met Glu Asp Leu His Arg His Ile Phe
        355                 360                 365

Trp Glu Pro Asp Ala Ser Lys Leu Asn Lys Asn Tyr Cys Arg Asn Pro
        370                 375                 380

Asp Asp Asp Ala His Gly Pro Trp Cys Tyr Thr Gly Asn Pro Leu Ile
385                 390                 395                 400

Pro Trp Asp Tyr Cys Pro Ile Ser Arg Cys Glu Gly Asp Thr Thr Pro
                405                 410                 415

Thr Ile Val Asn Leu Asp His Pro Val Ile Ser Cys Ala Lys Thr Lys
            420                 425                 430

Gln Leu Arg Val Val Asn Gly Ile Pro Thr Gln Thr Thr Val Gly Trp
        435                 440                 445

Met Val Ser Leu Arg Tyr Arg Asn Lys His Ile Cys Gly Gly Ser Leu
        450                 455                 460

Ile Lys Glu Ser Trp Val Leu Thr Ala Arg Gln Cys Phe Pro Ser Arg
465                 470                 475                 480

Asp Leu Lys Asp Tyr Glu Ala Trp Leu Gly Ile His Asp Val His Gly
                485                 490                 495

Arg Gly Asp Glu Lys Cys Lys Gln Val Leu Asn Val Ser Gln Leu Val
            500                 505                 510

Tyr Gly Pro Glu Gly Ser Asp Leu Val Leu Met Lys Leu Ala Arg Pro
        515                 520                 525

Ala Ile Leu Asp Asn Phe Val Ser Thr Ile Asp Leu Pro Ser Tyr Gly
        530                 535                 540

Cys Thr Ile Pro Glu Lys Thr Thr Cys Ser Ile Tyr Gly Trp Gly Tyr
545                 550                 555                 560

Thr Gly Leu Ile Asn Ala Asp Gly Leu Leu Arg Val Ala His Leu Tyr
                565                 570                 575

Ile Met Gly Asn Glu Lys Cys Ser Gln His His Gln Gly Lys Val Thr
            580                 585                 590

Leu Asn Glu Ser Glu Leu Cys Ala Gly Ala Glu Lys Ile Gly Ser Gly
        595                 600                 605

Pro Cys Glu Gly Asp Tyr Gly Gly Pro Leu Ile Cys Glu Gln His Lys
        610                 615                 620

Met Arg Met Val Leu Gly Val Ile Val Pro Gly Arg Gly Cys Ala Ile
625                 630                 635                 640

Pro Asn Arg Pro Gly Ile Phe Val Arg Val Ala Tyr Tyr Ala Lys Trp
                645                 650                 655

Ile His Lys Val Ile Leu Thr Tyr Lys Leu Cys Gly Arg His His His
            660                 665                 670

His His His
        675
```

HEPATOCYTE GROWTH FACTOR (HGF) BINDING PROTEINS

RELATED APPLICATIONS

This application is a divisional of U.S. patent application Ser. No. 13/051,481, filed Mar. 18, 2011, now U.S. Pat. No. 8,273,355, which is a divisional of U.S. patent application Ser. No. 12/632,765, filed Dec. 7, 2009, now U.S. Pat. No. 7,943,344, which is a divisional of U.S. patent application Ser. No. 11/757,059, filed Jun. 1, 2007, now U.S. Pat. No. 7,649,083, which claims the benefit of and priority to U.S. Provisional Application Nos. 60/810,714, filed Jun. 2, 2006, and 60/860,509, filed Nov. 21, 2006, the entire disclosures of which are incorporated by reference herein.

SEQUENCE LISTING

The instant application contains a Sequence Listing which has been submitted in ASCII format via EFS-Web and is hereby incorporated by reference in its entirety. Said ASCII copy, created on Mar. 28, 2013, is named AVO-001BDV3 SL.txt and is 285,675 bytes in size.

FIELD OF THE INVENTION

The field of the invention is molecular biology, immunology and oncology. More particularly, the field is antibody-based binding proteins that bind human hepatocyte growth factor (HGF).

BACKGROUND

Hepatocyte Growth Factor (HGF), also known as Scatter Factor (SF), is a multi-functional heterodimeric protein produced predominantly by mesenchymal cells, and is an effector of cells expressing the Met tyrosine kinase receptor (Bottaro et al. (1991) SCIENCE 251: 802-804, Rubin et al. (1993) BIOCHIM. BIOPHYS. ACTA 1155: 357-371). The human Met receptor is also known as "c-Met." Mature HGF contains two polypeptide chains, the α-chain and the β-chain. Published studies suggest it is the α-chain that contains HGF's c-Met receptor binding domain.

When it binds to its cognate receptor, HGF mediates a number of cellular activities. The HGF-Met signaling pathway plays a role in liver regeneration, wound healing, neural regeneration, angiogenesis and malignancies. See, e.g., Cao et al. (2001) PROC. NATL. ACAD. SCI. USA 98: 7443-7448, Burgess et al. (2006) CANCER RES. 66: 1721-1729, and U.S. Pat. Nos. 5,997,868 and 5,707,624. Investigators have been developing a number of HGF modulators, including antibodies, to treat various disorders that involve HGF activity, for example, certain HGF responsive cancers. See, e.g., International Application Publication No. WO 2005/017107.

The basic structure common to all antibodies is shown schematically in FIG. 1. Antibodies are multimeric proteins that contain four polypeptide chains. Two of the polypeptide chains are called heavy or H chains and two of the polypeptide chains are called light or L chains. The immunoglobulin heavy and light chains are connected by an interchain disulfide bond. The immunoglobulin heavy chains are connected by a number of interchain disulfide bonds. A light chain is composed of one variable region ($V_L$ in FIG. 1) and one constant region ($C_L$ in FIG. 1), while the heavy chain is composed of one variable region ($V_H$ in FIG. 1) and at least three constant regions ($CH_1$, $CH_2$ and $CH_3$ in FIG. 1). The variable regions determine the specificity of the antibody and the constant regions have other functions.

Amino acid and structural information indicate that each variable region comprises three hypervariable regions (also known as complementarity determining regions or CDRs) flanked by four relatively conserved framework regions or FRs. The three CDRs, referred to as $CDR_1$, $CDR_2$, and $CDR_3$, are responsible for the binding specificity of individual antibodies. When antibodies are to be used as diagnostic and therapeutic agents, typically it is desirable to create antibodies that have the highest binding specificity and affinity to the target molecule. It is believed that differences in the variable regions can have profound effects on the specificity and affinity of the antibody.

U.S. Pat. No. 5,707,624 describes the use of anti-HGF antibodies in the treatment of Kaposi's sarcoma. Similarly, U.S. Pat. No. 5,997,868 describes treating a tumor by administering an anti-HGF antibody to the patient to be treated so as to block the ability of endogeneous HGF to promote angiogenesis in the tumor. More recently, investigators propose that antibodies that bind the β-chain of HGF may have potential as therapeutic agents in patients with HGF-dependent tumors (Burgess (2006) supra).

Notwithstanding, there is still a need for additional HGF modulators that can be used as therapeutic and diagnostic agents.

SUMMARY OF THE INVENTION

The invention is based, in part, upon the discovery of a family of binding proteins that specifically bind HGF, in particular, human HGF. The binding proteins are antibody-based in so far as they contain antigen (i.e., HGF) binding sites based on the CDRs of a family of antibodies that specifically bind HGF. The CDRs confer the binding specificity of the binding proteins to HGF. The binding proteins can be used as diagnostic and therapeutic agents. When used as a therapeutic agent, the binding proteins are engineered (e.g., humanized) so as to reduce or eliminate the risk of inducing an immune response against the binding protein when administered to the recipient (e.g., a human).

The binding proteins neutralize the activity of HGF and, therefore, can be used as a therapeutic agent. In certain embodiments, the binding proteins prevent HGF from binding to its cognate receptor, c-Met, thereby neutralizing HGF activity. In other embodiments, the binding proteins bind to HGF and neutralize its biological activity but without preventing HGF from binding to the c-Met receptor. Because HGF has been implicated in the growth and proliferation of cancer cells, the binding proteins can be used to inhibit the proliferation of cancer cells. Furthermore, when administered to a mammal, the binding proteins can inhibit or reduce tumor growth in the mammal.

These and other aspects and advantages of the invention will become apparent upon consideration of the following figures, detailed description, and claims.

DESCRIPTION OF THE DRAWINGS

The invention can be more completely understood with reference to the following drawings.

FIG. 2 is a schematic diagram showing the amino acid sequence defining the complete immunoglobulin heavy chain variable region of the antibodies denoted as 1A3, 1D3, 1F3, 2B8, 2F8, 3A12, 3B6 and 3D11. The amino acid sequences for each antibody are aligned against one another and the regions defining the signal peptide, $CDR_1$, $CDR_2$, and $CDR_3$ are identified in boxes. The unboxed sequences represent FR sequences.

FIG. 3 is a schematic diagram showing the $CDR_1$, $CDR_2$, and $CDR_3$ sequences for each of the immunoglobulin heavy chain variable region sequences presented in FIG. 2.

FIG. 4 is a schematic diagram showing the amino acid sequence defining the complete immunoglobulin light chain variable region of the antibodies 1A3, 1D3, 1F3, 2B8, 2F8, 3A12, 3B6, and 3D11. The amino acid sequences for each antibody are aligned against one another and the regions defining the signal peptide, $CDR_1$, $CDR_2$, and $CDR_3$ are identified in boxes. The unboxed sequences represent FR sequences.

FIG. 5 is a schematic diagram showing the $CDR_1$, $CDR_2$, and $CDR_3$ sequences for each of the immunoglobulin light chain variable region sequences presented in FIG. 4.

FIG. 8 is a table summarizing surface plasmon resonance data on antigen-binding affinity and kinetics of interaction between human HGF and chimeric, chimeric/humanized, or humanized 2B8 antibodies. The table lists the pairs of Kappa light chain and IgG1 heavy chain tested. Those antibodies with standard deviations (STDEV) listed were analyzed in three independent experiments.

DETAILED DESCRIPTION OF THE INVENTION

Figure 1:
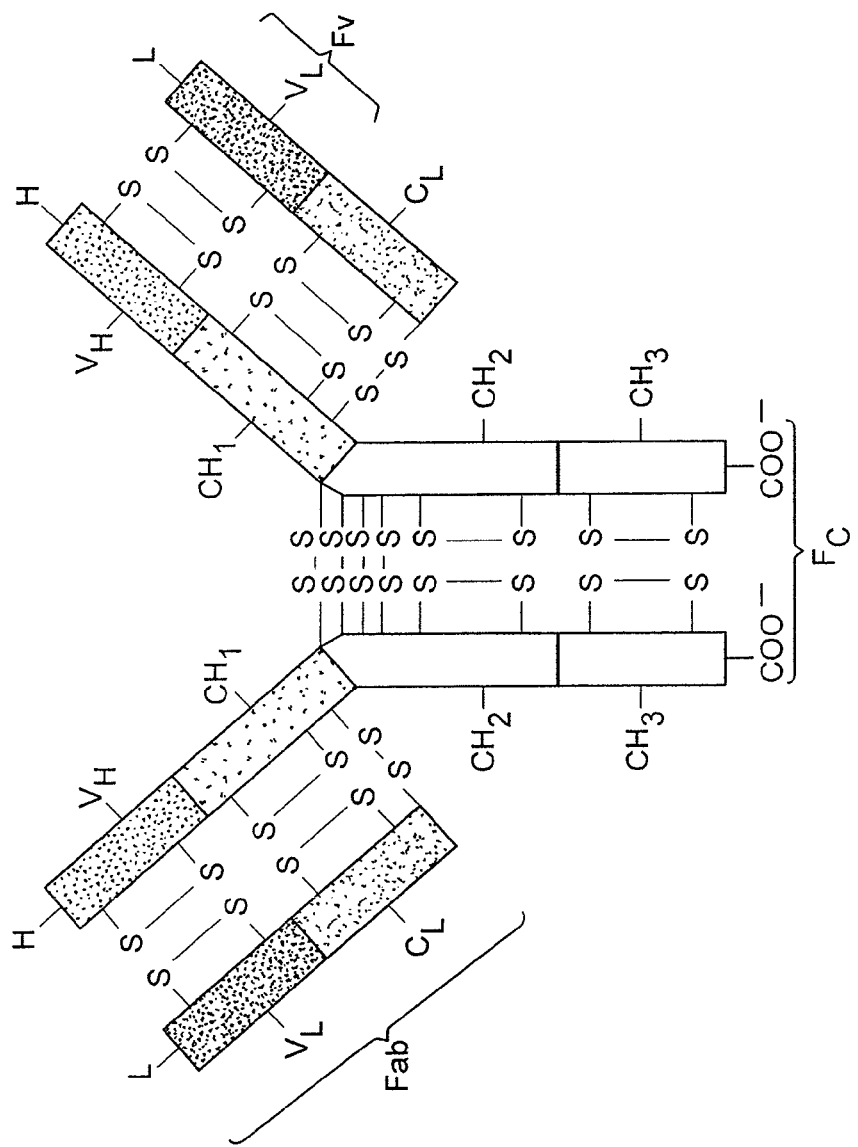
FIG. 1 is a schematic representation of a typical antibody.

The invention is based, in part, upon the discovery of a family of binding proteins that specifically bind, and neutralize the activity of, HGF, in particular, human HGF. The binding proteins can be used in a variety of diagnostic and therapeutic applications. The binding proteins are based upon the antigen binding sites of certain monoclonal antibodies that have been selected for their ability to bind, and neutralize the activity of, HGF. In particular, the binding proteins contain immunoglobulin variable region CDR sequences that together define a binding site for HGF.

In view of the neutralizing activity of these antibodies, they are particularly useful in modulating the growth and/or pro-liferation of HGF responsive cells, for example, cancer cells. When used as a therapeutic agent, the binding proteins can be engineered so as to minimize or eliminate the risk of inducing an immune response against the binding proteins when administered to the recipient. Furthermore, depending upon the particular application, it is contemplated that the binding proteins can be conjugated to other moieties, for example, detectable labels, for example, radiolabels, and effector molecules, for example, other protein and small molecule-based therapeutics. Each of these features and aspects of the invention are discussed in more detail below.

I—Binding Proteins That Bind HGF

In one aspect, the invention provides an isolated binding protein that binds human HGF. The binding protein comprises (i) an immunoglobulin light chain variable region comprising the structure $CDR_{L1}$-$CDR_{L2}$-$CDR_{L3}$, and (ii) an immunoglobulin heavy chain variable region comprising three complementarity determining regions (CDRs), wherein the immunoglobulin light chain variable region and the immunoglobulin heavy chain variable region together define a single binding site for binding human HGF. $CDR_{L1}$ comprises the amino acid sequence $X_1$ $X_2$ Ser $X_4$ $X_5$ $X_6$ $X_7$ $X_8$ $X_9$ $X_{10}$ $X_{11}$ $X_{12}$ $X_{13}$ $X_{14}$ $X_{15}$, wherein amino acid $X_1$ is Arg, Lys, or Ser, $X_2$ is Ala or Thr, $X_4$ is Glu, Gln, or Ser, $X_5$ is Asn, Asp, or Ser, $X_6$ is Ile or Val, $X_7$ is Asp, Lys, Ser, Val, or Tyr, $X_8$ is a peptide bond or Tyr, $X_9$ is a peptide bond or Asp, $X_{10}$ is a peptide bond or Gly, $X_{11}$ is a peptide bond or Asn, $X_{12}$ is a peptide bond, Ile, or Ser, $X_{13}$ is Asn or Tyr, $X_{14}$ is Ile, Leu, Met, or Val, $X_{15}$ is Ala, Asn, His, or Ser. $CDR_{L2}$ comprises the amino acid sequence $X_{16}$ $X_{17}$ $X_{18}$ $X_{19}$ $X_{20}$ $X_{21}$ $X_{22}$, wherein amino acid $X_{16}$ is Ala, Asp, Arg, Gly, or Val, $X_{17}$ is Ala, Thr, or Val, $X_{18}$ is Asn, Ser, or Thr, $X_{19}$ is Arg, Asn, Lys, or His, $X_{20}$ is Leu or Arg, $X_{21}$ is Ala, Asn, Glu, Val, or Pro, $X_{22}$ is Asp, Ser, or Thr. $CDR_{L3}$ comprises the amino acid sequence $X_{23}$ $X_{24}$ $X_{25}$ $X_{26}$ $X_{27}$ $X_{28}$ Pro $X_{30}$ Thr, wherein amino acid $X_{23}$ is Leu, Gly, or Gln, $X_{24}$ is His or Gln, $X_{25}$ is Phe, Ser, Trp, or Tyr, $X_{26}$ is Asp, Ile, Ser, Trp, or Tyr, $X_{27}$ is Gly, Glu, Asn, or Ser, $X_{28}$ is Asp, Asn, Phe, Thr, or Tyr, $X_{30}$ is Leu, Phe, Pro, or Tyr.

In another aspect, the invention provides an isolated binding protein that binds human HGF comprising (i) an immunoglobulin heavy chain variable region comprising the structure $CDR_{H1}$-$CDR_{H2}$-$CDR_{H3}$ and (ii) an immunoglobulin light chain variable region comprising three complementarity determining regions (CDRs), wherein the immunoglobulin heavy chain variable region and the immunoglobulin light chain variable region together define a single binding site for binding human HGF. $CDR_{H1}$ comprises the amino acid sequence $X_1$ Tyr $X_3$ $X_4$ $X_5$, wherein amino acid $X_1$ is Asp, Asn, Ser, or Thr, $X_3$ is Phe, Ser, Trp, or Tyr, $X_4$ is Ile, Leu, or Met, $X_5$ is Asn, His, or Ser. $CDR_{H2}$ comprises the amino acid sequence $X_6$ Ile $X_8$ $X_9$ $X_{10}$ $X_{11}$ Gly $X_{13}$ $X_{14}$ $X_{15}$ Tyr $X_{17}$ $X_{18}$ $X_{19}$ $X_{20}$ $X_{21}$ $X_{22}$, wherein amino acid $X_6$ is Lys, Gln, Glu, Val, or Tyr, $X_8$ is Asn, Gly, Ser, Trp, or Tyr, $X_9$ is Ala, Pro or Ser, $X_{10}$ is Gly or Thr, $X_{11}$ is a peptide bond, Asp, Asn, Gly, or Ser, $X_{13}$ is Asp, Asn, His, or Ser, $X_{14}$ is Ser or Thr, $X_{15}$ is Asn or Tyr, $X_{17}$ is Asn or Pro, $X_{18}$ is Ala, Asp, Gly, Gln, Glu, Pro, or Ser, $X_{19}$ is Asn, Lys, Met, or Ser, $X_{20}$ is Leu, Phe or Val, $X_{21}$ is Lys, Met, or Gln, $X_{22}$ is Asp, Gly or Ser. $CDR_{H3}$ comprises the amino acid sequence $X_{23}$ $X_{24}$ $X_{25}$ $X_{26}$ $X_{27}$ $X_{28}$ $X_{29}$ $X_{30}$ $X_{31}$ $X_{32}$ $X_{33}$ $X_{34}$ Tyr, wherein amino acid $X_{23}$ is Arg, Asn, Gln, or Glu, $X_{24}$ is Gly, Leu, Arg, or Tyr, $X_{25}$ is a peptide bond, Asp, or Gly, $X_{26}$ is a peptide bond or Gly, $X_{27}$ is a peptide bond or Tyr, $X_{28}$ is a peptide bond, Leu, or Tyr, $X_{29}$ is a peptide bond, Gly, Leu, Arg, or Val, $X_{30}$ is a peptide bond, Asp, Gly, or Glu, $X_{31}$ is a peptide bond, Asn, Arg, Ser, or Tyr, $X_{32}$ is peptide bond, Ala, Gly, Ile, or Tyr, $X_{33}$ is Met or Phe, $X_{34}$ is Ala or Asp.

It is understood that the binding protein can comprise both the immunoglobulin light chain and the immunoglobulin heavy chain sequences or the fragments thereof, noted above. Furthermore, it is understood that the binding protein can be an intact antibody or an antigen binding fragment thereof, or a biosynthetic antibody site.

In certain embodiments, the CDR sequences of the immunoglobulin light chain and the immunoglobulin heavy chain are interposed with framework regions (FR).

In certain other embodiments, the CDR sequences of the immunoglobulin light chain and the immunoglobulin heavy chain are interposed between human or humanized framework regions.

In another aspect, the invention provides an isolated binding protein that specifically binds human HGF. The binding protein comprises: (a) an immunoglobulin light chain variable region comprising the structure $CDR_{L1}$-$CDR_{L2}$-$CDR_{L3}$ and (b) immunoglobulin heavy chain variable region, wherein the immunoglobulin light chain variable region and the immunoglobulin heavy chain variable region together define a single binding site for binding human HGF. The $CDR_{L1}$ comprises a sequence selected from the group consisting of SEQ ID NO. 8 (1A3), SEQ ID NO. 18 (2B8), SEQ ID NO. 28 (2F8), SEQ ID NO. 38 (3B6), SEQ ID NO. 48 (3D11), SEQ ID NO. 58 (1D3), SEQ ID NO. 68 (1F3), and SEQ ID NO. 78 (3A12). The $CDR_{L2}$ comprises a sequence selected from the group consisting of SEQ ID NO. 9 (1A3), SEQ ID NO. 19 (2B8), SEQ ID NO. 29 (2F8), SEQ ID NO. 39 (3B6), SEQ ID NO. 49 (3D11), SEQ ID NO. 59 (1D3), SEQ ID NO. 69 (1F3), SEQ ID NO. 79 (3A12) and SEQ ID NO. 206 (LRMR2B8LC). The $CDR_{L3}$ comprises a sequence selected from the group consisting of SEQ ID NO. 10 (1A3), SEQ ID NO. 20 (2B8), SEQ ID NO. 30 (2F8), SEQ ID NO. 40 (3B6), SEQ ID NO. 50 (3D11), SEQ ID NO. 60 (1D3), SEQ ID NO. 70 (1F3), and SEQ ID NO. 80 (3A12). Throughout the specification and claims, the sequences denoted by a particular SEQ ID NO. are followed in parentheses by the antibody that was the origin of the particular sequence. By way of example, SEQ ID NO. 8 (1A3) indicates that the sequence of SEQ ID NO. 8 is based upon the sequence present in antibody 1A3.

In one embodiment, the binding protein comprises an immunoglobulin light chain variable region comprising a $CDR_{L1}$ comprising the sequence of SEQ ID NO. 8 (1A3), a $CDR_{L2}$ comprising the sequence of SEQ ID NO. 9 (1A3), and a $CDR_{L3}$ comprising the sequence of SEQ ID NO. 10 (1A3).

In another embodiment, the binding protein comprises an immunoglobulin light chain variable region comprising a $CDR_{L1}$ comprising the sequence of SEQ ID NO. 18 (2B8), a $CDR_{L2}$ comprising the sequence of SEQ ID NO. 19 (2B8) or SEQ ID NO. 206 (LRMR2B8LC), and a $CDR_{L3}$ comprising the sequence of SEQ ID NO. 20 (2B8).

In another embodiment, the binding protein comprises an immunoglobulin light chain variable region comprising a $CDR_{L1}$ comprising the sequence of SEQ ID NO. 28 (2F8), a $CDR_{L2}$ comprising the sequence of SEQ ID NO. 29 (2F8), and a $CDR_{L3}$ comprising the sequence of SEQ ID NO. 30 (2F8).

In another embodiment, the binding protein comprises an immunoglobulin light chain variable region comprising a $CDR_{L1}$ comprising the sequence of SEQ ID NO. 38 (3B6), a $CDR_{L2}$ comprising the sequence of SEQ ID NO. 39 (3B6), and a $CDR_{L3}$ comprising the sequence of SEQ ID NO. 40 (3B6).

In another embodiment, the binding protein comprises an immunoglobulin light chain variable region comprising a $CDR_{L1}$ comprising the sequence of SEQ ID NO. 48 (3D11), a $CDR_{L2}$ comprising the sequence of SEQ ID NO. 49 (3D11), and a $CDR_{L3}$ comprising the sequence of SEQ ID NO. 50 (3D11).

In another embodiment, the binding protein comprises an immunoglobulin light chain variable region comprising a $CDR_{L1}$ comprising the sequence of SEQ ID NO. 58 (1D3), a $CDR_{L2}$ comprising the sequence of SEQ ID NO. 59 (1D3), and a $CDR_{L3}$ comprising the sequence of SEQ ID NO. 60 (1D3).

In another embodiment, the binding protein comprises an immunoglobulin light chain variable region comprising a $CDR_{L1}$ comprising the sequence of SEQ ID NO. 68 (1F3), a $CDR_{L2}$ comprising the sequence of SEQ ID NO. 69 (1F3), and a $CDR_{L3}$ comprising the sequence of SEQ ID NO. 70 (1F3).

In another embodiment, the binding protein comprises an immunoglobulin light chain variable region comprising a $CDR_{L1}$ comprising the sequence of SEQ ID NO. 78 (3A12), a $CDR_{L2}$ comprising the sequence of SEQ ID NO. 79 (3A12), and a $CDR_{L3}$ comprising the sequence of SEQ ID NO. 80 (3A12).

In each of the foregoing embodiments, the $CDR_{L1}$, $CDR_{L2}$, and $CDR_{L3}$ sequences preferably are interposed between human or humanized immunoglobulin FRs. It is understood that the binding protein can be an intact antibody, an antigen binding fragment thereof, or a biosynthetic antibody site.

In another aspect, the invention provides an isolated binding protein that binds human HGF. The binding protein comprises (a) an immunoglobulin heavy chain variable region comprising the structure $CDR_{H1}$-$CDR_{H2}$-$CDR_{H3}$, and (b) an immunoglobulin light chain variable region, wherein the immunoglobulin heavy chain variable region and the immunoglobulin light chain variable region together define a single binding site for binding human HGF. The $CDR_{Hn}$ comprises a sequence selected from the group consisting of SEQ ID NO. 5 (1A3), SEQ ID NO. (2B8), SEQ ID NO. 25 (2F8), SEQ ID NO. 35 (3B6), SEQ ID NO. 45 (3D11), SEQ ID NO. 55 (1D3), SEQ ID NO. 65 (1F3), and SEQ ID NO. 75 (3A12); the $CDR_{H2}$ comprises a sequence selected from the group consisting of SEQ ID NO. 6 (1A3), SEQ ID NO. 16 (2B8), SEQ ID NO. 26 (2F8), SEQ ID NO. 36 (3B6), SEQ ID NO. 46 (3D11), SEQ ID NO. 56 (1D3), SEQ ID NO. 66 (1F3), SEQ ID NO. 76 (3A12), SEQ ID NO. 202 (Hu2B8 Hv1f.1), SEQ ID NO. 203 (Hu2B8 Hv5a.1 or Hu2B8 Hv5-51.1), SEQ ID NO. 204 (LR₂B8HC) and SEQ ID NO. 205 (LRMR₂B8HC); and the $CDR_{H3}$ comprises a sequence selected from the group consisting of SEQ ID NO. 7 (1A3), SEQ ID NO. 17 (2B8), SEQ ID NO. 27 (2F8), SEQ ID NO. 37 (3B6), SEQ ID NO. 47 (3D11), SEQ ID NO. 57 (1D3), SEQ ID NO. 67 (1F3), and SEQ ID NO. 77 (3A12).

In one embodiment, the binding protein comprises an immunoglobulin heavy chain variable region comprising: a $CDR_{H1}$ comprising the sequence of SEQ ID NO. 5 (1A3); a $CDR_{H2}$ comprising the sequence of SEQ ID NO. 6 (1A3); and a $CDR_{H3}$ comprising the sequence of SEQ ID NO. 7 (1A3).

In another embodiment, the binding protein comprises an immunoglobulin heavy chain variable region comprising: a $CDR_{H1}$ comprising the sequence of SEQ ID NO. 15 (2B8); a $CDR_{H2}$ comprising the sequence of SEQ ID NO. 16 (2B8), SEQ ID NO. 202 (Hu2B8 Hv1f.1), SEQ ID NO. 203 (Hu2B8 Hv5a.1 or Hu2B8 Hv5-51.1), SEQ ID NO. 204 (LR2B8HC) or SEQ ID NO. 205 (LRMR2B8HC); and a $CDR_{H3}$ comprising the sequence of SEQ ID NO. 17 (2B8).

In another embodiment, the binding protein comprises an immunoglobulin heavy chain variable region comprising: a $CDR_{H1}$ comprising the sequence of SEQ ID NO. 25 (2F8); a CDR$_{H2}$ comprising the sequence of SEQ ID NO. 26 (2F8); and a CDR$_{H3}$ comprising the sequence of SEQ ID NO. 27 (2F8).

In another embodiment, the binding protein comprises an immunoglobulin heavy chain variable region comprising a CDR$_{H1}$ comprising the sequence of SEQ ID NO. 35 (3B6); a CDR$_{H2}$ comprising the sequence of SEQ ID NO. 36 (3B6); and a CDR$_{H3}$ comprising the sequence of SEQ ID NO. 37 (3B6).

In another embodiment, the binding protein comprises an immunoglobulin heavy chain variable region comprising: a CDR$_{H1}$ comprising the sequence of SEQ ID NO. 45 (3D11); a CDR$_{H2}$ comprising the sequence of SEQ ID NO. 46 (3D11); and a CDR$_{H3}$ comprising the sequence of SEQ ID NO. 47 (3D11).

In another embodiment, the binding protein comprises an immunoglobulin heavy chain variable region comprising: a CDR$_{H1}$ comprising the sequence of SEQ ID NO. 55 (1D3); a CDR$_{H2}$ comprising the sequence of SEQ ID NO. 56 (1D3); and a CDR$_{H3}$ comprising the sequence of SEQ ID NO. 57 (1D3).

In another embodiment, the binding protein comprises an immunoglobulin heavy chain variable region comprising: a CDR$_{H1}$ comprising the sequence of SEQ ID NO. 65 (1F3); a CDR$_{H2}$ comprising the sequence of SEQ ID NO. 66 (1F3); and a CDR$_{H3}$ comprising the sequence of SEQ ID NO. 67 (1F3).

In another embodiment, the binding protein comprises an immunoglobulin heavy chain variable region comprising: a CDR$_{H1}$ comprising the sequence of SEQ ID NO. 75 (3A12); CDR$_{H2}$ comprising the sequence of SEQ ID NO. 76 (3A12); and a CDR$_{H3}$ comprising the sequence of SEQ ID NO. 77 (3A12).

In each of the foregoing embodiments, the CDR$_{H1}$, CDR$_{H2}$, and CDR$_{H3}$ sequences preferably are interposed between human or humanized immunoglobulin FRs. It is understood that the binding protein can be an intact antibody, an antigen binding fragment thereof, or a biosynthetic antibody site.

In another aspect, the invention provides a binding protein that binds human HGF. The binding protein comprises an immunoglobulin heavy chain variable region selected from the group consisting of residues 20-141 of SEQ ID NO. 2 (1A3), residues 20-137 of SEQ ID NO. 12 (2B8), residues 20-137 of SEQ ID NO. 22 (2F8), residues 20-139 of SEQ ID NO. 32 (3B6), residues 20-132 of SEQ ID NO. 42 (3D11), residues 20-141 of SEQ ID NO. 52 (1D3), residues 20-141 of SEQ ID NO. 62 (1F3), and residues 20-141 of SEQ ID NO. 72 (3A12) and an immunoglobulin light chain variable region selected from the group consisting of residues 21-127 of SEQ ID NO. 4 (1A3), residues 21-127 of SEQ ID NO. 14 (2B8), residues 20-131 of SEQ ID NO. 24 (2F8), residues 23-129 of SEQ ID NO. 34 (3B6), residues 23-128 of SEQ ID NO. 44 (3D11), residues 21-127 of SEQ ID NO. 54 (1D3), residues 21-127 of SEQ ID NO. 64 (1F3), and residues 21-127 of SEQ ID NO. 74 (3A12).

In another embodiment, the binding protein comprises an immunoglobulin heavy chain variable region comprising the amino acid sequence of residues 20-141 of SEQ ID NO. 2 (1A3), and an immunoglobulin light chain variable region comprising the amino acid sequence of residues 21-127 of SEQ ID NO. 4 (1A3).

In one embodiment, the binding protein comprises an immunoglobulin heavy chain variable region comprising the amino acid sequence of residues 20-137 of SEQ ID NO. 12 (2B8), and an immunoglobulin light chain variable region comprising the amino acid sequence of residues 21-127 of SEQ ID NO. 14 (2B8).

In another embodiment, the binding protein comprises an immunoglobulin heavy chain variable region comprising the amino acid sequence of residues 20-137 of SEQ ID NO. 22 (2F8), and an immunoglobulin light chain variable region comprising the amino acid sequence of residues 20-131 of SEQ ID NO. 24 (2F8).

In another embodiment, the binding protein comprises an immunoglobulin heavy chain variable region comprising the amino acid sequence of residues 20-139 of SEQ ID NO. 32 (3B6), and an immunoglobulin light chain variable region comprising the amino acid sequence of residues 23-129 of SEQ ID NO. 34 (3B6).

In another embodiment, the binding protein comprises an immunoglobulin heavy chain variable region comprising the amino acid sequence of residues 20-132 of SEQ ID NO. 42 (3D11), and an immunoglobulin light chain variable region comprising the amino acid sequence of residues 23-128 of SEQ ID NO. 44 (3D11).

In another embodiment, the binding protein comprises an immunoglobulin heavy chain variable region comprising the amino acid sequence of residues 20-141 of SEQ ID NO. 52 (1D3), and an immunoglobulin light chain variable region comprising the amino acid sequence of residues 21-127 of SEQ ID NO. 54 (1D3).

In another embodiment, the binding protein comprises an immunoglobulin heavy chain variable region comprising the amino acid sequence of residues 20-141 of SEQ ID NO. 62 (1F3), and an immunoglobulin light chain variable region comprising the amino acid sequence of residues 21-127 of SEQ ID NO. 64 (1F3).

In another embodiment, the binding protein comprises an immunoglobulin heavy chain variable region comprising the amino acid sequence of residues 20-141 of SEQ ID NO. 72 (3A12), and an immunoglobulin light chain variable region comprising the amino acid sequence of residues 21-127 of SEQ ID NO. 74 (3A12).

In each of the foregoing embodiments, the binding protein can be an intact antibody, an antigen binding fragment thereof, or a biosynthetic antibody site.

In another aspect, the invention provides an isolated binding protein that binds human HGF. The binding protein comprises (i) an immunoglobulin light chain variable region selected from the group consisting of SEQ ID NO. 173 (Hu2B8 Kv1-39.1 light chain variable region), SEQ ID NO. 179 (Hu2B8 Kv3-15.1 light chain variable region), SEQ ID NO. 193 (LR2B8LC light chain variable region), and SEQ ID NO. 199 (LRMR2B8LC light chain variable region); and (ii) an immunoglobulin heavy chain variable region selected from the group consisting of SEQ ID NO. 159 (Hu2B8 Hv1f.1 heavy chain variable region), SEQ ID NO. 165 (Hu2B8 Hv5a.1 heavy chain variable region), SEQ ID NO. 169 (Hu2B8 Hv5-51.1 heavy chain variable region), SEQ ID NO. 183 (LR2B8HC heavy chain variable region), and SEQ ID NO. 189 (LRMR2B8LC light chain variable region). The binding protein can be an intact antibody, an antigen binding fragment thereof, or a biosynthetic antibody site.

In another aspect, the invention provides an isolated binding protein that binds human HGF. The binding protein comprises (i) an immunoglobulin light chain selected from the group consisting of SEQ ID NO. 177 (Hu2B8 Kv1-39.1+kappa constant (Km(3) allotype (allele 2)), SEQ ID NO. 181 (Hu2B8 Kv3-15.1+Kappa constant (Km(3) allotype (allele 2)), SEQ ID NO. 197 (LR2B8LC+Kappa constant (Km(3) allotype (allele 1)), and SEQ ID NO. 201 (LRMR2B8LC+

Kappa constant (Km(3) allotype (allele 1)); and (ii) an immunoglobulin heavy chain selected from the group consisting of SEQ ID NO. 163 (Hu2B8 Hv1f.1+IgG1 Constant (G1m(17,1) allotype)), SEQ ID NO. 167 (Hu2B8 Hv5a.1+IgG1 Constant (G1m(17,1) allotype)), SEQ ID NO. 171 (Hu2B8 Hv5-51.1+IgG1 Constant (G1m(17,1) allotype)), SEQ ID NO. 187 (LR2B8HC+IgG1 Constant (G1m(3) allotype) (allele 1)), and SEQ ID NO. 191 (LRMR2B8HC IgG1 Constant (G1m (3) allotype) (allele 1)). The binding protein can be an intact antibody, an antigen binding fragment thereof, or a biosynthetic antibody site.

In another aspect, the invention provides an isolated binding protein that binds reduced human HGF. The binding protein comprises (i) an immunoglobulin light chain variable region comprising three CDRs, and (ii) an immunoglobulin heavy chain variable region comprising three CDRs. The CDRs typically are interposed between FRs. The CDRs of the immunoglobulin light chain and the immunoglobulin heavy chain together define a binding site that binds reduced human HGF, for example, the α-chain of reduced HGF. Reduced HGF refers to HGF treated with an amount of reducing agent, for example, dithiothreitol (DTT), 2-mercaptoethanol, or glutathione sufficient to reduce the disulfide linkage between the α-chain and the β-chain. Exemplary concentrations include, for example, 100 mM DTT and 5% 2-mercaptoethanol.

In certain embodiments, the binding protein comprises an immunoglobulin light chain variable region comprising at least one CDR selected from the group consisting of $CDR_{L1}$, $CDR_{L2}$ and $CDR_{L3}$. Optionally, the binding protein comprises two CDRs, for example, $CDR_{L1}$ and $CDR_{L2}$, or $CDR_{L1}$ and $CDR_{L3}$, or $CDR_{L1}$ and $CDR_{L3}$. Optionally, the binding protein comprises all three CDRs, i.e., $CDR_{L1}$, $CDR_{L2}$ and $CDR_{L3}$. $CDR_{L1}$ comprises the amino acid sequence $X_1 X_2$ Ser $X_4 X_5 X_6 X_7 X_8 X_9 X_{10} X_{11} X_{12} X_{13} X_{14} X_{15}$, wherein amino acid $X_1$ is Arg or Lys, $X_2$ is Ala or Thr, $X_4$ is Glu or Gln, $X_5$ is Asn, Ser, or Asp, $X_6$ is Ile or Val, $X_7$ is Tyr, Asp, or Lys, $X_8$ is a peptide bond or Tyr, $X_9$ is a peptide bond or Asp, $X_{10}$ is a peptide bond or Gly, $X_{11}$ is a peptide bond or Asn, $X_{12}$ is a peptide bond or Ser, $X_{13}$ is Asn or Tyr, $X_{14}$ is Ile or Leu, $X_{15}$ is Ala, Asn, or Ser. $CDR_{L2}$ comprises the amino acid sequence $X_{16} X_{17} X_{18} X_{19}$ Leu $X_{21} X_{22}$, wherein amino acid $X_{16}$ is Ala, Asp, Val, or Arg, $X_{17}$ is Ala or Val, $X_{18}$ is Asn, Ser, or Thr, $X_{19}$ is Arg, Asn, or His, $X_{21}$ is Ala, Glu, Val, or Pro, $X_{22}$ is Asp or Ser. $CDR_{L3}$ comprises the amino acid sequence $X_{23} X_{24} X_{25} X_{26} X_{27} X_{28}$ Pro $X_{30}$ Thr, wherein amino acid $X_{23}$ is Leu or Gln, $X_{24}$ is H is or Gln, $X_{25}$ is Phe, Ser, or Tyr, $X_{26}$ is Asp, Ile, or Trp, $X_{27}$ is Gly or Glu, $X_{28}$ is Asp, Phe, or Thr, $X_{30}$ is Phe, Pro, or Tyr.

In another embodiment, the binding protein comprises an immunoglobulin heavy chain variable region comprising at least one CDR selected from the group consisting of $CDR_{H1}$, $CDR_{H2}$, and $CDR_{H3}$. Optionally, the binding protein comprises two CDRs, for example, $CDR_{H1}$ and $CDR_{H2}$, or $CDR_{H1}$ and $CDR_{H3}$, or $CDR_{H1}$ and $CDR_{H3}$. Optionally, the binding protein comprises all three CDRs, i.e., $CDR_{H1}$, $CDR_{H2}$ and $CDR_{H3}$. $CDR_{H1}$ comprises the amino acid sequence $X_1$ Tyr $X_3 X_4 X_5$, wherein amino acid $X_1$ is Asp, Asn, Ser, or Thr, $X_3$ is Phe, Trp, or Tyr, $X_4$ is Ile or Met, $X_5$ is Asn, His, or Ser. $CDR_{H2}$ comprises the amino acid sequence $X_6$ Ile $X_8 X_9$ Gly $X_{11}$ Gly $X_{13} X_{14} X_{15}$ Tyr $X_{17} X_{18} X_{19} X_{20}$ Lys $X_{22}$, wherein amino acid $X_6$ is Lys, Gln, or Tyr, $X_8$ is Gly, Ser, or Tyr, $X_9$ is Pro or Ser, $X_{11}$ is Asp, Gly, or Ser, $X_{13}$ is Asp or Ser, $X_{14}$ is Ser or Thr, $X_{15}$ is Asn or Tyr, $X_{17}$ is Asn or Pro, $X_{18}$ is Ala, Asp, Gly, or Glu, $X_{19}$ is Asn, Met, or Ser, $X_{20}$ is Phe or Val, $X_{22}$ is Asp or Gly. $CDR_{H3}$ comprises the amino acid sequence $X_{23} X_{24} X_{25} X_{26} X_{27} X_{28} X_{29} X_{30} X_{31} X_{32} X_{33}$ Asp Tyr, wherein amino acid $X_{23}$ is Arg or Gln, $X_{24}$ is Gly or Leu, $X_{25}$ is Asp, Gly, or a peptide bond, $X_{26}$ is Gly or a peptide bond, $X_{27}$ is a peptide bond or Tyr, $X_{28}$ is Leu, a peptide bond or Tyr, $X_{29}$ is a Gly, Arg or Leu, $X_{30}$ is Asp, Gly or Glu, $X_{31}$ is a Tyr, Arg or Asn, $X_{32}$ is Ala, Gly or Tyr, $X_{33}$ is Met or Phe.

It is understood that the binding protein can comprise both the immunoglobulin heavy chain and the immunoglobulin light chain sequences or the fragments thereof, noted above. Furthermore, it is understood that the binding protein can be an intact antibody or an antigen binding fragment thereof, or a biosynthetic antibody site.

In certain embodiments, the binding protein comprises an immunoglobulin light chain variable region comprising (i) a $CDR_{L1}$ having a sequence selected from the group consisting of SEQ ID NO. 8 (1A3), SEQ ID NO. 28 (2F8), SEQ ID NO. 38 (3B6), SEQ ID NO. 58 (1D3), and SEQ ID NO. 68 (1F3), (ii) a $CDR_{L2}$ having a sequence selected from the group consisting of SEQ ID NO. 9 (1A3), SEQ ID NO. 29 (2F8), SEQ ID NO. 39 (3B6), SEQ ID NO. 59 (1D3), and SEQ ID NO. 69 (1F3), and (iii) a $CDR_{L3}$ having a sequence selected from the group consisting of SEQ ID NO. 10 (1A3), SEQ ID NO. 30 (2F8), SEQ ID NO. 40 (3B6), SEQ ID NO. 60 (1D3), and SEQ ID NO. 70 (1F3). The CDR sequences can be interposed between human or humanized FRs. In other embodiments, the binding protein comprises an immunoglobulin light chain variable region comprising an amino acid sequence selected from the group consisting of residues 21-127 of SEQ ID NO. 4 (1A3), residues 20-131 of SEQ ID NO. 24 (2F8), residues 23-129 of SEQ ID NO. 34 (3B6), residues 21-127 of SEQ ID NO. 54 (1D3), and residues 21-127 of SEQ ID NO. 64 (1F3).

In certain other embodiments, the binding protein comprises an immunoglobulin heavy chain variable region comprising (i) a $CDR_{H1}$ having a sequence selected from the group consisting of SEQ ID NO. 5 (1A3), SEQ ID NO. 25 (2F8), SEQ ID NO. 35 (3B6), SEQ ID NO. 55 (1D3), and SEQ ID NO. 65 (1F3), (ii) a $CDR_{H2}$ having a sequence selected from the group consisting of SEQ ID NO. 6 (1A3), SEQ ID NO. 26 (2F8), SEQ ID NO. 36 (3B6), SEQ ID NO. 56 (1D3), and SEQ ID NO. 66 (1F3), and (iii) a $CDR_{H3}$ having a sequence selected from the group consisting of SEQ ID NO. 7 (1A3), SEQ ID NO. 27 (2F8), SEQ ID NO. 37 (3B6), SEQ ID NO. 57 (1D3), and SEQ ID NO. 67 (1F3). The CDR sequences can be interposed between human or humanized FRs. In another embodiment, the immunoglobulin heavy chain variable region comprises an amino acid sequence selected from the group consisting of residues 20-141 of SEQ ID NO. 2 (1A3), residues 20-137 of SEQ ID NO. 22 (2F8), residues 20-139 of SEQ ID NO. 32 (3B6), residues 20-141 of SEQ ID NO. 52 (1D3), and residues 20-141 of SEQ ID NO. 62 (1F3).

In another aspect, the invention provides an isolated binding protein that binds human HGF and comprises an immunoglobulin light chain variable region and an immunoglobulin heavy chain variable region. The isolated binding protein competes for binding to HGF with at least one reference antibody selected from the group consisting of (i) an antibody having an immunoglobulin light chain variable region of residues 20-131 of SEQ ID NO. 24 (2F8), and an immunoglobulin heavy chain variable region of residues 20-137 of SEQ ID NO. 22 (2F8), (ii) an antibody having an immunoglobulin light chain variable region of residues 23-129 of SEQ ID NO. 34 (3B6), and an immunoglobulin heavy chain variable region of residues 20-139 of SEQ ID NO. 32 (3B6), and (iii) an antibody having an immunoglobulin light chain variable region of residues 23-128 of SEQ ID NO. 44 (3D11), and an immunoglobulin heavy chain variable region of residues 20-132 of SEQ ID NO. 42 (3D11). Under certain circumstances, the binding protein binds the same epitope of HGF as one of the reference antibodies.

It is understood that each of the binding proteins discussed above can be an intact antibody, for example, a monoclonal antibody. Alternatively, the binding protein can be an antigen binding fragment of an antibody, or can be a biosynthetic antibody binding site. Antibody fragments include Fab, Fab', $(Fab')_2$ or Fv fragments. Techniques for making such antibody fragments are known to those skilled in the art. A number of biosynthetic antibody binding sites are known in the art and include, for example, single Fv or sFv molecules, described, for example, in U.S. Pat. Nos. 5,476,786. Other biosynthetic antibody binding sites include bispecific or bifunctional binding proteins, for example, bispecific or bifunctional antibodies, which are antibodies or antibody fragments that bind at least two different antigens. For example, bispecific binding proteins can bind HGF, for example, human HGF, and another antigen of interest. Methods for making bispecific antibodies are known in art and, include, for example, by fusing hybridomas or by linking Fab' fragments. See, e.g., Songsivilai et al. (1990) CLIN. EXP. IMMUNOL. 79: 315-325; Kostelny et al. (1992) J. IMMUNOL. 148: 1547-1553.

The binding proteins of the invention can bind hHGF containing a cysteine to arginine substitution at position 561 or a glycine to glutamate substitution at position 555.

In another aspect, the invention provides an isolated binding protein that binds human HGF with a $k_d$ of $4.0\times10^{-5}$ $s^{-1}$ or lower, $3.0\times10^{-5}$ $s^{-1}$ or lower, or $2.0\times10^{-5}$ $s^{-1}$ or lower. The isolated binding proteins can bind human HGF with a $k_d$ from $5.0\times10^{-5}$ $s^{-1}$ to $0.5\times10^{-5}s^{-1}$, or from $4.0\times10^{-5}$ $s^{-1}$ to $1.0\times10^{-5}s^{-1}$, or from $3.0\times10^{-5}$ $s^{-1}$ to $1.5\times10^{-5}$ $s^{-1}$. In another aspect, the invention provides an isolated binding protein that binds human HGF with a $K_D$ of 100 pM or lower, or 20 pM or lower, or 10 pM or lower, or 5 pM or lower. The isolated binding proteins can bind human HGF with a $K_D$ from 100 pM to 5 pM, or from 20 pM to 5 pM, or from 15 pM to 10 pM, or from 20 pM to 10 pM, or from 15 pM to 5 pM. Unless otherwise specified, $K_D$ values are determined by the methods, and under the conditions, described in Example 6.

In another aspect, the invention provides an isolated binding protein that binds human HGF, wherein the antibody binds to human HGF with lower $K_D$ at 37° C. than at 25° C. The binding protein optionally binds human HGF with a $K_D$ less than 5 pM at 37° C.

In other aspects and embodiments, the binding proteins can inhibit hHGF from binding to c-Met. For example, the binding proteins can have an $IC_{50}$ (concentration at 50% of maximum inhibition) of at least about 4.0, 4.5, 5.0, 5.5, 6.0, 6.5, and 7.0 nM when assayed using the protocol described in Example 7(a). In certain other embodiments, the binding proteins can neutralize HGF BrdU incorporation in 4 MBr-5 cells (ATCC, Catalog No. CCL208) using the method described in Example 7(b).

The binding proteins have an $IC_{50}$ of 50 nM or lower, preferably 45, 40, 35, 30, 25, 20, 15, 10, 5, 1, 0.5 nM or lower, when assayed using the protocol described in Example 7(b). In certain other embodiments, the binding proteins can be used to inhibit HGF stimulated c-Met phosphorylation in PC-3 cells (ATCC, Manassus, Va. Catalog No. CRL-1435) using the assay described in Example 9. The binding proteins inhibit HGF-stimulated (1.25 nM) c-Met phosphorylation in PC-3 cells with an $IC_{50}$ of 2 nM or less (Table 8), using the assay described in Example 9.

II—Production of Binding Proteins

Binding proteins of the invention can be produced in various ways using approaches know in the art. For example, DNA molecules encoding light chain variable regions and heavy chain variable regions can be chemically synthesized, using a commercial synthesizer and sequence information provided herein. Such synthetic DNA molecules can be ligated to other appropriate nucleotide sequences, including, e.g., constant region coding sequences, and expression control sequences, to produce conventional gene expression constructs encoding the desired binding proteins. Production of defined gene constructs is within routine skill in the art. Alternatively, the sequences provided herein can be cloned out of hybridomas by conventional hybridization techniques or PCR techniques, using synthetic nucleic acid probes whose sequences are based on sequence information provided herein or prior art sequence information regarding genes encoding the heavy and light chains of murine antibodies in hybridoma cells. Production and use of such probes is within ordinary skill in the art.

The nucleic acids encoding the desired binding proteins can be introduced (ligated) into expression vectors, which can be introduced into a host cell via standard transfection or transformation techniques known in the art. Exemplary host cells include, for example, E. coli cells, Chinese hamster ovary (CHO) cells, HeLa cells, baby hamster kidney (BHK) cells, monkey kidney cells (COS), human hepatocellular carcinoma cells (e.g., Hep G2), and myeloma cells that do not otherwise produce immunoglobulin protein. Transfected host cells can be grown under conditions that permit the host cells to express the genes of interest, for example, the genes that encode the immunoglobulin light or heavy chain variable regions. The resulting expression products can be harvested using techniques known in the art.

The particular expression and purification conditions will vary depending upon what expression system is employed. For example, if the gene is to be expressed in E. coli, it is first cloned into an expression vector. This is accomplished by positioning the engineered gene downstream from a suitable bacterial promoter, e.g., Trp or Tac, and a signal sequence, e.g., a sequence encoding fragment B of protein A (FB). The resulting expressed fusion protein typically accumulates in refractile or inclusion bodies in the cytoplasm of the cells, and may be harvested after disruption of the cells by French press or sonication. The refractile bodies then are solubilized, and the expressed proteins refolded and cleaved by the methods already established for many other recombinant proteins.

If the engineered gene is to be expressed in eukayotic host cells, for example, myeloma cells or CHO cells, it is first inserted into an expression vector containing a suitable eukaryotic promoter, a secretion signal, immunoglobulin enhancers, and various introns. This expression vector optionally can contain sequences encoding all or part of a constant region, enabling an entire, or a part of, a heavy or light chain to be expressed. The gene construct can be transfected into myeloma cells or CHO cells using established transfection protocols. Such transfected cells can express $V_L$ or $V_H$ fragments, $V_L$-$V_H$ heterodimers, $V_H$-$V_L$ or $V_L$-$V_H$ single chain polypeptides, complete heavy or light immunoglobulin chains, or portions thereof, each of which may be attached to a protein domain having another function (e.g., cytotoxicity).

III—Modifications to the Binding Proteins

It is understood that the binding proteins can be modified to optimize performance depending upon the intended use of the binding proteins. For example, when the binding protein is being used as a therapeutic agent, the binding protein can be modified to reduce its immunogenicity in the intended recipient. Alternatively or in addition, the binding protein can be fused or coupled to another protein or peptide, for example, a growth factor, cytokine, or cytotoxin. Such modifications can be achieved by using routine gene manipulation techniques known in the art.

Various techniques for reducing the antigenicity of antibodies and antibody fragments are known in the art. These techniques can be used to reduce or eliminate the antigenicity of the binding proteins of the invention. For example, when the binding proteins are to be administered to a human, the binding proteins preferably are engineered to reduce their antigenicity in humans. This process often is referred to as humanization. Preferably, the humanized binding proteins have the same or substantially the same affinity for the antigen as the original non-humanized binding protein it was derived from.

In one well known humanization approach, chimeric proteins are created in which immunoglobulin constant regions of antibodies from one species, e.g., mouse, are replaced with immunoglobulin constant regions from a second, different species, e.g., a human. In this example, the resulting antibody is a mouse-human chimera, where the human constant region sequences, in principle, are less immunogenic than the counterpart murine sequences. This type of antibody engineering is described, for example, Morrison, et al. (1984) PROC. NAT. ACAD. SCI. 81: 6851-6855, Neuberger et al. (1984) NATURE 312: 604-608; U.S. Pat. Nos. 6,893,625 (Robinson); 5,500, 362 (Robinson); and 4,816,567 (Cabilly).

In another approach, known as CDR grafting, the CDRs of the light and heavy chain variable regions of an antibody of interest are grafted into frameworks (FRs) from another species. For example, murine CDRs can be grafted into human FR sequences. In some embodiments, the CDRs of the light and heavy chain variable regions of an anti-HGF antibody are grafted into human FRs or consensus human FRs. In order to create consensus human FRs, FRs from several human heavy chain or light chain amino acid sequences are aligned to identify a consensus amino acid sequence. CDR grafting is described, for example, in U.S. Pat. Nos. 7,022,500 (Queen); 6,982,321 (Winter); 6,180,370 (Queen); 6,054,297 (Carter); 5,693,762 (Queen); 5,859,205 (Adair); 5,693,761 (Queen); 5,565,332 (Hoogenboom); 5,585,089 (Queen); 5,530,101 (Queen); Jones et al. (1986) NATURE 321: 522-525; Riechmann et al. (1988) NATURE 332: 323-327; Verhoeyen et al. (1988) SCIENCE 239: 1534-1536; and Winter (1998) FEBS LETT 430: 92-94.

In an approach called "superhumanization," antibodies in which human immunogenicity is reduced or eliminated are created by an alternative form of grafting. In superhumanization, human FR sequences are chosen from a set of human germline genes based on the structural similarity of the human CDRs to those of the mouse antibody to be humanized. This approach is described, for example, in U.S. Pat. No. 6,881,557 (Foote) and in Tan et al. (2002) J. IMMUNOL 169: 1119-1125.

Other approaches to reduce immunogenicity include, techniques are known as "reshaping," "hyperchimerization," or "veneering/resurfacing" to produce humanized antibodies. See, e.g., Vaswami et al. (1998) ANNALS OF ALLERGY, ASTHMA, & IMMUNOL. 81: 105; Roguska et al. (1996) PROT. ENGINEER 9: 895-904; and U.S. Pat. No. 6,072,035 (Hardman). In the veneering/resurfacing approach, the surface accessible amino acid residues in the murine antibody are replaced by amino acid residues more frequently found at the same positions in a human antibody. This type of antibody resurfacing is described, for example, in U.S. Pat. No. 5,639,641 (Pedersen).

One exemplary approach for converting a mouse antibody into a form suitable for medical use in humans is known as ACTIVMAB™ technology (Vaccinex, Inc., Rochester, N.Y.), which involves a vaccinia virus-based vector to express antibodies in mammalian cells. High levels of combinatorial diversity of immunoglobulin heavy and light chains are said to be produced. See, e.g., U.S. Pat. Nos. 6,706,477 (Zauderer); 6,800,442 (Zauderer); and 6,872,518 (Zauderer).

Another exemplary approach for converting a mouse antibody into a form suitable for use in humans is technology practiced commercially by KaloBios Pharmaceuticals, Inc. (Palo Alto, Calif.). This technology involves the use of a proprietary human "acceptor" library to produce an "epitope focused" library for antibody selection.

Another exemplary approach for modifying a mouse antibody into a form suitable for medical use in humans is HUMAN ENGINEERING™ (HE™) technology, which is practiced commercially by XOMA (US) LLC. See, e.g., International Application Publication No. WO 93/11794 and U.S. Pat. Nos. 5,766,886; 5,770,196; 5,821,123; and 5,869, 619.

Any suitable approach, including any of the above approaches, can be used to reduce or eliminate human immunogenicity of a binding protein of interest.

In addition, it is possible to create fully human antibodies in mice. In this approach, human antibodies are prepared using a transgenic mouse in which the mouse's antibody-producing genes have been replaced by a substantial portion of the human antibody producing genes. Such mice produce human immunoglobulin instead of murine immunoglobulin molecules. See, e.g., WO 98/24893 (Jacobovitz et al.) and Mendez et al. (1997) NATURE GENETICS 15: 146-156. Fully human anti-HGF monoclonal antibodies can be produced using the following approach. Transgenic mice containing human immunoglobulin genes are immunized with the antigen of interest, e.g., HGF. Lymphatic cells from the mice then are obtained from the mice, which are then fused with a myeloid-type cell line to prepare immortal hybridoma cell lines. The hybridoma cell lines are screened and selected to identify hybridoma cell lines that produce antibodies specific to HGF.

Binding proteins of the invention can be conjugated with other molecules, depending upon their intended use. For example, if the binding protein is going to be used as a therapeutic, then the binding protein can be conjugated with another agent, for example, an effector molecule that modulates or otherwise promotes the therapy. To the extent that the effector is non-protein based agent, for example, a small molecule drug, a radiolabel or toxin, then, the agent can be chemically coupled to the binding protein using standard in vitro coupling chemistries. If, on the other hand, the effector molecule is a protein or peptide, for example, an enzyme, receptor, toxin, growth factor, cytokine or other immuno-modulator, then the binding protein can either be chemically coupled to the effector using in vitro coupling chemistries or can be coupled to the effector as a fusion protein. Fusion proteins can be constructed and expressed using the techniques similar to those discussed in section II.

IV—Use of Binding Proteins

The binding proteins described herein can be used as a diagnostic agent or a therapeutic agent.

(1) Therapeutic Applications

Because the binding proteins of the invention neutralize the activity of HGF, they can be used in various therapeutic applications. For example, certain binding proteins of the invention are useful in the prevention or treatment of hyperproliferative diseases or disorders, e.g., various forms of cancer.

The binding proteins can be used to inhibit or reduce the proliferation of tumor cells. In such an approach, the tumor cells are exposed to a therapeutically effective amount of the binding protein so as to inhibit or reduce proliferation of the tumor cell. In certain embodiments, the binding proteins inhibit tumor cell proliferation by at least 50%, 60%, 70%, 80%, 90%, 95% or 100%.

In certain embodiments, the binding protein is used to inhibit or reduce proliferation of a tumor cell wherein the binding protein reduces the ability of hHGF to bind to c-Met. In other embodiments, the binding protein is used to inhibit or reduce the proliferation of a tumor cell even when the binding protein binds hHGF but does not substantially inhibit hHGF binding to c-Met, as shown by antibody 3B6 in Tables 5 and 6.

In addition, the binding protein can be used to inhibit, or slow down tumor growth or development in a mammal. In such a method, an effective amount of the binding protein is administered to the mammal so as to inhibit or slow down tumor growth in the mammal. Accordingly, the binding proteins can be used to treat tumors, for example, in a mammal. The method comprises administering to the mammal a therapeutically effective amount of the binding protein. The binding protein can be administered alone or in combination with another pharmaceutically active molecule, so as to treat the tumor.

It is contemplated that the binding proteins of the invention can be used in the treatment of a variety of HGF responsive disorders, including, for example, HGF responsive tumor cells in lung cancer, breast cancer, colon cancer, prostate cancer, ovarian cancer, head and neck cancer, ovarian cancer, multiple myeloma, liver cancer, gastric cancer, esophageal cancer, kidney cancer, nasopharangeal cancer, pancreatic cancer, mesothelioma, melanoma and glioblastoma.

As used herein, "treat, "treating" and "treatment" refer to the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

Generally, a therapeutically effective amount of active component will be in the range of from about 0.1 mg/kg to about 100 mg/kg, optionally from about 1 mg/kg to about 100 mg/kg, optionally from about 1 mg/kg to 10 mg/kg. The amount administered will depend on variables such as the type and extent of disease or indication to be treated, the overall health status of the particular patient, the relative biological efficacy of the binding protein delivered, the formulation of the binding protein, the presence and types of excipients in the formulation, and the route of administration. The initial dosage administered may be increased beyond the upper level in order to rapidly achieve the desired blood-level or tissue level, or the initial dosage may be smaller than the optimum and the daily dosage may be progressively increased during the course of treatment depending on the particular situation. Human dosage can be optimized, e.g., in a conventional Phase I dose escalation study designed to run from 0.5 mg/kg to 20 mg/kg. Dosing frequency can vary, depending on factors such as route of administration, dosage amount and the disease condition being treated. Exemplary dosing frequencies are once per day, once per week and once every two weeks. A preferred route of administration is parenteral, e.g., intravenous infusion. Formulation of monoclonal antibody-based drugs is within ordinary skill in the art. In some embodiments of the invention, the binding protein, e.g., monoclonal antibody, is lyophilized and reconstituted in buffered saline at the time of administration.

The binding proteins may be administered either alone or in combination with other pharmaceutically active ingredients. The other active ingredients, e.g., immunomodulators, can be administered together with the binding protein, or can be administered before or after the binding protein.

Formulations containing the binding proteins for therapeutic use, typically include the binding proteins combined with a pharmaceutically acceptable carrier. As used herein, "pharmaceutically acceptable carrier" means buffers, carriers, and excipients, that are, within the scope of sound medical judgment, suitable for use in contact with the tissues of human beings and animals without excessive toxicity, irritation, allergic response, or other problem or complication, commensurate with a reasonable benefit/risk ratio. The carrier(s) should be "acceptable" in the sense of being compatible with the other ingredients of the formulations and not deleterious to the recipient. Pharmaceutically acceptable carriers, in this regard, are intended to include any and all buffers, solvents, dispersion media, coatings, isotonic and absorption delaying agents, and the like, compatible with pharmaceutical administration. The use of such media and agents for pharmaceutically active substances is known in the art.

The formulations can be conveniently presented in a dosage unit form and can be prepared by any suitable method, including any of the methods well known in the pharmacy art. A pharmaceutical composition of the invention should be formulated to be compatible with its intended route of administration. Examples of routes of administration include parenteral administration or non-parenteral administration, for example, intravenous, intradermal, inhalation, transdermal (topical), transmucosal, and rectal administration. Useful solutions for oral or parenteral administration can be prepared by any of the methods well known in the pharmaceutical art, described, for example, in *Remington's Pharmaceutical Sciences,* 18th ed. (Mack Publishing Company, 1990).

Formulations suitable for oral administration can be in the form of: discrete units such as injectables, capsules, gelatin capsules, sachets, tablets, troches, or lozenges, each containing a predetermined amount of the binding protein; a powder or granular composition; a solution or a suspension in an aqueous liquid or non-aqueous liquid; or an oil-in-water emulsion or a water-in-oil emulsion.

Formulations suitable for parenteral administration include, for example, the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

In general, compositions suitable for injectable use include aqueous solutions (where water soluble) or dispersions and powders for the extemporaneous preparation of sterile injectable solutions or dispersion. For intravenous administration, suitable carriers include physiological saline, bacteriostatic water, Cremophor ELTM (BASF, Parsippany, N.J.) or phosphate buffered saline (PBS). It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol), and suitable mixtures thereof.

Pharmaceutical formulations preferably are sterile. Sterilization can be accomplished, for example, by filtration through sterile filtration membranes. Where the composition is lyophilized, sterilization using this method can be conducted prior to or following lyophilization and reconstitution. Once the pharmaceutical composition has been formulated, it can be stored, for example, in vials as a solution, suspension, gel, emulsion, solid, or as a dehydrated or lyophilized powder.

(2) Diagnostic Applications

Whenever the binding proteins are used for diagnostic purposes, either in vitro or in vivo, the binding proteins typically are labeled either directly or indirectly with a detectable moiety. The detectable moiety can be any moiety which is capable of producing, either directly or indirectly, a detectable signal. For example, the detectable moiety may be a radioisotope, such as $^3$Hydrogen ($^3$H), $^{14}$-Carbon ($^{14}$C), $^{32}$Phosphorus ($^{32}$P), "Sulfur ($^{35}$S), or $^{125}$Iodine ($^{125}$I); a fluorescent or chemiluminescent compound, such as fluorescein isothiocyanate, rhodamine, or luciferin; an enzyme, such as alkaline phosphatase, beta-galactosidase, or horseradish peroxidase; a spin probe, such as a spin label; or a colored particle, for example, a latex or gold particle. It is understood that the binding protein can be conjugated to the detectable moiety using a number of approaches known in the art, for example, as described in Hunter et al. (1962) NATURE 144: 945; David et al. (1974) BIOCHEMISTRY 13: 1014; Pain et al. (1981) J. IMMUNOL. METH. 40: 219; and Nygren (1982) J. HISTOCHEM. AND CYTOCHEM. 30: 407. The labels may be detected, e.g., visually or with the aid of a spectrophotometer or other detector.

The binding proteins can be employed in a wide range of immunoassay techniques available in the art. Exemplary immunoassays include, for example, sandwich immunoassays, competitive immunoassays, immunohistochemical procedures.

In a sandwich immunoassay, two antibodies that bind an analyte or antigen of interest are used, e.g., one immobilized onto a solid support, and one free in solution and labeled with a detectable moiety. When a sample containing the antigen is introduced into this system, the antigen binds to both the immobilized antibody and the labeled antibody, to form a "sandwich" immune complex on the surface of the support. The complexed protein is detected by washing away non-bound sample components and excess labeled antibody, and measuring the amount of labeled antibody complexed to protein on the support's surface. Alternatively, the antibody free in solution can be detected by a third antibody labeled with a detectable moiety which binds the free antibody. A detailed review of immunological assay design, theory and protocols can be found in numerous texts, including Butt, ed., (1984) PRACTICAL IMMUNOLOGY, Marcel Dekker, New York; Harlow et al. eds. (1988) ANTIBODIES, A LABORATORY APPROACH, Cold Spring Harbor Laboratory; and Diamandis et al., eds. (1996) IMMUNOASSAY, Academic Press, Boston.

It is contemplated that the labeled binding proteins are useful as in vivo imaging agents, whereby the binding proteins can target the imaging agents to particular tissues of interest in the recipient. A preferred remotely detectable moiety for in vivo imaging includes the radioactive atom Technetium$^{-99m}$ ($^{99m}$Tc), a gamma emitter with a half-life of about six hours. Non-radioactive moieties also useful in in vivo imaging include nitroxide spin labels as well as lanthanide and transition metal ions all of which induce proton relaxation in situ. In addition to immunoimaging, the complexed radioactive moieties may be used in standard radioimmunotherapy protocols to destroy the targeted cell. Preferred nucleotides for high dose radioimmunotherapy include the radioactive atoms $^{90}$Yttrium ($^{90}$Yt), $^{131}$Iodine ($^{131}$I) and $^{111}$Indium ($^{111}$In). The binding protein can be labeled with $^{131}$I, $^{111}$In and $^{99m}$TC using coupling techniques known in the imaging arts. Similarly, procedures for preparing and administering the imaging agent as well as capturing and processing images are well known in the imaging art and so are not discussed in detail herein. Similarly, methods for performing antibody-based immunotherapies are well known in the art. See, for example, U.S. Pat. No. 5,534,254.

Throughout the description, where compositions are described as having, including, or comprising specific components, it is contemplated that compositions also consist essentially of, or consist of, the recited components. Similarly, where processes are described as having, including, or comprising specific process steps, the processes also consist essentially of, or consist of, the recited processing steps. Except where indicated otherwise, the order of steps or order for performing certain actions are immaterial so long as the invention remains operable. Moreover, unless otherwise noted, two or more steps or actions may be conducted simultaneously.

EXAMPLES

The following Examples discuss the production and characterization of a number of anti-hHGF monoclonal antibodies.

Example 1

Production of Anti-hHGF Monoclonal Antibodies

This Example describes the production of a number of anti-hHGF monoclonal antibodies.

Immunizations, fusions, and primary screens were conducted at MBS Inc. (Portland, Me.), following the Repetitive Immunization Multiple Sites (RIMMS) protocol. Five AJ mice and Five Balb/c mice were immunized with recombinant human HGF (R&D Systems, Minneapolis, Minn.; Catalog No. 294-HGN-025). Two mice with sera displaying highest anti-HGF activity by Enzyme Linked Immunosorbent Assay (ELISA) were chosen for subsequent fusion. Spleens and lymph nodes from the appropriate mice were harvested. B-cells then were harvested and fused with an myeloma line. Fusion products were serially diluted on one or more plates to near clonality. Supernatants from the resulting fusions were screened for their binding to hHGF by ELISA. Supernatants identified as containing antibodies to HGF were further characterized by in vitro functional testing as discussed in the following examples. A panel of hybridomas was selected and the hybridomas were subcloned and expanded. The monoclonal antibodies then were purified by affinity chromatography on Protein A/G resin under standard conditions.

Example 2

Sequence Analysis of anti-hHGF Monoclonal Antibodies

This Example describes isotype and sequence analyses of the anti-hHGF monoclonal antibodies produced in Example 1.

a. Determination of HGF Murine Monoclonal Antibody Isotypes

The light-chain type and heavy chain isotype of each monoclonal antibody were determined using the IsoStrip Mouse Monoclonal Antibody Isotyping Kit in accordance the manufacturer's instructions (Roche Applied Science).

All the antibodies were determined to contain a Kappa immunoglobulin light chain and an IgG1 immunoglobulin heavy chain.

b. Determination of Nucleotide Sequences Encoding Immunoglobulin Heavy and Light Chain Variable Regions Total RNA was extracted from each monoclonal hybridoma cell line using the RNeasy Miniprep kit according to the manufacturer's instructions (Qiagen Venlo, The Netherlands). Full-length first strand cDNA was generated using the BD SMART™ RACE cDNA Amplification Kit according to the manufacturer's instructions (Clontech) using the oligonucleotide primers BD SMART II A (5' aagcagtggtatcaacgcagagtacgcggg 3') (SEQ ID NO. 85) and 5'-RACE CDS Primer (5' ttttttttttttttttttttttttttvn 3', where v=a, g, or c and n=a, g, c, or t) (SEQ ID NO. 86) for the purpose of 5' RACE (Rapid Amplification of cDNA Ends).

The variable regions of the Kappa and Heavy (IgG1) immunoglobulin chains were amplified by PCR (Polymerase Chain Reaction) using the Expand High-Fidelity PCR System (Roche Applied Science) according to the manufacturer's instructions. Heavy chain variable regions were amplified with the 5' oligonucleotide primer mix Universal Primer Mix A (mix of 5' ctaatacgactcactatagggcaagcagtggtatcaacgcagagt 3' (SEQ ID NO. 87) and 5' ctaatacgactcactatagggc 3'(SEQ ID NO. 88)) and a 3' IgG1 Constant Region specific primer, either 5' tatgcaaggcttacaaccaca 3' (SEQ ID NO. 89) or 5' gccagtggatagacagatgggggtgtcg 3' (SEQ ID NO. 90). Kappa chain variable regions were amplified with the 5' oligonucleotide primer mix Universal Primer Mix A and a 3' Kappa Constant Region specific primer, either 5' ctcattcctgttgaagctcttgacaat 3' (SEQ ID NO. 91) or 5' cgactgaggcacctccagatgtt 3' (SEQ ID NO. 92).

Individual PCR products were fractionated by agarose gel electrophoresis and purified using the Qiaquick Gel Purification kit according to the manufacturer's instructions (Qiagen). The PCR products were subsequently cloned into the pCR2.1 TOPO plasmid using the topoisomerase based cloning kit TOPO TA Cloning® Kit (with pCR®2.1-TOPO® vector) according to the manufacturer's instructions (Invitrogen, Carlsbad, Calif.) and transformed into DH5 bacteria using standard transformation techniques. Plasmid DNA isolated from transformed bacterial clones was sequenced using T7 (5' TAATACGACTCACTATAGGG 3') (SEQ ID NO. 93), M13 Forward (5' GTAAAACGACGGCCAGT 3') (SEQ ID NO. 94), and M13 Reverse primers (5' CAGGAAACAGCTATGACC 3') (SEQ ID NO. 95) by Agencourt Bioscience using standard dideoxy DNA sequencing methods to identify the sequence of the variable region sequences. The sequences were analyzed using Vector NTI software (Invitrogen, Carlsbad, Calif.) and the IMGT/V-Quest webserver (http://imgt.cines.fr/textes/vquest) to identify and confirm variable region sequences.

c. Determination of Nucleotide Sequences Encoding Immunoglobulin Heavy and Light Chain Constant Region Sequences for 1A3, 1D3, 1F3, and 2B8 Kappa and IgG1 Chains Full Length cDNAs for the 1A3, 1D3, and 1F3 IgG1 chains were PCR amplified from the cDNA created above using the forward primer 5' ggggacaagtttgtacaaaaaagcaggctgccacc atgaactttgggctcagattgattttcc 3' (start codon underlined) (SEQ ID NO. 96) and the reverse primer 5' ggggaccactttgtacaagaaagctgggttcatttaccaggagagtgggagagg 3' (stop codon underlined) (SEQ ID NO. 97). Full Length cDNA for the 2B8 IgG1 chain was amplified from the cDNA created above using the forward primer 5' ggggacaagtttgtacaaaaaagcaggctgccacc atgggatggagctatatcatcctcttt 3' (start codon underlined) (SEQ ID NO. 98) and reverse primer 5' ggggaccactttgtacaagaaagctgggttcatttaccaggagagtgggagag 3' (stop codon underlined) (SEQ ID NO. 99).

Full Length cDNA for the 2B8 Kappa Chain was amplified using the forward primer 5' ggggacaagtttgtacaaaaaagcaggctgccaccatggaatcacagactctggtcttcata 3' (start codon underlined) (SEQ ID NO. 100) and the reverse primer 5' ggggaccactttgtacaagaaagctgggtctaacactcattcctgttgaagctc 3' (stop codon underlined) (SEQ ID NO. 101). PCR fragments were subcloned into pDONR221 (Invitrogen, Carlsbad, Calif.) by Gateway BP recombination reaction (Invitrogen, Carlsbad, Calif.) and sequenced by Agencourt Bioscience using standard dideoxy DNA sequencing methods to identify the sequence of the constant region and further confirm variable region sequences.

d. Sequence Analysis

Variable Regions (normal text) were identified using IMGT/V-QUEST webserver software (http://imgt.cines.fr/textes/vquest/). Signal Peptide sequences were predicted based on identification of the in frame start codon (ATG) that was upstream of the identified Variable Region. Signal Peptide sequences were identified and are underlined below.

The last nucleotide of each variable region is the first base of the next codon generated by the variable/constant region junction. This nucleotide is included in the variable region because it is part of that exon. Amino acid sequences of the constant regions listed below include the translation of this junction codon.

In order to create the complete heavy or kappa chain antibody sequences, the variable region sequences noted below are combined with their respective constant region sequences (the signal sequences are underlined).

(1) 1A3 Heavy Chain Variable Region (SEQ ID NO. 1)

```
  1  atgaactttg ggctcagatt gattttcctt gtccttgttt taaaaggtgt gaagtgtgaa 61  gtgcagctgg tggagtctgg gggaggctta gtgcagcctg gagggtccct gaaactctcc 121  tgtgcagcct ctgaattcac tttcagtaac tattacatgt cttgggttcg ccagactcca 181  gagaagaggc tgcagtgggt cgcatacatt agtcctggtg gtggtagctc ctactatcca 241  gccagtgtga agggtcgatt caccatctcc agagacaatg ccaagaacac cctgtacctg 301  caaatgagca gtctgaagtc tgaggacaca gccatgtatt actgtgcaag acaaggggat 361  ggttactacg gggactatgc tatggactac tggggtcaag gaacctcagt caccgtctcc 421  tcag
```

(2) 1A3 Kappa Light Chain Variable Region (SEQ ID NO. 3)

```
  1  atgagtgtgc ccactcaggt cctggggttg ctgctgctgt ggcttacaga tgccagatgt
 61  gacatccaga tgactcagtc tccagcctcc ctatctgttt ctgtgggaga aactgtcacc
121  atcacatgtc gagcaagtga aaatatttat agtaatttag catggtatca gcagaaacag
181  ggaaaatctc ctcagctcct ggtctatgct gcaacaaact tagcagatgg tgtgccatca
241  aggttcagtg gcagtggatc aggcacacag ttttccctca agatcaacag cctgcagtct
301  gaagattttg ggacttatta ctgtcaacat ttttggggta ctccgtacac gttcggaggg
361  gggaccaagc tggaaataaa ac
```

(3) 2B8 Heavy Chain Variable Region (SEQ ID NO. 11)

```
  1  atgggatgga gctatatcat cctcttttg gtagcaacag ctacagatgt ccactcccag
 61  gtccaactgc agcagcctgg ggctgaactg gtgaagcctg gacttcagt gaagctgtcc
121  tgcaaggctt ctggctacac cttcaccacc tactggatgc actgggtgaa tcagaggcct
181  ggacaaggcc ttgagtggat tggagagatt aatcctacca acggtcatac taactacaat
241  gagaagttca gagcaaggc cacactgact gtagacaaat cctccagcac agcctacatg
301  caactcagca gcctgacatc tgaggactct gcggtctatt actgtgcaag aaactatgtt
361  ggtagcatct ttgactactg gggccaaggc accactctca cagtctcctc ag
```

(4) 2B8 Kappa Light Chain Variable Region (SEQ ID NO. 13)

```
  1  atggaatcac agactctggt cttcatatcc atactgctct ggttatatgg tgctgatggg
 61  aacattgtaa tgacccaatc tcccaaatcc atgtccatgt cagtaggaga gagggtcacc
121  ttgagctgca aggccagtga aaatgtggtt tcttatgtat cctggtatca acagaaacca
181  gcgcagtctc ctaaactgct gatatacggg gcatccaacc ggaacactgg gtccccgat
241  cgcttcacag gcagtggatc tgcaacagat ttcactctga ccatcagcag tgtgcgggct
301  gaagaccttg cagattatca ctgtgggcag agttacaact atccgtacac gttcggaggg
361  gggaccaggc tggaaataaa ac
```

(5) 2F8 Heavy Chain Variable Region (SEQ ID NO. 21)

```
  1  atggaatgga gctgggtctt tctcttcctc ctgtcagtaa ctgcaggtgt ccactgccag
 61  gtccagctga agcagtctgg agctgagctg gtgaggcctg gacttcagt gaagatgtcc
121  tgcaaggctt ctggctacac cttcactacc tactatatac actgggtgaa tcagaggcct
181  ggacagggcc ttgagtggat tggaaagatt ggtcctggaa gtggtagtac ttactacaat
241  gagatgttca agacaaggc cacattgact gtagacacat cctccagcac agcctacatg
301  cagctcagca gcctgacatc tgacgactct gcggtctatt tctgtgcaag aaggggactg
361  ggacgtggct ttgactactg gggccaaggc accactctca cagtctcctc ag
```

(6) 2F8 Kappa Light Chain Variable Region (SEQ ID NO. 23)

```
  1  atggagacag acacaatcct gctatgggtg ctgctgctct gggttccagg ctccactggt
 61  gacattgtgc tgacccaatc tccagcttct ttggctgtgt ctctagggca gagggccacc
121  atctcctgca aggccagcca agtgttgat tatgatggta atagttatat caactggtac
```

```
181  caacagaaac caggacagcc acccaaagtc ctcatctatg ttgcatccaa tctagaatct 241  gggatcccag ccaggtttag tggcagtggg tctgggacag acttcaccct caacatccat 301  cctgtggagg aggaggatgc tgcaacctat tactgtcagc aaagtattga ggatcctccc 361  acgttcggtg ctgggaccaa gctggagctg aaac
```

(7) 3B6 Heavy Chain Variable Region (SEQ ID NO. 31)

```
  1  atggaatggc cttgtatctt tctcttcctc ctgtcagtaa ctgaaggtgt ccactcccag 61  gttcagctgc agcagtctgg ggctgaactg gtgaggcctg gtcctcagt gaagatttcc 121  tgcaaggctt ctggctatgt attcagtagc tactggatga actgggtgaa gcagaggcct 181  ggacagggtc ttgagtggat tggacagatt tatcctggag atggtgatag taactacaat 241  ggaaacttca agggtaaagc cacactgact gcagacaaat cctccagtac agcctacatg 301  cagctcagca gcctaacatc tgaggactct gcggtctatt tctgtgcatc ccagctcggg 361  ctacgtgaga actactttga ctactggggc caaggcacca ctctcacagt ctcctcag
```

(8) 3B6 Kappa Light Chain Variable Region (2 possible ATG start codons (uppercase)) (SEQ ID NO. 33)

```
  1  ATGgacATGa ggacccctgc tcagtttctt ggaatcttgt tgctctggtt tccaggtatc 61  aaatgtgaca tcaagatgac ccagtctcca tcttccatgt atgcatctct aggagagaga 121  gtcacaatca cttgcaaggc gagtcaggac attaaaagct atttaagctg gttccagcag 181  aaaccaggga aatctcctaa gaccctgatc tatcgtgtaa acagattggt agatggggtc 241  ccatcaaggt tcagtggcag tggatctggg caagattctt ctctcaccat caccagcctg 301  gagaatgaag atatgggaat ttattattgt ctacagtatg atgagtttcc gttcacgttc 361  ggaggggggga ccaagctgga ataaagc
```

(9) 3B11 Heavy Chain Variable Region (SEQ ID NO. 41)

```
  1  atggctgtcc cggtgctgtt cctctgcctg gttgcatttc caagctgtgt cctgtcccag 61  gtacagctga aggagtcagg acctggcctg gtggcgccct cacagagcct gtccatcact 121  tgcactgtct ctgggttttc attaaccagc tatagtttac actgggttcg ccagcctcca 181  ggaaagggtc tggaatggct gggagtaata tgggctggtg aaacacaaa ttataattcg 241  tctctcatgt ccagactgac catcaggaaa gacaactcca agagccaagt tttcttaaaa 301  atgaacagtc tgcaaactga tgacacagcc atgtactact gtgccagaga gaggtttgct 361  tactggggcc aagggactct ggtcactgtc tctgcag
```

(10) 3D11 Kappa Light Chain Variable Region (SEQ ID NO. 43)

```
  1  atggattttc aagtgcagat tttcagcttc ctgctaatca gtgcctcagt caaaatatcc 61  agaggacaaa ttgttctcac ccagtctcca gcaatcatgt ctgcatatcc aggggagaag 121  gtcaccatga cctgcagtgc cagctcaagt gtaagttaca tgcactggta ccagcagaag 181  tcaggcacct cccccaaaag atggatttat gacacatcca aactggcttc tggagtccct 241  gctcgcttca gtggcagtgg gtctgggacc tcttactccc tcacaatcag tagtatggag
```

-continued

```
301 gctgaagatg ctgccactta ttactgccag cagtggagta gtaacccact cacgttcggt
361 gctgggacca agctggagct gaaac
```

(11) 1D3 Heavy Chain Variable Region (SEQ ID NO. 51)

```
  1 atgaactttg ggctcagatt gattttcctt gtccttgttt taaaaggtgt gaagtgtgaa
 61 gtgcagctgg tggagtctgg gggaggctta gtgcagcctg agggtccct gaaactctcc
121 tgtgcagcct ctggattcac tttcagtgac tattacatgt cttgggttcg ccagactcca
181 gagaagaggc tggagtgggt cgcatacatt agtagtggtg gtggtagcac ctactatcca
241 gacagtgtga agggtcgatt caccatctcc cgagacaatg ccaagaacac cctgtacctg
301 caaatgagca gtctgaagtc tgaggacaca gccatatatt actgtgtgag acaaggggat
361 ggttattacg gggactatgc tatggactac tggggtcaag aacctcagt catcgtctcc
421 tcag
```

(12) 1D3 Kappa Light Chain Variable Region (SEQ ID NO. 53)

```
  1 atgagtgtgc ccactcaggt cctggggttg ctgctgctgt ggcttacaga tgtcagatgt
 61 gacatccaga tgactcagtc tccagcctcc ctatctgtat ctgtgggaga aactgtcacc
121 atcacatgtc gaacaagtga gaatatttac agtaatttag cgtggtatca gcagaaacag
181 ggaaaatctc ctcagctcct aatctatgct gcaacaaact tagcagatgg tgtgccatca
241 aggttcagtg gcagtggatc aggcacacag ttttcccctca ggatcaacag cctgcagtct
301 gaagattttg ggaggtatta ctgtcaacat ttttggggga ctccgtacac gttcggaggg
361 gggaccaaac tggaaataaa ac
```

(12) 1F3 Heavy Chain Variable Region (SEQ ID NO. 61)

```
  1 atgaactttg ggctcagatt gattttcctt gtccttgttt taaaaggtgt gaagtgtgag
 61 gtgcagctgg tggagtctgg gggaggctta gtgcagtctg agggtccct gaaactctcc
121 tgtgcggcct ctggattcac tttcagtaac tatttcatgt cttgggttcg ccagactcca
181 gagaagaggc tggagtgggt cgcatatatt agtagtggtg gtggtagcac ctactatcca
241 gacagtgtga agggtcgatt caccatctct agagacaatg ccaagaacac cctgtacctg
301 caaatgagca gtctgaagtc tgaggacaca gccatgtatt actgtgtaag acaaggggat
361 ggttactacg gggactatgc tatggactac tggggtcaag aacctcagt caccgtctcc
421 tcag
```

(14) 1F3 Kappa Light Chain Variable Region (SEQ ID NO. 63)

```
  1 atgagtgtgc ccactcaggt cctggggttg ctgctgctgt ggcttacaga tgccagatgt
 61 gacatccaga tgactcagtc tccagcctcc ctatctgtat ctgtgggaga aactgtcacc
121 atcacatgtc gagcaagtga gaatatttac agtaatttag catggtatca gcagaaacag
181 ggaaaatctc ctcagctcct ggtctatgat gcaacacact taccagatgg tgtgccatca
241 aggttcagtg gcagtggatc aggcacacag ttttcccctca agatcaacag cctgcagtct
```

-continued

```
301  gaagattttg ggagttatta ctgtcaacat ttttggggta ctccgtacac gtttggaggg
361  gggaccagac tggaaattaa ac
```

(15) 3A12 Heavy Chain Variable Region (SEQ ID NO. 71)

```
  1  atgaactttg ggctcagatt gattttcctt gtccttgttt taaaaggtgt gaagtgtgaa
 61  gtgcagctgg tggagtctgg gggaggctta gtgcagcctg agggtccct gaaaatctcc
121  tgtgcagcct ctggatttac tttcagtaac tatttcatgt cttgggttcg ccagactcca
181  gagaagaggc tggagtgggt cgcatacatt agtagtggtg gtggtagcac ctactatcca
241  gacagtgtga agggtcgatt caccatctcc agagacaatg ccaagaacac cctgtacctg
301  caaatgaaca gtctgaagtc tgaggacaca gccatgtatt actgtgtaag acaaggagat
361  ggttactatg gggactatgc tatggactac tggggtcaag aacctcagt caccgtctcc
421  tcag
```

(16) 2A12 Kappa Light Chain Variable Region (SEQ ID NO. 73)

```
  1  atgagtgtgc ccactcaggt cctggggttg ctgctgctgt ggcttacaga tgccagatgt
 61  gacatccaga tgactcagtc gccagcctcc ctatctgtat ctgtgggaga aactgtcacc
121  atcacatgtc gagcaagtga aatatttac attaatttag catggtatca gcagaaacag
181  ggaaaatctc ctcagctcct ggtccatgct gcaacaaagt tagcagatgg tgtgccatca
241  aggttcagtg gcagtggatc aggcacacag tattccctca agatcaacag cctgcagtct
301  gaagattttg ggagttatta ctgtcaacat ttttggggta ctccgtacac gttcggaggg
361  gggaccaaac tagaaataaa ac
```

(17) Reference Mouse IgG1 Heavy Chain Sonctant Region (J00453) (SEQ ID NO. 81)

```
  1  ccaaaacgac accccatct gtctatccac tggccctgg atctgctgcc caaactaact
 61  ccatggtgac cctgggatgc ctggtcaagg gctatttccc tgagccagtg acagtgacct
121  ggaactctgg atccctgtcc agcggtgtgc acaccttccc agctgtcctg gagtctgacc
181  tctacactct gagcagctca gtgactgtcc cctccagccc tcggcccagc gagaccgtca
241  cctgcaacgt tgcccacccg gccagcagca ccaaggtgga caagaaaatt gtgcccaggg
301  attgtggttg taagccttgc atatgtacag tcccagaagt atcatctgtc ttcatcttcc
361  ccccaaagcc caaggatgtg ctcaccatta ctctgactcc taaggtcacg tgtgttgtgg
421  tagacatcag caaggatgat cccgaggtcc agttcagctg gtttgtagat gatgtggagg
481  tgcacacagc tcagacgcaa ccccgggagg agcagttcaa cagcactttc cgctcagtca
541  gtgaacttcc catcatgcac caggactggc tcaatggcaa ggagttcaaa tgcagggtca
601  acagtgcagc tttccctgcc cccatcgaga aaaccatctc caaaaccaaa ggcagaccga
661  aggctccaca ggtgtacacc attccacctc caaggagca gatggccaag ataaagtca
721  gtctgacctg catgataaca gacttcttcc ctgaagacat tactgtggag tggcagtgga
781  atgggcagcc agcggagaac tacaagaaca ctcagcccat catgaacacg aatggctctt
841  acttcgtcta cagcaagctc aatgtgcaga gagcaactg ggaggcagga aatactttca
```

```
901 cctgctctgt gttacatgag ggcctgcaca accaccatac tgagaagagc ctctcccact
961 ctcctggtaa atga
```

(18) Mouse IgG1 Heavy Chain Constant Region Determined
for 1A3, 1D3, 1F3, and 2B8 (derived from AJ strain mice)
(SEQ ID NO. 82)

```
  1 ccaaaacgac acccccatct gtctatccac tggcccctgg atctgctgcc caaactaact
 61 ccatggtgac cctgggatgc ctggtcaagg gctatttccc tgagccagtg acagtgacct
121 ggaactctgg atccctgtcc agcggtgtgc acaccttccc agctgtcctg cagtctgacc
181 tctacactct gagcagctca gtgactgtcc cctccagcac ctggcccagc gagaccgtca
241 cctgcaacgt tgcccacccg gccagcagca caaggtgga caagaaaatt gtgcccaggg
301 attgtggttg taagccttgc atatgtacag tcccagaagt atcatctgtc ttcatcttcc
361 ccccaaagcc caaggatgtg ctcaccatta ctctgactcc taaggtcacg tgtgttgtgg
421 tagacatcag caaggatgat cccgaggtcc agttcagctg gtttgtagat gatgtggagg
481 tgcacacagc tcagacgcaa ccccgggagg agcagttcaa cagcactttc cgctcagtca
541 gtgaacttcc catcatgcac caggactggc tcaatggcaa ggagttcaaa tgcagggtca
601 acagtgcagc tttccctgcc cccatcgaga aaccatctc caaaccaaa ggcagaccga
661 aggctccaca ggtgtacacc attccacctc ccaaggagca gatggccaag ataaagtca
721 gtctgacctg catgataaca gacttcttcc ctgaagacat tactgtggag tggcagtgga
781 atgggcagcc agcggagaac tacaagaaca ctcagcccat catggacaca gatggctctt
841 acttcgtcta cagcaagctc aatgtgcaga agagcaactg ggaggcagga aatactttca
901 cctgctctgt gttacatgag ggcctgcaca accaccatac tgagaagagc ctctcccact
961 ctcctggtaa atga
```

(19) Reference Mouse Kappa Light Chain Constant Region
(V00807) and Mouse Kappa Light Chain constant Region
Determined for 1D3, 1F3, and 2B8 (derived from AJ strain
mice) (SEQ ID NO. 83)

```
  1 gggctgatgc tgcaccaact gtatccatct tcccaccatc cagtgagcag ttaacatctg
 61 gaggtgcctc agtcgtgtgc ttcttgaaca acttctaccc caaagacatc aatgtcaagt
121 ggaagattga tggcagtgaa cgacaaaatg gcgtcctgaa cagttggact gatcaggaca
181 gcaaagacag cacctacagc atgagcagca ccctcacgtt gaccaaggac gagtatgaac
241 gacataacag ctatacctgt gaggccactc acaagacatc aacttcaccc attgtcaaga
301 gcttcaacag gaatgagtgt tag
```

(20) Mouse Kappa Light Chain Constant Region Determined
for 1A3, containing one *altered* nucleotide compared to 1D3,
1F3, and 2B8 (underlined) (SEQ ID NO. 84)

```
  1 gggctgatgc tgcaccaact gtatccatct tcccaccatc cagtgagcag ttaacatctg
 61 gaggtgcctc agtcgtgtgc ttcttgaaca acttctaccc caaagacatc aatgtcaagt
121 ggaagattga tggcagtgaa cgacaaaatg gcgtcctgaa cagttggact gatcaggaca
181 gcaaagacag cacctacagc atgagcagca ccctcatgtt gaccaaggac gagtatgaac
```

```
241 gacataacag ctatacctgt gaggccactc acaagacatc aacttcaccc attgtcaaga 301 gcttcaacag gaatgagtgt tag
```

Each of the amino acid sequences defining the immunoglobulin heavy chain variable regions for the antibodies produced in Example 1 are set forth in FIG. 2. Each of the sequences are aligned with one another and the sequences defining the signal peptide, $CDR_1$, $CDR_2$ and $CDR_3$ are identified by boxes. FIG. 3 shows an alignment of the separate $CDR_1$, $CDR_2$ and $CDR_3$ sequences for each of the antibodies.

Each of the amino acid sequences defining the immunoglobulin light chain variable regions for each of the antibodies produced in Example 1 are set forth in FIG. 4. Each of the sequences are aligned with one another and the sequences defining the signal peptide, $CDR_1$, $CDR_2$ and $CDR_3$ are identified by boxes. FIG. 5 shows an alignment of the separate $CDR_1$, $CDR_2$ and $CDR_3$ sequences for each of the antibodies.

For convenience, Table 1 provides a concordance chart showing the correspondence between the antibody sequences discussed in this Example with those presented in the Sequence Listing.

TABLE 1

| SEQ. ID NO. | Protein or Nucleic Acid |
| --- | --- |
| 1 | Heavy Chain Variable Region 1A3 - nucleic acid |
| 2 | Heavy Chain Variable Region 1A3 - protein |
| 3 | Light (kappa) Chain Variable Region 1A3 - nucleic acid |
| 4 | Light (kappa) Chain Variable Region 1A3 - protein |
| 5 | Heavy Chain $CDR_1$ 1A3 |
| 6 | Heavy Chain $CDR_2$ 1A3 |
| 7 | Heavy Chain $CDR_3$ 1A3 |
| 8 | Light (kappa) Chain $CDR_1$ 1A3 |
| 9 | Light (kappa) Chain $CDR_2$ 1A3 |
| 10 | Light (kappa) Chain $CDR_3$ 1A3 |
| 11 | Heavy Chain Variable Region 2B8 - nucleic acid |
| 12 | Heavy Chain Variable Region 2B8 - protein |
| 13 | Light (kappa) Chain Variable Region 2B8 - nucleic acid |
| 14 | Light (kappa) Chain Variable Region 2B8 - protein |
| 15 | Heavy Chain $CDR_1$ 2B8 |
| 16 | Heavy Chain $CDR_2$ 2B8 |
| 17 | Heavy Chain $CDR_3$ 2B8 |
| 18 | Light (kappa) Chain $CDR_1$ 2B8 |
| 19 | Light (kappa) Chain $CDR_2$ 2B8 |
| 20 | Light (kappa) Chain $CDR_3$ 2B8 |
| 21 | Heavy Chain Variable Region 2F8 - nucleic acid |
| 22 | Heavy Chain Variable Region 2F8 - protein |
| 23 | Light (kappa) Chain Variable Region 2F8 - nucleic acid |
| 24 | Light (kappa) Chain Variable Region 2F8 - protein |
| 25 | Heavy Chain $CDR_1$ 2F8 |
| 26 | Heavy Chain $CDR_2$ 2F8 |
| 27 | Heavy Chain $CDR_3$ 2F8 |
| 28 | Light (kappa) Chain $CDR_1$ 2F8 |
| 29 | Light (kappa) Chain $CDR_2$ 2F8 |
| 30 | Light (kappa) Chain $CDR_3$ 2F8 |
| 31 | Heavy Chain Variable Region 3B6 - nucleic acid |
| 32 | Heavy Chain Variable Region 3B6 - protein |
| 33 | Light (kappa) Chain Variable Region 3B6 - nucleic acid |
| 34 | Light (kappa) Chain Variable Region 3B6 - protein |
| 35 | Heavy Chain $CDR_1$ 3B6 |
| 36 | Heavy Chain $CDR_2$ 3B6 |
| 37 | Heavy Chain $CDR_3$ 3B6 |
| 38 | Light (kappa) Chain $CDR_1$ 3B6 |
| 39 | Light (kappa) Chain $CDR_2$ 3B6 |

TABLE 1-continued

| SEQ. ID NO. | Protein or Nucleic Acid |
| --- | --- |
| 40 | Light (kappa) Chain $CDR_3$ 3B6 |
| 41 | Heavy Chain Variable Region 3D11 - nucleic acid |
| 42 | Heavy Chain Variable Region 3D11 - protein |
| 43 | Light (kappa) Chain Variable Region 3D11 - nucleic acid |
| 44 | Light (kappa) Chain Variable Region 3D11 - protein |
| 45 | Heavy Chain $CDR_1$ 3D11 |
| 46 | Heavy Chain $CDR_2$ 3D11 |
| 47 | Heavy Chain $CDR_3$ 3D11 |
| 48 | Light (kappa) Chain $CDR_1$ 3D11 |
| 49 | Light (kappa) Chain $CDR_2$ 3D11 |
| 50 | Light (kappa) Chain $CDR_3$ 3D11 |
| 51 | Heavy Chain Variable Region 1D3 - nucleic acid |
| 52 | Heavy Chain Variable Region 1D3 - protein |
| 53 | Light (kappa) Chain Variable Region 1D3 - nucleic acid |
| 54 | Light (kappa) Chain Variable Region 1D3 - protein |
| 55 | Heavy Chain $CDR_1$ 1D3 |
| 56 | Heavy Chain $CDR_2$ 1D3 |
| 57 | Heavy Chain $CDR_3$ 1D3 |
| 58 | Light (kappa) Chain $CDR_1$ 1D3 |
| 59 | Light (kappa) Chain $CDR_2$ 1D3 |
| 60 | Light (kappa) Chain $CDR_3$ 1D3 |
| 61 | Heavy Chain Variable Region 1F3 - nucleic acid |
| 62 | Heavy Chain Variable Region 1F3 - protein |
| 63 | Light (kappa) Chain Variable Region 1F3 - nucleic acid |
| 64 | Light (kappa) Chain Variable Region 1F3 - protein |
| 65 | Heavy Chain $CDR_1$ 1F3 |
| 66 | Heavy Chain $CDR_2$ 1F3 |
| 67 | Heavy Chain $CDR_3$ 1F3 |
| 68 | Light (kappa) Chain CDR, 1F3 |
| 69 | Light (kappa) Chain CDR2 1F3 |
| 70 | Light (kappa) Chain CDR3 1F3 |
| 71 | Heavy Chain Variable Region 3A12 - nucleic acid |
| 72 | Heavy Chain Variable Region 3A12 - protein |
| 73 | Light (kappa) Chain Variable Region 3A12 - nucleic acid |
| 74 | Light (kappa) Chain Variable Region 3A12 - protein |
| 75 | Heavy Chain $CDR_1$ 3A12 |
| 76 | Heavy Chain $CDR_2$ 3A12 |
| 77 | Heavy Chain $CDR_3$ 3A12 |
| 78 | Light (kappa) Chain $CDR_1$ 3A12 |
| 79 | Light (kappa) Chain $CDR_2$ 3A12 |
| 80 | Light (kappa) Chain $CDR_3$ 3A12 |

Also, for convenience, the following sequences represent the actual or contemplated full length heavy and light chain sequences (i.e., containing both the variable and constant region sequences) for each of the antibodies described in this Example. It is noted that the constant regions of the murine antibodies 2F8, 3A12, 3B6, and 3D11 were not sequenced but are presumed to have the same constant region sequences as the 1D3, 1F3, and 2B8 antibodies, which were sequenced, as they were all derived from AJ strain mice. It is appreciated, however, that the variable region sequences described herein can be ligated to each of a number of other constant region sequences known to those skilled in the art to produce active full length immunoglobulin heavy and light chains.

(1) Nucleic Acid Sequence Encoding the Full Length 1A3 Heavy Chain Sequence (1A3 Heavy Chain Variable Region and IgG1 Constant Region) (Signal Sequence Underlined) (SEQ ID NO. 122)

```
 1   atgaacttlg ggctcagatt gattttcctt gtccttgttt taaaaggtgt gaagtgtgaa 61   gtgcagctgg tggagtctgg gggaggctta gtgcagcctg gagggtccct gaaactctcc
```

-continued

```
 121   tgtgcagcct ctgaattcac tttcagtaac tattacatgt cttgggttcg ccagactcca 181   gagaagaggc tgcagtgggt cgcatacatt agtcctggtg gtggtagctc ctactatcca 241   gccagtgtga agggtcgatt caccatctcc agagacaatg ccaagaacac cctgtacctg 301   caaatgagca gtctgaagtc tgaggacaca gccatgtatt actgtgcaag acaagggat 361   ggttactacg gggactatgc tatggactac tggggtcaag gaacctcagt caccgtctcc 421   tcagccaaaa cgacaccccc atctgtctat ccactggccc ctggatctgc tgcccaaact 481   aactccatgg tgaccctggg atgcctggtc aagggctatt ccctgagcc agtgacagtg 541   acctggaact ctggatccct gtccagcggt gtgcacacct tcccagctgt cctgcagtct 601   gacctctaca ctctgagcag ctcagtgact gtcccctcca gcacctggcc cagcgagacc 661   gtcacctgca acgttcccca ccggccagc agcaccaagg tggacaagaa aattgtgccc 721   agggattgtg gttgtaagcc ttgcatatgt acagtcccag aagtatcatc tgtcttcatc 781   ttccccccaa agcccaagga tgtgctcacc attactctga ctcctaaggt cacgtgtgtt 841   gtggtagaca tcagcaagga tgatcccgag gtccagttca gctggtttgt agatgatgtg 901   gaggtgcaca cagctcagac gcaaccccgg gaggagcagt tcaacagcac tttccgctca 961   gtcagtgaac ttcccatcat gcaccaggac tggctcaatg gcaaggagtt caaatgcagg 1021   gtcaacagtg cagctttccc tgcccccatc gagaaaacca tctccaaaac caaaggcaga 1081   ccgaaggctc cacaggtgta caccattcca cctcccaagg agcagatggc caaggataaa 1141   gtcagtctga cctgcatgat aacagacttc ttccctgaag acattactgt ggagtggcag 1201   tggaatgggc agccagcgga gaactacaag aacactcagc ccatcatgga cacagatggc 1261   tcttacttcg tctacagcaa gctcaatgtg cagaagagca ctgggaggc aggaaatact 1321   ttcacctgct ctgtgttaca tgagggcctg cacaaccacc atactgagaa gagcctctcc 1381   cactctcctg gtaaatga
```

(2) Protein Sequence Defining the Full Length 1A3 Heavy Chain Sequence (1A3 Heavy Chain Variable Region and IgG1 Constant Region) (without signal sequence) (SEQ ID NO. 123)

```
  1   evqlvesggg lvqpggslkl scaaseftfs nyymswvrqt pekrlqwvay ispgggssyy 61   pasvkgrfti srdnakntly lqmsslksed tamyycarqg dgyygdyamd ywgqgtsvtv 121   ssakttppsv yplapgsaaq tnsmvtlgcl vkgyfpepvt vtwnsgslss gvhtfpavlq 181   sdlytlsssv tvpsstwpse tvtcnvahpa sstkvdkkiv prdcgckpci ctvpevssvf 241   ifppkpkdvl titltpkvtc vvvdiskddp evqfswfvdd vevhtaqtqp reeqfnstfr 301   syselpimhq dwlngkefkc rvnsaafpap iektisktkg rpkapqvyti pppkeqmakd 361   kvsltcmitd ffpeditvew qwngqpaeny kntqpimdtd gsyfvyskln vqksnweagn 421   tftcsvlheg lhnhhteksl shspgk
```

(3) Nucleic Acid Sequence Encoding the Full Length 1A3 Light Chain Sequence (1A3 Kappa Variable Region and Constant Region) (Signal Sequence Underlined) (SEQ ID NO. 124)

```
  1   atgagtgtgc ccactcaggt cctggggttg ctgctgctgt ggcttacaga tgccagatgt 61   gacatccaga tgactcagtc tccagcctcc ctatctgttt ctgtgggaga aactgtcacc
```

-continued

```
121  atcacatgtc gagcaagtga gaatatttat agtaatttag catggtatca gcagaaacag 181  ggaaaatctc ctcagctcct ggtctatgct gcaacaaact tagcagatgg tgtgccatca 241  aggttcagtg gcagtggatc aggcacacag ttttccctca agatcaacag cctgcagtct 301  gaagattttg ggacttatta ctgtcaacat ttttggggta ctccgtacac gttcggaggg 361  gggaccaagc tggaaataaa acgggctgat gctgcaccaa ctgtatccat cttcccacca 421  tccagtgagc agttaacatc tggaggtgcc tcagtcgtgt gcttcttgaa caacttctac 481  cccaaagaca tcaatgtcaa gtggaagatt gatggcagtg aacgacaaaa tggcgtcctg 541  aacagttgga ctgatcagga cagcaaagac agcacctaca gcatgagcag caccctcatg 601  ttgaccaagg acgagtatga acgacataac agctatacct gtgaggccac tcacaagaca 661  tcaacttcac ccattgtcaa gagcttcaac aggaatgagt gttag
```

(4) Protein Sequence Defining the Full Length 1A3 Light Chain Sequence (1A3 Kappa Variable Region and Constant Region) (without Signal Sequence) (SEQ ID NO. 125)

```
  1  diqmtqspas lsvsvgetvt itcraseniy snlawyqqkq gkspqllvya atnladgvps 61  rfsgsgsgtq fslkinslqs edfgtyycqh fwgtpytfgg gtkleikrad aaptvsifpp 121  sseqltsgga svvcflnnfy pkdinvkwki dgserqngvl nswtdqdskd stysmsstlm 181  ltkdeyerhn sytceathkt stspivksfn rnec
```

(5) Nucleic Acid Sequence Encoding the Full Length 2B8 Heavy Chain Sequence (2B8 Heavy Chain Variable Region and IgG1 Constant Region) (Signal Sequence Underlined) (SEQ ID NO. 126)

```
   1  atgggatgga gctatatcat cctcttttg gtagcaacag ctacagatgt ccactcccag 61  gtccaactgc agcagcctgg ggctgaactg gtgaagcctg gacttcagt gaagctgtcc 121  tgcaaggctt ctggctacac cttcaccacc tactggatgc actgggtgaa tcagaggcct 181  ggacaaggcc ttgagtggat tggagagatt aatcctacca acggtcatac taactacaat 241  gagaagttca agagcaaggc cacactgact gtagacaaat cctccagcac agcctacatg 301  caactcagca gcctgacatc tgaggactct gcggtctatt actgtgcaag aaactatgtt 361  ggtagcatct ttgactactg gggccaaggc accactctca cagtctcctc agccaaaacg 421  acacccccat ctgtctatcc actggcccct ggatctgctg cccaaactaa ctccatggtg 481  accctgggat gcctggtcaa gggctatttc cctgagccag tgacagtgac ctggaactct 541  ggatccctgt ccagcggtgt gcacaccttc ccagctgtcc tgcagtctga cctctacact 601  ctgagcagct cagtgactgt cccctccagc acctggccca gcgagaccgt cacctgcaac 661  gttgcccacc cggccagcag caccaaggtg gacaagaaaa ttgtgcccag ggattgtggt 721  tgtaagcctt gcatatgtac agtcccagaa gtatcatctg tcttcatctt cccccaaag 781  cccaaggatg tgctcaccat tactctgact cctaaggtca cgtgtgttgt ggtagacatc 841  agcaaggatg atcccgaggt ccagttcagc tggtttgtag atgatgtgga ggtgcacaca 901  gctcagacgc aaccccggga ggagcagttc aacagcactt tccgctcagt cagtgaactt 961  cccatcatgc accaggactg gctcaatggc aaggagttca atgcaggt caacagtgca 1021  gctttccctg ccccatcga gaaaaccatc tccaaaacca aggcagacc gaaggctcca 1081  caggtgtaca ccattccacc tcccaaggag cagatggcca aggataaagt cagtctgacc
```

```
1141  tgcatgataa cagacttctt ccctgaagac attactgtgg agtggcagtg gaatgggcag 1201  ccagcggaga actacaagaa cactcagccc atcatggaca cagatggctc ttacttcgtc 1261  tacagcaagc tcaatgtgca gaagagcaac tgggaggcag gaaatacttt cacctgctct 1321  gtgttacatg agggcctgca caaccaccat actgagaaga gcctctccca ctctcctggt 1381  aaatga
```

(6) Protein Sequence Defining the Full Length 2B8 Heavy Chain Sequence (2B8 Heavy Chain Variable Region and IgG1 Constant Region) (without Signal Sequence) (SEQ ID NO. 127)

```
  1  qvqlqqpgae lvkpgtsvkl sckasgytft tywmhwvnqr pgqglewige inptnghtny 61  nekfkskatl tvdkssstay mqlssltsed savyycarny vgsifdywgq gttltvssak 121  ttppsvypla pgsaaqtnsm vtlgclvkgy fpepvtvtwn sgslssgvht fpavlqsdly 181  tlsssvtvps stwpsetvtc nvahpasstk vdkkivprdc gckpcictvp evssvfifpp 241  kpkdvltitl tpkvtcvvvd iskddpevqf swfvddvevh taqtqpreeq fnstfrsvse 301  lpimhqdwln gkefkcrvns aafpapiekt isktkgrpka pqvytipppk eqmakdkvsl 361  tcmitdffpe ditvewqwng qpaenykntq pimdtdgsyf vysklnvqks nweagntftc 421  svlheglhnh htekslshsp gk
```

(7) Nucleic Acid Sequence Encoding the Full Length 2B8 Light Chain Sequence (2B8 Kappa Variable Region and Constant Region) (Signal Sequence Underlined) (SEQ ID NO. 128)

```
  1  atggaatcac agactctggt cttcatatcc atactgctct ggttatatgg tgctgatggg 61  aacattgtaa tgacccaatc tcccaaatcc atgtccatgt cagtaggaga gagggtcacc 121  ttgagctgca aggccagtga gaatgtggtt tcttatgtat cctggtatca acagaaacca 181  gcgcagtctc ctaaactgct gatatacggg gcatccaacc ggaacactgg ggtccccgat 241  cgcttcacag gcagtggatc tgcaacagat ttcactctga ccatcagcag tgtgcgggct 301  gaagaccttg cagattatca ctgtgggcag agttacaact atccgtacac gttcggaggg 361  gggaccaggc tggaaataaa acgggctgat gctgcaccaa ctgtatccat cttcccacca 421  tccagtgagc agttaacatc tggaggtgcc tcagtcgtgt gcttcttgaa caacttctac 481  cccaaagaca tcaatgtcaa gtggaagatt gatggcagtg aacgacaaaa tggcgtcctg 541  aacagttgga ctgatcagga cagcaaagac agcacctaca gcatgagcag cacctcacg 601  ttgaccaagg acgagtatga acgacataac agctatacct gtgaggccac tcacaagaca 661  tcaacttcac ccattgtcaa gagcttcaac aggaatgagt gttag
```

(8) Protein Sequence Defining the Full Length 2B8 Light Chain Sequence (2B8 Kappa Variable Region and Constant Region) (without Signal Sequence) (SEQ ID NO. 129)

```
  1  nivmtqspks msmsvgervt lsckasenvv syvswyqqkp aqspklliyg asnrntgvpd 61  rftgsgsatd ftltissvra edladyhcgq synypytfgg gtrleikrad aaptvsifpp 121  sseqltsgga svvcflnnfy pkdinvkwki dserqngvl nswtdqdskd stysmsstlt 181  ltkdeyerhn sytceathkt stspivksfn rnec
```

(9) Nucleic Acid Sequence Encoding the Full Length 2F8 Heavy Chain Sequence (2F8 Heavy Chain Variable Region and IgG1 Constant Region) (Signal Sequence Underlined) (SEQ ID NO. 130)

```
   1  atggaatgga gctgggtctt tctcttcctc ctgtcagtaa ctgcaggtgt ccactgccag
  61  gtccagctga agcagtctgg agctgagctg gtgaggcctg ggacttcagt gaagatgtcc
 121  tgcaaggctt ctggctacac cttcactacc tactatatac actgggtgaa tcagaggcct
 181  ggacagggcc ttgagtggat tggaaagatt ggtcctggaa gtggtagtac ttactacaat
 241  gagatgttca agacaaggc cacattgact gtagacacat cctccagcac agcctacatg
 301  cagctcagca gcctgacatc tgacgactct gcggtctatt tctgtgcaag aaggggactg
 361  ggacgtggct ttgactactg gggccaaggc accactctca gtctcctc agccaaaacg
 421  acacccccat ctgtctatcc actggcccct ggatctgctg cccaaactaa ctccatggtg
 481  accctgggat gcctggtcaa gggctatttc cctgagccag tgacagtgac ctggaactct
 541  ggatccctgt ccagcggtgt gcacaccttc ccagctgtcc tgcagtctga cctctacact
 601  ctgagcagct cagtgactgt cccctccagc acctggccca gcgagaccgt cacctgcaac
 661  gttgcccacc cggccagcag caccaaggtg gacaagaaaa ttgtgcccag ggattgtggt
 721  tgtaagcctt gcatatgtac agtcccagaa gtatcatctg tcttcatctt ccccccaaag
 781  cccaaggatg tgctcaccat tactctgact cctaaggtca cgtgtgttgt ggtagacatc
 841  agcaaggatg atcccgaggt ccagttcagc tggtttgtag atgatgtgga ggtgcacaca
 901  gctcagacgc aacccgggga ggagcagttc aacagcactt tccgctcagt cagtgaactt
 961  cccatcatgc accaggactg gctcaatggc aaggagttca atgcaggt caacagtgca
1021  gctttccctg ccccatcga gaaaaccatc tccaaaacca aaggcagacc gaaggctcca
1081  caggtgtaca ccattccacc tcccaaggag cagatggcca aggataaagt cagtctgacc
1141  tgcatgataa cagacttctt ccctgaagac attactgtgg agtggcagtg gaatgggcag
1201  ccagcggaga actacaagaa cactcagccc atcatggaca cagatggctc ttacttcgtc
1261  tacagcaagc tcaatgtgca gaagagcaac tgggaggcag gaaatacttt cacctgctct
1321  gtgttacatg agggcctgca caaccaccat actgagaaga gcctctccca ctctcctggt
1381  aaatga
```

(10) Protein Sequence Defining the Full Length 2F8 Heavy Chain Sequence (2F8 Heavy Chain Variable Region and IgG1 Constant Region) (without Signal Sequence) (SEQ ID NO. 131)

```
   1  qvqlkqsgae lvrpgtsvkm sckasgytft tyyihwvnqr pgqglewigk igpgsgstyy
  61  nemfkdkatl tvdtssstay mqlssltsdd savyfcarrg lgrgfdywgq gttltvssak
 121  ttppsvypla pgsaaqtnsm vtlgclvkgy fpepvtvtwn sgslssgvht fpavlqsdly
 181  tlsssvtvps stwpsetvtc nvahpasstk vdkkivprdc gckpcictvp evssvfifpp
 241  kpkdvltitl tpkvtcvvvd iskddpevqf swfvddvevh taqtqpreeq fnstfrsvse
 301  lpimhqdwln gkefkcrvns aafpapiekt isktkgrpka pqvytippk eqmakdkvsl
 361  tcmitdffpe ditvewqwng qpaenykntq pimdtdgsyf vysklnvqks nweagntftc
 421  svlheglhnh htekslshsp gk
```

(11) Nucleic Acid Sequence Encoding the Full Length 2F8 Light Chain Sequence (2F8 Kappa Variable Region and Constant Region) (Signal Sequence Underlined) (SEQ ID NO. 132)

```
  1   atggagacag acacaatcct gctatgggtg ctgctgctct gggttccagg ctccactggt
 61   gacattgtgc tgacccaatc tccagcttct ttggctgtgt ctctagggca gagggccacc
121   atctcctgca aggccagcca aagtgttgat tatgatggta atagttatat caactggtac
181   caacagaaac caggacagcc acccaaagtc ctcatctatg ttgcatccaa tctagaatct
241   gggatcccag ccaggtttag tggcagtggg tctgggacag acttcaccct caacatccat
301   cctgtggagg aggaggatgc tgcaacctat tactgtcagc aaagtattga ggatcctccc
361   acgttcggtg ctgggaccaa gctggagctg aaacgggctg atgctgcacc aactgtatcc
421   atcttcccac catccagtga gcagttaaca tctggaggtg cctcagtcgt gtgcttcttg
481   aacaacttct accccaaaga catcaatgtc aagtggaaga ttgatggcag tgaacgacaa
541   aatggcgtcc tgaacagttg gactgatcag gacagcaaag acagcaccta cagcatgagc
601   agcaccctca cgttgaccaa ggacgagtat gaacgacata acagctatac ctgtgaggcc
661   actcacaaga catcaacttc acccattgtc aagagcttca acaggaatga gtgttag
```

(12) Protein Sequence Defining the Full Length 2F8 Light Chain Sequence (2F8 Kappa Variable Region and Constant Region) (without Signal Sequence) (SEQ ID NO. 133)

```
  1   divltqspas lavslgqrat isckasqsvd ydgnsyinwy qqkpgqppkv liyvasnles
 61   giparfsgsg sgtdftlnih pveeedaaty ycqqsiedpp tfgagtklel kradaaptvs
121   ifppsseqlt sggasvvcfl nnfypkdinv kwkidgserq ngvlnswtdq dskdstysms
181   stltltkdey erhnsytcea thktstspiv ksfnrnec
```

(13) Nucleic Acid Sequence Encoding the Full Length 3B6 Heavy Chain Sequence (3B6 Heavy Chain Variable Region and IgG1 Constant Region) (Signal Sequence Underlined) (SEQ ID NO. 134)

```
  1   atggaatggc cttgtatctt tctcttcctc ctgtcagtaa ctgaaggtgt ccactcccag
 61   gttcagctgc agcagtctgg ggctgaactg gtgaggcctg ggtcctcagt gaagatttcc
121   tgcaaggctt ctggctatgt attcagtagc tactggatga actgggtgaa gcagaggcct
181   ggacagggtc ttgagtggat tggacagatt tatcctggag atggtgatag taactacaat
241   ggaaacttca agggtaaagc cacactgact gcagacaaat cctccagtac agcctacatg
301   cagctcagca gcctaacatc tgaggactct gcggtctatt tctgtgcatc ccagctcggg
361   ctacgtgaga actactttga ctactggggc caaggcacca ctctcacagt ctcctcagcc
421   aaaacgacac ccccatctgt ctatccactg gcccctggat ctgctgccca aactaactcc
481   atggtgaccc tgggatgcct ggtcaagggc tatttccctg agccagtgac agtgacctgg
541   aactctggat ccctgtccag cggtgtgcac accttcccag ctgtcctgca gtctgacctc
601   tacactctga gcagctcagt gactgtcccc tccagcacct ggcccagcga gaccgtcacc
661   tgcaacgttg cccacccggc cagcagcacc aaggtggaca agaaaattgt gcccagggat
721   tgtggttgta agccttgcat atgtacagtc ccagaagtat catctgtctt catcttcccc
781   ccaaagccca aggatgtgct caccattact ctgactccta aggtcacgtg tgttgtggta
841   gacatcagca aggatgatcc cgaggtccag ttcagctggt ttgtagatga tgtggaggtg
```

```
 901  cacacagctc agacgcaacc ccgggaggag cagttcaaca gcactttccg ctcagtcagt 961  gaacttccca tcatgcacca ggactggctc aatggcaagg agttcaaatg cagggtcaac 1021  agtgcagctt tccctgcccc catcgagaaa accatctcca aaccaaagg cagaccgaag 1081  gctccacagg tgtacaccat tccacctccc aaggagcaga tggccaagga taaagtcagt 1141  ctgacctgca tgataacaga cttcttccct gaagacatta ctgtggagtg gcagtggaat 1201  gggcagccag cggagaacta caagaacact cagcccatca tggacacaga tggctcttac 1261  ttcgtctaca gcaagctcaa tgtgcagaag agcaactggg aggcaggaaa tactttcacc 1321  tgctctgtgt tacatgaggg cctgcacaac caccatactg agaagagcct ctcccactct 1381  cctggtaaat ga
```

(14) Protein Sequence Defining the Full Length 3B6 Heavy Chain Sequence (3B6 Heavy Chain Variable Region and IgG1 Constant Region) (without Signal Sequence) (SEQ ID NO. 135)

```
  1  qvqlqqsgae lvrpgssvki sckasgyvfs sywmnwvkqr pgqglewigq iypgdgdsny 61  ngnfkgkatl tadkssstay mqlssltsed savyfcasql glrenyfdyw gqgttltvss 121  akttppsvyp lapgsaaqtn smvtlgclvk gyfpepvtvt wnsgslssgv htfpavlqsd 181  lytlsssvtv psstwpsetv tcnvahpass tkvdkkivpr dcgckpcict vpevssvfif 241  ppkpkdvlti tltpkvtcvv vdiskddpev qfswfvddve vhtaqtqpre eqfnstfrsv 301  selpimhqdw lngkefkcrv nsaafpapie ktisktkgrp kapqvytipp pkeqmakdkv 361  sltcmitdff peditvewqw ngqpaenykn tqpimdtdgs yfvysklnvq ksnweagntf 421  tcsvlheglh nhhtekslsh spgk
```

(15) Nucleic Acid Sequence Encoding the Full Length 3B6 Light Chain Sequence (3B6 Kappa Variable Region and Constant Region) (Signal Sequence Underlined) (SEQ ID NO. 136)

```
  1  ATGgacATGa gggaccctgc tcagtttctt ggaatcttgt tgctctggtt tccaggtatc 61  aaatgtgaca tcaagatgac ccagtctcca tcttccatgt atgcatctct aggagagaga 121  gtcacaatca cttgcaaggc gagtcaggac attaaaagct atttaagctg gttccagcag 181  aaaccaggga aatctcctaa gaccctgatc tatcgtgtaa acagattggt agatggggtc 241  ccatcaaggt tcagtggcag tggatctggg caagattctt ctctcaccat caccagcctg 301  gagaatgaag atatgggaat ttattattgt ctacagtatg atgagtttcc gttcacgttc 361  ggagggggga ccaagctgga aataaagcgg gctgatgctg caccaactgt atccatcttc 421  ccaccatcca gtgagcagtt aacatctgga ggtgcctcag tcgtgtgctt cttgaacaac 481  ttctacccca aagacatcaa tgtcaagtgg aagattgatg cagtgaacg acaaaatggc 541  gtcctgaaca gttggactga tcaggacagc aaagacagca cctacagcat gagcagcacc 601  ctcacgttga ccaaggacga gtatgaacga cataacagct atacctgtga ggccactcac 661  aagacatcaa cttcacccat tgtcaagagc ttcaacagga atgagtgtta g
```

(16) Protein Sequence Defining the Full Length 3B6 Light Chain Sequence (3B6 Kappa Variable Region and Constant Region) (without Signal Sequence) (SEQ ID NO. 137)

```
  1  dikmtqspss myaslgervt itckasqdik sylswfqqkp gkspktliyr vnrlvdgvps
 61  rfsgsgsgqd ssltitslen edmgiyyclq ydefpftfgg gtkleikrad aaptvsifpp
121  sseqltsgga svvcflnnfy pkdinvkwki dgserqngvl nswtdqdskd stysmsstlt
181  ltkdeyerhn sytceathkt stspivksfn rnec
```

(17) Nucleic Acid Sequence Encoding the Full Length 3D11 Heavy Chain Sequence (3D11 Heavy Chain Variable Region and IgG1 Constant Region) (Signal Sequence Underlined) (SEQ ID NO. 138)

```
   1  atggctgtcc cggtgctgtt cctctgcctg gttgcatttc caagctgtgt cctgtcccag
  61  gtacagctga aggagtcagg acctggcctg gtggcgccct cacagagcct gtccatcact
 121  tgcactgtct ctgggttttc attaaccagc tatagtttac actgggttcg ccagcctcca
 181  ggaaagggtc tggaatggct gggagtaata tgggctggtg aaacacaaa ttataattcg
 241  tctctcatgt ccagactgac catcaggaaa gacaactcca agagccaagt tttcttaaaa
 301  atgaacagtc tgcaaactga tgacacagcc atgtactact gtgccagaga gaggtttgct
 361  tactggggcc aagggactct ggtcactgtc tctgcagcca aaacgacacc cccatctgtc
 421  tatccactgg ccctggatc tgctgcccaa actaactcca tggtgaccct gggatgcctg
 481  gtcaagggct atttccctga gccagtgaca gtgacctgga actctggatc cctgtccagc
 541  ggtgtgcaca ccttcccagc tgtcctgcag tctgacctct acactctgag cagctcagtg
 601  actgtcccct ccagcacctg gcccagcgag accgtcacct gcaacgttgc ccaccggcc
 661  agcagcacca aggtggacaa gaaaattgtg cccagggatt gtggttgtaa gccttgcata
 721  tgtacagtcc cagaagtatc atctgtcttc atcttccccc caaagcccaa ggatgtgctc
 781  accattactc tgactcctaa ggtcacgtgt gttgtggtag acatcagcaa ggatgatccc
 841  gaggtccagt tcagctggtt tgtagatgat gtggaggtgc acacagctca gacgcaaccc
 901  cgggaggagc agttcaacag cactttccgc tcagtcagtg aacttcccat catgcaccag
 961  gactggctca atggcaagga gttcaaatgc agggtcaaca gtgcagcttt ccctgccccc
1021  atcgagaaaa ccatctccaa aaccaaaggc agaccgaagg ctccacaggt gtacaccatt
1081  ccacctccca aggagcagat ggccaaggat aaagtcagtc tgacctgcat gataacagac
1141  ttcttccctg aagacattac tgtggagtgg cagtggaatg ggcagccagc ggagaactac
1201  aagaacactc agcccatcat ggacacagat ggctcttact tcgtctacag caagctcaat
1261  gtgcagaaga gcaactggga ggcaggaaat actttcacct gctctgtgtt acatgagggc
1321  ctgcacaacc accatactga gaagagcctc tcccactctc ctggtaaatg a
```

(18) Protein Sequence Defining the Full Length 3D11 Heavy Chain Sequence (3D11 Heavy Chain Variable Region and IgG1 Constant Region) (without Signal Sequence) (SEQ ID NO. 139)

```
  1  qvqlkesgpg lvapsqslsi tctvsgfslt syslhwvrqp pgkglewlgv iwaggntnyn
 61  sslmsrltir kdnksqvfl kmnslqtddt amyycarerf aywgqgtlvt vsaakttpps
121  vyplapgsaa qtnsmvtlgc lvkgyfpepv tvtwnsgsls sgvhtfpavl qsdlytlsss
181  vtvpsstwps etvtcnvahp asstkvdkki vprdcgckpc ictpevssv fifppkpkdv
```

-continued

```
241   ltitltpkvt cvvvdiskdd pevqfswfvd dvevhtaqtq preeqfnstf rsvselpimh
301   qdwlngkefk crvnsaafpa piektisktk grpkapqvyt ipppkeqmak dkvsltcmit
361   dffpeditve wqwngqpaen ykntqpimdt dgsyfvyskl nvqksnweag ntftcsvlhe
421   glhnhhteks lshspgk
```

(19) Nucleic Acid Sequence Encoding the Full Length 3D11 Light Chain Sequence (3D11 Kappa Variable Region and Constant Region) (Signal Sequence Underlined) (SEQ ID NO. 140)

```
  1   atggattttc aagtgcagat tttcagcttc ctgctaatca gtgcctcagt caaaatatcc
 61   agaggacaaa ttgttctcac ccagtctcca gcaatcatgt ctgcatatcc aggggagaag
121   gtcaccatga cctgcagtgc cagctcaagt gtaagttaca tgcactggta ccagcagaag
181   tcaggcacct cccccaaaag atggatttat gacacatcca aactggcttc tggagtccct
241   gctcgcttca gtggcagtgg gtctgggacc tcttactccc tcacaatcag tagtatggag
301   gctgaagatg ctgccactta ttactgccag cagtggagta gtaacccact cacgttcggt
361   gctgggacca gctggagct gaaacgggct gatgctgcac caactgtatc catcttccca
421   ccatccagtg agcagttaac atctggaggt gcctcagtcg tgtgcttctt gaacaacttc
481   taccccaaag acatcaatgt caagtggaag attgatggca gtgaacgaca aaatggcgtc
541   ctgaacagtt ggactgatca ggacagcaaa gacagcacct acagcatgag cagcaccctc
601   acgttgacca aggacgagta tgaacgacat aacagctata cctgtgaggc cactcacaag
661   acatcaactt cacccattgt caagagcttc aacaggaatg agtgttag
```

(20) Protein Sequence Defining the Full Length 3D11 Light Chain Sequence (3D11 Kappa Variable Region and Constant Region) (without signal sequence) (SEQ ID NO. 141)

```
  1   qivltqspai msaypgekvt mtcsasssvs ymhwyqqksg tspkrwiydt sklasgvpar
 61   fsgsgsgtsy sltissmeae daatyycqqw ssnpltfgag tklelkrada aptvsifpps
121   seqltsggas vvcflnnfyp kdinvkwkid gserqngvln swtdqdskds tysmsstltl
181   tkdeyerhns ytceathkts tspivksfnr nec
```

(21) Nucleic Acid Sequence Encoding the Full Length 1D3 Heavy Chain Sequence (1D3 Heavy Chain Variable Region and IgG1 Constant Region) (Signal Sequence Underlined) (SEQ ID NO. 142)

```
  1   atgaactttg ggctcagatt gattttcctt gtccttgttt taaaaggtgt gaagtgtgaa
 61   gtgcagctgg tggagtctgg gggaggctta gtgcagcctg gagggtccct gaaactctcc
121   tgtgcagcct ctggattcac tttcagtgac tattacatgt cttgggttcg ccagactcca
181   gagaagaggc tggagtgggt cgcatacatt agtagtggtg gtggtagcac ctactatcca
241   gacagtgtga agggtcgatt caccatctcc cgagacaatg ccaagaacac cctgtacctg
301   caaatgagca gtctgaagtc tgaggacaca gccatatatt actgtgtgag acaaggggat
361   ggttattacg gggactatgc tatggactac tggggtcaag gaacctcagt catcgtctcc
421   tcagccaaaa cgacaccccc atctgtctat ccactggccc ctggatctgc tgcccaaact
481   aactccatgg tgaccctggg atgcctggtc aagggctatt tccctgagcc agtgacagtg
```

-continued

```
 541   acctggaact ctggatccct gtccagcggt gtgcacacct tcccagctgt cctgcagtct
 601   gacctctaca ctctgagcag ctcagtgact gtcccctcca gcacctggcc cagcgagacc
 661   gtcacctgca acgttgccca cccggccagc agcaccaagg tggacaagaa aattgtgccc
 721   agggattgtg gttgtaagcc ttgcatatgt acagtcccag aagtatcatc tgtcttcatc
 781   ttccccccaa agcccaagga tgtgctcacc attactctga ctcctaaggt cacgtgtgtt
 841   gtggtagaca tcagcaagga tgatcccgag gtccagttca gctggtttgt agatgatgtg
 901   gaggtgcaca cagctcagac gcaaccccgg gaggagcagt tcaacagcac tttccgctca
 961   gtcagtgaac ttcccatcat gcaccaggac tggctcaatg gcaaggagtt caaatgcagg
1021   gtcaacagtg cagctttccc tgcccccatc gagaaaacca tctccaaaac caaaggcaga
1081   ccgaaggctc cacaggtgta caccattcca cctcccaagg agcagatggc caaggataaa
1141   gtcagtctga cctgcatgat aacagacttc ttccctgaag acattactgt ggagtggcag
1201   tggaatgggc agccagcgga gaactacaag aacactcagc ccatcatgga cacagatggc
1261   tcttacttcg tctacagcaa gctcaatgtg cagaagagca ctgggaggc aggaaatact
1321   ttcacctgct ctgtgttaca tgagggcctg cacaaccacc atactgagaa gagcctctcc
1381   cactctcctg gtaaatga
```

(22) Protein Sequence Defining the Full Length 1D3 Heavy chain sequence (1D3 Heavy Chain Variable Region and IgG1 Constant Region) (without Signal Sequence) (SEQ ID NO. 143)

```
  1   evqlvesggg lvqpggslkl scaasgftfs dyymswvrqt pekrlewvay issgggstyy
 61   pdsvkgrfti srdnakntly lqmsslksed taiyycvrqg dgyygdyamd ywgqgtsviv
121   ssakttppsv yplapgsaaq tnsmvtlgcl vkgyfpepvt vtwnsgslss gvhtfpavlq
181   sdlytlsssv tvpsstwpse tvtcnvahpa sstkvdkkiv prdcgckpci ctvpevssvf
241   ifppkpkdvl titltpkvtc vvvdiskddp evqfswfvdd vevhtaqtqp reeqfnstfr
301   svselpimhq dwlngkefkc rvnsaafpap iektisktkg rpkapqvyti pppkeqmakd
361   kvsltcmitd ffpeditvew qwngqpaeny kntqpimdtd gsyfvyskln vqksnweagn
421   tftcsvlheg lhnhhteksl shspgk
```

(23) Nucleic Acid Sequence Encoding the Full Length 1D3 Light Chain Sequence (1D3 Kappa Variable Region and Constant Region) (Signal Sequence Underlined) (SEQ ID NO. 144)

```
  1   atgagtgtgc ccactcaggt cctggggttg ctgctgctgt ggcttacaga tgtcagatgt
 61   gacatccaga tgactcagtc tccagcctcc ctatctgtat ctgtgggaga aactgtcacc
121   atcacatgtc gaacaagtga gaatatttac agtaatttag cgtggtatca gcagaaacag
181   ggaaaatctc ctcagctcct aatctatgct gcaacaaact agcagatgg tgtgccatca
241   aggttcagtg gcagtggatc aggcacacag ttttcccctca ggatcaacag cctgcagtct
301   gaagattttg ggaggtatta ctgtcaacat ttttggggga ctccgtacac gttcggaggg
361   gggaccaaac tggaaataaa acgggctgat gctgcaccaa ctgtatccat cttcccacca
421   tccagtgagc agttaacatc tggaggtgcc tcagtcgtgt gcttcttgaa caacttctac
481   cccaaagaca tcaatgtcaa gtggaagatt gatggcagtg aacgacaaaa tggcgtcctg
```

```
541  aacagttgga ctgatcagga cagcaaagac agcacctaca gcatgagcag caccctcacg 601  ttgaccaagg acgagtatga acgacataac agctatacct gtgaggccac tcacaagaca 661  tcaacttcac ccattgtcaa gagcttcaac aggaatgagt gttag
```

(24) Protein Sequence Defining the Full Length 1D3 Light Chain Sequence (1D3 Kappa Variable Region and Constant Region) (without signal sequence) (SEQ ID NO. 145)

```
  1  diqmtqspas lsvsvgetvt itcrtseniy snlawyqqkq gkspqlliya atnladgvps 61  rfsgsgsgtq fslrinslqs edfgryycqh fwgtpytfgg gtkleikrad aaptvsifpp 121  sseqltsgga svvcflnnfy pkdinvkwki dgserqngvl nswtdqdskd stysmsstlt 181  ltkdeyerhn sytceathkt stspivksfn rnec
```

(25) Nucleic Acid Sequence Encoding the Full Length 1F3 Heavy Chain Sequence (1F3 Heavy Chain Variable Region and IgG1 Constant Region) (signal sequence underlined) (SEQ ID NO. 146)

```
   1  atgaactttg ggctcagatt gatttttcctt gtccttgttt taaaaggtgt gaagtgtgag 61  gtgcagctgg tggagtctgg gggaggctta gtgcagtctg gagggtccct gaaactctcc 121  tgtgcggcct ctggattcac tttcagtaac tatttcatgt cttgggttcg ccagactcca 181  gagaagaggc tggagtgggt cgcatatatt agtagtggtg gtggtagcac ctactatcca 241  gacagtgtga agggtcgatt caccatctct agagacaatg ccaagaacac cctgtacctg 301  caaatgagca gtctgaagtc tgaggacaca gccatgtatt actgtgtaag acaaggggat 361  ggttactacg gggactatgc tatggactac tggggtcaag gaacctcagt caccgtctcc 421  tcagccaaaa cgacaccccc atctgtctat ccactggccc ctggatctgc tgcccaaact 481  aactccatgg tgaccctggg atgcctggtc aagggctatt tccctgagcc agtgacagtg 541  acctggaact ctggatccct gtccagcggt gtgcacacct tcccagctgt cctgcagtct 601  gacctctaca ctctgagcag ctcagtgact gtcccctcca gcacctggcc cagcgagacc 661  gtcacctgca acgttgccca cccggccagc agcaccaagg tggacaagaa aattgtgccc 721  agggattgtg gttgtaagcc ttgcatatgt acagtcccag aagtatcatc tgtcttcatc 781  ttccccccaa agcccaagga tgtgctcacc attactctga ctcctaaggt cacgtgtgtt 841  gtggtagaca tcagcaagga tgatcccgag gtccagttca gctggtttgt agatgatgtg 901  gaggtgcaca cagctcagac gcaaccccgg gaggagcagt tcaacagcac tttccgctca 961  gtcagtgaac ttcccatcat gcaccaggac tggctcaatg gcaaggagtt caaatgcagg 1021  gtcaacagtg cagctttccc tgcccccatc gagaaaacca tctccaaaac caaaggcaga 1081  ccgaaggctc cacaggtgta caccattcca cctcccaagg agcagatggc caaggataaa 1141  gtcagtctga cctgcatgat aacagacttc ttccctgaag acattactgt ggagtggcag 1201  tggaatgggc agccagcgga gaactacaag aacactcagc ccatcatgga cacagatggc 1261  tcttacttcg tctacagcaa gctcaatgtg cagaagagca actgggaggc aggaaatact 1321  ttcacctgct ctgtgttaca tgagggcctg cacaaccacc atactgagaa gagcctctcc 1381  cactctcctg gtaaatga
```

(26) Protein Sequence Defining the Full Length 1F3 Heavy Chain Sequence (1F3 Heavy Chain Variable Region and IgG1 Constant Region) (without Signal Sequence) (SEQ ID NO. 147)

```
  1  evqlvesggg lvqsggslkl scaasgftfs nyfmswvrqt pekrlewvay issgggstyy
 61  pdsvkgrfti srdnakntly lqmsslksed tamyycvrqg dgyygdyamd ywgqgtsvtv
121  ssakttppsv yplapgsaaq tnsmvtlgcl vkgyfpepvt vtwnsgslss gvhtfpavlq
181  sdlytlsssv tvpsstwpse tvtcnvahpa sstkvdkkiv prdcgckpci ctvpevssvf
241  ifppkpkdvl titltpkvtc vvvdiskddp evqfswfvdd vevhtaqtqp reeqfnstfr
301  syselpimhq dwlngkefkc rvnsaafpap iektisktkg rpkapqvyti pppkeqmakd
361  kvsltcmitd ffpeditvew qwngqpaeny kntqpimdtd gsyfvyskln vqksnweagn
421  tftcsvlheg lhnhhteksl shspgk
```

(27) Nucleic Acid Sequence Encoding the Full Length 1F3 Light Chain Sequence (1F3 Kappa Variable Region and Constant Region) (Signal Sequence Underlined) (SEQ ID NO. 148)

```
  1  atgagtgtgc ccactcaggt cctggggttg ctgctgctgt ggcttacaga tgccagatgt
 61  gacatccaga tgactcagtc tccagcctcc ctatctgtat ctgtgggaga aactgtcacc
121  atcacatgtc gagcaagtga aatatttac agtaatttag catggtatca gcagaaacag
181  ggaaaatctc ctcagctcct ggtctatgat gcaacacact taccagatgg tgtgccatca
241  aggttcagtg gcagtggatc aggcacacag ttttccctca agatcaacag cctgcagtct
301  gaagattttg ggagttatta ctgtcaacat ttttggggta ctccgtacac gtttggaggg
361  gggaccagac tggaaattaa acgggctgat gctgcaccaa ctgtatccat cttcccacca
421  tccagtgagc agttaacatc tggaggtgcc tcagtcgtgt gcttcttgaa caacttctac
481  cccaaagaca tcaatgtcaa gtggaagatt gatggcagtg aacgacaaaa tggcgtcctg
541  aacagttgga ctgatcagga cagcaaagac agcacctaca gcatgagcag cccctcacg
601  ttgaccaagg acgagtatga acgacataac agctatacct gtgaggccac tcacaagaca
661  tcaacttcac ccattgtcaa gagcttcaac aggaatgagt gttag
```

(28) Protein Sequence Defining the Full Length 1F3 Light Chain Sequence (1F3 Kappa Variable Region and Constant Region) (without Signal Sequence) (SEQ ID NO. 149)

```
  1  diqmtqspas lsvsvgetvt itcraseniy snlawyqqkq gkspqllvyd athlpdgvps
 61  rfsgsgsgtq fslkinslqs edfgsyycqh fwgtpytfgg gtrleikrad aaptvsifpp
121  sseqltsgga svvcflnnfy pkdinvkwki dgserqngvl nswtdqdskd stysmsstlt
181  ltkdeyerhn sytceathkt stspivksfn rnec
```

(29) Nucleic Acid Sequence Encoding the Full Length 3A12 Heavy Chain Sequence (3A12 Heavy Chain Variable Region and IgG1 Constant Region) (Signal Sequence Underlined) (SEQ ID NO. 150)

```
  1  atgaactttg ggctcagatt gatttteett gtccttgttt taaaaggtgt gaagtgtgaa
 61  gtgcagctgg tggagtctgg gggaggctta gtgcagcctg gagggtccct gaaaatctcc
121  tgtgcagcct ctggatttac tttcagtaac tatttcatgt cttgggttcg ccagactcca
```

-continued

```
 181   gagaagaggc tggagtgggt cgcatacatt agtagtggtg gtggtagcac ctactatcca
 241   gacagtgtga agggtcgatt caccatctcc agagacaatg ccaagaacac cctgtacctg
 301   caaatgaaca gtctgaagtc tgaggacaca gccatgtatt actgtgtaag acaaggagat
 361   ggttactatg gggactatgc tatggactac tggggtcaag gaacctcagt caccgtctcc
 421   tcagccaaaa cgacaccccc atctgtctat ccactggccc ctggatctgc tgcccaaact
 481   aactccatgg tgaccctggg atgcctggtc aagggctatt tccctgagcc agtgacagtg
 541   acctggaact ctggatccct gtccagcggt gtgcacacct tcccagctgt cctgcagtct
 601   gacctctaca ctctgagcag ctcagtgact gtcccctcca gcctggcc cagcgagacc
 661   gtcacctgca acgttgccca cccggccagc agcaccaagg tggacaagaa aattgtgccc
 721   agggattgtg gttgtaagcc ttgcatatgt acagtcccag aagtatcatc tgtcttcatc
 781   ttcccccaa agcccaagga tgtgctcacc attactctga ctcctaaggt cacgtgtgtt
 841   gtggtagaca tcagcaagga tgatcccgag gtccagttca gctggtttgt agatgatgtg
 901   gaggtgcaca cagctcagac gcaaccccgg gaggagcagt tcaacagcac tttccgctca
 961   gtcagtgaac ttcccatcat gcaccaggac tggctcaatg gcaaggagtt caaatgcagg
1021   gtcaacagtg cagctttccc tgcccccatc gagaaaacca tctccaaaac caaaggcaga
1081   ccgaaggctc acaggtgta caccattcca cctcccaagg agcagatggc caaggataaa
1141   gtcagtctga cctgcatgat aacagacttc ttccctgaag acattactgt ggagtggcag
1201   tggaatgggc agccagcgga gaactacaag aacactcagc ccatcatgga cacagatggc
1261   tcttacttcg tctacagcaa gctcaatgtg cagaagagca actgggaggc aggaaatact
1321   ttcacctgct ctgtgttaca tgagggcctg cacaaccacc atactgagaa gagcctctcc
1381   cactctcctg gtaaatga
```

(30) Protein Sequence Defining the Full Length 3A12 Heavy Chain Sequence (3A12 Heavy Chain Variable Region and IgG1 Constant Region) (without Signal Sequence) (SEQ ID NO. 151)

```
  1   evqlvesggg lvqpggslki scaasgftfs nyfmswvrqt pekrlewvay issgggstyy
 61   pdsvkgrfti srdnakntly lqmnslksed tamyycvrqg dgyygdyamd ywgqgtsvtv
121   ssakttppsv yplapgsaaq tnsmvtlgcl vkgyfpepvt vtwnsgslss gvhtfpavlq
181   sdlytlsssv tvpsstwpse tvtcnvahpa sstkvdkkiv prdcgckpci ctvpevssvf
241   ifppkpkdvl titltpkvtc vvvdiskddp evqfswfvdd vevhtaqtqp reeqfnstfr
301   svselpimhq dwlngkefkc rvnsaafpap iektisktkg rpkapqvyti pppkeqmakd
361   kvsltcmitd ffpeditvew qwngqpaeny kntqpimdtd gsyfvyskln vqksnweagn
421   tftcsvlheg lhnhhteksl shspgk
```

(31) Nucleic Acid Sequence Encoding the Full Length 3A12 Light Chain Sequence (3A12 Kappa Variable Region and Constant Region) (signal sequence underlined) (SEQ ID NO. 152)

```
  1   atgagtgtgc ccactcaggt cctgggttg ctgctgctgt ggcttacaga tgccagatgt
 61   gacatccaga tgactcagtc gccagcctcc ctatctgtat ctgtgggaga aactgtcacc
121   atcacatgtc gagcaagtga gaatatttac attaatttag catggtatca gcagaaacag
```

-continued

```
181   ggaaaatctc ctcagctcct ggtccatgct gcaacaaagt tagcagatgg tgtgccatca 241   aggttcagtg gcagtggatc aggcacacag tattccctca agatcaacag cctgcagtct 301   gaagattttg ggagttatta ctgtcaacat ttttggggta ctccgtacac gttcggaggg 361   gggaccaaac tagaaataaa acgggctgat gctgcaccaa ctgtatccat cttcccacca 421   tccagtgagc agttaacatc tggaggtgcc tcagtcgtgt gcttcttgaa caacttctac 481   cccaaagaca tcaatgtcaa gtggaagatt gatggcagtg aacgacaaaa tggcgtcctg 541   aacagttgga ctgatcagga cagcaaagac agcacctaca gcatgagcag caccctcacg 601   ttgaccaagg acgagtatga acgacataac agctatacct gtgaggccac tcacaagaca 661   tcaacttcac ccattgtcaa gagcttcaac aggaatgagt gttag
```

(32) Protein Sequence Defining the Full Length 3A12 Light Chain Sequence (3A12 Kappa Variable Region and Constant Region) (without Signal Sequence) (SEQ ID NO. 153)

```
  1   diqmtqspas lsvsvgetvt itcraseniy inlawyqqkq gkspqllvha atkladgvps 61   rfsgsgsgtq yslkinslqs edfgsyycqh fwgtpytfgg gtkleikrad aaptvsifpp 121   sseqltsgga svvcflnnfy pkdinvkwki dgserqngvl nswtdqdskd stysmsstlt 181   ltkdeyerhn sytceathkt stspivksfn rnec
```

For convenience, Table 2 provides a concordance chart showing the correspondence between the full length sequences of the antibodies discussed in this Example with those presented in the Sequence Listing.

TABLE 2

| SEQ. ID NO. | Protein or Nucleic Acid |
|---|---|
| 122 | 1A3 Heavy Variable + IgG1 constant - nucleic acid |
| 123 | 1A3 Heavy Variable + IgG1 constant - protein |
| 124 | 1A3 Light Variable + constant - nucleic acid |
| 125 | 1A3 Light Variable + constant - protein |
| 126 | 2B8 Heavy Variable + IgG1 constant - nucleic acid |
| 127 | 2B8 Heavy Variable + IgG1 constant - protein |
| 128 | 2B8 Light Variable + constant - nucleic acid |
| 129 | 2B8 Light Variable + constant - protein |
| 130 | 2F8 Heavy Variable + IgG1 constant - nucleic acid |
| 131 | 2F8 Heavy Variable + IgG1 constant - protein |
| 132 | 2F8 Light Variable + constant - nucleic acid |
| 133 | 2F8 Light Variable + constant - protein |
| 134 | 3B6 Heavy Variable + IgG1 constant - nucleic acid |
| 135 | 3B6 Heavy Variable + IgG1 constant - protein |
| 136 | 3B6 Light Variable + constant - nucleic acid |
| 137 | 3B6 Light Variable + constant - protein |
| 138 | 3D11 Heavy Variable + IgG1 constant - nucleic acid |
| 139 | 3D11 Heavy Variable + IgG1 constant - protein |
| 140 | 3D11 Light Variable + constant - nucleic acid |
| 141 | 3D11 Light Variable + constant - protein |
| 142 | 1D3 Heavy Variable + IgG1 constant - nucleic acid |
| 143 | 1D3 Heavy Variable + IgG1 constant - protein |
| 144 | 1D3 Light Variable + constant - nucleic acid |
| 145 | 1D3 Light Variable + constant - protein |
| 146 | 1F3 Heavy Variable + IgG1 constant - nucleic acid |
| 147 | 1F3 Heavy Variable + IgG1 constant - protein |
| 148 | 1F3 Light Variable + constant - nucleic acid |
| 149 | 1F3 Light Variable + constant - protein |
| 150 | 3A12 Heavy Variable + IgG1 constant - nucleic acid |
| 151 | 3A12 Heavy Variable + IgG1 constant - protein |
| 152 | 3A12 Light Variable + constant - nucleic acid |
| 153 | 3A12 Light Variable + constant - protein |

Example 3

Production of Various Recombinant hHGF Proteins

This Example describes the cloning and expression of a number of recombinant proteins used to characterize the antibodies created in Example 1 and in Example 14. In particular, this Example describes the cloning and expression of recombinant hHGF protein, a recombinant hHGF protein containing a glycine to glutamate substitution at position 555 (G555E), a recombinant hHGF protein containing a cysteine to arginine substitution at position 561 (C561R), a recombinant mouse-human-mouse (mhm) chimeric HGF protein containing the human V495-L585 HGF sequence disposed within mouse HGF sequence, a recombinant mhm chimeric HGF protein containing the human I499-R566 HGF sequence disposed within mouse HGF sequence, and a recombinant mhm chimeric HGF protein containing human W507-L585 HGF sequence disposed within mouse HGF sequence.

The following expression constructs were generated using standard molecular techniques and the resulting cDNA sequences were confirmed by DNA sequencing:

a. hHGF-Fc

In a first round of PCR, two overlapping PCR fragments were generated introducing a Not I site and encoding a 6×His tag between hHGF and hIgFc. The overlapping PCR fragments served as template in a second round to amplify hHGF-his-IgFc. The resulting fragment was digested by NheI and BamHI and cloned into pcDNA5/FRT (Invitrogen, #35-3014). Then, hHGF was amplified from Invitrogen clone ID: 10H29794 (human HGF cDNA). The sequence was found to correspond to the sequence deposited at the NCBI under accession number NM_000601.4.

(1) 5' hHGF NheI Primer
ACTGGCTAGCATGTGGGTGACCAAACTCCT (SEQ ID NO. 102)

(2) 3' hHGF NotI His Tag Primer
GTGATGGTGATGGTGATGGCGGCCGCAT-
GACTGTGGTACCTTATATG (SEQ ID NO. 103)
(3) 5' HisIgFc Primer
ACTGGCGGCCGCCATCACCATCACCATCAC (SEQ ID NO. 104)
(4) 3' IgFc BamHI Primer
ACTGGGATCCTCACTATTTACCCGGGGACAG (SEQ ID NO. 105)

b. hHGF-Fc G555E and hHGF-Fc C561R hHGF-Fc mutants G555E and C561R were generated by site directed mutagenesis using the QuikChange II XL site-directed mutagenesis kit (Stratagene) according to manufacturer's instructions.

(1) hHGF-Fc (G555E) Sense Primer
CATGATGTCCACGAAAGAGGAGATGAG (SEQ ID NO. 106)
(2) hHGF-Fc (G555E) Anti-Sense Primer
CTCATCTCCTCTTTCGTGGACATCATG (SEQ ID NO. 107)
(3) hHGF-Fc (C561R) Sense Primer
GGAAGAGGAGATGAGAAACGCAAACAG-GTTCTCAATG (SEQ ID NO. 108)
(4) hHGF-Fc (C561R) Anti-sense Primer
CATTGAGAACCTGTTTGCGTTTCT-CATCTCCTCTTCC (SEQ ID NO. 109)

c. Mouse-Human-Mouse Chimera Fc

The mouse-human-mouse chimera IgFc construct contains mHGF alpha chain-hHGF, β-chain amino acids Val 495-Leu 585 of human HGF, and mHGF C-terminal beta chain followed by 6xHis tag and IgG-Fc.

Human HGF cDNA encoding amino acids V495-L585 was amplified from Invitrogen clone ID: IOH29794 (human HGF cDNA). The sequence corresponds to the sequence deposited at the NCBI under accession number NM_000601.4. Mouse HGF sequences were amplified by RT-PCR from mouse liver total RNA (Clontech, #636603) using the Super Script One Step RT-PCR kit from Invitrogen (#10928-034) according to manufacturer's instructions. The mHGF cDNA sequence corresponds to the sequence deposited at the NCBI under accession number D10213.1.

Three fragments, referred to as Fragments 1, 2, and 3, were generated using overlapping PCR primers and annealed in consecutive rounds of PCR amplification. The final product was cleaved with NheI and NotI and cloned into pcDNA5/FRT IgFc.)

(1) Fragment 1 Primers for mHGF Alpha Chain 5'NheI
5'ATCGGCTAGCATGATGTGGGGGACCAAAC (SEQ ID NO. 110)
3'    GAATCCCATTTACAACCCGCAGT-TGTTTTGTTTTGG (SEQ ID NO. 111)
(2) Fragment 2 Primers for hHGF Beta Chain aa V495-L585
5'    CCAAAACAAAACAACTGCGGGTTG-TAAATGGGATTC (SEQ ID NO. 112)
3'    CAGGATTGCAGGTCGAGCAAGCTTCAT-TAAAACCAGATCT (SEQ ID NO. 113)
(3) Fragment 3 Primer for mHGF Beta Chain C-terminus 3'NotI
5'    AGATCTGGTTTTAATGAAGCTTGCTC-GACCTGCAATCCTG (SEQ ID NO. 114)
3'    GTAATTTTGACATACAAGTTGTGCGGC-CGCCATCACCATCACCATCAC (SEQ ID NO. 115)

d. Construction of hHGF and mhm Chimera

The vectors encoding hHGF and mhm chimera (V495-L585), pcDNA5/FRT hHGF and pcDNA5/FRT-mhm chimera (V495-L585), without Fc-tag were generated by site directed mutagenesis. A stop codon was introduced 3' of the 6xHis tag using the QuikChange II XL site-directed mutagenesis kit (Stratagene) according to manufacturer's instructions. The mutagenesis primer included Primer 1: CATCAC-CATCACCATCACTAAGCGGGTCTGGTGCCACG (SEQ ID NO. 116), and Primer 2: CGTGGCACCAGACCCGCT-TAGTGATGGTGATGGTGATG (SEQ ID NO. 117).

In addition, two additional mhm chimeras were created from the pcDNA5/FRT-mhm (V495-L585) construct by site directed mutagenesis using the QuikChange II XL site-directed mutagenesis kit (Stratagene) according to manufacturer's instructions. One mhm construct contained the region of I499-R556 of hHGF disposed between murine sequences. The other mhm construct contained the region of W507-L585 of hHGF disposed between murine sequences.

For the mhm chimera (I1499-R556), the following point mutations were made in order in the template pcDNA5/FRT-mhm chimera (V495-L585) construct: D558E, C561R, V564I, V567I and M583L, using the appropriate oligonucleotide sequences. For the mhm chimera (W507-L585), the following point mutations were introduced in one step in the template pcDNA5/FRT-mhm chimera (V495-L585) construct: Q502R, $N_{504}T$ and I505V, using the appropriate oligonucleotide sequences.

The resulting nucleotide sequence of the hHGF-Fc protein is set forth as SEQ ID NO. 118, including signal sequence (nucleotides 1-93) and prodomain (nucleotides 94-162). The amino acid sequence of the hHGF-Fc protein is set forth as SEQ ID NO. 119.

The resulting nucleotide sequence encoding the mhm (V495-L585)-Fc chimeric protein is set forth in SEQ ID NO. 120, including signal sequence (nucleotides 1-96) and prodomain (nucleotides 97-165). The amino acid sequence of the mhm (V495-L585)-Fc chimeric protein is set forth in SEQ ID NO. 121.

The resulting nucleotide sequence encoding, and the protein sequence defining, the mhm (V495-L585) construct are set forth in SEQ ID NOS. 211 and 212, respectively. The nucleic acid sequence set forth in SEQ ID NO. 211 includes the signal sequence (nucleotides 1-96) and the prodomain (nucleotides 97-165), and the protein sequence set forth in SEQ ID NO. 212 includes the active protein sequence (without the signal sequence or the prodomain). The resulting nucleotide sequence encoding, and the protein sequence defining, the mhm (I499-R556) construct are set forth in SEQ ID NOS. 213 and 214, respectively. The nucleic acid sequence set forth in SEQ ID NO. 213 includes the signal sequence (nucleotides 1-96) and the prodomain (nucleotides 97-165), and the protein sequence set forth in SEQ ID NO. 214 includes the active protein sequence (without the signal sequence or the prodomain). The resulting nucleotide sequence encoding, and the protein sequence defining, the mhm (W507-L585) are set forth in SEQ ID NOS. 215 and 216, respectively. The nucleic acid sequence set forth in SEQ ID NO. 215 includes the signal sequence (nucleotides 1-96) and the prodomain (nucleotides 97-165), and the protein sequence set forth in SEQ ID NO. 216 includes the active protein sequence (without the signal sequence or the prodomain).

e. Protein Expression (1) Cell Culture

CHO FlpIn cells (Invitrogen, Catalog No. R758-07)) were grown in F12K media (ATCC, Catalog No. 30-2004), 10% FCS (Invitrogen, Catalog No. 10438026), 1% Penicillin (10000 units/mL)/Streptomycin (10,000 µg/mL) (Invitrogen, Catalog No. 15140-122) at 37° C., 5% $CO_2$, 100 µg/mL Zeocin (Invitrogen, Catalog No. R250-01).

(2) Generation of Stable CHO FlpIn Cell Lines

CHO FlpIn host cells were transfected with a 9:1 ratio of pOG44:pcDNA5/FRT expression plasmid DNA using lipofectamine 2000 according to the manufacturer's instructions (Invitrogen, Catalog No. 11668-027). As controls, cells were transfected with empty pcDNA5/FRT vector/pOG44 and pOG44 plasmid (Invitrogen, Catalog No. 35-3018) alone. Twenty four hours after transfection, the cells were split, and after forty eight hours 0.5 mg/mL Hygromycin B (Sigma, Catalog No. H0654-SPEC) was added to the cells. Polyclonal selection of stable cells was performed in F12K, 10% FCS, 1% Penicillin/Streptomycin, 0.5 mg/mL Hygromycin B.

(3) Protein Expression in Stable CHO Flpin Cell Lines

Approximately $2 \times 10^6$ cells were seeded in 15 cm plates and grown in F12K (ATCC, Catalog No. 30-2004)/DMEM high glucose (Invitrogen, Catalog No. 11995065) 1:1, 5% ultra low IgG FCS (Invitrogen, #16250-78) at 37° C., 5% $CO_2$ for 5-6 days. Supernatants were harvested and resulting proteins analyzed by ELISA and by surface plasmon resonance.

Example 4

Binding Characteristics of Anti-hHGF Monoclonal Antibodies

The monoclonal antibodies produced in Example 1 were characterized by their ability to bind hHGF, and certain of the recombinant HGF proteins produced in Example 3.

The antibodies were analyzed by surface-plasmon resonance using a BIAcore T100 instrument to assess their ability to bind HGF and certain of the fusion proteins discussed in Example 3. Each antibody was immobilized on a carboxymethylated dextran CM5 sensor chip (BIAcore, Catalog No. BR-1006-68) by amine coupling (BIAcore, Catalog No. BR-1000-50) using a standard coupling protocol according to manufacturer's instructions.

Analyses were performed at 25° C. using PBS (GIBCO, Catalog No. 14040-133) containing 0.05% surfactant P20 (BIAcore, Catalog No. R-1000-54), 2 mg/mL BSA (EMD, Catalog No. 2930) and 10 mg/mL CM-Dextran Sodium salt (Fluka, Catalog No. 86524) as running buffer. Supernatant containing different HGF fusion proteins or supernatant from cells transfected with empty vector were injected over each antibody at a flow rate of 30 µL/min for 3 minutes. The resulting binding was determined as resonance units (RU) over baseline 30 seconds after the end of injection. Binding was compared to human HGF (R&D Systems, Catalog No. 294-HGN-025) diluted in running buffer. Non-specific binding was monitored by comparing binding to a control surface where mouse IgG (Rockland, Catalog No. 010-0102) was immobilized using the same amine coupling procedure.

The results are summarized in the Table 3.

TABLE 3

| Antibody | rhHGF (R & D Systems) | mHGF (R & D Systems) | mhm chimera (V495-L585) | human HGF | G555E | C561R |
|---|---|---|---|---|---|---|
| 1A3 | Yes | No | No | Yes | Yes | Yes |
| 1D3 | Yes | No | Yes | Yes | Yes | Yes |
| 1F3 | Yes | Yes | Yes | Yes | Yes | Yes |
| 2B8 | Yes | No | Yes | Yes | Yes | Yes |
| 2F8 | Yes | Yes | No | Yes | Yes | Yes |
| 3A12 | Yes | No | No | Yes | Yes | Yes |
| 3B6 | Yes | No | No | Yes | Yes | Yes |
| 3D11 | Yes | No | No | Yes | Yes | Yes |

The results in Table 3 demonstrate that each of the antibodies bind rHGF and purified human HGF. Furthermore, all of the antibodies bind hHGF containing point mutations G555E and C561R. In general, all of the antibodies except for 1F3 and 2F8 did not bind murine HGF demonstrating that the antibodies 1A3, 1D3, 2B8, 3A12, 3B6, and 3D11 specifically bind human HGF. Antibodies 1D3, 1F3, and 2B8 bind the mouse-human-mouse chimera whereas the remaining antibodies did not. The results suggest that the antibodies 1D3 and 2B8 at least in part bind to residues 495-585 of human HGF. The antibodies 1A3, 3A12, 3B6, and 3D11 appear to bind portions of human hHGF other than residues 495-585. At present, it is uncertain why 2F8 does not bind the mhm chimera as it appears to bind both hHGF and mHGF.

Example 5

Ability of Anti-hHGF Monoclonal Antibodies to Bind Reduced and Non-Reduced HGF

In this Example, the anti-hHGF monoclonal antibodies produced in Example 1 were analyzed for their ability to bind reduced and non-reduced HGF.

The reactivity of the anti-HGF sera with the recombinant hHGF was assessed by immunoblotting. Eight µg of recombinant hHGF protein in NuPAGE MOPS SDS running buffer (Invitrogen) with or without NuPAGE sample reducing buffer (Invitrogen) was fractionated on a 4-12% Bis-Tris 1.0 mm×2D well gel (Invitrogen, Carlsbad, Calif.). The fractionated proteins then were transferred onto a nitrocellulose membrane using standard procedures. The nitrocellulose membranes were blocked with 5% nonfat milk powder solution in Tris buffered Saline with 0.1% Tween-20® (TBST), and then mounted onto a Mini Protean II Multi-Screen apparatus (BioRad) for further blocking.

The resulting membranes were probed with the purified antibodies on a Multi-Screen apparatus. The purified antibodies were diluted to 5 µg/mL in blocking buffer. The nitrocellulose membrane then was removed from the apparatus, and incubated with horseradish peroxidase-labeled anti-mouse IgG antibodies. The results are summarized in Table 4, where the numbers reflect the extent of binding with—representing the least (little or no binding) and 3+ representing the most binding.

TABLE 4

| Antibody | Reduced (exposure: 3-5 min) | Non-Reduced (exposure: 20 sec) |
|---|---|---|
| 1A3 | 2+ | 2+ |
| 1D3 | 2+ | 2+ |
| 1F3 | 2+ | 2+ |
| 2B8 | — | 1+ |
| 2F8 | 2+ | 2+ |
| 3A12 | — | 2+ |
| 3B6 | 3+ | 2+ |
| 3D11 | — | 3+ |

The data in Table 4 demonstrate that all the antibodies bind non-reduced rhHGF. In contrast, monoclonal antibodies 1A3, 1D3, 1F3, 2F8, 3B6 bound reduced rhHGF but antibodies 2B8, 3A12, and 3D11 did not bind to reduced rhHGF.

Example 6

Binding Affinities

The binding affinities and kinetics of interaction of each of the antibodies produced in Example 1 against hHGF were measured by surface plasmon resonance.

Rabbit anti-mouse immunoglobulins (BIAcore, Catalog No. BR-1005-14) were immobilized on carboxymethylated dextran CM5 sensor chips (BIAcore, Catalog No. BR-1006-68) by amine coupling (BIAcore, Catalog No. BR-1000-50) using a standard coupling protocol according to manufacturer's instructions. The analyses were performed at 25° C. using PBS (GIBCO, Catalog No. 14040-133) containing 0.05% surfactant P20 (BIAcore, Catalog No. BR-1000-54), 2 mg/mL BSA (EMD, Catalog No. 2930), and 10 mg/mL CM-Dextran Sodium salt (Fluka, Catalog No. 86524) as running buffer.

The antibodies were captured in an individual flow cell at a flow rate of 10 µL/min. Injection time was variable for each antibody to yield approximately 20 RU of antibody captured for each cycle. Buffer or HGF (R&D Systems, Catalog No. 294-HGN-025) diluted in running buffer was injected sequentially over a reference surface (no antibody captured) and the active surface (antibody to be tested) for 2 minutes at 60 µL/min. The dissociation phase was monitored for 15 or 90 minutes, depending on concentration. The surface then was regenerated with 10 mM Glycine-HCl, pH 1.7 (BIAcore, Catalog No. BR-1003-54) injected for 3 minutes at a flow rate of 60 µL/min before another cycle was initiated. HGF concentrations tested were 0.46 nM to 7.5 nM.

Kinetic parameters were determined using the kinetic function of the BIAevalutation software with reference subtraction. Kinetic parameters for each antibody, $k_a$ (association rate constant), $k_d$ (dissociation rate constant) and $K_D$ (equilibrium dissociation constant) are summarized in Table 5.

TABLE 5

| Antibody | ka (1/Ms) | SE (ka) | kd (1/s) | SE (kd) | $K_D$ (pM) | SD |
|---|---|---|---|---|---|---|
| 1A3 | $1.7 \times 10^6$ | $7.3 \times 10^4$ | $5.2 \times 10^{-5}$ | $8.4 \times 10^{-7}$ | 30.1 | 5.6 |
| 1D3 | $1.7 \times 10^6$ | $3.1 \times 10^4$ | $8.2 \times 10^{-5}$ | $1.7 \times 10^{-6}$ | 54.2 | 27.4 |
| 1F3 | $1.5 \times 10^6$ | $5.0 \times 10^4$ | $2.6 \times 10^{-5}$ | $6.6 \times 10^{-7}$ | 18.1 | 8.2 |
| 2B8 | $1.6 \times 10^6$ | $2.9 \times 10^4$ | $2.1 \times 10^{-5}$ | $1.4 \times 10^{-7}$ | 13.5 | 4.4 |
| 3A12 | $1.6 \times 10^6$ | $3.7 \times 10^4$ | $1.6 \times 10^{-4}$ | $1.6 \times 10^{-6}$ | 103.0 | 10.4 |
| 3B6 | $2.0 \times 10^6$ | $6.5 \times 10^4$ | $3.9 \times 10^{-5}$ | $3.2 \times 10^{-7}$ | 17.0 | 3.4 |

The data in Table 5 demonstrate that the antibodies bind hHGF with a $K_D$ of about 100 pM or less, about 50 pM or less, or 20 pM or less.

Example 7

Neutralization Activity of Anti-hHGF Antibodies

In this Example, the antibodies produced in Example 1 were characterized for their ability to (a) inhibit the binding of hHGF to c-Met, and (b) inhibit HGF stimulated BrdU incorporation in 4 MBr-5 cells.

a. HGF-Met Binding Inhibition Assay (Neutralization Assay)

The antibodies were tested by ELISA for their ability to inhibit hHGF binding to c-Met.

Specifically, Wallac 96-well DELFIA assay plates (Wallac Inc., Catalog No. AAAND-0001) were coated with 100 µL of 6.25 µg/mL HGF (R&D Systems, Catalog No. 294-HGN-025) in carbonate coating buffer (15 mM $Na_2CO_3$ and 34 mM $NaHCO_3$, pH 9.0) for 16 hours at 4° C. The plates then were blocked with 200l of 5% non-fat dry milk in PBS for 1 hour at room temperature. The antibodies were prepared in a separate plate by adding increasing concentrations of the antibodies under investigation (0.033-667 nM, 3-fold-serial dilution) to 2 nM c-Met (R&D Systems, Catalog No. 358-MT/CF) in 5% non-fat dry milk in PBS. 100 µL of sample per well was transferred to the assay plate and incubated overnight at 4° C. The assay plates then were washed 3 times with PBS-0.1% Tween 20, and incubated for 2 hours at room temperature with 100 µL/well of 2 µg/mL biotinylated anti-human c-Met antibody (R&D Systems, Catalog No. BAF358) prepared in 5% non-fat dry milk in PBS.

The resulting plates then were washed three times with PBS-0.1% Tween 20, and incubated for 1 hour at room temperature with Eu-labeled Streptavidin (Wallac, Catalog No. 1244-360) diluted 1:1000 in DELFIA assay buffer (Wallac, Catalog No. 4002-0010). The resulting plates were washed 3 times with DELFIA wash solution (Wallac, Catalog No. 4010-0010) and incubated with 100 µL/well DELFIA enhancement solution (Wallac #4001-0010) for 15 minutes at room temperature with agitation.

The plates were read on Victor$^3$V instrument (Perkin Elmer) using the Europium method. The $IC_{50}$ values were calculated and are summarized in Table 6.

TABLE 6

| Antibody | $IC_{50}$ (nM) | SD |
|---|---|---|
| 1A3 | 5.65 | 0.91 |
| 1D3 | 4.43 | 2.27 |
| 1F3 | 6.57 | 0.28 |
| 2B8 | 5.57 | 1.19 |
| 2F8 | 5.36 | 0.88 |
| 3A12 | 5.26 | 2.11 |
| 3B6 | — | — |
| 3D11 | 5.66 | 2.75 |

The results demonstrate that all the antibodies (i.e., 1D3, 1A3, 2B8, 3A12, 1F3, 3D11, and 2F8) other than 3B6 efficiently neutralize HGF binding to c-Met.

b. Neutralization of HGF Stimulated BrdU Incorporation in 4 MBr-5 Cells

Ten µL of 12.5 nM of hHGF was dispensed into individual wells of a 96-well tissue culture microtiter plate (Costar Catalog No. 3903). Ten µL of serially diluted antibodies at concentrations of 6667, 2222, 740, 247, 82, 27, 9.1, 3.0, 1.0, 0.33 nM were added to each well. The HGF antibody mixture then was incubated at room temperature for 30 minutes. Monkey bronchial epithelial cells 4 MBr-5 (ATCC, CCL208) cultured in F-12K (ATCC, 30-2004), 15% FBS (Gibco 10438-026), 30 ng/mL EGF (Sigma E9644), 1% penicillin/streptomycin (PS, Gibco Catalog No. 15140-122) were dissociated with Trypsin (Gibco Catalog No. 25200-056), resuspended in assay media (F-12K, 2.5% FBS, 1% PS) at 75,000 cells/mL, and 80 µL of the cell suspension was dispensed to the HGF antibody mixture.

The resulting cells were incubated at 37° C., 5% $CO_2$. Forty eight hours later, 10 µL of 100 µM BrdU (Roche Catalog No. 1669915) was added. Seventy two hours later, the media was removed, the plates were dried with a hair dryer and were processed with the BrdU ELISA in accordance with manufacturer's instructions (Roche Catalog No. 1669915).

The luminescent signal was quantified by a Synergy HT plate reader (Bio-Tek). The data were fit to a sigmoidal dose response with variable slope with the equation y=bottom+(top-bottom)/(1+10^(log(EC50-x)*hill slope)) in GraphPad Prism (GraphPad Software). Each experiment was repeated at least 3 times in duplicates, and average $EC_{50}$ values are presented in Table 7.

TABLE 7

| Antibody | IC$_{50}$ (nM) |
|---|---|
| 1A3 | 4.69 |
| 1D3 | 4.99 |
| 1F3 | 1.94 |
| 2B8 | 1.41 |
| 2F8 | 19.24 |
| 3A12 | 30.30 |
| 3B6 | 36.08 |
| 3D11 | 51.12 |

The results in Table 7 demonstrate that all of the antibodies, 1A3, 1D3, 1F3, 2B8, 2F8, 3A12, 3B6, and 3D11 inhibit HGF induced proliferation in 4 MBr-5 cells.

Example 8

Anti-Scatter Activity of Anti-hHGF Antibodies

This Example describes a characterization of the antibodies produced in Example 1 for their ability to inhibit HGF induced scatter activity. HGF induces "scattering" (motility) of clusters in MDCK cells (ATCC, Manassas, Va., Catalog No. CCL-34).

MDCK cells were seeded in 96-well Costar tissue culture plates (Corning Incorporated, Corning, N.Y., Catalog No. 3595) at a density of 4×10$^3$ cells per well in 80 µl MEM (ATCC, Manassas, Va., Catalog No. 30-2003) containing 10% Fetal Bovine Serum (Invitrogen Catalog No. 10438026), and 1% penicillin-streptomycin (Invitrogen Catalog No. 15140122). Each of the antibodies to be investigated was diluted to 6,667 nM in MEM containing 10% Fetal Bovine Serum and 1% penicillin-streptomycin. Each of the different antibody dilutions, as well as MEM containing 10% Fetal Bovine Serum and 1% penicillin-streptomycin without antibody, then was separately combined with an equal volume of MEM containing 10% Fetal Bovine Serum and 1% penicillin-streptomycin, and 100 ng/ml HGF (R&D Systems Catalog No. 294-HGN-025). The antibody/HGF dilutions were incubated for 30 minutes at 25° C. Twenty µL of each antibody/HGF dilution was added separately to individual wells, yielding a final antibody concentration of 666.7 nM, and a final HGF concentration of 10 ng/ml. The MDCK cells then were incubated for 24 hours at 37° C. with 5% CO$_2$.

After 24 hours incubation, the MDCK cells were carefully washed once with 100 µl, per well of ice-cold PBS (Invitrogen Catalog No. 14190144), and fixed with 100 µL per well of ice-cold methanol while rocking for 10 minutes at 25° C. The plates then were washed carefully once with distilled water. A volume of 100 µL crystal violet solution, consisting of 0.5% crystal violet (Sigma, St. Louis, Mo., Catalog No. C3886) and 50% ethanol in distilled water, was added to each well, and the cells were incubated for 20 minutes at 25° C. while rocking.

Following staining with crystal violet solution, the cells were washed carefully three times with distilled water. Then, PBS was added to each well to prevent drying of samples. The cells were imaged using the Leica DMIRB microscope (Leica Microsystems GmbH, Wetzler, Germany), DC500 camera (Leica Microsystems GmbH, Wetzler, Germany), and MagnaFire 2.1C software (Optronics, Goleta, Calif.), and samples were rated for level of scattering. The results are summarized in Table 8.

TABLE 8

| | Inhibition of HGF-induced MDCK Cell Scattering | |
|---|---|---|
| Antibody | Trial 1 | Trial 2 |
| 1A3 | ++ | + |
| 1D3 | ++ | ++ |
| 1F3 | + | + |
| 2B8 | +++ | +++ |
| 2F8 | + | + |
| 3A12 | − | −/+ |
| 3B6 | ++ | ++ |
| 3D11 | − | − |

− No Inhibition+
+++ Very strong, nearly complete inhibition
++ Strong inhibition
+ Detectable inhibition The results in Table 8 demonstrate that antibody 2B8 inhibited HGF-induced scattering more than the other antibodies. Antibodies 1D3 and 3B6 displayed an intermediate level of inhibition; antibody 1A3 displayed a low to intermediate level of inhibition: antibodies 1F3 and 2F8 displayed a low level of inhibition; and antibodies 3A12 and 3D11 gave little or no detectable inhibition.

Example 9

Inhibition of HGF-Stimulated c-Met Phosphorylation

This Example describes a characterization of the antibodies produced in Example 1 for their ability to inhibit the HGF-stimulated c-Met phosphorylation in PC-3 cells. HGF induces phosphorylation of Met in PC-3 cells (ATCC No. CRL-1435).

PC-3 cells were seeded into individual wells of 96-well Costar tissue culture plates (Corning Catalog No. 3595) at a density of 4.5×10$^4$ cells per well in 100 µl F-12K (ATCC, Manassas, Va., Catalog No. 30-2004) containing 10% Fetal Bovine Serum (Invitrogen Catalog No. 10438026) and 1% penicillin-streptomycin (Invitrogen Catalog No. 15140122). After 24 hours at 37° C. with 5% CO$_2$, the media was removed, and cells were rinsed once with serum-free F-12K containing 1% penicillin-streptomycin. Cells then were incubated for 24 hours in 100 µL serum-free F-12K containing 1% penicillin-streptomycin.

The following 10 different dilutions of each of the antibodies being investigated were prepared in serum-free F-12K containing 1% penicillin-streptomycin: 6667 nM, 2222 nM, 741 nM, 247 nM, 82.3 nM, 27.4 nM, 9.1 nM, 3.0 nM, 1.0 nM, and 0.3 nM. Each antibody dilution, and, serum-free F-12K containing 1% penicillin-streptomycin without antibody, were separately combined with an equal volume of serum-free F-12K containing 1% penicillin-streptomycin and 500 ng/mL HGF (R&D Systems Catalog No. 294-HGN-025). These antibody/HGF dilutions were incubated for 30 minutes at 25° C. This resulted in a final concentration of 1.25 nM HGF.

The PC-3 cells then were rinsed once with serum-free F-12K containing 1% penicillin-streptomycin. Next, 70 µL of serum-free F-12K containing 1% penicillin-streptomycin was added to the cells, followed by 10 µL of 10 mM Na$_3$VO$_4$ (Sigma Catalog No. S6508) in serum-free F-12K containing 1% penicillin-streptomycin. The cells then were incubated for 60 minutes at 37° C. with 5% CO$_2$. Following this incubation, 20 µL of each antibody/HGF dilution was added separately to separate wells, yielding a final HGF concentration of 50 ng/mL, and the following final concentrations of each antibody: 666.7 nM, 222.2 nM, 74.1 nM, 24.7 nM, 8.23 nM, 2.74 nM, 0.91 nM, 0.30 nM, 0.10 nM, 0.03 nM. The cells then were incubated for 10 minutes at 37° C. with 5% $CO_2$, after which point the media/antibody/HGF mixture was removed, the plates were placed on ice. The cells then were rinsed once with 100 µL per well of ice-cold PBS (Invitrogen Catalog No. 14190144) containing 1 mM $Na_3VO_4$. The cells then were incubated for 30 minutes at 4° C. in 100 µL per well ice-cold lysis buffer consisting of 1% OmniPur Triton X-100 (MERCK KGaA, Darmstadt, Germany, Catalog No. 9410), 50 mM Tris-HCl pH 8.0, 100 mM NaCl, 0.3 mM $Na_3VO_4$, 1× protease inhibitor cocktail (Sigma Catalog No. P8340), and 1× phosphatase inhibitor cocktail 2 (Sigma Catalog No. 5726).

Biotinylated anti-human HGF-R (c-met) antibody (R&D Systems Catalog No. BAF358) was diluted to a concentration of 2 µg/mL in DELFIA Assay Buffer (PerkinElmer, Turku, Finland, Catalog No. 4002-0010) containing 1% bovine serum albumin (Sigma Catalog No. A2153), and 50 µL of this dilution was added per well of yellow streptavidin microtitration plates (PerkinElmer Catalog No. AAAND-0005). The plates then were incubated with antibody for 30 minutes at 25° C. with rocking. Following incubation, the plates were washed with DELFIA wash solution (PerkinElmer Catalog No. 4010-0010), and 80 µL of each of the different PC-3 cell lysates was added separately to individual wells of the washed streptavidin microtitration plates.

The streptavidin microtitration plates containing PC-3 cell lysates were incubated for 60 minutes at 25° C. with shaking, and then washed with DELFIA wash solution. 100 µL of 600 ng/mL DELFIA Eu-N1 P-Tyr-100 antibody (PerkinElmer Catalog No. AD0159) diluted in DELFIA Assay Buffer containing 1% bovine serum albumin was added to each well of the washed streptavidin microtitration plates previously incubated with PC-3 cell lysates. The plates were incubated for 60 minutes at 25° C., with rocking. The plates were washed a final time with DELFIA wash solution. Then 200 µL of DELFIA Enhancement Solution (PerkinElmer Catalog No. 4001-0010) was added to each well of the washed streptavidin microtitration plates, and the plates were incubated in the dark for 5 minutes at 25° C., with shaking.

Signal then was measured using the Europium protocol on the Victor3V reader (PerkinElmer). $EC_{50}$ values were calculated using Prism 4 for Windows (GraphPad Software, Inc., San Diego, Calif.) and the sigmoidal dose-response equation.

The results summarized as EC50s in nM are tabulated in Table 9.

TABLE 9

| Antibody | Average of Two Trials | Standard Deviation |
|---|---|---|
| 1A3 | 0.684 | 0.242 |
| 1D3 | 0.984 | 0.129 |
| 1F3 | 1.19 | 1.01 |
| 2B8 | 0.287 | 0.104 |
| 2F8 | 1.39 | 2.12 |
| 3A12 | 2.00 | 0.553 |
| 3B6 | 1.01 | 1.11 |
| 3D11 | 2.28 | N/A |

The data in Table 9 demonstrate that all eight antibodies are potent inhibitors of HGF-induced c-Met phosphorylation in PC-3 cells.

Example 10

Tumor Inhibition in U87MG Xenograft Model

The ability of murine monoclonal antibodies of the invention to inhibit tumor growth was tested in an U87MG xenograft model. U87MG cells (ATCC) were expanded in culture at 37° C. in an atmosphere containing 5% CO2 and 95% air, using a medium comprising Dulbecco's Modified Eagle medium (DMEM) with 10% fetal bovine serum, 100 units/mL penicillin and 100 µg/mL streptomycin. The cells were subcultured and maintained by detaching the cells from the wall of the culture dish using trypsin-EDTA.

Near-confluent cells were collected by trypsinization and then $5 \times 10^6$ cells in 50% Matrigel (BD Biosciences; catalog no. 356237) were injected subcutaneously into the upper dorsal area between the shoulder blades of 7-week old female ICR SCID mice (Taconic Labs). The long (L) and short (W) diameters (mm) of tumors were measured with a caliper. Tumor volume (vol.) was calculated as: volume $(mm^3)= L \times W^2/2$. When the tumors grew to approximately 200 $mm^3$, the tumor-bearing mice were randomized into 5 groups of 10 mice each. One group received PBS. Each of the other 4 groups received one of the antibody 1A3, 1D3, 1F3 or 2B8. All antibodies were dosed at 1 mg/kg body weight, twice per week, by intra-peritoneal injections of 5 doses. Tumor volumes and mouse body weights were recorded twice per week. Tumor growth inhibition was analyzed using Student's t-test. The results are summarized in FIG. 6 and Table 10.

TABLE 10

| | Percent Inhibition | |
|---|---|---|
| 2B8 vs PBS | 93% | p = 0.001 |
| 1A3 vs PBS | 73% | p = 0.0075 |
| 1D3 vs PBS | 51% | p = 0.075 |
| 1F3 vs PBS | 60% | p = 0.027 |

Figure 6:
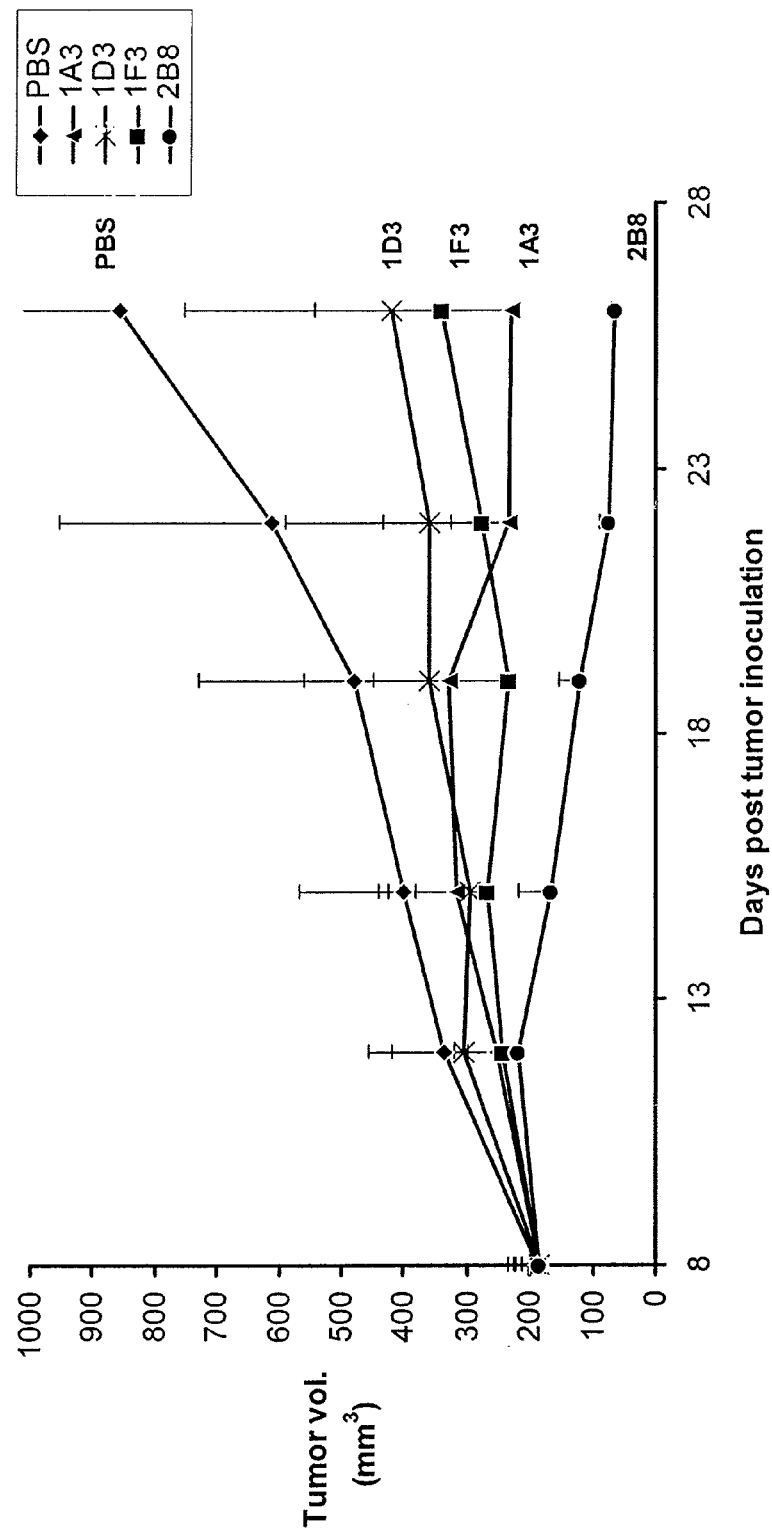
FIG. 6 is a graph summarizing results from an experiment to measure tumor inhibitory activity of anti-HGF antibodies 1D3, 1F3, 1A3 and 2B8 in a U87MG xenograft model. Diamonds correspond to PBS; triangles correspond to anti-HGF antibody 1A3; X corresponds to anti-HGF antibody 1D3; squares correspond to anti-HGF antibody 1F3, and circles correspond to anti-HGF antibody 2B8.

Partial regression was achieved in 2B8 treated group (FIG. 6). Statistically significant growth inhibition was observed in the 1A3-treated and 1F3-treated groups (Table 10). There was 51% tumor growth inhibition for 1D3 with a p value of 0.075. No significant body weight loss was observed.

Example 11

Tumor Inhibition in U118 Xenograft Model

The ability of the antibodies 1A3, 1D3, 1F3 and 2B8 to inhibit tumor growth was tested in an U118 xenograft model. U118 cells (ATCC) were expanded as described in Example 10 (above) with respect to the U87MG cells.

Subcutaneous tumors were established as described in Example 10 above, except that the mice used were 7 weeks old female NCr nude mice (Taconic), and treatment was started when the tumors grew to approximately 80 $mm^3$. As in the U87MG model, all the antibodies were dosed at 1 mg/kg body weight twice a week by intra-peritoneal injections for 4 doses. Tumor volumes and body weights of the mice were recorded twice per week. Tumor growth inhibition was analyzed using Student's t-test. The results are summarized in FIG. 7 and Table 11.

TABLE 11

| | Percent Inhibition | |
|---|---|---|
| 2B8 vs IgG | 75% | p = 0.007 |
| 1A3 vs IgG | 57% | p = 0.01 |
| 1D3 vs IgG | 47% | p = 0.12 |
| 1F3 vs IgG | 30% | p = 0.39 |

Figure 7:
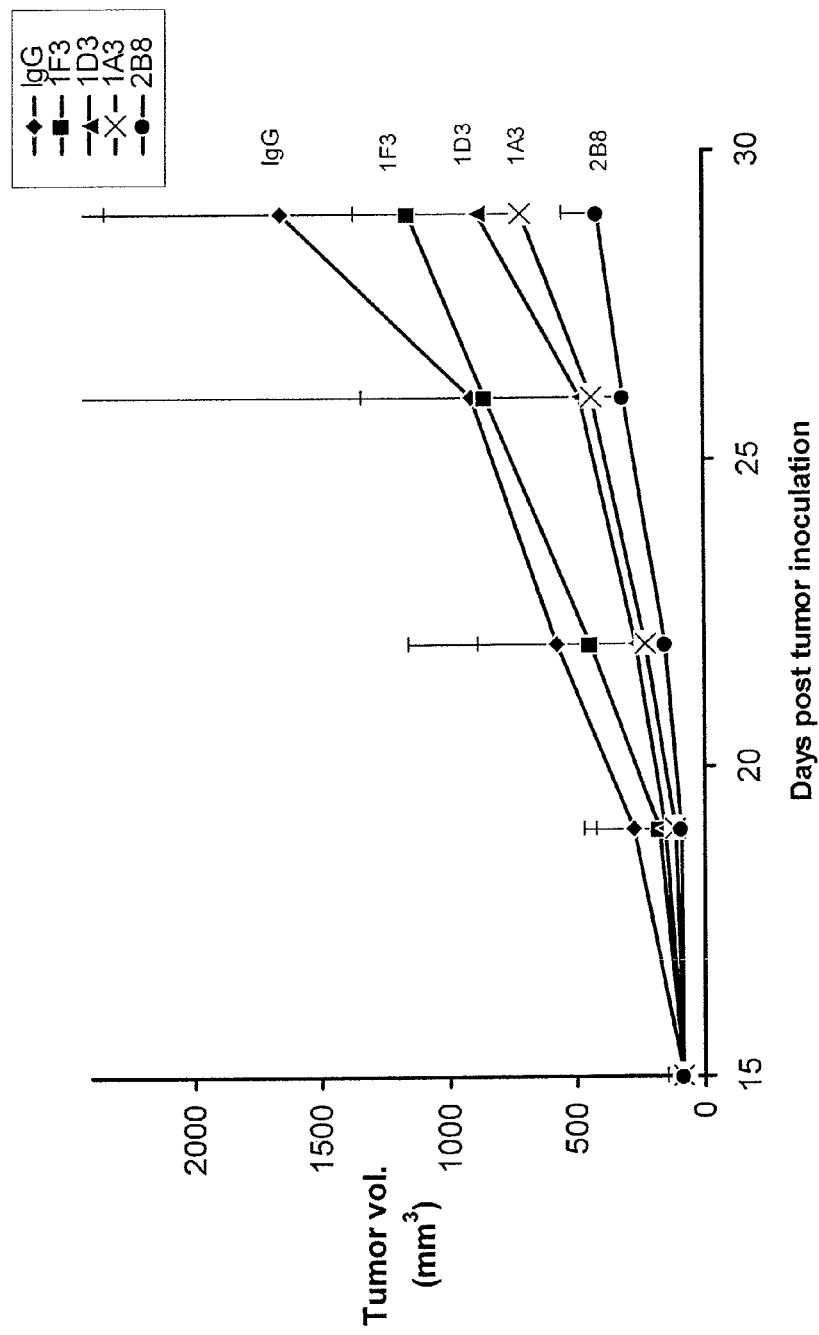
FIG. 7 is a graph summarizing results from an experiment to measure tumor inhibitory activity of anti-HGF antibodies 1D3, 1F3, 1A3 and 2B8 in a U118 xenograft model. Diamonds correspond to IgG; squares correspond to anti-HGF antibody 1F3, triangles to anti-HGF antibody 1D3; X corresponds to anti-HGF antibody 1A3; and circles correspond to anti-HGF antibody 2B8.

Statistically significant tumor growth inhibition was observed in 2B8 and 1A3 treated groups (FIG. 7). There was modest tumor growth inhibition in 1F3 and 1D3 groups with p values less than 0.05, which was defined as statistical significance in this study (Table 11). No significant body weight loss was observed.

Example 12

Humanization of Murine Monoclonal Antibodies

This Example describes the humanization of the murine 2B8 antibody, together with a characterization of the resulting humanized antibodies. The murine 2B8 Heavy and Light Variable Regions were "humanized" by two methods.

A. Humanization Procedure I

In the first method, three humanized heavy chain variable regions and two humanized kappa light chain variable regions were designed based on the "superhumanization" method described in Hwang et al. (2005) METHODS 36:35-42; Tan et al. (2002) J. IMMUNOL. 169:1119-1125; U.S. Pat. No. 6,881,557.

The Chothia canonical structural class was determined for each mouse 2B8 CDR based on CDR length and amino acid composition. Human germline variable regions consisting of the same Chothia canonical structural class light and heavy variable regions were identified based on known human germline variable region reference alleles described at the International Immunogenics Information System (IMGT) website (available on the world wide web at imgt.cines.fr and biochem.unizh.ch/antibody/Sequences/index.html). These human germline variable regions of the same structural class were compared to murine 2B8 variable regions by calculating the percent identity or similarity between CDR amino acid residues. Those human germline variable regions with the highest identity and/or similarity with mouse 2B8 CDR residues were chosen for CDR grafting. The framework residues of the human germline variable regions were preserved while the mouse 2B8 CDR residues were used to replace the corresponding human germline variable region residues that were different between mouse 2B8 CDR and human germline CDRs. The human J region that was most similar to the 2B8 mouse J region was then added to the carboxyl terminus of the "superhumanized" variable region. A signal sequence was then added to the amino terminus of the "superhumanized" variable regions and these amino acid sequences were converted into nucleic acid sequences.

The complete variable region nucleic acid sequence was constructed using gene synthesis PCR methods (Young et al. (2004) NUCL. ACIDS RES. 32:e59) and cloned into a mammalian expression vector (based on pcDNA3.2 DEST (Invitrogen)) containing human constant IgG1 (G1m(17,1) allotype) or Kappa (Km(3) allotype (allele 2)) regions (downstream of the variable regions) using standard molecular biology techniques. All four heavy chain IgG1 antibodies (chimeric 2B8 and 3 humanized heavy chains (Hu2B8 Hv1-f1, Hu2B8 Hv5-a.1, Hu2B8 Hv5-51.1) were expressed in the possible combinations with all 3 kappa chain antibodies (chimera 2B8 and 2 humanized light chains (Hu2B8 Kv1-39.1 and Hu2B8 Kv3-15.1) creating 12 different antibody proteins. Binding of the chimeric, chimeric/humanized, and humanized antibodies to human HGF was then measured as described below and the results are summarized in FIG. 8. Each of the possible combinations of immunoglobulin heavy chain and immunoglobulin light chain variable regions are set forth below in Table 12A.

TABLE 12A

| Heavy Chain Variable Region | Light Chain Variable Region |
|---|---|
| Chimeric 2B8 (SEQ ID NO: 12) | Chimeric 2B8 (SEQ ID NO: 14) |
| Chimeric 2B8 (SEQ ID NO: 12) | Hu2B8 Kv1-39.1 (SEQ ID NO: 173) |
| Chimeric 2B8 (SEQ ID NO: 12) | Hu2B8 Kv3-15.1 (SEQ ID NO: 179) |
| Hu2B8 Hv1-f.1 (SEQ ID NO: 159) | Chimeric 2B8 (SEQ ID NO: 14) |
| Hu2B8 Hv1-f.1 (SEQ ID NO: 159) | Hu2B8 Kv1-39.1 (SEQ ID NO: 173) |
| Hu2B8 Hv1-f.1 (SEQ ID NO: 159) | Hu2B8 Kv3-15.1 (SEQ ID NO: 179) |
| Hu2B8 Hv5-a.1 (SEQ ID NO: 165) | Chimeric 2B8 (SEQ ID NO: 14) |
| Hu2B8 Hv5-a.1 (SEQ ID NO: 165) | Hu2B8 Kv1-39.1 (SEQ ID NO: 173) |
| Hu2B8 Hv5-a.1 (SEQ ID NO: 165) | Hu2B8 Kv3-15.1 (SEQ ID NO: 179) |
| Hu2B8 Hv5-51.1 (SEQ ID NO: 169) | Chimeric 2B8 (SEQ ID NO: 14) |
| Hu2B8 Hv5-51.1 (SEQ ID NO: 169) | Hu2B8 Kv1-39.1 (SEQ ID NO: 173) |
| Hu2B8 Hv5-51.1 (SEQ ID NO: 169) | Hu2B8 Kv3-15.1 (SEQ ID NO: 179) |

Each of the possible combinations of immunoglobulin heavy chains and immunoglobulin light chains are set forth below in Table 12B.

TABLE 12B

| Immunoglobulin Heavy Chain | Immunoglobulin Light Chain |
|---|---|
| Chimeric 2B8 IgG1 (SEQ ID NO: 155) | Chimeric 2B8 Kappa (Km(3)) (SEQ ID NO: 157) |
| Chimeric 2B8 IgG1 (SEQ ID NO: 155) | Hu2B8 Kv1-39.1 + Kappa Constant (Km(3) allotype) (allele 2) (SEQ ID NO: 177) |
| Chimeric 2B8 IgG1 (SEQ ID NO: 155) | Hu2B8 Kv3-15.1 + Kappa Constant (Km(3) allotype) (allele 2) (SEQ ID NO: 181) |
| Hu2B8 Hv1-f.1 + IgG1 Constant (G1M(17,1)) allotype (SEQ ID NO: 163) | Chimeric 2B8 Kappa (Km(3)) (SEQ ID NO: 157) |
| Hu2B8 Hv1-f.1 + IgG1 Constant (G1M(17,1)) allotype (SEQ ID NO: 163) | Hu2B8 Kv1-39.1 + Kappa Constant (Km(3) allotype) (allele 2) (SEQ ID NO: 177) |
| Hu2B8 Hv1-f.1 + IgG1 Constant (G1M(17,1)) allotype (SEQ ID NO: 163) | Hu2B8 Kv3-15.1 + Kappa Constant (Km(3) allotype) (allele 2) (SEQ ID NO: 181) |
| Hu2B8 Hv5-a.1 + IgG1 Constant (G1M(17,1)) allotype (SEQ ID NO: 167) | Chimeric 2B8 Kappa (Km(3)) (SEQ ID NO: 157) |
| Hu2B8 Hv5-a.1 + IgG1 Constant (G1M(17,1)) allotype (SEQ ID NO: 167) | Hu2B8 Kv1-39.1 + Kappa Constant (Km(3) allotype) (allele 2) (SEQ ID NO: 177) |
| Hu2B8 Hv5-a.1 + IgG1 Constant (G1M(17,1)) allotype (SEQ ID NO: 167) | Hu2B8 Kv3-15.1 + Kappa Constant (Km(3) allotype) (allele 2) (SEQ ID NO: 181) |
| Hu2B8 Hv5-51.1 + IgG1 Constant (G1M(17,1)) allotype (SEQ ID NO: 171) | Chimeric 2B8 Kappa (Km(3)) (SEQ ID NO: 157) |
| Hu2B8 Hv5-51.1 + IgG1 Constant (G1M(17,1)) allotype (SEQ ID NO: 171) | Hu2B8 Kv1-39.1 + Kappa Constant (Km(3) allotype) (allele 2) (SEQ ID NO: 177) |
| Hu2B8 Hv5-51.1 + IgG1 Constant (G1M(17,1)) allotype (SEQ ID NO: 171) | Hu2B8 Kv3-15.1 + Kappa Constant (Km(3) allotype) (allele 2) (SEQ ID NO: 181) |

Two of the possible antibody constructs containing the full length immunoglobulin heavy and light chains containing humanized variable regions are designated below:

sh2B8-9 (G1m(17,1))=hu2B8 Hv5-51.1 (+IgG1 constant region (G1m(17,1) allotype) (SEQ ID NO. 171) plus hu2B8 Kv 1-39.1 (+Kappa constant region (Km(3) allotype (allele 2))) (SEQ ID NO. 177)

sh2B8-12 (G1m(17,1))=hu2B8 Hv5-51.1 (+IgG1 constant region (G1m(17,1) allotype)) (SEQ ID NO. 171) plus hu2B8 Kv 3-15.1 (+Kappa constant region (Km(3) allotype (allele 2))) (SEQ ID NO. 181).

The nucleic acid sequences encoding and the protein sequences defining each of the humanized antibodies are summarized below. In this section, the last nucleotide of each variable region is the first base of the next codon generated by the variable/constant region junction. This nucleotide is included in the Variable Region because it is part of that exon. Amino acid sequences of Constant Regions listed below include the translation of this junction codon.

(1) Nucleic Acid Sequence Encoding the Full Length Chimeric 2B8 Heavy Chain (Mouse Variable Region and Human IgG1 Constant Region) (allotype G1m(17,1)) (Signal Sequence Underlined) (SEQ ID NO. 154)

```
   1 atgggatgga gctatatcat cctcttttg gtagcaacag ctacagatgt ccactcccag
  61 gtccaactgc agcagcctgg ggctgaactg gtgaagcctg gacttcagt gaagctgtcc
 121 tgcaaggctt ctggctacac cttcaccacc tactggatgc actgggtgaa tcagaggcct
 181 ggacaaggcc ttgagtggat tggagagatt aatcctacca acggtcatac taactacaat
 241 gagaagttca gagcaaggc cacactgact gtagacaaat cctccagcac agcctacatg
 301 caactcagca gcctgacatc tgaggactct gcggtctatt actgtgcaag aaactatgtt
 361 ggtagcatct ttgactactg gggccaaggc accactctca ccgtctcctc agcctccacc
 421 aagggcccat cggtcttccc cctggcaccc tcctccaaga gcacctctgg gggcacagcg
 481 gccctgggct gcctggtcaa ggactacttc cccgaaccgg tgacggtgtc gtggaactca
 541 ggcgccctga ccagcggcgt gcacaccttc ccggctgtcc tacagtcctc aggactctac
 601 tccctcagca gcgtggtgac cgtgccctcc agcagcttgg gcacccagac ctacatctgc
 661 aacgtgaatc acaagcccag caacaccaag gtggacaaga agttgagcc caaatcttgt
 721 gacaaaactc acacatgccc accgtgccca gcacctgaac tcctgggggg accgtcagtc
 781 ttcctcttcc cccaaaaacc caaggacacc ctcatgatct cccggacccc tgaggtcaca
 841 tgcgtggtgg tggacgtgag ccacgaagac cctgaggtca agttcaactg gtacgtggac
 901 ggcgtggagg tgcataatgc caagacaaag ccgcgggagg agcagtacaa cagcacgtac
 961 cgtgtggtca gcgtcctcac cgtcctgcac caggactggc tgaatggcaa ggagtacaag
1021 tgcaaggtct ccaacaaagc cctcccagcc cccatcgaga aaaccatctc caaagccaaa
1081 gggcagcccc gagaaccaca ggtgtacacc ctgcccccat cccgggatga gctgaccaag
1141 aaccaggtca gcctgacctg cctggtcaaa ggcttctatc ccagcgacat cgccgtggag
1201 tgggagagca atgggcagcc ggagaacaac tacaagacca cgcctcccgt gctggactcc
1261 gacggctcct tcttcctcta cagcaagctc accgtggaca agagcaggtg gcagcagggg
1321 aacgtcttct catgctccgt gatgcatgag gctctgcaca accactacac gcagaagagc
1381 ctctccctgt ctccgggtaa atga
```

(2) Protein Sequence Defining the Full Length Chimeric 2B8 Heavy Chain (Chimeric 2B8 IgG1 (G1m(17,1) allotype) (without Signal Sequence) (SEQ ID NO. 155)

```
  1 qvqlqqpgae lvkpgtsvkl sckasgytft tywmhwvnqr pgqglewige inptnghtny
 61 nekfkskatl tvdkssstay mqlssltsed savyycarny vgsifdywgq gttltvssas
121 tkgpsvfpla psskstsggt aalgclvkdy fpepvtvswn sgaltsgvht fpavlqssgl
181 yslssvvtvp ssslgtqtyi cnvnhkpsnt kvdkkvepks cdkthtcppc papellggps
241 vflfppkpkd tlmisrtpev tcvvvdvshe dpevkfnwyv dgvevhnakt kpreeqynst
301 yrvvsvltvl hqdwlngkey kckvsnkalp apiektiska kgqprepqvy tlppsrdelt
361 knqvsltclv kgfypsdiav ewesngqpen nykttppvld sdgsfflysk ltvdksrwqq
421 gnvfscsvmh ealhnhytqk slslspgk
```

(3) Nucleic Acid Sequence Encoding the Full Length Chimeric 2B8 Light Chain (Mouse Variable Region and Human Constant Region) (Chimeric 2B8 Kappa (Km(3))) (Signal Sequence Underlined) (SEQ ID NO. 156)

```
  1   atggaatcac agactctggt cttcatatcc atactgctct ggttatatgg tgctgatggg 61   aacattgtaa tgacccaatc tcccaaatcc atgtccatgt cagtaggaga gagggtcacc 121   ttgagctgca aggccagtga aatgtggtt tcttatgtat cctggtatca acagaaacca 181   gcgcagtctc ctaaactgct gatatacggg gcatccaacc ggaacactgg ggtccccgat 241   cgcttcacag gcagtggatc tgcaacagat ttcactctga ccatcagcag tgtgcgggct 301   gaagaccttg cagattatca ctgtgggcag agttacaact atccgtacac gttcggaggg 361   gggaccaggc tggaaataaa acgaactgtg gctgcaccat ctgtcttcat cttcccgcca 421   tctgatgagc agttgaaatc tggaactgcc tctgttgtgt gcctgctgaa taacttctat 481   cccagagagg ccaaagtaca gtggaaggtg gataacgccc tccaatcggg taactcccag 541   gagagtgtca cagagcagga cagcaaggac agcacctaca gcctcagcag caccctgacg 601   ctgagcaaag cagactacga gaaacacaaa gtctacgcct gcgaagtcac ccatcagggc 661   ctgagctcgc ccgtcacaaa gagcttcaac aggggagagt gttga
```

(4) Protein Sequence Defining the Full Length Chimeric 2B8 Light Chain (Chimeric 2B8 Kappa (Km(3))) (without Signal Sequence) (SEQ ID NO. 157)

```
  1   nivmtqspks msmsvgervt lsckasenvv syvswyqqkp aqspklliyg asnrntgvpd 61   rftgsgsatd ftltissvra edladyhcgq synypytfgg gtrleikrtv aapsvfifpp 121   sdeqlksgta svvcllnnfy preakvqwkv dnalqsgnsq esvteqdskd styslsstlt 181   lskadyekhk vyacevthqg lsspvtksfn rgec
```

(5) Nucleic Acid Sequence Encoding Humanized Hu2B8 Hv1-f.1 Heavy Chain Variable Region (Signal Sequence Underlined) (SEQ ID NO. 158)

```
  1   atggactgca cctggaggat cctcctcttg gtggcagcag ctacaggcac ccacgccgag 61   gtccagctgg tacagtctgg ggctgaggtg aagaagcctg ggctacagt gaaaatctcc 121   tgcaaggttt ctggatacac cttcaccacc tactggatgc actgggtgca acaggcccct 181   ggaaaagggc ttgagtggat gggagagatt aatcctacca acggtcatac taactacaat 241   gagaagttcc agggcagagt caccataacc gcggacacgt ctacagacac agcctacatg 301   gagctgagca gcctgagatc tgaggacacg gccgtgtatt actgtgcaac aaactatgtt 361   ggtagcatct ttgactactg gggccaagga accctggtca ccgtctcctc ag
```

(6) Protein Sequence Defining Humanized Hu2B8 Hv1-f.1 Heavy Chain Variable Region (without signal sequence) (SEQ ID NO. 159)

```
  1   evqlvqsgae vkkpgatvki sckvsgytft tywmhwvqqa pgkglewmge inptnghtny 61   nekfqgrvti tadtstdtay melsslrsed tavyycatny vgsifdywgq gtlvtvss
```

(7) Nucleic Acid Sequence Encoding Human IgG1 Heavy Chain Constant Region (G1m(17,1) Allotype) (SEQ ID NO. 160)

```
  1  cctccaccaa gggcccatcg gtcttccccc tggcaccctc ctccaagagc acctctgggg
 61  gcacagcggc cctgggctgc ctggtcaagg actacttccc cgaaccggtg acggtgtcgt
121  ggaactcagg cgccctgacc agcggcgtgc acaccttccc ggctgtccta cagtcctcag
181  gactctactc cctcagcagc gtggtgaccg tgccctccag cagcttgggc acccagacct
241  acatctgcaa cgtgaatcac aagcccagca acaccaaggt ggacaagaaa gttgagccca
301  aatcttgtga caaaactcac acatgcccac cgtgcccagc acctgaactc ctggggggac
361  cgtcagtctt cctcttcccc ccaaaaccca aggacaccct catgatctcc cggacccctg
421  aggtcacatg cgtggtggtg gacgtgagcc acgaagaccc tgaggtcaag ttcaactggt
481  acgtggacgg cgtggaggtg cataatgcca agacaaagcc gcgggaggag cagtacaaca
541  gcacgtaccg tgtggtcagc gtcctcaccg tcctgcacca ggactggctg aatggcaagg
601  agtacaagtg caaggtctcc aacaaagccc tcccagcccc catcgagaaa accatctcca
661  aagccaaagg gcagccccga gaaccacagg tgtacaccct gcccccatcc cgggatgagc
721  tgaccaagaa ccaggtcagc ctgacctgcc tggtcaaagg cttctatccc agcgacatcg
781  ccgtggagtg ggagagcaat gggcagccgg agaacaacta caagaccacg cctcccgtgc
841  tggactccga cggctccttc ttcctctaca gcaagctcac cgtggacaag agcaggtggc
901  agcagggaa cgtcttctca tgctccgtga tgcatgaggc tctgcacaac cactacacgc
961  agaagagcct ctccctgtct ccgggtaaat ga
```

(8) Protein Sequence Defining Human IgG1 Heavy Chain Constant Region (G1m(17,1) Allotype) (SEQ ID NO. 161).

The first amino acid is derived from translation of the last nucleotide of variable region and beginning two nucleotides of the IgG1 Heavy Chain sequence.

```
  1  astkgpsvfp lapsskstsg gtaalgclvk dyfpepvtvs wnsgaltsgv htfpavlqss
 61  glyslssvvt vpssslgtqt yicnvnhkps ntkvdkkvep kscdkthtcp pcpapellgg
121  psvflfppkp kdtlmisrtp evtcvvvdvs hedpevkfnw yvdgvevhna ktkpreeqyn
181  styrvvsvlt vlhqdwlngk eykckvsnka lpapiektis kakgqprepq vytlppsrde
241  ltknqvsltc lvkgfypsdi avewesngqp ennykttppv ldsdgsffly skltvdksrw
301  qqgnvfscsv mhealhnhyt qkslslspgk
```

(9) Nucleic Acid Sequence Encoding the Full Length Heavy Chain Humanized Hu2B8 Hv1f.1 Variable Region and Human IgG1 (G1m(17,1) allotype) Heavy Chain Constant Region (Signal Sequence Underlined) (SEQ ID NO. 162)

```
  1  atggactgca cctggaggat cctcctcttg gtggcagcag ctacaggcac ccacgccgag
 61  gtccagctgg tacagtctgg ggctgaggtg aagaagcctg ggctacagt gaaaatctcc
121  tgcaaggttt ctggatacac cttcaccacc tactggatgc actgggtgca acaggcccct
181  ggaaagggc ttgagtggat gggagagatt aatcctacca acggtcatac taactacaat
241  gagaagttcc agggcagagt caccataacc gcggacacgt ctacagacac agcctacatg
301  gagctgagca gcctgagatc tgaggacacg gccgtgtatt actgtgcaac aaactatgtt
361  ggtagcatct ttgactactg gggccaagga accctggtca ccgtctcctc agcctccacc
```

-continued

```
 421   aagggcccat cggtcttccc cctggcaccc tcctccaaga gcacctctgg gggcacagcg
 481   gccctgggct gcctggtcaa ggactacttc cccgaaccgg tgacggtgtc gtggaactca
 541   ggcgccctga ccagcggcgt gcacaccttc ccggctgtcc tacagtcctc aggactctac
 601   tccctcagca gcgtggtgac cgtgccctcc agcagcttgg gcacccagac ctacatctgc
 661   aacgtgaatc acaagcccag caacaccaag gtggacaaga agttgagcc caaatcttgt
 721   gacaaaactc acacatgccc accgtgccca gcacctgaac tcctgggggg accgtcagtc
 781   ttcctcttcc ccccaaaacc caaggacacc ctcatgatct cccggacccc tgaggtcaca
 841   tgcgtggtgg tggacgtgag ccacgaagac cctgaggtca agttcaactg gtacgtggac
 901   ggcgtggagg tgcataatgc caagacaaag ccgcgggagg agcagtacaa cagcacgtac
 961   cgtgtggtca gcgtcctcac cgtcctgcac caggactggc tgaatggcaa ggagtacaag
1021   tgcaaggtct ccaacaaagc cctcccagcc cccatcgaga aaaccatctc caaagccaaa
1081   gggcagcccc gagaaccaca ggtgtacacc ctgcccccat cccgggatga gctgaccaag
1141   aaccaggtca gcctgacctg cctggtcaaa ggcttctatc ccagcgacat cgccgtggag
1201   tgggagagca atgggcagcc ggagaacaac tacaagacca cgcctcccgt gctggactcc
1261   gacggctcct tcttcctcta cagcaagctc accgtggaca agagcaggtg gcagcagggg
1321   aacgtcttct catgctccgt gatgcatgag gctctgcaca accactacac gcagaagagc
1381   ctctccctgt ctccgggtaa atga
```

(10) Protein Sequence Defining the Full Length Heavy Chain Humanized Hu2B8 Hv1f.1 Variable Region and Human IgG1 Heavy Chain Constant Region (G1m(17,1) Allotype) (without Signal Sequence) (SEQ ID NO. 163)

```
  1   evqlvqsgae vkkpgatvki sckvsgytft tywmhwvqqa pgkglewmge inptnghtny
 61   nekfqgrvti tadtstdtay melsslrsed tavyycatny vgsifdywgq gtlvtvssas
121   tkgpsvfpla psskstsggt aalgclvkdy fpepvtvswn sgaltsgvht fpavlqssgl
181   yslssvvtvp ssslgtqtyi cnvnhkpsnt kvdkkvepks cdkthtcppc papellggps
241   vflfppkpkd tlmisrtpev tcvvvdvshe dpevkfnwyv dgvevhnakt kpreeqynst
301   yrvvsvltvl hqdwlngkey kckvsnkalp apiektiska kgqprepqvy tlppsrdelt
361   knqvsltclv kgfypsdiav ewesngqpen nykttppvld sdgsfflysk ltvdksrwqq
421   gnvfscsvmh ealhnhytqk slslspgk
```

(11) Nucleic Acid Sequence Encoding Humanized Hu2B8 Hv5a.1 Heavy Chain Variable Region (Signal Sequence Underlined) (SEQ ID NO. 164)

```
  1   atggggtcaa ccgccatcct cgccctcctc ctggctgttc tccaaggagt ctgtgccgaa
 61   gtgcagctgg tgcagtctgg agcagaggtg aaaaagcccg gggagtctct gaggatctcc
121   tgtaagggtt ctggatacag ctttaccacc tactggatgc actgggtgcg ccagatgccc
181   gggaaaggcc tggagtggat gggggagatt aatcctacca cggtcatac taactacaat
241   ccgtccttcc aaggccacgt caccatctca gctgacaagt ccatcagcac tgcctacctg
301   cagtggagca gcctgaaggc ctcggacacc gccatgtatt actgtgcgag aaactatgtt
361   ggtagcatct ttgactactg ggccaagga accctggtca ccgtctcctc ag
```

(12) Protein Sequence Defining Humanized Hu2B8 Hv5a.1 Heavy Chain Variable Region (without Signal Sequence) (SEQ ID NO. 165)

```
  1 evqlvqsgae vkkpgeslri sckgsgysft tywmhwvrqm pgkglewmge inptnghtny
 61 npsfqghvti sadksistay lqwsslkasd tamyycarny vgsifdywgq gtivtvss
```

(13) Nucleic Acid Sequence Encoding the Full Length Humanized Hu2B8 Hv5a.1 Heavy Chain Variable Region and Human IgG1 (G1m(17,1) Allotype) Heavy Chain Constant Region (Signal Sequence Underlined) (SEQ ID NO. 166)

```
    1 atggggtcaa ccgccatcct cgccctcctc ctggctgttc tccaaggagt ctgtgccgaa
   61 gtgcagctgg tgcagtctgg agcagaggtg aaaaagcccg ggagtctct gaggatctcc
  121 tgtaagggtt ctggatacag ctttaccacc tactggatgc actgggtgcg ccagatgccc
  181 gggaaaggcc tggagtggat ggggagatt aatcctacca acggtcatac taactacaat
  241 ccgtccttcc aaggccacgt caccatctca gctgacaagt ccatcagcac tgcctacctg
  301 cagtggagca gcctgaaggc ctcggacacc gccatgtatt actgtgcgag aaactatgtt
  361 ggtagcatct ttgactactg gggccaagga accctggtca ccgtctcctc agcctccacc
  421 aagggcccat cggtcttccc cctggcaccc tcctccaaga gcacctctgg gggcacagcg
  481 gccctgggct gcctggtcaa ggactacttc cccgaaccgg tgacggtgtc gtggaactca
  541 ggcgccctga ccagcggcgt gcacaccttc ccggctgtcc tacagtcctc aggactctac
  601 tccctcagca gcgtggtgac cgtgccctcc agcagcttgg gcacccagac ctacatctgc
  661 aacgtgaatc acaagcccag caacaccaag gtggacaaga agttgagcc caaatcttgt
  721 gacaaaactc acacatgccc accgtgccca gcacctgaac tcctgggggg accgtcagtc
  781 ttcctcttcc ccccaaaacc caaggacacc ctcatgatct cccggacccc tgaggtcaca
  841 tgcgtggtgg tggacgtgag ccacgaagac cctgaggtca agttcaactg gtacgtggac
  901 ggcgtggagg tgcataatgc caagacaaag ccgcgggagg agcagtacaa cagcacgtac
  961 cgtgtggtca gcgtcctcac cgtcctgcac caggactggc tgaatggcaa ggagtacaag
 1021 tgcaaggtct ccaacaaagc cctcccagcc cccatcgaga aaaccatctc caaagccaaa
 1081 gggcagcccc gagaaccaca ggtgtacacc ctgcccccat cccgggatga gctgaccaag
 1141 aaccaggtca gcctgacctg cctggtcaaa ggcttctatc ccagcgacat cgccgtggag
 1201 tgggagagca atgggcagcc ggagaacaac tacaagacca cgcctcccgt gctggactcc
 1261 gacggctcct tcttcctcta cagcaagctc accgtggaca agagcaggtg gcagcagggg
 1321 aacgtcttct catgctccgt gatgcatgag gctctgcaca accactacac gcagaagagc
 1381 ctctccctgt ctccgggtaa atga
```

(14) Protein Sequence Defining the Full Length Humanized Hu2B8 Hv5a.1 Heavy Chain Variable Region and Human IgG1 (G1m(17,1) allotype) Heavy Chain Constant Region (without Signal Sequence) (SEQ ID NO. 167)

```
  1 evqlvqsgae vkkpgeslri sckgsgysft tywmhwvrqm pgkglewmge inptnghtny
 61 npsfqghvti sadksistay lqwsslkasd tamyycarny vgsifdywgq gtlvtvssas
121 tkgpsvfpla psskstsggt aalgclvkdy fpepvtvswn sgaltsgvht fpavlqssgl
181 yslssvvtvp ssslgtqtyi cnvnhkpsnt kvdkkvepks cdkthtcppc papellggps
241 vflfppkpkd tlmisrtpev tcvvvdvshe dpevkfnwyv dgvevhnakt kpreeqynst
301 yrvvsvltvl hqdwlngkey kcksvnkalp apiektiska kgqprepqvy tlppsrdelt
361 knqvsltclv kgfypsdiav ewesngqpen nykttppvld sdgsfflysk ltvdksrwqq
421 gnvfscsvmh ealhnhytqk slslspgk
```

(15) Nucleic Acid Sequence Encoding Humanized Hu2B8 Hv5-51.1 Heavy Chain Variable Region (Signal Sequence Underlined) (SEQ ID NO. 168)

```
  1   atggggtcaa ccgccatcct cgccctcctc ctggctgttc tccaaggagt ctgtgccgaa
 61   gtgcagctgg tgcagtctgg agcagaggtg aaaaagcccg gggagtctct gaagatctcc
121   tgtaagggtt ctggatacag ctttaccacc tactggatgc actgggtgcg ccagatgccc
181   gggaaaggcc tggagtggat gggggagatt aatcctacca acggtcatac taactacaat
241   ccgtccttcc aaggccaggt caccatctca gctgacaagt ccatcagcac tgcctacctg
301   cagtggagca gcctgaaggc ctcggacacc gccatgtatt actgtgcgag aaactatgtt
361   ggtagcatct ttgactactg gggccaagga accctggtca ccgtctcctc ag
```

(16) Protein Sequence Defining Humanized Hu2B8 Hv5-51.1 Heavy Chain Variable Sequence (without Signal Sequence) (SEQ ID NO. 169)

```
  1   evqlvqsgae vkkpgeslki sckgsgysft tywmhwvrqm pgkglewmge inptnghtny
 61   npsfqgqvti sadksistay lqwsslkasd tamyycarny vgsifdywgq gtlvtvss
```

(17) Nucleic Acid Sequence Encoding the Full Length Humanized Hu2B8 Hv5-51.1 Heavy Chain Variable Region and Human IgG1 (G1m(17,1) Allotype) Heavy Chain Constant Region (Signal Sequence Underlined) (SEQ ID NO. 170)

```
   1   atggggtcaa ccgccatcct cgccctcctc ctggctgttc tccaaggagt ctgtgccgaa
  61   gtgcagctgg tgcagtctgg agcagaggtg aaaaagcccg gggagtctct gaagatctcc
 121   tgtaagggtt ctggatacag ctttaccacc tactggatgc actgggtgcg ccagatgccc
 181   gggaaaggcc tggagtggat gggggagatt aatcctacca acggtcatac taactacaat
 241   ccgtccttcc aaggccaggt caccatctca gctgacaagt ccatcagcac tgcctacctg
 301   cagtggagca gcctgaaggc ctcggacacc gccatgtatt actgtgcgag aaactatgtt
 361   ggtagcatct ttgactactg gggccaagga accctggtca ccgtctcctc agcctccacc
 421   aagggcccat cggtcttccc cctggcaccc tcctccaaga gcacctctgg gggcacagcg
 481   gccctgggct gcctggtcaa ggactacttc cccgaaccgg tgacggtgtc gtggaactca
 541   ggcgccctga ccagcggcgt gcacaccttc ccggctgtcc tacagtcctc aggactctac
 601   tccctcagca gcgtggtgac cgtgccctcc agcagcttgg gcacccagac ctacatctgc
 661   aacgtgaatc acaagcccag caacaccaag gtggacaaga agttgagcc caaatcttgt
 721   gacaaaactc acacatgccc accgtgccca gcacctgaac tcctgggggg accgtcagtc
 781   ttcctcttcc ccccaaaacc caaggacacc ctcatgatct cccggacccc tgaggtcaca
 841   tgcgtggtgg tggacgtgag ccacgaagac cctgaggtca agttcaactg gtacgtggac
 901   ggcgtggagg tgcataatgc caagacaaag ccgcgggagg agcagtacaa cagcacgtac
 961   cgtgtggtca gcgtcctcac cgtcctgcac caggactggc tgaatggcaa ggagtacaag
1021   tgcaaggtct ccaacaaagc cctcccagcc cccatcgaga aaccatctc caaagccaaa
1081   gggcagcccc gagaaccaca ggtgtacacc ctgccccat cccgggatga gctgaccaag
1141   aaccaggtca gcctgacctg cctggtcaaa ggcttctatc ccagcgacat cgccgtggag
1201   tgggagagca atgggcagcc ggagaacaac tacaagacca cgcctcccgt gctggactcc
1261   gacggctcct tcttcctcta cagcaagctc accgtggaca gagcaggtg gcagcagggg
```

```
1321  aacgtcttct catgctccgt gatgcatgag gctctgcaca accactacac gcagaagagc 1381  ctctccctgt ctccgggtaa atga
```

(18) Protein Sequence Defining the Full Length Humanized Hu2B8 Hv5-51.1 Heavy Chain Variable Region and Human IgG1 (G1m(17,1) Allotype) Heavy Chain Constant Region (without Signal Sequence) (SEQ ID NO. 171)

```
  1  evqlvqsgae vkkpgeslki sckgsgysft tywmhwvrqm pgkglewmge inptnghtny
 61  npsfqgqvti sadksistay lqwsslkasd tamyycarny vgsifdywgq gtlvtvssas
121  tkgpsvfpla psskstsggt aalgclvkdy fpepvtvswn sgaltsgvht fpavlqssgl
181  yslssvvtvp ssslgtqtyi cnvnhkpsnt kvdkkvepks cdkthtcppc papellggps
241  vflfppkpkd tlmisrtpev tcvvvdvshe dpevkfnwyv dgvevhnakt kpreeqynst
301  yrvvsvltvl hqdwlngkey kckvsnkalp apiektiska kgqprepqvy tlppsrdelt
361  knqvsltclv kgfypsdiav ewesngqpen nykttppvld sdgsfflysk ltvdksrwqq
421  gnvfscsvmh ealhnhytqk slslspgk
```

(19) Nucleic Acid Sequence Encoding Humanized Hu2B8 Kv1-39.1 Kappa Chain Variable Region (Signal Sequence Underlined) (SEQ ID NO. 172).

Two possible start ATGs are shown in uppercase.

```
  1  ATGgacATGa gggtccccgc tcagctcctg gggctcctgc tactctggct ccgaggtgcc
 61  agatgtgaca tccagatgac ccagtctcca tcctccctgt ctgcatctgt aggagacaga
121  gtcaccatca cttgcaaggc cagtgagaat gtggtttctt atgtatcctg gtatcagcag
181  aaaccaggga agcccctaa gctcctgatc tatggggcat ccaaccggaa cactggggtc
241  ccatcaaggt tcagtggcag tggatctggg acagatttca ctctcaccat cagcagtctg
301  caacctgaag attttgcaac ttactactgt gggcagagtt acaactatcc gtacacgttt
361  ggccagggga ccaagctgga gatcaaac
```

(20) Protein Sequence Defining Humanized Hu2B8 Kv1-39.1 Kappa Chain Variable Region (without Signal Sequence) (SEQ ID NO. 173)

```
  1  diqmtqspss lsasvgdrvt itckasenvv syvswyqqkp gkapklliyg asnrntgvps
 61  rfsgsgsgtd ftltisslqp edfatyycgq synypytfgq gtkleik
```

(21) Nucleic Acid Sequence Encoding Human Kappa Chain Constant Region (Km(3) Allotype) (allele 2) (SEQ ID NO. 174)

```
  1  gaactgtggc tgcaccatct gtcttcatct tcccgccatc tgatgagcag ttgaaatctg
 61  gaactgcctc tgttgtgtgc ctgctgaata acttctatcc cagagaggcc aaagtacagt
121  ggaaggtgga taacgccctc caatcgggta actcccagga gagtgtcaca gagcaggaca
181  gcaaggacag cacctacagc ctcagcagca cctgacgct gagcaaagca gactacgaga
241  aacacaaagt ctacgcctgc gaagtcaccc atcagggcct gagctcgccc gtcacaaaga
301  gcttcaacag gggagagtgt tga
```

(22) Protein Sequence Defining Human Kappa Chain Constant Region (Km(3) Allotype) (Allele 2) (SEQ ID NO. 175).
The first amino acid is derived from translation of the last nucleotide of variable region and beginning two nucleotides of the Kappa Light Chain sequence.

```
  1   rtvaapsvfi fppsdeqlks gtasvvclln nfypreakvq wkvdnalqsg nsqesvteqd
 61   skdstyslss tltlskadye khkvyacevt hqglsspvtk sfnrgec
```

(23) Nucleic Acid Sequence Encoding the Full Length Humanized Hu2B8 Kv1-39.1 Light Chain Variable Region and Human Kappa Chain Constant Region (Km(3) Allotype) (Allele 2) (Signal Sequence Underlined) (SEQ ID NO. 176)

```
  1   atggacatga gggtccccgc tcagctcctg gggctcctgc tactctggct ccgaggtgcc
 61   agatgtgaca tccagatgac ccagtctcca tcctccctgt ctgcatctgt aggagacaga
121   gtcaccatca cttgcaaggc cagtgagaat gtggtttctt atgtatcctg gtatcagcag
181   aaaccaggga agcccctaa gctcctgatc tatggggcat ccaaccggaa cactggggtc
241   ccatcaaggt tcagtggcag tggatctggg acagatttca ctctcaccat cagcagtctg
301   caacctgaag attttgcaac ttactactgt gggcagagtt acaactatcc gtacacgttt
361   ggccagggga ccaagctgga gatcaaacga actgtggctg caccatctgt cttcatcttc
421   ccgccatctg atgagcagtt gaaatctgga actgcctctg ttgtgtgcct gctgaataac
481   ttctatccca gagaggccaa agtacagtgg aaggtggata cgcctcca atcgggtaac
541   tcccaggaga gtgtcacaga gcaggacagc aaggacagca cctacagcct cagcagcacc
601   ctgacgctga gcaaagcaga ctacgagaaa cacaaagtct acgcctgcga agtcacccat
661   cagggcctga gctcgcccgt cacaaagagc ttcaacaggg gagagtgttg a
```

(24) Protein Sequence Defining the Full Length Humanized Hu2B8 Kv1-39.1 Light Chain Variable Region and Human Kappa Chain Constant Region (Km(3) Allotype) (Allele 1) (SEQ ID NO. 177)

```
  1   diqmtqspss lsasvgdrvt itckasenvv syvswyqqkp gkapklliyg asnrntgvps
 61   rfsgsgsgtd ftltisslqp edfatyycgq synypytfgq gtkleikrtv aapsvfifpp
121   sdeqlksgta svvcllnnfy preakvqwkv dnalqsgnsq esvteqdskd styslsstlt
181   lskadyekhk vyacevthqg lsspvtksfn rgec
```

(25) Nucleic Acid Sequence Encoding Humanized Hu2B8 Kv3-15.1 Light Chain Variable Region (Signal Sequence Underlined) (SEQ ID NO. 178)

```
  1   atggaagccc cagcgcagct tctcttcctc ctgctactct ggctcccaga taccactgga
 61   gaaatagtga tgacgcagtc tccagccacc ctgtctgtgt ctccagggga aagagccacc
121   ctctcctgca aggccagtga gaatgtggtt tcttatgtat cctggtacca gcagaaacct
181   ggccaggctc ccaggctcct catctatggg gcatccaacc ggaacactgg tatcccagcc
241   aggttcagtg gcagtgggtc tgggacagag ttcactctca ccatcagcag cctgcagtct
301   gaagattttg cagtttatta ctgtgggcag agttacaact atccgtacac gtttggccag
361   gggaccaagc tggagatcaa ac
```

(26) Protein Sequence Defining Humanized Hu2B8 Kv3-15.1 Light Chain Variable Region (without Signal Sequence) (SEQ ID NO. 179)

```
  1   eivmtqspat lsyspgerat lsckasenvv syvswyqqkp gqaprlliyg asnrntgipa
 61   rfsgsgsgte ftltisslqs edfavyycgq synypytfgq gtkleik
```

(27) Nucleic Acid Encoding the Full Length Humanized Hu2B8 Kv3-15.1 Light Chain Variable Region and Human Kappa Chain Constant Region (Km(3) Allotype) (Allele 2) (Signal Sequence Underlined) (SEQ ID NO. 180)

```
  1   atggaagccc cagcgcagct tctcttcctc ctgctactct ggctcccaga taccactgga
 61   gaaatagtga tgacgcagtc tccagccacc ctgtctgtgt ctccagggga aagagccacc
121   ctctcctgca aggccagtga aaatgtggtt tcttatgtat cctggtacca gcagaaacct
181   ggccaggctc ccaggctcct catctatggg gcatccaacc ggaacactgg tatcccagcc
241   aggttcagtg gcagtgggtc tgggacagag ttcactctca ccatcagcag cctgcagtct
301   gaagattttg cagtttatta ctgtgggcag agttacaact atccgtacac gtttggccag
361   gggaccaagc tggagatcaa acgaactgtg gctgcaccat ctgtcttcat cttcccgcca
421   tctgatgagc agttgaaatc tggaactgcc tctgttgtgt gcctgctgaa taacttctat
481   cccagagagg ccaaagtaca gtggaaggtg gataacgccc tccaatcggg taactcccag
541   gagagtgtca cagagcagga cagcaaggac agcacctaca gcctcagcag caccctgacg
601   ctgagcaaag cagactacga gaaacacaaa gtctacgcct gcgaagtcac ccatcagggc
661   ctgagctcgc ccgtcacaaa gagcttcaac aggggagagt gttga
```

(28) Protein Sequence Defining Humanized Hu2B8 Kv3-15.1 Light Chain Variable Region and Human Kappa Chain Constant Region (Km(3) Allotype) (Allele 2) (without Signal Sequence) (SEQ ID NO. 181)

```
  1   eivmtqspat lsvspgerat lsckasenvv syvswyqqkp gqaprlliyg asnrntgipa
 61   rfsgsgsgte ftltisslqs edfavyycgq synypytfgq gtkleikrtv aapsvfifpp
121   sdeqlksgta svvcllnnfy preakvqwkv dnalqsgnsq esvteqdskd styslsstlt
181   lskadyekhk vyacevthqg lsspvtksfn rgec
```

For convenience, Table 13 provides a concordance chart showing the correspondence between the full length sequences and of the antibodies discussed in this section with those presented in the Sequence Listing.

TABLE 13

| SEQ. ID NO. | Protein or Nucleic Acid |
| --- | --- |
| 154 | Chimeric 2B8 IgG1 (G1m(17,1)) - nucleic acid |
| 155 | Chimeric 2B8 IgG1 (G1m(17,1)) - protein |
| 156 | Chimeric 2B8 Kappa (Km(3)) - nucleic acid |
| 157 | Chimeric 2B8 Kappa (Km(3)) - protein |
| 158 | Hu2B8 Hv1f.1 Heavy Chain Variable Region - nucleic acid |
| 159 | Hu2B8 Hv1f.1 Heavy Chain Variable Region - protein |
| 160 | Human IgG1 Heavy Chain Constant Region (G1m(17,1)) allotype - nucleic acid |
| 161 | Human IgG1 Heavy Chain Constant Region (G1m(17,1)) allotype - protein |
| 162 | Hu2B8 Hv1f.1 + IgG1 Constant (G1m(17,1) allotype) - nucleic acid |
| 163 | Hu2B8 Hv1f.1 + IgG1 Constant (G1m(17,1) allotype) - protein |
| 164 | Hu2B8 Hv5a.1 Heavy Chain Variable Region - nucleic acid |
| 165 | Hu2B8 Hv5a.1 Heavy Chain Variable Region - protein |
| 166 | Hu2B8 Hv5a.1 + IgG1 Constant (G1m(17,1) allotype) - nucleic acid |
| 167 | Hu2B8 Hv5a.1 + IgG1 Constant (G1m(17,1) allotype) - protein |
| 168 | Hu2B8 Hv5-51.1 Heavy Chain Variable Region - nucleic acid |
| 169 | Hu2B8 Hv5-51.1 Heavy Chain Variable Region - protein |
| 170 | Hu2B8 Hv5-51.1 + IgG1 Constant (G1m(17,1) allotype) - nucleic acid |
| 171 | Hu2B8 Hv5-51.1 + IgG1 Constant (G1m(17,1) allotype) - protein |
| 172 | Hu2B8 Kv1-39.1 Kappa Chain Variable Region - nucleic acid |
| 173 | Hu2B8 Kv1-39.1 Kappa Chain Variable Region - protein |

TABLE 13-continued

| SEQ. ID NO. | Protein or Nucleic Acid |
|---|---|
| 174 | Human Kappa Chain Constant Region (Km(3) allotype) (allele 2) - nucleic acid |
| 175 | Human Kappa Chain Constant Region (Km(3) allotype) (allele 2) - protein |
| 176 | Hu2B8 Kv1-39.1 + Kappa Constant (Km(3) allotype) (allele 2) - nucleic acid |
| 177 | Hu2B8 Kv1-39.1 + Kappa Constant (Km(3) allotype) (allele 2) - protein |
| 178 | Hu2B8 Kv3-15.1 Kappa Chain Variable Region - nucleic acid |
| 179 | Hu2B8 Kv3-15.1 Kappa Chain Variable Region - protein |
| 180 | Hu2B8 Kv3-15.1 + Kappa Constant (Km(3) allotype) (allele 2) - nucleic acid |
| 181 | Hu2B8 Kv3-15.1 + Kappa Constant (Km(3) allotype) (allele 2) - protein |

B. Humanization Procedure 2

The second humanization method employed for reducing immunogenicity of the mouse 2B8 antibody is based on the method described in Studnicka et al. (1994) PROTEIN ENG. 7:805-814. The heavy and kappa human germline variable regions most identical (at the amino acid level) to those of mouse 2B8 were identified. Residues that differed between mouse and human were converted into the human sequence depending on the likely risk that such a change would affect binding or immunogenicity. Low risk residues (i.e., residues that when changed would likely not affect antigen binding and would also reduce potential immunogenicity) were changed to the human amino acid in the heavy variable region (creating LR2B8HC) and the kappa variable region (creating LR2B8LC). Additionally, low risk and medium risk (i.e., residues that when changed are somewhat likely to have an effect on antigen binding residues and would also reduce potential immunogenicity) were changed to the human amino acid in the heavy variable region (creating LRMR2B81-1C) and the kappa variable region (creating LRMR2B8LC). The human IgG1 heavy chain constant region (G1m(3) allotype (allele 1)) was added to the carboxyl terminus of the two human engineered heavy variable regions and the human Kappa constant region (Km(3) allotype (allele 1)) was added to the carboxyl terminus of two human engineered light variable regions, thus creating four human engineered antibody chains. Variable region nucleic acid sequences were first synthesized by gene synthesis methods and then added to human constant region sequences. These human engineered antibodies were cloned into mammalian protein expression vectors, and protein was expressed in the four possible combinations of heavy chain plus light chain. Binding of the chimeric, chimeric/humanized, or humanized antibodies to human HGF was measured using conventional techniques, as described below.

The nucleic acid sequences encoding and the protein sequences defining each of the humanized antibodies are summarized below. In this section, the last nucleotide of each variable region is the first base of the next codon generated by the variable/constant region junction. This nucleotide is included in the Variable Region because it is part of that exon. Amino acid sequences of Constant Regions listed below include the translation of this junction codon.

(1) Nucleic Acid Sequence Encoding the Humanized LR2B8HC Heavy Chain Variable Region (Signal Sequence Underlined) (SEQ ID NO. 182)

```
  1 atgggctggt catatattat tctctttctt gttgctaccg ctaccgatgt gcactctcaa
 61 gtccaactcg tacaaccagg cgctgaagtc gtaaaacccg gaacatctgt taaactctca
121 tgcaaagcct caggatacac tttcacaact tactggatgc attgggtcaa tcaagccccc
181 ggacaaggcc tcgaatggat tggcgaaatt aacccaacta acggacatac taattataat
241 gaaaaattta agggcaaagc tacactcacc gtcgataaat caacctctac agcttatatg
301 gaactttcat ccctgagatc agaagataca gccgtctact attgcgccag aaactacgta
361 ggatcaatat tcgattactg gggtcaaggc actctcctca cagtcagctc ag
```

(2) Protein Sequence Defining Humanized LR2B8HC Heavy Chain Variable Region (without Signal Sequence) (SEQ ID NO. 183)

```
  1 qvqlvqpgae vvkpgtsvkl sckasgytft tywmhwvnqa pgqglewige inptnghtny
 61 nekfkgkatl tvdkststay melsslrsed tavyycarny vgsifdywgq gtlltvss
```

(3) Nucleic Acid Sequence Encoding the Human IgG1 Heavy Chain Constant Region (G1m(3) Allotype) (Allele 1) (SEQ ID NO. 184)

```
  1 ccagcacaaa gggcccatcg gtcttccccc tggcaccctc ctccaagagc acctctgggg
 61 gcacagcggc cctgggctgc ctggtcaagg actacttccc cgaaccggtg acggtgtcgt
121 ggaactcagg cgccctgacc agcggcgtgc acaccttccc ggctgtccta cagtcctcag
181 gactctactc cctcagcagc gtggtgaccg tgccctccag cagcttgggc acccagacct
241 acatctgcaa cgtgaatcac aagcccagca acaccaaggt ggacaagaga gttgagccca
```

-continued

```
301  aatcttgtga caaaactcac acatgtccac cgtgcccagc acctgaactc ctgggggggac
361  cgtcagtctt cctcttcccc ccaaaaccca aggacaccct catgatctcc cggacccctg
421  aggtcacatg cgtggtggtg gacgtgagcc acgaagaccc tgaggtcaag ttcaactggt
481  acgtggacgg cgtggaggtg cataatgcca agacaaagcc gcgggaggag cagtacaaca
541  gcacgtaccg tgtggtcagc gtcctcaccg tcctgcacca ggactggctg aatggcaagg
601  agtacaagtg caaggtctcc aacaaagccc tcccagcccc atcgagaaa accatctcca
661  aagccaaagg gcagccccga gaaccacagg tgtacaccct gcccccatcc cgggaggaga
721  tgaccaagaa ccaggtcagc ctgacctgcc tggtcaaagg cttctatccc agcgacatcg
781  ccgtggagtg ggagagcaat gggcagccgg agaacaacta caagaccacg cctcccgtgc
841  tggactccga cggctccttc ttcctctata gcaagctcac cgtggacaag agcaggtggc
901  agcaggggaa cgtcttctca tgctccgtga tgcatgaggc tctgcacaac cactacacgc
961  agaagagcct ctccctgtcc ccgggtaaat ga
```

(4) Protein Sequence Defining Human IgG1 Heavy Chain Constant Region (G1m(3) Allotype) (Allele 1 or 2) (SEQ ID NO. 185).

The first amino acid is derived from translation of the last nucleotide of variable region and the beginning two nucleotides of the IgG1 Heavy Chain sequence.

```
  1 astkgpsvfp lapsskstsg gtaalgclvk dyfpepvtvs wnsgaltsgv htfpavlqss
 61 glyslssvvt vpssslgtqt yicnvnhkps ntkvdkrvep kscdkth-tcp pcpapellgg
121 psvflfppkp kdtlmisrtp evtcvvvdvs hedpevkfnw yvdgvevhna ktkpreeqyn
181 styrvvsvlt vlhqdwlngk eykckvsnka lpapiektis kakgqprepq vytlppsree
241 mtknqvsltc lvkgfypsdi avewesngqp ennykttppv ldsdgsffly skltvdksrw
301 qqgnvfscsv mhealhnhyt qkslslspgk
```

(5) Nucleic Acid Sequence Encoding the Full Length Heavy Chain Humanized LR2B8HC Heavy Chain Variable Region and Human IgG1 Heavy Chain Constant Region (G1m(3) Allotype) (Allele 1) (Signal Sequence Underlined) (SEQ ID NO. 186)

```
   1 atgggctggt catatattat tctctttctt gttgctaccg ctaccgatgt gcactctcaa
  61 gtccaactcg tacaaccagg cgctgaagtc gtaaaacccg gaacatctgt taaactctca
 121 tgcaaagcct caggatacac tttcacaact tactgatgc attgggtcaa tcaagccccc
 181 ggacaaggcc tcgaatggat tggcgaaatt aacccaacta acggacatac taattataat
 241 gaaaaattta agggcaaagc tacactcacc gtcgataaat caacctctac agcttatatg
 301 gaactttcat ccctgagatc agaagataca gccgtctact attgcgccag aaaactacgta
 361 ggatcaatat tcgattactg gggtcaaggc actctcctca gtcagctc agccagcaca
 421 aagggcccat cggtcttccc cctggcaccc tcctccaaga gcacctctgg gggcacagcg
 481 gccctgggct gcctggtcaa ggactacttc cccgaaccgg tgacggtgtc gtggaactca
 541 ggcgccctga ccagcggcgt gcacaccttc ccggctgtcc tacagtcctc aggactctac
 601 tccctcagca gcgtggtgac cgtgccctcc agcagcttgg gcacccagac ctacatctgc
 661 aacgtgaatc acaagcccag caacaccaag gtggacaaga gagttgagcc caaatcttgt
 721 gacaaaactc acacatgtcc accgtgccca gcacctgaac tcctgggggg accgtcagtc
 781 ttcctcttcc ccccaaaacc caaggacacc ctcatgatct cccggacccc tgaggtcaca
 841 tgcgtggtgg tggacgtgag ccacgaagac cctgaggtca agttcaactg gtacgtggac
 901 ggcgtggagg tgcataatgc caagacaaag ccgcgggagg agcagtacaa cagcacgtac
 961 cgtgtggtca gcgtcctcac cgtcctgcac caggactggc tgaatggcaa ggagtacaag
1021 tgcaaggtct ccaacaaagc cctcccagcc cccatcgaga aaaccatctc caaagccaaa
1081 gggcagcccc gagaaccaca ggtgtacacc ctgcccccat cccgggagga gatgaccaag
```

```
1141  aaccaggtca gcctgacctg cctggtcaaa ggcttctatc cagcgacat cgccgtggag 1201  tgggagagca atgggcagcc ggagaacaac tacaagacca cgcctcccgt gctggactcc 1261  gacggctcct tcttcctcta tagcaagctc accgtggaca agagcaggtg gcagcagggg 1321  aacgtcttct catgctccgt gatgcatgag gctctgcaca accactacac gcagaagagc 1381  ctctccctgt ccccgggtaa atga
```

(6) Protein Sequence Defining the Full Length Heavy Chain Humanized LR2B8HC Heavy Chain Variable Region and Human IgG1 Heavy Chain Constant Region (G1m(3) Allotype) (Allele 1) (without Signal Sequence) (SEQ ID NO. 187)

```
  1  qvqlvqpgae vvkpgtsvkl sckasgytft tywmhwvnqa pgqglewige inptnghtny
 61  nekfkgkatl tvdkststay melsslrsed tavyycarny vgsifdywgq gtlltvssas
121  tkgpsvfpla psskstsggt aalgclvkdy fpepvtvswn sgaltsgvht fpavlqssgl
181  yslssvvtvp ssslgtqtyi cnvnhkpsnt kvdkrvepks cdkthtcppc papellggps
241  vflfppkpkd tlmisrtpev tcvvvdvshe dpevkfnwyv dgvevhnakt kpreeqynst
301  yrvvsvltvl hqdwlngkey kckvsnkalp apiektiska kgqprepqvy tlppsreemt
361  knqvsltclv kgfypsdiav ewesngqpen nykttppvld sdgsfflysk ltvdksrwqq
421  gnvfscsvmh ealhnhytqk slslspgk
```

(7) Nucleic Acid Sequence Encoding the Humanized LRMR2B8HC Heavy Chain Variable Region (Signal Sequence Underlined) (SEQ ID NO. 188)

```
  1  atgggttggt catatattat actctttctc gtagccaccg ccaccgacgt acactctcag
 61  gttcaactcg tacaacccgg cgccgaagtc aagaaaccag gaacatcagt caaactctca
121  tgtaaagcaa gcggatacac ctttactact tattggatgc attgggtaag acaagccccc
181  ggacaaggac tcgaatggat aggcgaaata atcccacta atggacatac aaattataat
241  caaaaatttc aaggacgcgc tacactcacc gtcgataaat caacctcaac cgcatacatg
301  gaactcagct ccctccgatc cgaagacact gccgtttatt attgtgccag aaactatgta
361  ggatctattt tcgattactg gggacaagga acacttctca ccgtaagctc ag
```

(8) Protein Sequence Defining Humanized LRMR2B8HC Heavy Chain Variable Region (without Signal Sequence) (SEQ ID NO. 189)

```
  1  qvqlvqpgae vkkpgtsvkl sckasgytft tywmhwvrqa pgqglewige inptnghtny
 61  nqkfqgratl tvdkststay melsslrsed tavyycarny vgsifdywgq gtlltvss
```

(9) Nucleic Acid Sequence Encoding the Full Length Heavy Chain Humanized LRMR2B8HC Heavy Chain Variable Region and Human IgG1 Heavy Chain Constant Region (G1m(3) Allotype) (Allele 1) (Signal Sequence Underlined) (SEQ ID NO. 190)

```
  1  atgggttggt catatattat actctttctc gtagccaccg ccaccgacgt acactctcag
 61  gttcaactcg tacaacccgg cgccgaagtc aagaaaccag gaacatcagt caaactctca
121  tgtaaagcaa gcggatacac ctttactact tattggatgc attgggtaag acaagccccc
```

-continued

```
 181   ggacaaggac tcgaatggat aggcgaaata atcccacta atggacatac aaattataat
 241   caaaaattc aaggacgcgc tacactcacc gtcgataaat caacctcaac cgcatacatg
 301   gaactcagct ccctccgatc cgaagacact gccgtttatt attgtgccag aaactatgta
 361   ggatctattt tcgattactg gggacaagga acacttctca ccgtaagctc agccagcaca
 421   aagggcccat cggtcttccc cctggcaccc tcctccaaga gcacctctgg gggcacagcg
 481   gccctgggct gcctggtcaa ggactacttc cccgaaccgg tgacggtgtc gtggaactca
 541   ggcgccctga ccagcggcgt gcacaccttc ccggctgtcc tacagtcctc aggactctac
 601   tccctcagca gcgtggtgac cgtgccctcc agcagcttgg gcacccagac ctacatctgc
 661   aacgtgaatc acaagcccag caacaccaag gtggacaaga gagttgagcc caaatcttgt
 721   gacaaaactc acacatgtcc accgtgccca gcacctgaac tcctgggggg accgtcagtc
 781   ttcctcttcc ccccaaaacc caaggacacc ctcatgatct cccggacccc tgaggtcaca
 841   tgcgtggtgg tggacgtgag ccacgaagac cctgaggtca agttcaactg gtacgtggac
 901   ggcgtggagg tgcataatgc caagacaaag ccgcgggagg agcagtacaa cagcacgtac
 961   cgtgtggtca gcgtcctcac cgtcctgcac caggactggc tgaatggcaa ggagtacaag
1021   tgcaaggtct ccaacaaagc cctcccagcc cccatcgaga aaccatctc caaagccaaa
1081   gggcagcccc gagaaccaca ggtgtacacc ctgcccccat cccgggagga tgaccaag
1141   aaccaggtca gcctgacctg cctggtcaaa ggcttctatc ccagcgacat cgccgtggag
1201   tgggagagca atgggcagcc ggagaacaac tacaagacca cgcctcccgt gctggactcc
1261   gacggctcct tcttcctcta tagcaagctc accgtggaca gagcaggtg gcagcagggg
1321   aacgtcttct catgctccgt gatgcatgag gctctgcaca accactacac gcagaagagc
1381   ctctccctgt ccccgggtaa atga
```
35

(10) Protein Sequence Defining the Full Length Heavy Chain Humanized LRMR2B8HC Heavy Chain Variable Region and Human IgG1 Heavy Chain Constant Region (G1m(3) Allotype) (Allele 1) (without Signal Sequence) (SEQ ID NO. 191)

```
  1   qvqlvqpgae vkkpgtsvkl sckasgytft tywmhwvrqa pgqglewige inptnghtny
 61   nqkfqgratl tvdkststay melsslrsed tavyycarny vgsifdywgq gtlltvssas
121   tkgpsvfpla ppsskstsggt aalgclvkdy fpepvtvswn sgaltsgvht fpavlqssgl
181   yslssvvtvp ssslgtqtyi cnvnhkpsnt kvdkrvepks cdkthtcppc papellggps
241   vflfppkpkd tlmisrtpev tcvvvdvshe dpevkfnwyv dgvevhnakt kpreeqynst
301   yrvvsvltvl hqdwlngkey kckvsnkalp apiektiska kgqprepqvy tlppsreemt
361   knqvsltclv kgfypsdiav ewesngqpen nykttppvld sdgsfflysk ltvdksrwqq
421   gnvfscsvmh ealhnhytqk slslspgk
```
55

(11) Nucleic Acid Sequence Encoding the Humanized LR2B8LC Light Chain Variable Region (Signal Sequence Underlined) (SEQ ID NO. 192)

```
  1   atggaaagtc agacccttgt attcatctct attcttcttt ggttgtatgg agcagacggc
 61   gacattgtga tgacccaatc ccccgatagt atggccatga gtgtaggaga aagagtcacc
121   cttaattgca aagcctccga aaatgtcgtt tcatatgtgt cttggtatca acaaaaaccc
181   ggccaatcac ccaaacttct catatacggc gcttcaaaca gaaacacagg cgttcccgac
```

```
241 agatttagtg gatccggatc agctacagat ttcaccctta ccatcagttc agttcaagca 301 gaagacgttg cagactatca ttgcggacaa tcttataact acccttacac attcggacaa
```

(12) Protein Sequence Defining Humanized LR2B8LC Light Chain Variable Region (without Signal Sequence) (SEQ ID NO. 193)

```
1   divmtqspds mamsvgervt lnckasenvv syvswyqqkp gqspklliyg asnrntgvpd 61  rfsgsgsatd ftltissvqa edvadyhcgq synypytfgq gtkleik
```

(13) Nucleic Acid Sequence Encoding the Human Kappa Chain Constant Region (Km(3) Allotype) (Allele 1) (SEQ ID NO. 194)

```
1   gtacggtggc tgcaccatct gtcttcatct tcccgccatc tgatgagcag ttgaaatctg 61  gaactgcctc tgttgtgtgc ctgctgaata acttctatcc cagagaggcc aaagtacagt 121 ggaaggtgga taacgccctc caatcgggta actcccagga gagtgtcaca gagcaggaca 181 gcaaggacag cacctacagc ctcagcagca ccctgacgct gagcaaagca gactacgaga 241 aacacaaagt ctacgcctgc gaagtcaccc atcagggcct gagctcgccc gtcacaaaga 301 gcttcaacag gggagagtgt tag
```

(14) Protein Sequence Defining the Human Kappa Chain Constant Region (Km(3) Allotype) (Allele 1) (SEQ ID NO. 195).

The first amino acid derived from translation of the last nucleotide of variable region and beginning two nucleotides of the Kappa Light Chain sequence.

```
1 rtvaapsvfi fppsdeqlks gtasvvclln nfypreakvq wkvdnalqsg nsqesvteqd 61 skdstyslss tltlskadye khkvyacevt hqglsspvtk sfnrgec
```

(15) Nucleic Acid Sequence Encoding the Full Length Humanized LR2B8LC Light Chain Variable Region and the Human Kappa Chain Constant Region (Km(3) Allotype) (Allele 1) (SEQ ID NO. 196)

```
1   atggaaagtc agacccttgt attcatctct attcttcttt ggttgtatgg agcagacggc 61  gacattgtga tgacccaatc ccccgatagt atggccatga gtgtaggaga aagagtcacc 121 cttaattgca aagcctccga aaatgtcgtt tcatatgtgt cttggtatca acaaaaaccc 181 ggccaatcac ccaaacttct catatacggc gcttcaaaca gaaacacagg cgttcccgac 241 agatttagtg gatccggatc agctacagat ttcaccctta ccatcagttc agttcaagca 301 gaagacgttg cagactatca ttgcggacaa tcttataact acccttacac attcggacaa 361 ggaaccaaac tcgaaattaa acgtacggtg gctgcaccat ctgtcttcat cttcccgcca 421 tctgatgagc agttgaaatc tggaactgcc tctgttgtgt gcctgctgaa taacttctat 481 cccagagagg ccaaagtaca gtggaaggtg gataacgccc tccaatcggg taactcccag 541 gagagtgtca cagagcagga cagcaaggac agcacctaca gcctcagcag caccctgacg 601 ctgagcaaag cagactacga gaaacacaaa gtctacgcct gcgaagtcac ccatcagggc 661 ctgagctcgc ccgtcacaaa gagcttcaac aggggagagt gttag
```

(16) Protein Sequence Encoding the Full Length Humanized LR2B8LC Light Chain Variable Region and the Human Kappa Chain Constant Region (Km(3) Allotype) (Allele 1) (SEQ ID NO. 197)

```
1   divmtqspds mamsvgervt lnckasenvv syvswyqqkp gqspklliyg asnrntgvpd 61  rfsgsgsatd ftltissvqa edvadyhcgq synypytfgq gtkleikrtv aapsvfifpp
```

```
121  sdeqlksgta svvcllnnfy preakvqwkv dnalqsgnsq esvteqdskd styslsstlt 181  lskadyekhk vyacevthqg lsspvtksfn rgec
```

(17) Nucleic Acid Sequence Encoding the Humanized LRMR2B8LC Light Chain Variable Region (Signal Sequence Underlined) (SEQ ID NO. 198)

```
  1  atggaatccc aaaccttgt tttcatctct atccttctct ggctttatgg cgccgacgga 61  gacatcgtaa tgacacaatc ccctgactct cttgctatga gcttgggcga acgagtaaca 121  cttaactgca aagcatccga aaatgtcgta tcttacgtat cctggtatca gcaaaaacct 181  ggtcaaagtc ctaaacttct tatatatggt gcaagtaatc gtgaaagtgg cgtcccagac 241  agatttagcg gttcaggttc agcaactgac tttacactta caatttctag cgttcaggcc 301  gaagacgttg cagactatca ttgtggacaa tcttataact atccttatac tttcggacaa 361  ggcactaaac ttgaaattaa ac
```

(18) Protein Sequence Defining the Humanized LRMR2B8LC Light Chain Variable Region (without Signal Sequence) (SEQ ID NO. 199)

```
  1  divmtqspds lamslgervt lnckasenvv syvswyqqkp gqspklliyg asnresgvpd 61  rfsgsgsatd ftltissvqa edvadyhcgq synypytfgq gtkleik
```

(19) Nucleic Acid Sequence Encoding the Full Length Humanized LRMR2B8LC Light Chain Variable Region and the Human Kappa Chain Constant Region (Km(3) Allotype) (Allele 1) (Signal Sequence Underlined) (SEQ ID NO. 200)

```
  1  atggaatccc aaaccttgt tttcatctct atccttctct ggctttatgg cgccgacgga 61  gacatcgtaa tgacacaatc ccctgactct cttgctatga gcttgggcga acgagtaaca 121  cttaactgca aagcatccga aaatgtcgta tcttacgtat cctggtatca gcaaaaacct 181  ggtcaaagtc ctaaacttct tatatatggt gcaagtaatc gtgaaagtgg cgtcccagac 241  agatttagcg gttcaggttc agcaactgac tttacactta caatttctag cgttcaggcc 301  gaagacgttg cagactatca ttgtggacaa tcttataact atccttatac tttcggacaa 361  ggcactaaac ttgaaattaa acgtacggtg gctgcaccat ctgtcttcat cttcccgcca 421  tctgatgagc agttgaaatc tggaactgcc tctgttgtgt gcctgctgaa taacttctat 481  cccagagagg ccaaagtaca gtggaaggtg gataacgccc tccaatcggg taactcccag 541  gagagtgtca cagagcagga cagcaaggac agcacctaca gcctcagcag caccctgacg 601  ctgagcaaag cagactacga gaaacacaaa gtctacgcct gcgaagtcac ccatcagggc 661  ctgagctcgc ccgtcacaaa gagcttcaac aggggagagt gttag
```

(20) Protein Sequence Defining the Full Length Humanized LRMR2B8LC Light Chain Variable Region and the Human Kappa Chain Constant Region (Km(3) Allotype) (Allele 1) (SEQ ID NO. 201)

```
  1  divmtqspds lamslgervt lnckasenvv syvswyqqkp gqspklliyg asnresgvpd 61  rfsgsgsatd ftltissvqa edvadyhcgq synypytfgq gtkleikrtv aapsvfifpp 121  sdeqlksgta svvcllnnfy preakvqwkv dnalqsgnsq esvteqdskd styslsstlt 181  lskadyekhk vyacevthqg lsspvtksfn rgec
```

For convenience, Table 14 provides a concordance chart showing the correspondence between the full length sequences and of the antibodies discussed in this section with those presented in the Sequence Listing.

TABLE 14

| SEQ. ID NO. | Protein or Nucleic Acid |
|---|---|
| 182 | LR2B8HC Heavy Chain Variable Region - nucleic acid |
| 183 | LR2B8HC Heavy Chain Variable Region - protein |
| 184 | Human IgG1 Heavy Chain Constant Region (G1m(3) allotype) (allele 1) - nucleic acid |
| 185 | Human IgG1 Heavy Chain Constant Region (G1m(3) allotype) (allele 1) - protein |
| 186 | LR2B8HC + IgG1 Constant (G1m(3) allotype) (allele 1) - nucleic acid |
| 187 | LR2B8HC + IgG1 Constant (G1m(3) allotype) (allele 1) - protein |
| 188 | LRMR2B8HC Heavy Chain Variable Region - nucleic acid |
| 189 | LRMR2B8HC Heavy Chain Variable Region - protein |
| 190 | LRMR2B8HC + IgG1 Constant (G1m(3) allotype) (allele 1) - nucleic acid |
| 191 | LRMR2B8HC + I:G1 Constant (G1m(3) allotype) (allele 1) - protein |

TABLE 14-continued

| SEQ. ID NO. | Protein or Nucleic Acid |
|---|---|
| 192 | LR2B8LC Light Chain Variable Region - nucleic acid |
| 193 | LR2B8LC Light Chain Variable Region - protein |
| 194 | Human Kappa Chain Constant Region (Km(3) allotype) (allele 1) - nucleic acid |
| 195 | Human Kappa Chain Constant Region (Km(3) allotype) (allele 1) - protein |
| 196 | LR2B8LC + Kappa Constant (Km(3) allotype) (allele 1) - nucleic acid |
| 197 | LR2B8LC + Kappa Constant (Km(3) allotype) (allele 1) - protein |
| 198 | LRMR2B8LC Light Chain Variable Region - nucleic acid |
| 199 | LRMR2B8LC Light Chain Variable Region - protein |
| 200 | LRMR2B8LC + Kappa Constant (Km(3) allotype) (allele 1) - nucleic acid |
| 201 | LRMR2B8LC + Kappa Constant (Km(3) allotype) (allele 1) - protein |

Table 15 summarizes the heavy chain CDR sequences (Kabat Definition) of the humanized 2B8 antibodies prepared by humanization procedure 1 and by humanization procedure 2 described herein above in this Example.

TABLE 15

| Antibody | CDR1 | CDR2 | CDR3 | Full Length Heavy Chain Variable Region |
|---|---|---|---|---|
| Murine 2B8 Heavy | TYWMH (SEQ ID NO: 15) | EINPTNGHTNYNEKFKS (SEQ ID NO: 16) | NYVGSIFDY (SEQ ID NO: 17) | SEQ ID NO: 12 |
| Hu2B8 Hv1f.1 | TYWMH (SEQ ID NO: 15) | EINPTNGHTNYNEKFQG (SEQ ID NO: 202) | NYVGSIFDY (SEQ ID NO: 17) | SEQ ID NO: 159 |
| Hu2B8 Hv5a.1 | TYWMH (SEQ ID NO: 15) | EINPTNGHTNYNPSFQG (SEQ ID NO: 203) | NYVGSIFDY (SEQ ID NO: 17) | SEQ ID NO: 165 |
| Hu2B8 Hv5-51.1 | TYWMH (SEQ ID NO: 15) | EINPTNGHTNYNPSFQG (SEQ ID NO: 203) | NYVGSIFDY (SEQ ID NO: 17) | SEQ ID NO: 169 |
| LR2B8HC | TYWMH (SEQ ID NO: 15) | EINPTNGHTNYNEKFKG (SEQ ID NO: 204) | NYVGSIFDY (SEQ ID NO: 17) | SEQ ID NO: 183 |
| LRMR2B8HC | TYWMH (SEQ ID NO: 15) | EINPTNGHTNYNQKFQG (SEQ ID NO: 205) | NYVGSIFDY (SEQ ID NO: 17) | SEQ ID NO: 189 |

Table 16 summarizes the light chain CDR sequences (Kabat Definition) of the humanized 2B8 antibodies prepared by humanization procedure 1 and by humanization procedure 2 described herein above in this Example.

TABLE 16

| Antibody | CDR1 | CDR2 | CDR3 | Full Length Light Chain Variable Region |
|---|---|---|---|---|
| Murine 2B8 Light | KASENVVSYVS (SEQ ID NO: 18) | GASNRNT (SEQ ID NO: 19) | GQSYNYPYT (SEQ ID NO: 20) | SEQ ID NO: 14 |
| Hu2B8 Kv1-39.1 | KASENVVSYVS (SEQ ID NO: 18) | GASNRNT (SEQ ID NO: 19) | GQSYNYPYT (SEQ ID NO: 20) | SEQ ID NO: 173 |
| Hu2B8 Kv3-15.1 | KASENVVSYVS (SEQ ID NO: 18) | GASNRNT (SEQ ID NO: 19) | GQSYNYPYT (SEQ ID NO: 20) | SEQ ID NO: 179 |
| LR2B8LC | KASENVVSYVS (SEQ ID NO: 18) | GASNRNT (SEQ ID NO: 19) | GQSYNYPYT (SEQ ID NO: 20) | SEQ ID NO: 193 |
| LRMR2B8LC | KASENVVSYVS (SEQ ID NO: 18) | GASNRES (SEQ ID NO: 206) | GQSYNYPYT (SEQ ID NO: 20) | SEQ ID NO: 199 |

C. Binding Affinity of Humanized 2B8 Antibodies

Antigen-binding affinity and kinetics of interaction were assessed by surface plasmon resonance technology using a BIAcore T100 instrument. Mouse anti-human immunoglobulins (Jackson ImmunoResearch Labs, 209-005-098) were immobilized on carboxymethylated dextran CM4 sensor chips (BIAcore, Catalog No. BR-1005-34) by amine coupling (BIAcore, Catalog No. BR-1000-50) using a standard coupling protocol according to manufacturer's recommendations. The analyses were performed at 25° C. using PBS (GIBCO, Catalog No. 14040-133) containing 0.05% surfactant P20 (BIAcore, Catalog No. BR-1000-54), 2 mg/mL BSA (EMD, Catalog No. 2930) and 10 mg/mL CM-Dextran Sodium salt (Fluka, Catalog No. 86524) as running buffer.

The antibodies were captured on individual flow cell at a flow rate of 10 µL/min. Injection time was variable for each antibody to yield approximately 20 RU of antibody captured for each cycle. Buffer or HGF (R&D Systems, Catalog No. 294-HGN-025) diluted in running buffer was injected sequentially over a reference surface (no antibody captured) and the active surface (antibody to be tested) for 2 minutes at 60 µL/min. The dissociation phase was monitored for 15 or 90 minutes, depending on concentration. The surface then was regenerated with 10 mM Glycine-HCl, pH 2.0 (BIAcore, Catalog No. BR-1003-55) injected for 3 minutes at a flow rate of 60 µL/min before another cycle was initiated. HGF concentrations tested were 1.88, 3.75 and 7.5 nM. Determination of kinetic parameters was achieved using the kinetic function of the BIAevaluation software with reference subtraction. Kinetic parameters for each antibody, $k_a$ (association rate constant), $k_d$ (dissociation rate constant) and $K_D$ (equilibrium dissociation constant) are summarized in FIG. 8.

The results summarized in FIG. 8 show that certain combinations of superhumanized heavy chains (Hu2B8 Hv5a.1, Hu2B8 Hv5-51.1 or Hu2B8 Hv14.1) and light chains (Hu2B8 Kv1-39.1 or Hu2B8 Kv3-15.1) retain similar binding affinity ($K_D$) to HGF as chimeric 2B8 (mouse variable regions with human constant regions) and 2B8 (Table 5).

D. Mutually Exclusive Binding Assay

Mutually exclusive binding to HGF was assessed by surface plasmon resonance technology using a BIAcore T100 instrument. Mouse anti-human immunoglobulins (Jackson ImmunoResearch Labs, 209-005-098) were immobilized on carboxymethylated dextran CM5 sensor chips (BIAcore, Catalog No. BR-1006-68) by amine coupling (BIAcore, Catalog No. BR-1000-50) using a standard coupling protocol according to manufacturer's recommendations. The analyses were performed at 25° C. using PBS (GIBCO, Catalog No. 14040-133) containing 0.05% surfactant P20 (BIAcore, #BR-1000-54), 2 mg/mL BSA (EMD, Catalog No. 2930) and 10 mg/ml CM-Dextran Sodium salt (Fluka, Catalog No. 86524) as running buffer.

The humanized antibodies were captured on an individual flow cell at a flow rate of 30 µL/min. Injection time was variable for each antibody to yield approximately 150 RU of antibody captured for each cycle. HGF (R&D Systems, Catalog No. 294-HGN-025) diluted in running buffer at a final concentration of 7.5 µg/mL was injected for 90 sec at 30 µL/min over the captured humanized antibodies. Binding of HGF was monitored before subsequent injection of mouse 2B8 antibody or polyclonal goat anti-HGF antibody (R & D Systems, AF294) for 3 min at 30 µL/min. The surface then was regenerated with 10 mM Glycine-HCl, pH 2.0 (BIAcore, Catalog No. BR-1003-55) injected for 3 min at a flow rate of 60 µL/min before another antibody was tested. The results are summarized in FIG. 9.

Figure 9:
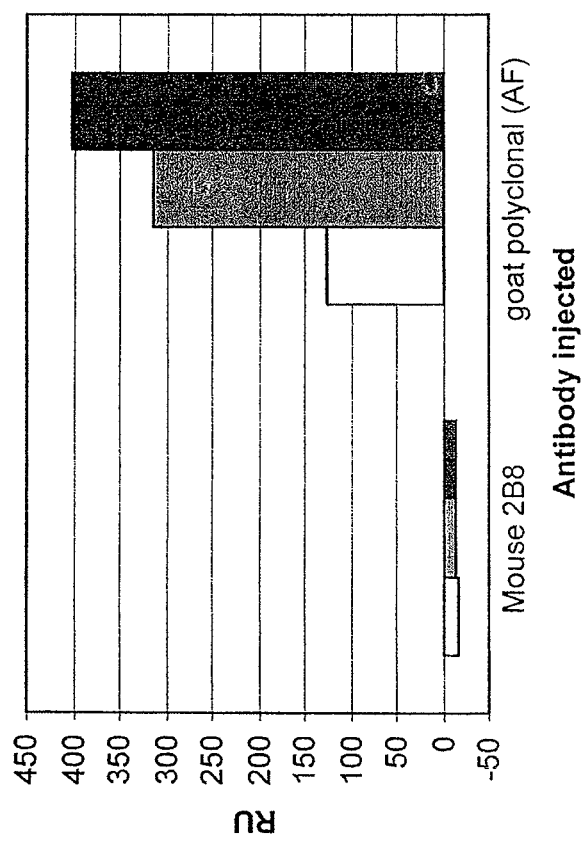
FIG. 9 is a bar chart summarizing experimental data indicating that Hu2B8 binds an epitope mutually exclusive to murine monoclonal antibody 2B8. Humanized or chimeric 2B8 was captured on an anti-human Fc chip. HGF then was bound to the humanized or chimeric 2B8. The ability of mouse 2B8 or the control antibody (polyclonal goat anti-HGF antibody) to bind the captured HGF was measured. Both humanized 2B8 antibodies and chimeric 2B8 prevent murine 2B8 from binding HGF. White bars correspond to the chimeric 2B8 antibody; gray bars correspond to the humanized Hu2B8 antibody (kappa variable region Kv1-39.1 and heavy chain variable region Hv5-51.1); black bars correspond to the humanized Hu2B8 antibody (kappa variable region Kv3-15.1 and heavy chain variable region Hv5-51.1).

Results summarized in FIG. 9 show that both humanized 2B8 antibodies and chimeric 2B8 antibodies prevent murine 2B8 from binding HGF. These results demonstrate that the humanized antibodies still bind the same HGF epitope as the original 2B8 antibody.

Example 13

Production of Humanized 2B8 Variants a. HUMAN ENGINEERED™ Antibodies

Codon- and expression-optimized low risk and low-plus-moderate risk Human Engineered light chain (LR2B8LC and LRMR2B8LC, respectively) and heavy chains (LR2B8HC and LRMR2B8HC, respectively) were cloned in-phase into XOMA's transient antibody expression vectors, which contain human Kappa and Gamma-1 constant regions modules. The four Human Engineered 2B8 variants were produced by transient transfection in HEK293E cells. The following four antibodies were produced:

HE2B8-1=LR2B8HC (+IgG1 constant region (G1m(3) allotype (allele 1)) (SEQ ID NO. 187) plus LR2B8LC (+Kappa constant region (Km(3) allotype (allele 1))) (SEQ ID NO. 197)

HE2B8-2=LR2B8HC (+IgG1 constant region (G1m(3) allotype (allele 1)) (SEQ ID NO. 187) plus LRMR2B8LC (+Kappa constant region (Km(3) allotype (allele 1))) (SEQ ID NO. 201)

HE2B8-3=LRMR2B8HC (+IgG1 constant region (G1m (3) allotype (allele 1)) (SEQ ID NO. 191) plus LR2B8LC (+Kappa constant region (Km(3) allotype (allele 1))) (SEQ ID NO. 197)

HE2B8-4=LRMR2B8HC (+IgG1 constant region (G1m (3) allotype (allele 1)) (SEQ ID NO. 191) plus LRMR2B8LC (+Kappa constant region (Km(3) allotype (allele 1))) (SEQ ID NO. 201)

The light and heavy chains were co-transfected into XOMA's suspension adapted HEK293E cells grown in IS293 media (Irvine Scientific, Irvine, Calif.) using 2 liter shake flasks. After 24 hours in the shake flasks, 200 mL of transfected cells were centrifuged, resuspended in 40 mL of fresh medium and transferred to Integra flasks (Wilson Wolf Manufacturing Inc., MN) for production. After incubation for seven days, the cell suspensions were removed from the Integra flasks, centrifuged and the culture supernatants retained.

The nucleic acid sequences encoding and the protein sequences defining the human IgG1 Heavy Constant Region G1m(3) allotype (allele 2) and each of the full length heavy chain sequences are set forth below. The light chain sequences were the same as described in Example 12.

(1) Nucleic Acid Sequence Encoding Human IgG1 Heavy Chain Constant Region (G1m(3) Allotype) (Allele 2) (SEQ ID NO. 207)

```
  1 cctccaccaa gggcccatcg gtcttccccc tggcaccctc ctccaagagc acctctgggg
 61 gcacagcggc cctgggctgc ctggtcaagg actacttccc cgaaccggtg acggtgtcgt
121 ggaactcagg cgccctgacc agcggcgtgc acaccttccc ggctgtccta cagtcctcag
181 gactctactc cctcagcagc gtggtgaccg tgccctccag cagcttgggc acccagacct
241 acatctgcaa cgtgaatcac aagcccagca acaccaaggt ggacaagaga gttgagccca
301 aatcttgtga caaaactcac acatgcccac cgtgcccagc acctgaactc ctggggggac
361 cgtcagtctt cctcttcccc ccaaaaccca aggacaccct catgatctcc cggacccctg
421 aggtcacatg cgtggtggtg gacgtgagcc acgaagaccc tgaggtcaag ttcaactggt
481 acgtggacgg cgtggaggtg cataatgcca agacaaagcc gcgggaggag cagtacaaca
541 gcacgtaccg tgtggtcagc gtcctcaccg tcctgcacca ggactggctg aatggcaagg
601 agtacaagtg caaggtctcc aacaaagccc tcccagcccc catcgagaag accatctcca
661 aagccaaagg gcagccccga gaaccacagg tgtacaccct gcccccatcc cgggaggaga
721 tgaccaagaa ccaggtcagc ctgacctgcc tggtcaaagg cttctatccc agcgacatcg
781 ccgtggagtg ggagagcaat gggcagccgg agaacaacta caagaccacg cctcccgtgc
841 tggactccga cggctccttc ttcctctaca gcaagctcac cgtggacaag agcaggtggc
901 agcaggggaa cgtcttctca tgctccgtga tgcatgaggc tctgcacaac cactacacgc
961 agaagagcct ctccctgtct ccgggtaaat ga
```

Antibodies in the culture supernatants were purified on protein A spin columns (Pro-Chem), dialyzed against PBS, concentrated and sterile filtered.

b. SUPERHUMANIZED™ Antibodies

Full length Hu2B8_Hv5-51.1+human IgG1 constant domain (G1m(3) allotype) cDNA was cloned into pEE6.4 (Lonza Biologics, Berkshire, UK) using HindIII and EcoRI restriction sites. Full length Hu2B8_Kv1-39.1 variable region+human Kappa constant domain cDNA and full length Hu2B8_Kv3-15.1 variable region+human Kappa constant domain cDNA were each cloned into pEE14.4 (Lonza Biologics) using HindIII and EcoRI restriction sites. The hCMV-MIE promoter+full length Hu2B8_Hv5-51.1+human IgG1 constant domain (G1m(3) allotype) cDNA+SV40 poly A fragment (in pEE6.4) was removed by NotI/SalI digestion and inserted into either Kappa chain pEE14.4 vector through NotI/SalI sites, thus creating 2 different expression vectors that each simultaneously express heavy and light chain to make the following antibodies:

sh2B8-9 (G1m(3))=hu2B8 Hv5-51.1 (+IgG1 constant region (G1m(3) allotype) (allele 2)) (SEQ ID NO. 210) plus hu2B8 Kv 1-39.1 (+Kappa constant region (Km(3) allotype (allele 2))) (SEQ ID NO: 177)

sh2B8-12 (G1m(3))=hu2B8 Hv5-51.1 (+IgG1 constant region (G1m(3) allotype) (allele 2)) (SEQ ID NO. 210) plus hu2B8 Kv 3-15.1 (+Kappa constant region (Km(3) allotype (allele 2))) (SEQ ID No. 181)

(2) Protein Sequence Defining Human IgG1 Heavy Chain Constant Region (G1m(3) Allotype) (Allele 1 or 2) (SEQ ID NO. 208).

The first amino acid is derived from translation of the last nucleotide of variable region and the beginning two nucleotides of the IgG1 Heavy Chain sequence.

1 astkgpsvfp lapsskstsg gtaalgclvk dyfpepvtvs wnsgaltsgv htfpavlqss 61 glyslssvvt vpssslgtqt yicnvnhkps ntkvdkrvep kscdkthtcp pcpapellgg 121 psvflfppkp kdtlmisrtp evtcvvvdvs hedpevkfnw yvdgvevhna ktkpreeqyn 181 styrvvsvlt vlhqdwlngk eykckvsnka lpapiektis kakgqprepq vytlppsree 241 mtknqvsltc lvkgfypsdi avewesngqp ennykttppv ldsdgsffly skltvdksrw 301 qqgnvfscsv mhealhnhyt qkslslspgk (3) Nucleic Acid Sequence Encoding the Full Length Chain Containing Humanized Hu2B8 Hv5-51.1 Heavy Chain Variable Region and the Human IgG1 Heavy Chain Constant Region G1m(3) Allotype (Allele 2) (Signal Sequence Underlined) (SEQ ID NO. 209)

```
   1  atggggtcaa ccgccatcct cgccctcctc ctggctgttc tccaaggagt ctgtgccgaa
  61  gtgcagctgg tgcagtctgg agcagaggtg aaaaagcccg gggagtctct gaagatctcc
 121  tgtaagggtt ctggatacag ctttaccacc tactggatgc actgggtgcg ccagatgccc
 181  gggaaaggcc tggagtggat gggggagatt aatcctacca acggtcatac taactacaat
 241  ccgtccttcc aaggccaggt caccatctca gctgacaagt ccatcagcac tgcctacctg
 301  cagtggagca gcctgaaggc ctcggacacc gccatgtatt actgtgcgag aaactatgtt
 361  ggtagcatct ttgactactg gggccaagga accctggtca ccgtctcctc agcctccacc
 421  aagggcccat cggtcttccc cctggcaccc tcctccaaga gcacctctgg gggcacagcg
 481  gccctgggct gcctggtcaa ggactacttc cccgaaccgg tgacggtgtc gtggaactca
 541  ggcgccctga ccagcggcgt gcacaccttc ccggctgtcc tacagtcctc aggactctac
 601  tccctcagca gcgtggtgac cgtgccctcc agcagcttgg gcacccagac ctacatctgc
 661  aacgtgaatc acaagcccag caacaccaag gtggacaaga gagttgagcc caaatcttgt
 721  gacaaaactc acacatgccc accgtcccca gcacctgaac tcctgggggg accgtcagtc
 781  ttcctcttcc ccccaaaacc caaggacacc ctcatgatct cccggacccc tgaggtcaca
 841  tgcgtggtgg tggacgtgag ccacgaagac cctgaggtca agttcaactg gtacgtggac
 901  ggcgtggagg tgcataatgc caagacaaag ccgcgggagg agcagtacaa cagcacgtac
 961  cgtgtggtca gcgtcctcac cgtcctgcac caggactggc tgaatggcaa ggagtacaag
1021  tgcaaggtct ccaacaaagc cctcccagcc cccatcgaga agaccatctc caaagccaaa
1081  gggcagcccc gagaaccaca ggtgtacacc ctgcccccat cccgggagga tgaccaagaa
1141  aaccaggtca gcctgacctg cctggtcaaa ggcttctatc ccagcgacat cgccgtggag
1201  tgggagagca atgggcagcc ggagaacaac tacaagacca cgcctcccgt gctggactcc
1261  gacggctcct tcttcctcta cagcaagctc accgtggaca agagcaggtg gcagcagggg
1321  aacgtcttct catgctccgt gatgcatgag gctctgcaca accactacac gcagaagagc
1381  ctctccctgt ctccgggtaa atga
```

(4) Protein Sequence Defining the Full Length Heavy Chain Containing Humanized Hu2B8 Hv5-51.1 and the Human IgG1 Heavy Chain Constant Region G1m(3) Allotype (Allele 2) (without Signal Sequence) (SEQ ID NO. 210)

```
   1  evqlvqsgae vkkpgeslki sckgsgysft tywmhwvrqm pgkglewmge inptnghtny
  61  npsfqgqvti sadksistay lqwsslkasd tamyycarny vgsifdywgq gtlvtvssas
 121  tkgpsvfpla psskstsggt aalgclvkdy fpepvtvswn sgaltsgvht fpavlqssgl
 181  yslssvvtvp ssslgtqtyi cnvnhkpsnt kvdkrvepks cdkthtcppc papellggps
 241  vflfppkpkd tlmisrtpev tcvvvdvshe dpevkfnwyv dgvevhnakt kpreeqynst
 301  yrvvsvltvl hqdwlngkey kckvsnkalp apiektiska kgqprepqvy tlppsreemt
 361  knqvsltclv kgfypsdiav ewesngqpen nykttppvld sdgsfflysk ltvdksrwqq
 421  gnvfscsvmh ealhnhytqk slslspgk
```

Each dual expression vector was transfected into 293T cells for transient expression using DMEM 10% fetal bovine serum. Forty-eight hours after transfection, cells were washed with and then replaced with serum free medium, IS GRO™ (Irvine Scientific, Santa Ana, Calif.) containing 4 mM L-Glutamine. Supernatant was harvested daily and replaced with fresh media for 10 days. The culture supernatants were centrifuged, filtered (0.45 μm) and concentrated 10-100 fold. Antibodies were purified on ProSep vA resin (Millipore), dialyzed against PBS, concentrated and sterile filtered.

Example 14

Binding Characteristics of Humanized 2B8 Variants

The humanized antibodies produced in Example 13 were characterized by their ability to bind hHGF and the recombinant HGF proteins produced in Example 3.

The antibodies were analyzed by surface-plasmon resonance using a BIAcore T100 instrument to assess their ability to bind hHGF and the fusion proteins discussed in Example 3. Each antibody was immobilized on a carboxymethylated dextran CM5 sensor chip (BIAcore, Catalog No. BR-1006-68) by amine coupling (BIAcore, Catalog No. BR-1000-50) using a standard coupling protocol according to manufacturer's instructions.

Analyses were performed at 25° C. using PBS (GIBCO, Catalog No. 14040-133) containing 0.05% surfactant P20 (BIAcore, Catalog No. R-1000-54), 2 mg/mL BSA (EMD, Catalog No. 2930) and 10 mg/mL CM-Dextran Sodium salt (Fluka, Catalog No. 86524) as running buffer. Supernatant containing different HGF fusion proteins or supernatant from cells transfected with empty vector were injected over each antibody at a flow rate of 30 µL/min for 3 minutes. The resulting binding was determined as resonance units (RU) over baseline 30 seconds after the end of injection. Binding was compared to human HGF (R&D Systems, Catalog No. 294-HGN-025) diluted in running buffer. Non-specific binding was monitored by comparing binding to a control surface. The results are summarized in the Table 17.

TABLE 17

| Antibody | rhHGF (R&D Systems) | mHGF (R&D Systems) | MHM chimera (495-585) | MHM chimera (507-585) | MHM chimera (499-556) |
|---|---|---|---|---|---|
| 2B8 | Yes | No | Yes | Yes | Yes |
| HE2B8-1 | Yes | No | Yes | Yes | Yes |
| HE2B8-2 | Yes | No | Yes | Yes | Yes |
| HE2B8-3 | Yes | No | Yes | Yes | Yes |
| HE2B8-4 | Yes | No | Yes | Yes | Yes |
| sh2B8-9 (G1m(3)) | Yes | No | Yes | Yes | Yes |
| sh2B8-12 (G1m(3)) | Yes | No | Yes | Yes | Yes |

The results in Table 17 demonstrate that each of the humanized 2B8-based antibodies bind rhHGF and all three mouse-human-mouse chimeras.

Example 15

Binding Affinities of Humanized 2B8 Variants

The binding affinities and kinetics of interaction of the antibodies listed in Table 15 were measured by surface plasmon resonance.

Mouse anti-human immunoglobulins (Jackson Labs, Catalog No. 209-005) were immobilized on carboxymethylated dextran CM4 sensor chips (BIAcore, Catalog No. BR-1006-68) by amine coupling (BIAcore, Catalog No. BR-1000-50) using a standard coupling protocol according to manufacturer's instructions. The analyses were performed at 25° C. using PBS (GIBCO, Catalog No. 14040-133) containing 0.05% surfactant P20 (BIAcore, Catalog No. BR-1000-54), and 2 mg/mL BSA (EMD, Catalog No. 2930).

The antibodies were captured in an individual flow cell at a flow rate of 10 µL/min. Injection time was variable for each antibody to yield approximately 20 RU of antibody captured for each cycle. Buffer or HGF (R&D Systems, Catalog No. 294-HGN-025) diluted in running buffer was injected sequentially over a reference surface (no antibody captured) and the active surface (antibody to be tested) for 2 minutes at 60 µL/min. The dissociation phase was monitored for 15 or 90 minutes, depending on concentration. The surface then was regenerated with 10 mM Glycine-HCl, pH 2.2 (BIAcore, Catalog No. BR-1003-54) injected for 3 minutes at a flow rate of 60 µL/min before another cycle was initiated. HGF concentrations tested were 0.46 nM to 7.5 nM.

Kinetic parameters were determined using the kinetic function of the BIAevalutation™ software with reference subtraction. Kinetic parameters for each antibody, $k_a$ (association rate constant), $k_d$ (dissociation rate constant) and $K_D$ (equilibrium dissociation constant) are summarized in Table 18.

TABLE 18

| Antibody | $k_a$ (1/MS) | $k_d$ (1/s) | $K_D$ (pM) | SD |
|---|---|---|---|---|
| 2B8 | $1.4 \times 10^6$ | $1.0 \times 10^{-5}$ | 7.3 | — |
| HE2B8-1 | $2.2 \times 10^6$ | $1.4 \times 10^{-5}$ | 7.1 | 5.2 |
| HE2B8-2 | $1.8 \times 10^6$ | $9.6 \times 10^{-6}$ | 5.2 | 2.7 |
| HE2B8-3 | $2.0 \times 10^6$ | $4.1 \times 10^{-6}$ | 2.0 | 1.1 |
| HE2B8-4 | $1.7 \times 10^6$ | $1.1 \times 10^{-5}$ | 6.5 | 1.3 |
| sh2B8-9 (G1m(17,1)) | $2.0 \times 10^6$ | $1.7 \times 10^{-5}$ | 8.1 | 5.3 |
| sh2B8-12 (G1m(17,1)) | $1.9 \times 10^6$ | $2.3 \times 10^{-5}$ | 12 | 0.4 |

These data show that the humanized antibodies have fast association rates ($k_a$), very slow dissociation rates ($k_d$), and very high affinities ($K_D$). In particular, the antibodies have affinities ranging from 2.0-12 pM.

Example 16

Comparison of Binding Affinities at 25° C. and 37° C.

The binding affinities and kinetics of interaction of antibody HE2B8-4, sh2B8-9, sh2B8-12, and murine 2B8 were measured by surface plasmon resonance under different conditions.

Mouse anti-human immunoglobulins (Jackson Labs, Catalog No. 209-005) or rabbit anti-mouse immunoglobulins (BIAcore, Catalog No. BR-1005-14) were immobilized on carboxymethylated dextran CM4 sensor chips (BIAcore, Catalog No. BR-1006-68) by amine coupling (BIAcore, Catalog No. BR-1000-50) using a standard coupling protocol according to manufacturer's instructions. In the case of 25° C. measurements for sh2b8-9 and sh2B8-12, a CM5 sensor chip (BIAcore, Catalog No. BR-1006-68) was used. The analyses were performed at 25° C. and 37° C. using PBS (GIBCO, Catalog No. 14040-133) containing 0.05% surfactant P20 (BIAcore, Catalog No. BR-1000-54), and 2 mg/mL BSA (EMD, Catalog No. 2930) as running buffer.

The antibodies were captured in an individual flow cell at a flow rate of 10 µL/min. Injection time was variable for each antibody to yield approximately 20 RU of antibody captured for each cycle. Buffer or HGF (R&D Systems, Catalog No. 294-HGN-025) diluted in running buffer was injected sequentially over a reference surface (no antibody captured) and the active surface (antibody to be tested) for 2 minutes at 60 µL/min. The dissociation phase was monitored for 15 or 90 minutes, depending on concentration. The surface of mouse anti-human immunoglobulins sensor chips was then regenerated with 10 mM Glycine-HCl, pH 2.2 (BIAcore, Catalog No. BR-1003-54) injected for 3 minutes at a flow rate of 60

µL/min before another cycle was initiated. The surface of rabbit anti-mouse immunoglobulins sensor chips was regenerated with 10 mM Glycine-HCl, pH 1.7 (BIAcore, Catalog No. BR-1003-54) injected for 3 minutes at a flow rate of 60 µL/min before another cycle was initiated. HGF concentrations tested were 0.46 nM to 7.5 nM.

Kinetic parameters were determined using the kinetic function of the BIAevaluation software with reference subtraction. Kinetic parameters for each antibody, $k_a$ (association rate constant), $k_d$ (dissociation rate constant) and $K_D$ (equilibrium dissociation constant) are summarized below in Table 19.

TABLE 19

| Antibody | Temp. (° C.) | $k_a$ (1/Ms) | $k_d$ (1/s) | $K_D$ (pM) |
|---|---|---|---|---|
| 2B8 | 25 | $1.6 \times 10^6$ | $2.1 \times 10^{-5}$ | 13.5 |
| 2B8 | 37 | $2.8 \times 10^6$ | $1.3 \times 10^{-5}$ | 4.5 |
| HE2B8-4 | 25 | $2.0 \times 10^6$ | $1.2 \times 10^{-5}$ | 5.6 |
| HE2B8-4 | 37 | $3.1 \times 10^6$ | $1.0 \times 10^{-5}$ | 3.3 |
| sh2B8-9 (G1m(17,1)) | 25 | $2.0 \times 10^6$ | $1.7 \times 10^{-5}$ | 8.1 |
| sh2B8-9 (G1m(3)) | 37 | $2.5 \times 10^6$ | $1.4 \times 10^{-5}$ | 5.8 |
| sh2B8-12 (G1m(17,1)) | 25 | $1.9 \times 10^6$ | $2.3 \times 10^{-5}$ | 12.0 |
| sh2B8-12 (G1m(3)) | 37 | $2.4 \times 10^6$ | $1.1 \times 10^{-5}$ | 4.8 |

As expected, the association rate constants increased with an increase in the temperature. Surprisingly, the dissociation constants did not change significantly with a corresponding increase in temperature. Consequently, the overall equilibrium dissociation constants ($K_D$) were approximately 1.4 to 3 times smaller (higher affinity) at physiological temperature (37° C.).

Example 17

Neutralization Activity of Humanized 2B8 Variants

The antibodies described in Example 14 were characterized for their ability to (a) inhibit the binding of hHGF to c-Met, and (b) inhibit HGF stimulated BrdU incorporation in 4 MBr-5 cells.

HGF-Met Binding Inhibition Assay (Neutralization Assay) was performed as described in as follows. The antibodies were tested by ELISA for their ability to inhibit hHGF binding to c-Met. Specifically, Wallac 96-well DELFIA assay plates (Wallac Inc., Catalog No. AAAND-0001) were coated with 100 µL of 6.25 µg/mL HGF (R&D Systems, Catalog No. 294-HGN-025) in carbonate coating buffer (15 mM $Na_2CO_3$ and 34 mM $NaHCO_3$, pH 9.0) for 16 hours at 4° C. The plates then were blocked with 200 µL of 5% non-fat dry milk in PBS for 1 hour at room temperature. The antibodies were prepared in a separate plate by adding increasing concentrations of the antibodies under investigation (0.033-250 nM, 2-fold-serial dilution) to 2 nM biotinylated c-Met in 5% non-fat dry milk in PBS. c-Met (R&D Systems, Catalog No. 358-MT/CF) is biotinylated according to manufacturer's instruction at 10:1 biotin to c-Met ratio (Pierce, Catalog No. 21335). 100 µL of sample per well was transferred to the assay plate and incubated for 2 hours at room temperature. The resulting plates were washed three times with PBS-0.1% Tween 20, and incubated for 1 hour at room temperature with Eu-labeled Streptavidin (Wallac, Catalog No. 1244-360) diluted 1:1000 in DELFIA assay buffer (Wallac, Catalog No. 4002-0010). The resulting plates were washed 3 times with DELFIA wash solution (Wallac, Catalog No. 4010-0010) and incubated with 100 µL/well DELFIA enhancement solution (Wallac #4001-0010) for 15 minutes at room temperature with agitation. The plates were read on Victor[3]V instrument (Perkin Elmer) using the Europium method. The $IC_{50}$ values were calculated using Prism.

The $IC_{50}$ values obtained are shown in Table 20.

TABLE 20

| Antibody | $IC_{50}$ (nM) | SD |
|---|---|---|
| 2B8 | 9.2 | 1.2 |
| HE2B8-1 | 6.0 | 1.2 |
| HE2B8-2 | 5.7 | 1.1 |
| HE2B8-3 | 5.9 | 1.1 |
| HE2B8-4 | 6.5 | 1.2 |
| sh2B8-9 (G1m(3)) | 4.2 | — |
| sh2B8-12 (G1m(3)) | 6.8 | — |

These results from Table 20 demonstrate that the humanized antibodies tested efficiently neutralize HGF binding to c-Met.

The antibodies in Table 17 were also tested in the cell proliferation assay described in Example 7(b). The results are summarized below in Table 21.

TABLE 21

| Antibody | $IC_{50}$ (nM) | SD |
|---|---|---|
| 2B8 | 0.86 | 0.35 |
| HE2B8-1 | 0.47 | 0.15 |
| HE2B8-2 | 0.66 | 0.13 |
| HE2B8-3 | 0.55 | 0.28 |
| HE2B8-4 | 0.58 | 0.26 |
| sh2B8-9 (G1m(3)) | 0.52 | 0.11 |
| sh2B8-12 (G1m(3)) | 0.81 | 0.22 |

The results from Table 21 demonstrate that all the humanized antibodies tested inhibit HGF-induced proliferation of 4 MBr-5 cells.

Example 18

Anti-Scatter Activity of Humanized 2B8 Variants

The antibodies in Table 17 were tested in the anti-scatter assay described in Example 8. The results are summarized below in Table 22.

TABLE 22

| | Inhibition of HGF-induced MDCK Cell Scattering | |
|---|---|---|
| Antibody | Trial 1 | Trial 2 |
| 2B8 | ++ | ++ |
| HE2B8-1 | ++ | ++ |
| HE2B8-2 | ++ | ++ |
| HE2B8-3 | ++ | ++ |
| HE2B8-4 | ++ | ++ |
| sh2B8-9 (G1m(3)) | ++ | ++ |
| sh2B8-12 (G1m(3)) | ++ | ++ |

− No Inhibition
+++ Very strong, nearly complete inhibition
++ Strong inhibition
+ Detectable inhibition The results in Table 22 demonstrate that all the humanized antibodies tested inhibited HGF-induced scattering to the same extent as the murine monoclonal antibody 2B8.

Example 19

Inhibition of HGF-Stimulated c-Met Phosphorylation

The antibodies in Table 17 were tested in the c-Met phosphorylation assay described in Example 9. The results are summarized below in Table 23.

TABLE 23

| Antibody | Average of Two Trials | Standard Deviation |
|---|---|---|
| 2B8 | 0.91 | 0.02 |
| he2B8-1 | 0.80 | 0.04 |
| he2B8-2 | 0.88 | 0.15 |
| he2B8-3 | 0.79 | 0.05 |
| he2B8-4 | 0.75 | 0.14 |
| sh2B8-9 (G1m(3)) | 0.93 | 0.03 |
| sh2B8-12 (G1m(3)) | 0.81 | 0.07 |

The results in Table 23 demonstrate that all the humanized antibodies tested are potent inhibitors of HGF-induced c-Met phosphorylation in PC-3 cells.

Example 20

Tumor Inhibition in U87MG Xenograft Model

The ability of the humanized monoclonal antibodies of the invention to inhibit tumor growth was tested in an U87MG xenograft model. U87MG cells (ATCC) were expanded in culture at 37° C. in an atmosphere containing 5% $CO_2$ and 95% air, using a medium comprising Dulbecco's Modified Eagle medium (DMEM) with 10% fetal bovine serum, 100 units/mL penicillin and 100 µg/mL streptomycin. The cells were subcultured and maintained by detaching the cells from the wall of the culture dish using trypsin-EDTA.

Near-confluent cells were collected by trypsinization and then $5 \times 10^6$ cells in 50% Matrigel (BD Biosciences; catalog no. 356237) were injected subcutaneously into the upper dorsal area between the shoulder blades of 7-week old female ICR SCID mice (Taconic Labs). The long (L) and short (W) diameters (mm) of tumors were measured with a caliper. Tumor volume (vol.) was calculated as: volume (mm$^3$)=L× $W^2$/2. When the tumors grew to approximately 200 mm$^3$, the tumor-bearing mice were randomized into 5 groups of 10 mice each. One group received PBS and one group received human IgG control. Each of the other 4 groups received one of the humanized antibodies (HE2B8-1, HE2B8-2, HE2B8-3, and HE2B8-4). All the antibodies were dosed at 0.25 mg/kg body weight, twice per week, by intra-peritoneal injections of 5 doses. Tumor volumes and mouse body weights were recorded twice per week. Tumor growth inhibition was analyzed using Student's t-test.

The humanized antibodies tested were active in vivo. There was 57% tumor growth inhibition for HE2B8-1 with a p value of 0.02, 61% tumor growth inhibition for HE2B8-2 with a p value of 0.02, 85% tumor growth inhibition for HE2B8-3, with a p value of 0.0004, and 74% tumor growth inhibition for HE2B8-4 with a p value of 0.001. No significant body weight loss was observed.

A subsequent study was performed as described above in female NCR nude mice (Taconic Labs) bearing subcutaneous U87MG tumors inoculated in the flank. Each group (10 mice each) received one of the following treatments at 0.5 mg/kg: PBS vehicle control, huIgG control, HE2B8-4, or sh2B8-9. Treatment was given intra-peritoneal twice weekly for a minimum of 5 weeks. Each treatment group demonstrated similar tumor regression with tumor growth inhibition of 113% for sh2B8-9 and 115% for HE2B8-4, and a minimum tumor growth delay of 30 days. Both treatments were well-tolerated with no significant body weight loss.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

---

What is claimed is:

1. An isolated antibody that binds human hepatocyte growth factor (HGF) comprising:
   (a) an immunoglobulin heavy chain variable region, comprising the structure $CDR_{H1}$-$CDR_{H2}$-$CDR_{H3}$, wherein
      (i) $CDR_{H1}$ comprises the amino acid sequence of SEQ ID NO. 15,
      (ii) $CDR_{H2}$ comprises the amino acid sequence of SEQ ID NO. 204, and
      (iii) $CDR_{H3}$ comprises the amino acid sequence of SEQ ID NO. 17; and
   (b) an immunoglobulin light chain variable region comprising the structure $CDR_{L1}$-$CDR_{L2}$-$CDR_{L3}$, wherein
      (i) $CDR_{L1}$ comprises the amino acid sequence of SEQ ID NO. 18,
      (ii) $CDR_{L2}$ comprises the amino acid sequence of SEQ ID NO. 19, and
      (iii) $CDR_{L3}$ comprises the amino acid sequence of SEQ ID NO. 20; or an antigen binding fragment of the antibody.

2. The antibody of claim 1, wherein the CDRs are interposed between human or humanized immunoglobulin framework regions.

3. The antibody of claim 1, wherein the antibody is a monoclonal antibody.

4. The antibody of claim 1, wherein the antibody binds human hepatocyte growth factor with a $K_d$ of $4.0 \times 10^{-5} s^{-1}$ or lower.

5. The antibody of claim 1, wherein the antibody binds human hepatocyte growth factor with a $K_D$ of 20 pM or lower.

6. An isolated antibody that binds human hepatocyte growth factor (HGF) comprising an immunoglobulin heavy chain variable region comprising the amino acid sequence of SEQ ID NO. 183 and an immunoglobulin light chain variable region comprising the amino acid sequence of SEQ ID NO. 193, or an antigen binding fragment of the antibody.

7. The antibody of claim 6, wherein the antibody is a monoclonal antibody.

8. An isolated antibody that binds human hepatocyte growth factor (HGF) comprising an immunoglobulin heavy chain sequence comprising the amino acid sequence of SEQ ID NO. 187 and an immunoglobulin light chain sequence comprising the amino acid sequence of SEQ ID NO. 197, or an antigen binding fragment of the antibody.

9. The antibody of claim 8, wherein the antibody is a monoclonal antibody.

* * * * *